US012433897B2

(12) United States Patent
Heimann et al.

(10) Patent No.: US 12,433,897 B2
(45) Date of Patent: Oct. 7, 2025

(54) PYRIDINE DERIVATIVES WITH N-LINKED CYCLIC SUBSTITUENTS AS cGAS INHIBITORS

(71) Applicant: BOEHRINGER INGELHEIM INTERNATIONAL GMBH, Ingelheim am Rhein (DE)

(72) Inventors: Annekatrin Charlotte Heimann, Biberach an der Riss (DE); Sandra Ruth Handschuh, Biberach an der Riss (DE); Christoph Hoenke, Biberach an der Riss (DE); Cédrickx Godbout, Attenweiler (DE); Christian Gnamm, Biberach an der Riss (DE); Patrick Gross, Biberach (DE); Joerg Kley, Mittelbiberach (DE); Christian Andreas Kuttruff, Schemmerhofen (DE); Dirk Reinert, Bad Duerkheim (DE); Raphael Stuber, Schwendi (DE); Marc Alexander Grundl, Biberach an der Riss (DE); Theodor Theis, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 17/741,009

(22) Filed: May 10, 2022

(65) Prior Publication Data

US 2023/0000878 A1 Jan. 5, 2023

(30) Foreign Application Priority Data

May 12, 2021 (EP) .................................... 21173689

(51) Int. Cl.

| | |
|---|---|
| ***A61K 31/5386*** | (2006.01) |
| ***A61K 31/4412*** | (2006.01) |
| ***A61K 31/496*** | (2006.01) |
| ***A61K 31/519*** | (2006.01) |
| ***A61K 31/5377*** | (2006.01) |

(Continued)

(52) U.S. Cl.

CPC ...... *A61K 31/5386* (2013.01); *A61K 31/4412* (2013.01); *A61K 31/496* (2013.01); *A61K 31/519* (2013.01); *A61K 31/5377* (2013.01); *A61K 39/3955* (2013.01); *A61K 45/06* (2013.01); *A61P 37/06* (2018.01); *C07D 491/048* (2013.01); *C07D 519/00* (2013.01)

(58) Field of Classification Search

CPC .............. A61K 31/4412; A61K 31/496; A61K 31/519; A61K 31/5377; A61K 31/5366; A61P 1/00; A61P 21/00; A61P 25/16; A61P 27/02; A61P 29/00; A61P 35/00; A61P 37/06; A61P 9/00; C07D 213/74; C07D 401/04; C07D 401/12; C07D 401/14; C07D 413/04; C07D 491/048; C07D 491/107; C07D 498/04; C07D 519/00

See application file for complete search history.

(56) References Cited

U.S. PATENT DOCUMENTS 5,654,299 A 8/1997 Shenvi et al.
12,043,625 B2 7/2024 Heimann et al.

(Continued)

FOREIGN PATENT DOCUMENTS

EP 000001710233 A1 10/2006
EP 000002409977 A1 1/2012

(Continued)

OTHER PUBLICATIONS

Wu et al, Toxicology, vol. 236, pp. 1-6 (Year: 2007).*
Ablasser et al., cGAS produces a 2'-5'-linked cyclic dinucleotide second messenger that activates STING, Nature, 2013, vol. 498, No. 7454, pp. 380-384.
Ahn et al., "STING manifests self DNA-dependent inflammatory disease", Proceedings of the National Academy of Sciences, 2012, vol. 109, No. 47, pp. 19386-19391.

(Continued)

*Primary Examiner* — Sarah Pihonak
(74) *Attorney, Agent, or Firm* — Philip I. Datlow

(57) ABSTRACT

The invention relates to new proline derivatives of formula (I) as cGAS inhibitors, (I)

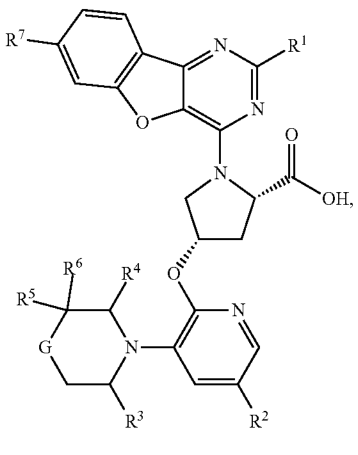

wherein
wherein $R^1$, $R^2$, $R^3$, $R^4$, $R^5$, $R^6$, $R^7$, $R^8$, $R^9$, $R^{10}$, $R^{11}$ and G are defined as in claim 1,
and prodrugs or pharmaceutically acceptable salts of these compounds
for the treatment of diseases such as systemic lupus erythematosus, systemic sclerosis (SSc), non-alcoholic steatotic hepatitis (NASH), interstitial lung disease (ILD) and idiopathic pulmonary fibrosis (IPF).

65 Claims, No Drawings

(51) Int. Cl.

| | |
|---|---|
| ***A61K 39/395*** | (2006.01) |
| ***A61K 45/06*** | (2006.01) |
| ***A61P 37/06*** | (2006.01) |
| ***C07D 491/048*** | (2006.01) |
| ***C07D 519/00*** | (2006.01) |

(56) References Cited

U.S. PATENT DOCUMENTS

| | | | |
|---|---|---|---|
| 2011/0082182 | A1 | 4/2011 | Buckman et al. |
| 2012/0220621 | A1 | 8/2012 | Carry et al. |
| 2019/0192668 | A1 | 6/2019 | Mainolfi et al. |
| 2023/0000878 | A1 | 1/2023 | Heimann et al. |
| 2024/0189315 | A1 | 6/2024 | Heimann et al. |
| 2024/0208997 | A1 | 6/2024 | Heimann et al. |
| 2024/0342186 | A1 | 10/2024 | Heimann et al. |

FOREIGN PATENT DOCUMENTS

| | | | |
|---|---|---|---|
| EP | 2680844 | A2 | 1/2014 |
| JP | 1994340625 | | 12/1991 |
| JP | 2016512203 | A | 4/2016 |
| WO | 2004002986 | A2 | 1/2004 |
| WO | 2005035525 | A2 | 4/2005 |
| WO | 2006047504 | A1 | 5/2006 |
| WO | 2010057126 | A1 | 5/2010 |
| WO | 2011092272 | A1 | 8/2011 |
| WO | 2011143129 | A1 | 11/2011 |
| WO | 2011143366 | A1 | 11/2011 |
| WO | 2011143495 | A1 | 11/2011 |
| WO | 2012037259 | A1 | 3/2012 |
| WO | 2012040242 | A1 | 3/2012 |
| WO | 2014011769 | A1 | 1/2014 |
| WO | 2016038581 | A1 | 3/2016 |
| WO | 2019180683 | A1 | 9/2019 |
| WO | 2019183636 | A1 | 9/2019 |
| WO | 2019195609 | A2 | 10/2019 |
| WO | 2019241787 | A1 | 12/2019 |
| WO | 2020014729 | A1 | 1/2020 |
| WO | 2020142729 | A1 | 7/2020 |
| WO | 2020210649 | A1 | 10/2020 |
| WO | 2020229982 | A1 | 11/2020 |
| WO | 2022174012 | A1 | 8/2022 |
| WO | 2022238327 | A1 | 11/2022 |
| WO | 2022238335 | A1 | 11/2022 |
| WO | 2023241627 | | 12/2023 |
| WO | 2024099907 | A1 | 5/2024 |

OTHER PUBLICATIONS

Barbalat et al., "Nucleic Acid Recognition by the Innate Immune System", Annual Review of Immunology, 2011, vol. 29, No. 1, pp. 185-214.
Chen et al., "cGAS suppresses genomic instability as a decelerator of replication forks", Science Advances, 2020, pp. 1-10.
Cho et al., "Lipotoxicity induces hepatic protein inclusions through TANK binding kinase 1-mediated p62/sequestosome 1 phosphorylation", Hepatology, 2018, vol. 68, No. 4, pp. 1331-1346.
Crow et al., "Mutations in the gene encoding the 3 ?- 5? DNA exonuclease TREX1 cause Aicardi-Goutières syndrome at the AGS1 locus", Nature Genetics, 2006, vol. 38, No. 8, pp. 917-920.
Gao et al., "Activation of cyclic GMP-AMP synthase by self-DNA causes autoimmune diseases", Proceedings of the National Academy of Sciences, 2015, vol. 112, No. 42, pp. E5699-E5705.
Gao et al., "Cyclic GMP-AMP Synthase Is an Innate Immune Sensor of HIV and Other Retroviruses", Science, 2013, vol. 341, pp. 903-907.
Glück et al., "Innate immune sensing of cytosolic chromatin fragments through cGAS promotes senescence", Nature Cell Biology, 2017, vol. 19, No. 9, pp. 1061-1070.
Gratia et al., "Bloom syndrome protein restrains innate immune sensing of micronuclei by cGAS", The Journal of Experimental Medicine, 2019, vol. 216, No. 5, pp. 1199-1213.
Gray et al., "Cutting Edge: cGAS Is Required for Lethal Autoimmune Disease in the Trex1-Deficient Mouse Model of Aicardi-Goutières Syndrome", The Journal of Immunology, 2015, vol. 195, No. 5, pp. 1939-1943.
Hall et al., "Discovery of PF-06928215 as a high affinity inhibitor of cGAS enabled by a novel fluorescence polarization assay", Plos One, 2017, vol. 12, No. 9, pp. e0184843.
Hansen et al., "Listeria monocytogenes induces IFN? expression through an IFI16?, cGAS? and STING?dependent pathway", The EMBO Journal, 2014, vol. 33, No. 15, pp. 1654-1666.
Harding et al., "Mitotic progression following DNA damage enables pattern recognition within micronuclei", Nature, 2017, vol. 548, No. 7668, pp. 466-470.
Hoong et al., "cGAS-STING pathway in oncogenesis and cancer therapeutics", Oncotarget, 2020, vol. 11, No. 30, pp. 2930-2955.
Hu et al., "Cytosolic DNA sensor cGAS plays an essential pathogenetic role in pressure overload-induced heart failure", American Journal of Physiology-Heart and Circulatory Physiology, 2020, vol. 318, No. 6, pp. H1525-H1537.
Kerur et al., "cGAS drives non-canonical inflammasome activation in age-related macular degeneration", Nature Medicine, 2018, vol. 24, No. 1, pp. 50-61.
Ma et al., "Gasdermin D in macrophages restrains colitis by controlling cGAS-mediated inflammation", Science Advances, 2020, vol. 6, No. 21, pp. eaaz6717.
Ma et al., "Modulation of the cGAS-STING DNA sensing pathway by gammaherpesviruses", Proceedings of the National Academy of Sciences, 2015, vol. 112, No. 31, pp. E4306-E4315.
Mackenzie et al., "cGAS surveillance of micronuclei links genome instability to innate immunity", Nature, 2017, vol. 548, No. 7668, pp. 461-465.
Nakamura et al., "Synthesis and evaluation of N-acylsulfonamide and N-acylsulfonylurea prodrugs of a prostacyclin receptor agonist", Bioorganic & Medicinal Chemistry, 2007, vol. 15, No. 24, pp. 7720-7725.
Nascimento et al., "Self-DNA release and STING-dependent sensing drives inflammation to cigarette smoke in mice", Scientific Reports, 2019, vol. 9, No. 1, pp. 14848.
Papinska et al., "Activation of Stimulator of Interferon Genes (STING) and Sjögren Syndrome", Journal of Dental Research, 2018, vol. 97, No. 8, pp. 893-900.
Pisetsky, "Anti-DNA antibodies—quintessential biomarkers of SLE", Nature Reviews Rheumatology, 2016, vol. 12, No. 2, pp. 102-110.
Sliter et al., "Parkin and PINK1 mitigate STING-induced inflammation", Nature, 2018, vol. 561, No. 7722, pp. 258-262.
Sun et al., "Cyclic GMP-AMP Synthase Is a Cytosolic DNA Sensor That Activates the Type I Interferon Pathway", Science, 2013, vol. 339, No. 6121, pp. 786-791.
Wu et al., "Cyclic GMP-AMP Is an Endogenous Second Messenger in Innate Immune Signaling by Cytosolic DNA", Science, 2013, vol. 339, pp. 826-831.
Yang et al., "cGAS is essential for cellular senescence", Proceedings of the National Academy of Sciences, 2017, vol. 114, No. 23, pp. E4612-E4620.
Bai & Liu, "cGAS-STING signaling and function in metabolism and kidney diseases", Journal of Molecular Cell Biology, 2021, 13(10), pp. 728-738.
International Search Report and Written Opinion for application, PCT/EP2022/062480, date of mailing Aug. 1, 2022.
STN Search Results entitled "[Kagoubutsu without Caplus, Chemcats Compounds]", pp. 1/6-6/6, listing Registry Nos. 2384889-55-6 (Nov. 28, 2019), 2229587-23-7 (Jun. 29, 2018), 1988901-31-0 (Sep. 8, 2016), 1875636-26-2 (Feb. 28, 2016), 1704945-82-3 (May 15, 2015), 1604285-51-9 (May 14, 2014), 1604282-32-7 (May 13, 2014), 1566463-09-9 (Mar. 11, 2014), 1566082-34-5 (Mar. 11, 2014), 1121613-72-6 (Mar. 16, 2009), 1121613-47-5 (Mar. 16, 2009).
Chauhan et al., "The role of cGAS-STING signaling in ischemic stroke: from immune response to therapeutic targeting", Drug Discovery Today, vol. 28, 2023, p. 1-9.
Shen et al., "STING mediates microglial pyroptosis via interaction with NLRP3 in cerebral ischaemic stroke", SVN, vol. 9, 2024, p. 153-164.

(56) References Cited

OTHER PUBLICATIONS

Guan et al., “Methylsulfone as a leaving group for synthesis of hyperbranched poly(arylene pyrimidine ether)s by nucleophilic aromatic substitutions”, RSC Advances, vol. 5, No. 17, 2015, p. 12821-12823.
Duo et al., “Cytoplasmic chromatin triggers inflammation in senescense and cancer”, Nature, vol. 550, 2017, p. 402-406.
ACS Chemical Abstracts Service Registry Nos., 1352719-62-0, Title Pyridine, 2-fluorp-3-(tetrahydro-2H-thiopyran-4-yl)- 2012, 8 pages.
An et al., “Expression of Cyclic GMP?AMP Synthase in Patients With Systemic Lupus Erythematosus”, Arthritis & Rheumatology, 2017, vol. 69, No. 4, pp. 800-807.
Bakhoum et al., “Chromosomal instability drives metastasis through a cytosolic DNA response”, Nature, 2018, vol. 553, No. 7689, pp. 467-472.
Beaumont et al., “Design of Ester Prodrugs to Enhance Oral Absorption of Poorly Permeable Compounds: Challenges to the Discovery Scientist”, Current Drug Metabolism, 2003, vol. 4, No. 6, pp. 461-485.
Chung et al., “Mitochondrial Damage and Activation of the STING Pathway Lead to Renal Inflammation and Fibrosis”, Cell Metabolism, 2019, vol. 30, No. 4, pp. 784-799.e5.
Domizio et al., “The cGAS-STING pathway drives type I IFN immunopathology in COVID-19”, Nature, 2022, vol. 603, No. 7899, pp. 145-151.
Dou et al., “Cytoplasmic chromatin triggers inflammation in senescence and cancer”, Nature, 2017, vol. 550, No. 7676, pp. 402-406.
Gao et al., “Cyclic GMP-AMP Is an Endogenous Second Messenger in Innate Immune Signaling by Cytosolic DNA”, Science, 2013, vol. 339, pp. 826-831.
Hamann et al., “First evidence for Sting Snp R293Q being protective regarding obesity-associated cardiovascular disease in age-advanced subjects—a cohort study”, Immunity & Ageing, 2020, vol. 17, No. 1, pp. 1-6.
Hamann et al., “Sting SNP R293Q Is Associated with a Decreased Risk of Aging-Related Diseases”, Gerontology, 2019, vol. 65, No. 2, pp. 145-154.
Hu et al., “Discovery of Phosphodiesterade 10A (PDE10A) Pet Tracer AMG 580 to Support Clinical Studies”, ACS Medicinal Chemistry Letters, 2016, vol. 7, No. 7, pp. 719-723.
Huang et al., “mtDNA Activates cGAS Signaling and Suppresses the YAP-Mediated Endothelial Cell Proliferation Program to Promote Inflammatory Injury”, IMMUNITY, 2020, vol. 52, No. 3, pp. 475-486.e5.
International Search Report and Written Opinion for PCT/EP2023/080705, mailed Feb. 5, 2024.
International Search Report and Written Opinion for PCT/EP2023/080711, mailed Feb. 5, 2024.
Kato et al., “Apoptosis-derived membrane vesicles drive the cGAS-STING pathway and enhance type I IFN production in systemic lupus erythematosus”, Annals of the Rheumatic Diseases, 2018, vol. 77, No. 10, pp. 1507-1515.
Kennedy et al., “Protective Groups in Organic Synthesis (3rd Edition) T.W. Greene, P.G.M. Wuts; John Wiley & Sons, Inc., New York, 1999, xxi+779 pages, £58-50, ISBN 0-471-16019-9”, Carbohydrate Polymers, 2001, vol. 45, No. 1, pp. 105-106.
Li et al., “Plasma-derived DNA containing-extracellular vesicles induce STING-mediated proinflammatory responses in dermatomyositis”, Theranostics, 2021, vol. 11, No. 15, pp. 7144-7158.
Maekawa et al., “Mitochondrial Damage Causes Inflammation via cGAS-STING Signaling in Acute Kidney Injury”, Cell Reports, 2019, vol. 29, No. 5, pp. 1261-1273.e6.
Mao et al., “STING-IRF3 Triggers Endothelial Inflammation in Response to Free Fatty Acid-Induced Mitochondrial Damage in Diet-Induced Obesity”, Arteriosclerosis, Thrombosis, and Vascular Biology, 2018, vol. 37, No. 5, pp. 920-929.
Moseley et al., “Investigation of an Alternative Route to ZD3638 and Cost-Benefit Analysis Comparison of Raw Materials with the Previous Route”, Organic Process Research & Development, 2001, vol. 5, No. 5, pp. 491-497.
Neufeldt et al., “SARS-COV-2 infection induces a pro-inflammatory cytokine response through cGAS-STING and NF-? B”, Communications Biology, 2022, vol. 5, No. 1, pp. 1-15.
Ryu et al., “Bioactive Plasma Mitochondrial DNA Is Associated With Disease Progression in Scleroderma?Associated Interstitial Lung Disease”, Arthritis & Rheumatology, 2020, vol. 72, No. 11, pp. 1905-1915.
Schuliga et al., “Self DNA perpetuates IPF lung fibroblast senescence in a cGAS-dependent manner”, Clinical Science, 2020, vol. 134, No. 7, pp. 889-905.
Steiner et al., “Deficiency in coatomer complex I causes aberrant activation of STING signalling”, Nature Communications, 2022, vol. 13, No. 1, pp. 2321.
Thim-Uam et al., “STING Mediates Lupus via the Activation of Conventional Dendritic Cell Maturation and Plasmacytoid Dendritic Cell Differentiation”, Iscience, 2020, vol. 23, No. 9, pp. 1-42.
Tonduti et al., “Novel and emerging treatments for Aicardi-Goutières syndrome”, Expert Review of Clinical Immunology, 2020, vol. 16, No. 2, pp. 189-198.
U.S. Appl. No. 18/734,077 filed Jun. 5, 2024 Inventor Annakatrin Charlotte Heimann (the cited pending US Application is stored in the USPTO IFW System MPEP 609.04(a)(II)C.
Visitchanakun et al., “Interference on Cytosolic DNA Activation Attenuates Sepsis Severity: Experiments on Cyclic GMP-AMP Synthase (cGAS) Deficient Mice”, International Journal of Molecular Sciences, 2021, vol. 22, No. 21, pp. 11450.
Wang et al., “Cyclic GMP-AMP Synthase Is Required for Cell Proliferation and Inflammatory Responses in Rheumatoid Arthritis Synoviocytes”, Mediators of Inflammation, 2015, vol. 2015, pp. 192329.
Willemsen et al., “TNF leads to mtDNA release and cGAS/STING-dependent interferon responses that support inflammatory arthritis”, Cell Reports, 2021, vol. 37, No. 6, pp. 109977.
Yu et al., “STING-mediated inflammation in Kupffer cells contributes to progression of nonalcoholic steatohepatitis”, Journal of Clinical Investigation, 2018, vol. 129, No. 2, pp. 546-555.
Yu et al., “TDP-43 Triggers Mitochondrial DNA Release via mPTP to Activate cGAS/STING in Als”, Cell, 2020, vol. 183, No. 3, pp. 636-649.
Zhou et al., “Activation of cGAS?STING pathway—A possible cause of myofiber atrophy/necrosis in dermatomyositis and immune? mediated necrotizing myopathy”, Journal of Clinical Laboratory Analysis, 2022, vol. 36, No. 10, pp. 1-10.
Patel, et al., “Human cGAS catalytic domain has an additional DNA-binding interface that enhances enzymatic activity and liquid-ohase condensation”, PNAS, vol. 116, 2019, p. 11946-11955.
Guo, et al., Targeting STING ROS induced intervertebral disc degeneration:, Osteoarthritis Cartilage, vol. 8, 2021, p. 1213-1224.
Liu, “Nuclear cGAS suppresses DNA repair and promotes tumorigenesis”, Nature, vol. 563, 2018, p. 131-136.
Irvine et al., “Causes and Consequences of Innate Immune Dysfunction in Cirrhosis”, Front Immunol., vol. 10, 2015, p. 1-14.
Keskitalo et al., “Novel TMEM173 Mutation and the Role of Disease Modifying Alleles” Front Immunol., vol. 10, 2019, p. 1-17.
Weidler et al., “A rare manifestation of STING-associated vasculopathy with onset in infancy: a case report”, Pediatric Rheumatol. Online, vol. 22, 2024, p. 1-9.
Debopam, “Multiple Autoimmune Disorders in Aicardi-Goutieres Syndrome”, Pediatric Neurology, vol. 96, 2019, p. 37-39.
Coquel et al., “SAMHD1 acts at stalled replication forks to prevent interferon induction”, Nature, vol. 557, 2018, p. 57-82.
Shehata et al., “Mitochondrial DNA copy marker as a diagnostic marker and indicator of degree of severity in alopecia areata”, J. of Immunoassay and Immunochemistry, vol. 44, 2023, p. 256-268.
Omar et al., IFN-? and TNF-? serum levels and their association with disease severity in Egytian children and adults with alopecia areata, Int. j. of Dermatology, vol. 60, 2021, p. 1397-1404.

(56) References Cited

OTHER PUBLICATIONS

Kessler et al., "Monocyte-derived macrophages aggravate pulmonary vasculitis via cGAS/STING/IFN-mediated nucleic acid sensing", J. Exp. Med., vol. 219, 2019, p. 1-19.
Staels et al., "Adult-onset ANCA-Associated Vasculitis in SAVI: Extension of the Phenotypic Spectrum, Case Report and Review of the Literature", Frontiers in Immunology, vol. 11, 2020, p. 1-5.
Roesing et al., "Chronic endoplasmic reticulum stress in myotonic dystrophy type 2 promotes autoimmunity via mitochondrial DNA release", Nature, vol. 15, 2024, p. 1-15.
Sun et al., "Mutant huntingtin protein induces MLH1 degredation, DNA hyperexcision, and cGAS-STING-dependent apoptosis", PNAS, vol. 121, 2024, p. 1-12.
Sharma et al. "Cyclic GMP-AMP synthase promotes the inflammatory and autophagy responses in Huntington disease", PNAS, vol. 117, 2020, p. 15989-15999.
Xie et al., "Activation of innate immune cGAS-STING pathway contributes to Alzheimer's pathogenesis in 5xFAD mice", Nature Aging, vol. 3, 2023, p. 202-212.

* cited by examiner

PYRIDINE DERIVATIVES WITH N-LINKED CYCLIC SUBSTITUENTS AS cGAS INHIBITORS

1 BACKGROUND OF THE INVENTION

1.1 cGAS Inhibitors

Innate immunity is considered a first line cellular stress response defending the host cell against invading pathogens and initiating signaling to the adaptive immune system. These processes are triggered by conserved pathogen-associated molecular patterns (PAMPs) through sensing by diverse pattern recognition receptors (PRRs) and subsequent activation of cytokine and type I interferon gene expression. The major antigen-presenting cells, such as monocytes, macrophages, and dendritic cells produce type I interferons and are critical for eliciting adaptive T- and B-cell immune system responses. The major PRRs detect aberrant, i.e. mislocalized, immature or unmodified nucleic acids on either the cell surface, the inside of lysosomal membranes or within other cellular compartments (Barbalat et al., Annu. Rev. Immunol. 29, 185-214 (2011)).

"Cyclic GMP-AMP Synthase" (cGAS, UniProtKB-Q8N884)) is the predominant sensor for aberrant double-stranded DNA (dsDNA) originating from pathogens or mislocalization or misprocessing of nuclear or mitochondrial cellular dsDNA (Sun et al., Science 339, 786-791 (2013); Wu et al., Science 339, 826-830 (2013); Ablasser et al., Nature 498, 380-384 (2013)). Binding of dsDNA to cGAS activates the reaction of GTP and ATP to form the cyclic dinucleotide GMP-AMP (referred to as cGAMP). cGAMP then travels to and activates the endoplasmatic reticulum membrane-anchored adaptor protein, "Stimulator of Interferon Genes" (STING). Activated STING recruits and activates TANK-binding kinase 1 (TBK1) which in turn phosporylates the transcription factor family of interferon regulatory factors (IRFs) inducing cytokine and type I interferon mRNA expression.

The critical role of cGAS in dsDNA sensing has been established in different pathogenic bacteria (Hansen et al., EMBOJ. 33, 1654 (2014)), viruses (Ma et al., PNAS 112, E4306 (2015)) and retroviruses (Gao et al., Science 341, 903-906 (2013)). Additionally, cGAS is essential in various other biological processes such as cellular senescence (Yang et al., PNAS 114, E4612 (2017), Glück et al., Nat. Cell Biol. 19, 1061-1070 (2017)) and recognition of ruptured micronuclei in the surveillance of potential cancer cells (Mackenzie et al., Nature 548, 461-465 (2017); Harding et al., Nature 548, 466-470 (2017)).

While the cGAS pathway is important for host defense against invading pathogens, cellular stress and genetic factors may also cause production of aberrant cellular dsDNA, e.g. by nuclear or mitochondrial leakage, and thereby trigger autoinflammatory responses. Aicardi-Goutieres syndrome (AGS; Crow et al., Nat. Genet. 38, 917-920 (2006))—a lupus-like severe autoinflammatory immune-mediated disorder—arises from loss-of-function mutations in TREX1, a primary DNA exonuclease responsible for degrading aberrant DNA in cytosol. Knock-out of cGAS in TREX1-deficient mice prevented otherwise lethal autoimmune responses, supporting cGAS as driver of interferonopathies (Gray et al., J. Immunol. 195, 1939-1943 (2015); Gao et al., PNAS 112, E5699-E5705 (2015)). Likewise, embryonic lethality caused by deficiency of DNAse2, an endonuclease responsible for degradation of excessive DNA in lysosomes during endocytosis, was completely rescued by additional knock-out of cGAS (Gao et. al, PNAS 112, E5699-E5705 (2015)) or STING (Ahn et al., PNAS 109, 19386-19391 (2012)). These observations support cGAS as a drug target and inhibition of cGAS may provide a therapeutic strategy for preventing autoinflammation and treating diseases such as systemic lupus erythematosus (SLE) with involvement of anti-dsDNA antibodies (Pisetsky et al., Nat. Rev. Rheumatol. 12, 102-110 (2016)).

1.2 Prior Art

Due to the observation that inhibition of the cGAS-pathway may provide a therapeutic strategy for preventing autoinflammation and for treating e.g. autoimmune diseases many efforts to develop cGAS inhibitors have been undertaken.

In WO 2019/241787 for example, methyl 4-amino-6-(phenylamino)-1,3,5-triazine-2-carboxylates such as CU-32 and CU-76 have been disclosed as cGAS-inhibitors with "in vitro hcGAS IC50-values" slightly below 1 μM (IC50(CU-32)=0.66 μM and IC50(CU-76=0.27 μM).

In Hall et al., PLoS ONE 12(9); e0184843 (2017), compound PF-06928215 has been published as an inhibitor of cGAS with an "in vitro hcGAS IC50-value" of 0.049 μM as measured by a fluorescence polarization assay. However, compound PF-06928215 showed no acceptable cellular activity as a cGAS inhibitor.

In WO 2020/142729, (benzofuro[3,2-d]pyrimidin-4-yl) pyrrolidine-2-carboxylic acid derivatives have been disclosed as cGAS inhibitors for the therapy of autoimmune disorders such as Aicardi-Goutieres Syndrome (AGS), lupus erythematosus, scleroderma, inflammatory bowel disease and non-alcoholic steatotic hepatitis (NASH). However, the compounds of this invention differ from the (benzofuro[3,2-d]pyrimidin-4-yl)pyrrolidine-2-carboxylic acid derivatives of WO 2020/142729 in their completely different substitution pattern in the 4-position of the pyrrolidine ring.

Recently provided cGAS inhibitors, such as the ones in WO 2020/142729, usually show an insufficient cellular cGAS inhibitory potency (with IC50-values regarding inhibition of the cGAS/STING pathway as measured in cellular assays of usually larger than 1 μM, often of larger than 5 μM). However, it is crucial to provide therapeutic cGAS inhibitors that do not only show a satisfying biochemical (in vitro) inhibitory potency ("hcGAS IC50"), but also a satisfying cellular inhibitory potency (for example by showing inhibition of IFN induction in virus-stimulated THP-1 cells (THP1$_{(vir)}$ IC50)) in order to ensure that the compound is able to show a therapeutic effect in a patient. Other important properties that may be predictive for successful development of a cGAS inhibitor as a therapeutic agent are satisfying cGAS-selectivity (versus off-target activity) and acceptable inhibitory potency in human whole blood.

Surprisingly it has now been found that the compounds of formula (I) and of formula (I') show at the same time the following three properties:

- a satisfying "biochemical (in vitro) IC50-value regarding cGAS inhibition" (with a hcGAS IC50 of ≤100 nM, preferably of ≤50 nM, in particular of ≤10 nM),
- a satisfying "inhibition of IFN induction in virus-stimulated THP-1 cells (with a THP1 IC50$_{(vir)}$ of ≤1 μM, preferably of ≤500 nM, more preferably of ≤100 nM, in particular of ≤50 nM) and
- a satisfying selectivity for cGAS-inhibition (with a ratio THP1 IC50$_{(cGAMP)}$/THP1 IC50$_{(vir)}$ of ≥10, more preferably ≥50, more preferably ≥500, in particular ≥1000).

Additionally the compounds of formula (I) and of formula (I') also show acceptable IC50-values with regard to inhibition of IFN induction in dsDNA-stimulated human whole blood assays, preferably with human whole blood IC50-values with regard to cGAS inhibition (hWB IC50) of ≤5000 nM, more preferably of ≤1000 nM, in particular of ≤100 nM.

The cGAS inhibitors of the invention with this particular pharmacological profile which combines an excellent in vitro inhibitory potency and an excellent cellular inhibitory potency with a high selectivity for cGAS inhibition have a high probability to also exhibit a good therapeutic effect in the patient. Due to their high cellular inhibitory potency compounds with this particular pharmacological profile should be able to pass the cell membrane barrier and therefore reach their intracellular target location and due to their selectivity to exclusively inhibit cGAS activity, these compounds should not show unwanted off target effects, for example side effects somewhere within the signaling pathway downstream of cGAS or cytotoxic effects.

2 DESCRIPTION OF THE INVENTION

The invention concerns compounds of formula (I), (I)

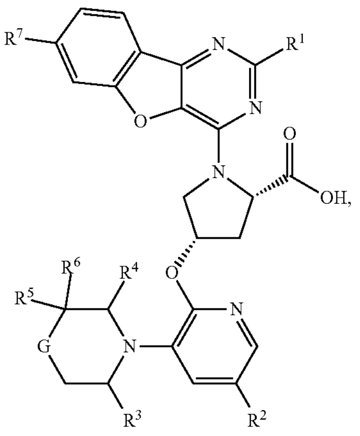

wherein $R^1$ is selected from methyl, ethyl, halomethyl, haloethyl, and halogen, wherein G is selected from O, $NR^8$, $CH_2$, C and $CR^8R^9$, wherein $R^2$ is selected from H, halogen, cyclopropyl, $C_{1-3}$-alkyl, $C_{2-5}$-alkynyl, —S-methyl and CN, or wherein $R^2$ is a cyclic group, wherein this cyclic group is selected from the group consisting of a phenyl and a five- to six-membered heteroaryl comprising 1, 2, 3 or 4 heteroatoms each independently selected from N, S and O, and wherein this cyclic group is substituted by one or two, identical or different substituents $R^{10}$, wherein $R^3$ is H or methyl $R^4$ is H or methyl $R^5$ is selected from H, methyl, —CN, -methylene-OH and —$CF_3$, or $R^5$ is absent, $R^6$ is selected from H, methyl, —CN, -methylene-OH and —$CF_3$, or $R^5$ and $R^6$ together with the C-atoms in between form a ring selected from oxetane, tetrahydrofurane and cyclopropane $R^7$ is selected from H, halogen, $(C_{1-3})$-alkyl and halo-$(C_{1-3})$-alkyl $R^8$ is selected from CN, H and methyl, $R^9$ is selected from H, methyl and halogen or $R^9$ is absent, wherein each $R^{10}$ is independently selected from the group consisting of hydrogen, halogen, haloalkyl, -methyl, -ethyl, —NH—CO-methyl, —$N(CH_3)_2$, —$CH_2$—OH, —$NH(CH_3)$, —O—$(C_{1-3}$-alkyl), —CN, —S—$CH_3$, —CO—$NH_2$, —$CH_2$—$NH(CH_3)$, —$CH_2$—$NH_2$, —SO—$(CH_3)$, cyclopropyl and —O—$R^{11}$, wherein each $R^{11}$ is independently selected from a five- or six-membered aromatic or non-aromatic heterocycle with one or two heteroatoms each independently selected from N, O and S, or G is $CR^8R^9$, $R^5$ and $R^9$ are absent, and $R^5$ and $R^6$ and the two C-atoms in between $R^5$ and $R^6$ form an annulated five-membered aromatic or non-aromatic heterocycle comprising one, two or three heteroatoms each independently selected from N, S and O, or G is $CR^8R^9$ and $R^8$ and $R^9$ form a diazirine ring together with the C-atom in between $R^8$ and $R^9$, and prodrugs or pharmaceutically acceptable salts of these compounds.

A preferred embodiment of the invention relates to the aforementioned compounds which fall into the scope of formula (I')

(I')

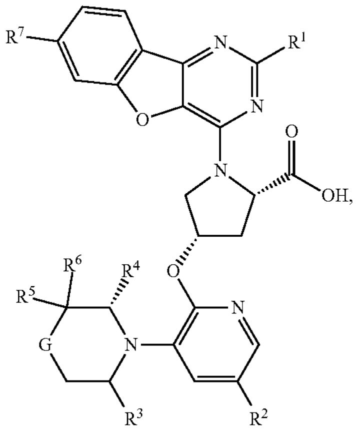

wherein $R^1$, $R^2$, $R^3$, $R^4$, $R^5$, $R^6$, $R^7$, $R^8$, $R^9$, $R^{10}$, $R^{11}$ and G are defined as mentioned above and prodrugs or pharmaceutically acceptable salts of these compounds.

Another preferred embodiment of the invention refers to the above-mentioned compounds of formula (I) or of formula (I'), wherein $R^7$ is H, F, Cl, methyl, ethyl, halomethyl or haloethyl, and prodrugs or pharmaceutically acceptable salts of these compounds.

In another preferred embodiment the invention relates to the above-mentioned compounds of formula (I) or of formula (I'), wherein $R^1$ is halomethyl, haloethyl or methyl, and prodrugs or pharmaceutically acceptable salts of these compounds.

A further preferred embodiment of the invention refers to the above-mentioned compounds of formula (I) or of formula (I'), wherein $R^1$ is a fluoromethyl selected from the group consisting of —$CF_3$, —$CHF_2$ and —$CH_2F$, and prodrugs or pharmaceutically acceptable salts of these compounds.

In another preferred embodiment the invention relates to the above-mentioned compounds of formula (I) or of formula (I'), wherein at least one of $R^3$ and $R^4$ is methyl and prodrugs or pharmaceutically acceptable salts of these compounds.

Another preferred embodiment of the invention relates to the aforementioned compounds of formula (I) or of formula (I'), wherein one of $R^3$ and $R^4$ is methyl and the other one is H and prodrugs or pharmaceutically acceptable salts of these compounds.

In another preferred embodiment the invention relates to the above-mentioned compounds of formula (I) or of formula (I'), wherein G is O and prodrugs or pharmaceutically acceptable salts of these compounds.

Another preferred embodiment of the invention relates to the aforementioned compounds of formula (I) or of formula (I'), wherein G is O and wherein one of $R^3$ and $R^4$ is methyl and the other one is H, and prodrugs or pharmaceutically acceptable salts of these compounds.

In another preferred embodiment the invention relates to the above-mentioned compounds of formula (I) or of formula (I'), wherein G is O, wherein $R^4$ is methyl and $R^3$ is H, and wherein $R^5$ and $R^6$ together form an oxetane ring and prodrugs or pharmaceutically acceptable salts of these compounds.

Another preferred embodiment of the invention relates to the aforementioned compounds of formula (I) or of formula (I'), wherein $R^2$ is selected from the group consisting of H, ethynyl, 1-propynyl, —S-methyl and halogen, and prodrugs or pharmaceutically acceptable salts of these compounds.

In another preferred embodiment the invention refers to the above-mentioned compounds of formula (I) or of formula (I'), wherein $R^2$ is ethynyl, and prodrugs or pharmaceutically acceptable salts of these compounds.

Another preferred embodiment of the invention relates to the aforementioned compounds of formula (I) or of formula (I'), wherein $R^4$ is methyl and $R^3$ is H, wherein G is O, wherein $R^5$ and $R^6$ together form an oxetane ring, wherein $R^2$ is selected from the group consisting of H, ethynyl, 1-propynyl, —S-methyl and halogen, and prodrugs or pharmaceutically acceptable salts of these compounds.

In another preferred embodiment the invention refers to the above-mentioned compounds of formula (I) or of formula (I'), wherein $R^2$ is a cyclic group, wherein this cyclic group is selected from the group consisting of a phenyl or a five- to six-membered heteroaryl comprising 1, 2 or 3 heteroatoms selected from N, S and O, and wherein this cyclic group is substituted by one or two, identical or different substituents $R_{10}$, wherein each $R^{10}$ is independently selected from the group consisting of hydrogen, halogen, haloalkyl, -methyl, -ethyl, —NH—CO-methyl, —$N(CH_3)_2$, —$CH_2$—OH, —$NH(CH_3)$, —O—$CH_3$, —CN, —S—$CH_3$, —CO—$NH_2$, —$CH_2$—$NH(CH_3)$, —$CH_2$—$NH_2$, —SO—$(CH_3)$, cyclopropyl and —O—$R^{11}$, wherein each $R^{11}$ is independently selected from a five- or six-membered aromatic or non-aromatic heterocycle with one or two heteroatoms each independently selected from N and O, and prodrugs or pharmaceutically acceptable salts of these compounds.

A further preferred embodiment of the invention refers to the aforementioned compounds of formula (I) or of formula (I'), wherein $R^2$ is a cyclic group selected from the group consisting of pyrazolyl, pyridinyl, imidazolyl, phenyl and isoxazolyl, wherein this cyclic group is substituted by one or two, identical or different substituents $R^{10}$ wherein each $R^{10}$ is independently selected from the group consisting of hydrogen, halogen, haloalkyl, -methyl, -ethyl, —NH—CO-methyl, —$N(CH_3)_2$, —$CH_2$—OH, —$NH(CH_3)$, —O—$CH_3$, —CN, —S—$CH_3$, —CO—$NH_2$, —$CH_2$—$NH(CH_3)$, —$CH_2$—$NH_2$, —SO—$(CH_3)$, cyclopropyl and —O—$R^{11}$, wherein each $R^{11}$ is tetrahydropyrane and prodrugs or pharmaceutically acceptable salts of these compounds.

In another preferred embodiment the invention refers to the above-mentioned compounds of formula (I) or of formula (I'), wherein G is O, wherein one of $R^3$ and $R^4$ is methyl and the other one is H, wherein $R^2$ is a cyclic group selected from the group consisting of pyrazolyl, pyridinyl, imidazolyl, phenyl and isoxazolyl, wherein this cyclic group is substituted by one or two, identical or different substituents $R^{10}$ wherein each $R^{10}$ is independently selected from the group consisting of hydrogen, halogen, haloalkyl, -methyl, -ethyl, —NH—CO-methyl, —$N(CH_3)_2$, —CH2-OH, —$NH(CH_3)$, —O—$CH_3$, —CN, —S—$CH_3$, —CO—$NH_2$, —$CH_2$—$NH(CH_3)$, —$CH_2$—$NH_2$, —SO—$(CH_3)$, cyclopropyl and —O—$R^{11}$, wherein each $R^{11}$ is tetrahydropyrane, and prodrugs or pharmaceutically acceptable salts of these compounds.

In another preferred embodiment the invention refers to the above-mentioned compounds of formula (I) or of formula (I'), wherein $R^2$ is a cyclic group selected from the group consisting of pyrazolyl, pyridinyl, imidazolyl, phenyl and isoxazolyl, wherein this cyclic group is substituted by one or two, identical or different substituents $R^{10}$ wherein each $R^{10}$ is independently selected from the group consisting of hydrogen, halogen, haloalkyl, -methyl, -ethyl, —NH—CO-methyl, —$N(CH_3)_2$, —CH2-OH, —NH($CH_3$), —O—$CH_3$, —CN, —S—$CH_3$, —CO—$NH_2$, —$CH_2$—NH($CH_3$), —$CH_2$—$NH_2$, —SO—($CH_3$), cyclopropyl and —O—$R^{11}$, wherein each $R^{11}$ is tetrahydropyrane, wherein G is O, wherein one of $R^3$ and $R^4$ is methyl and the other one is H, and wherein $R^5$ and $R^6$ together form an oxetane ring, and prodrugs or pharmaceutically acceptable salts of these compounds.

In another preferred embodiment the invention refers to the above-mentioned compounds of formula (I) or of formula (I'), wherein G is $CR^8R^9$, wherein $R^8$ and $R^6$ and the two C-atoms in between $R^8$ and $R^6$ form an annulated five-membered aromatic heterocycle comprising one or two heteroatoms each independently selected from N and O, which is selected from an annulated isoxazolyl ring, an annulated pyrazolyl ring, an annulated pyrrolyl ring and an annulated furanyl ring, and wherein $R^9$ and $R^5$ are absent, and prodrugs or pharmaceutically acceptable salts of these compounds.

Another particularly preferred embodiment of the invention relates to compounds of formula (I) or of formula (I'), which are selected from the group consisting of

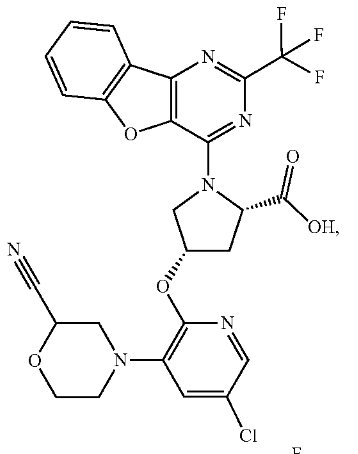

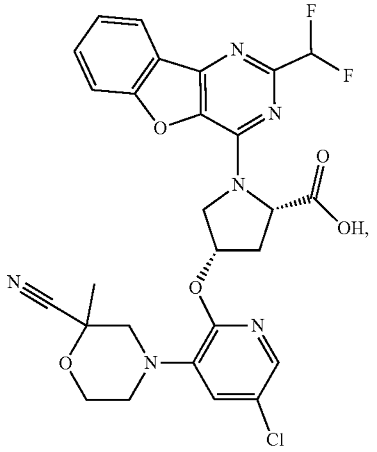

-continued

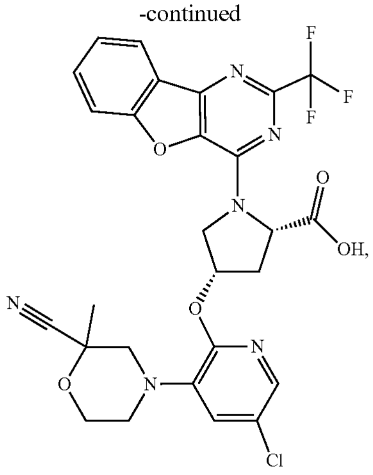

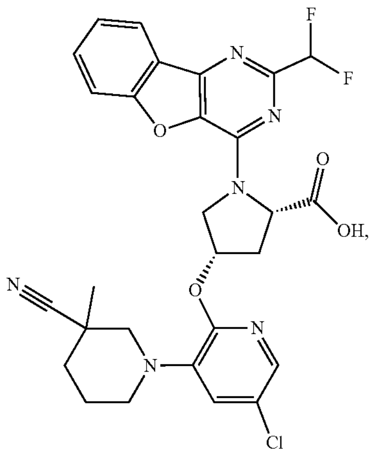

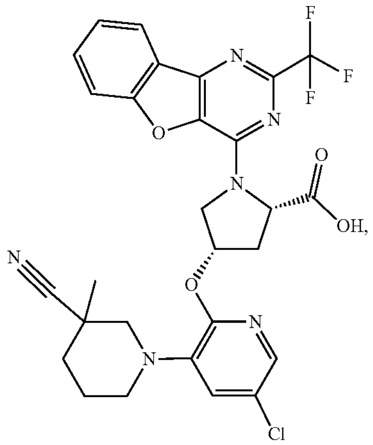

-continued
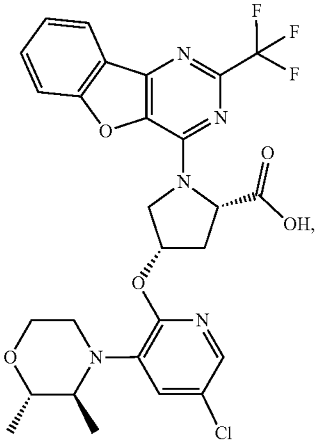
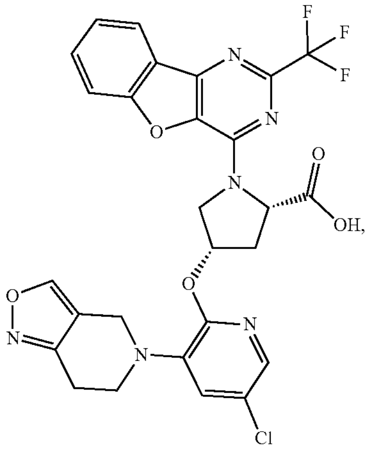
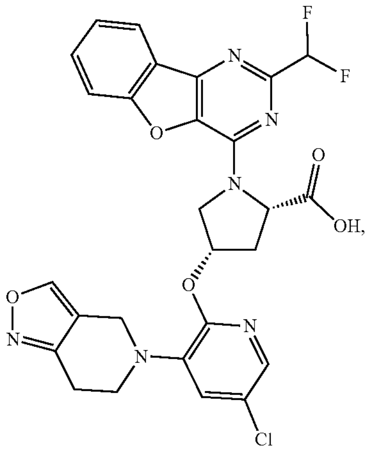
-continued
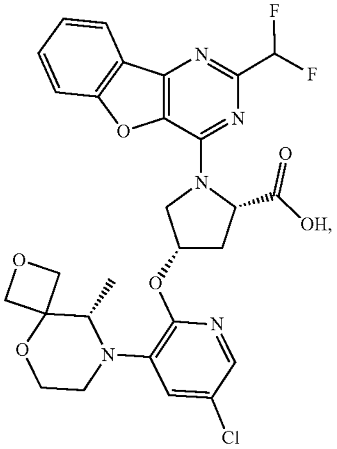
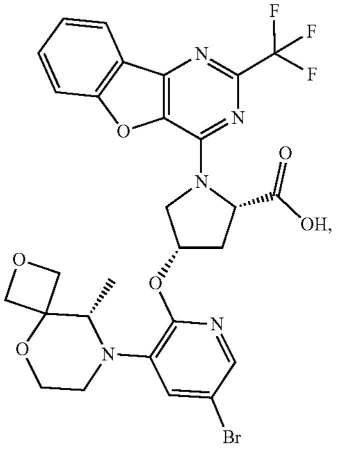
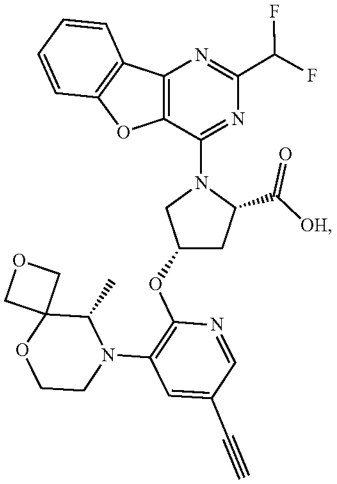

-continued
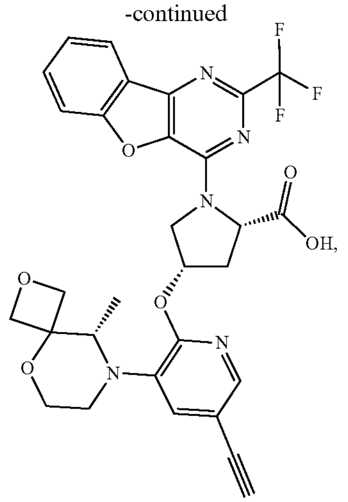
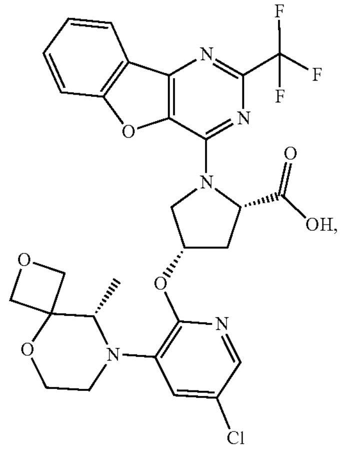
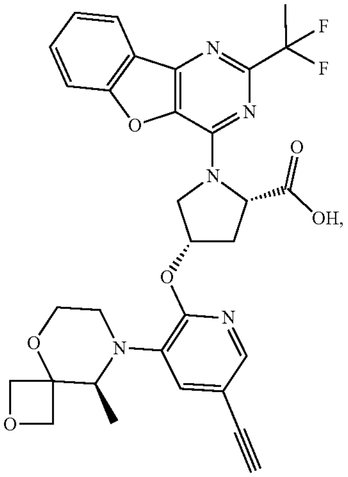
-continued
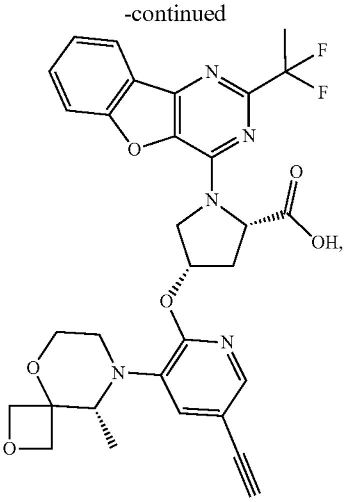
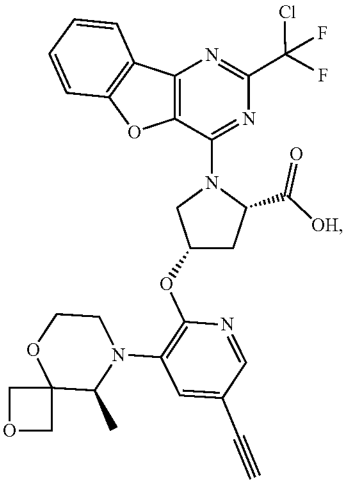
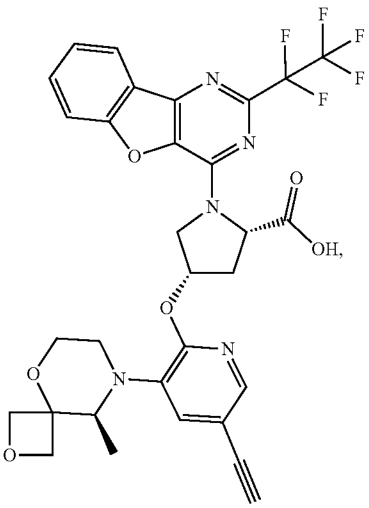

-continued
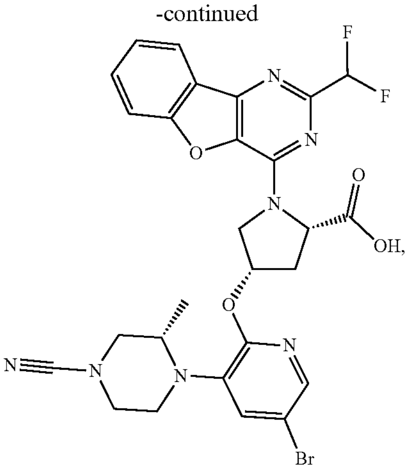
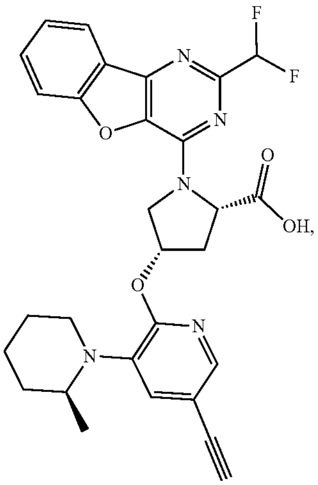
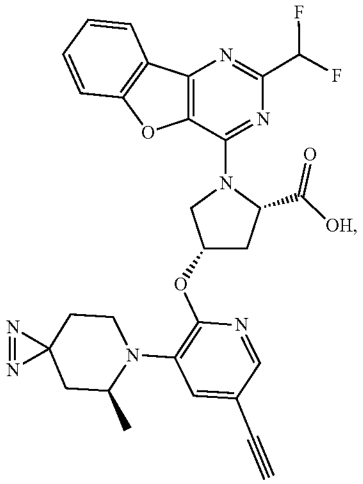
-continued
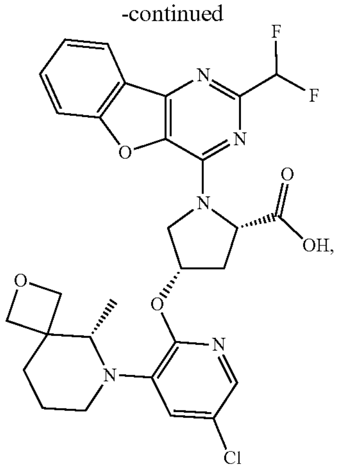
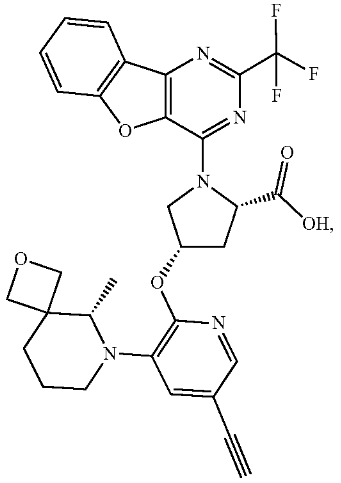
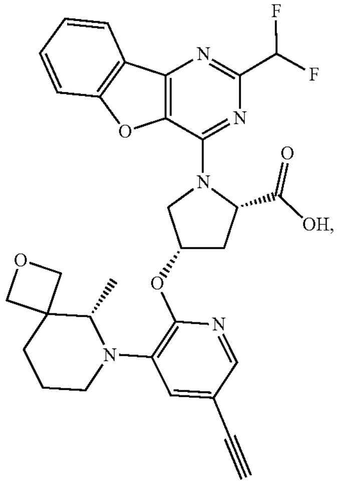

-continued
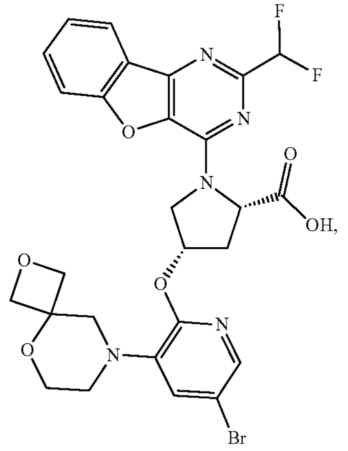
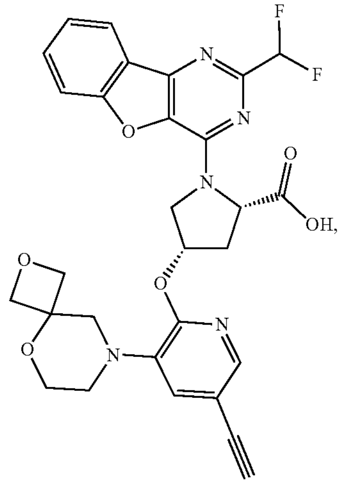
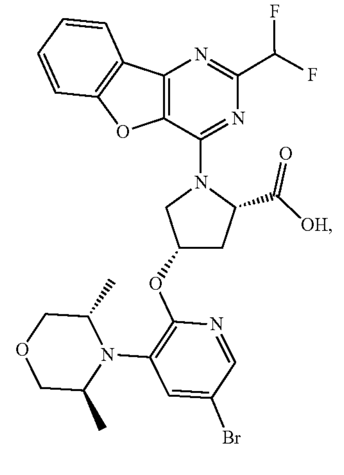
-continued
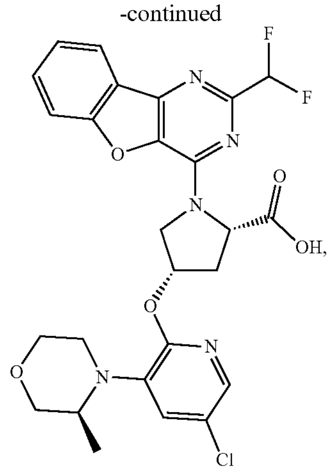
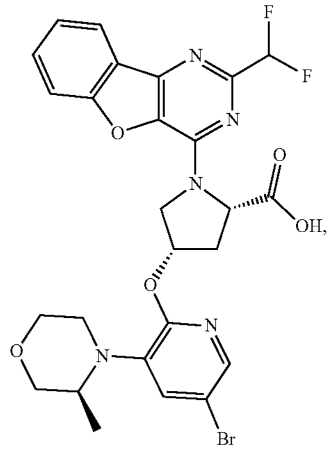
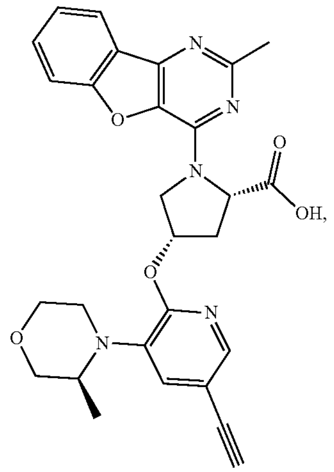

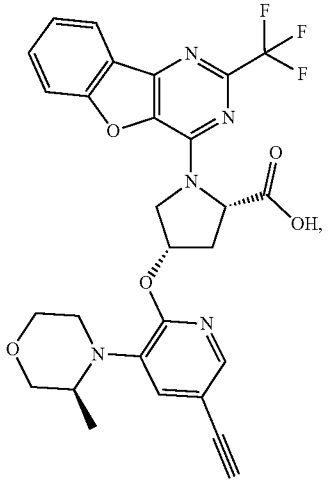
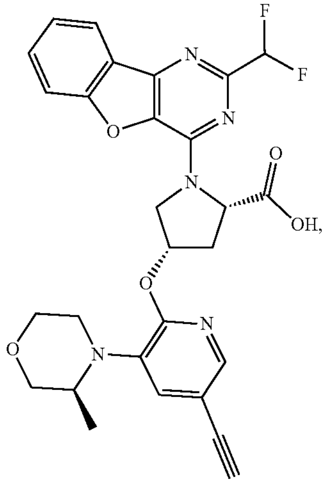
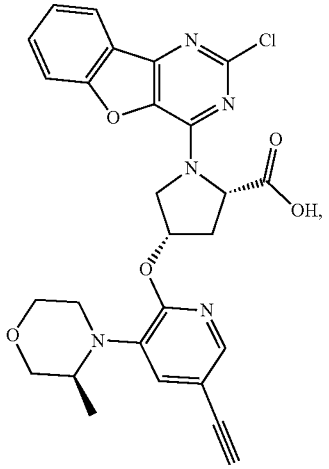
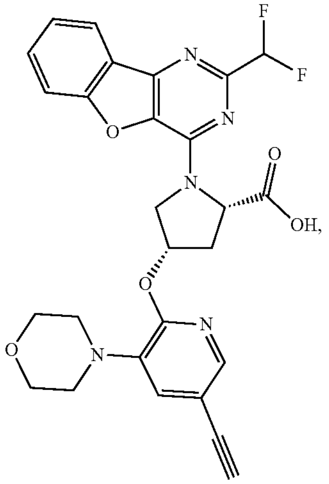
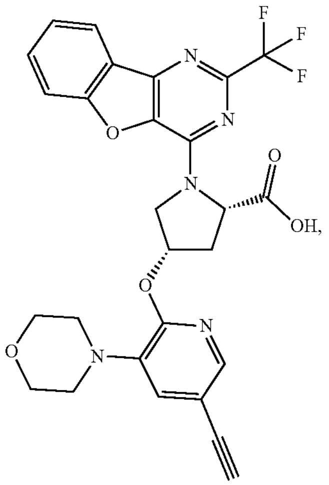
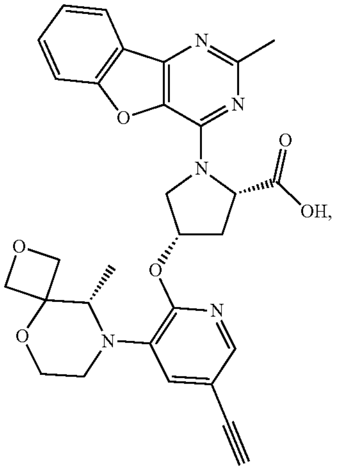

-continued
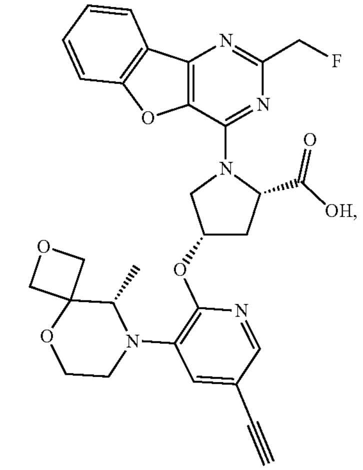
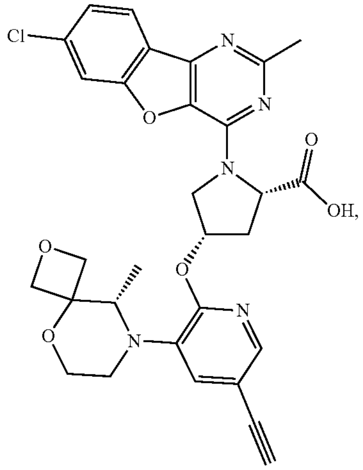
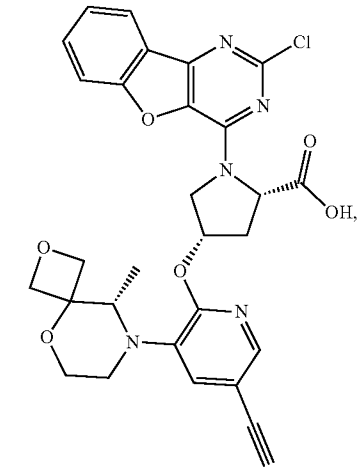
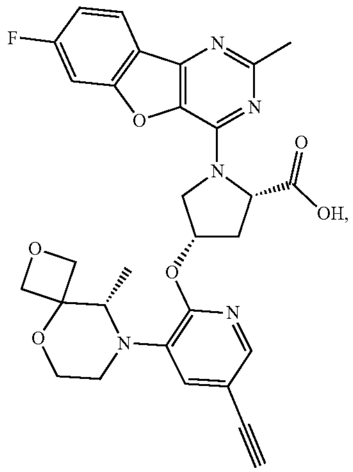
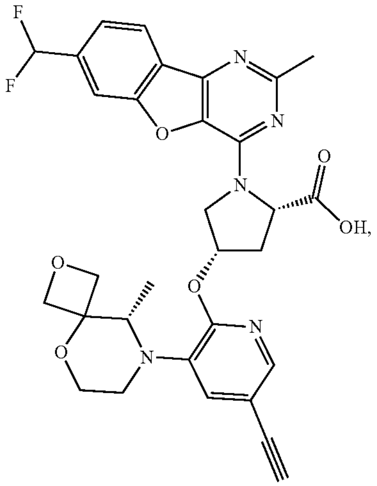
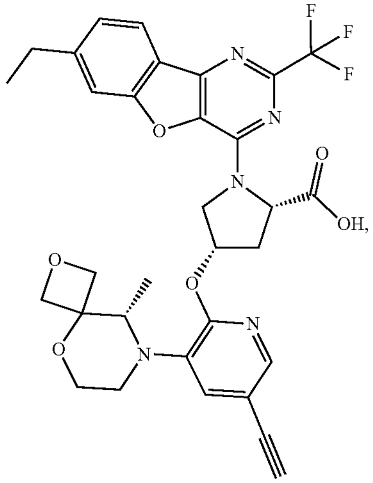
-continued -continued
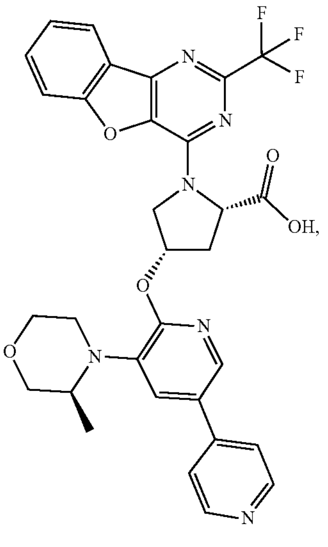
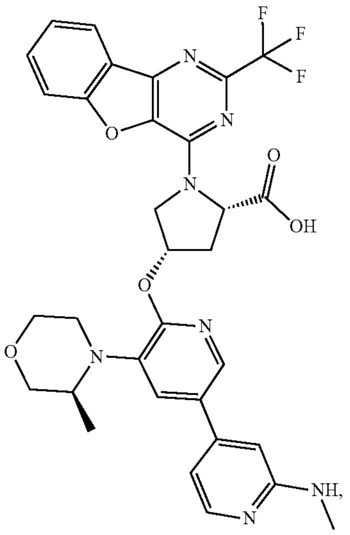
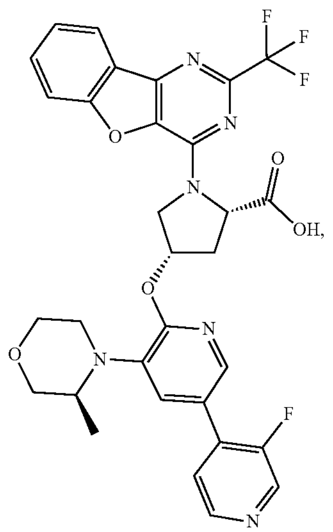
-continued
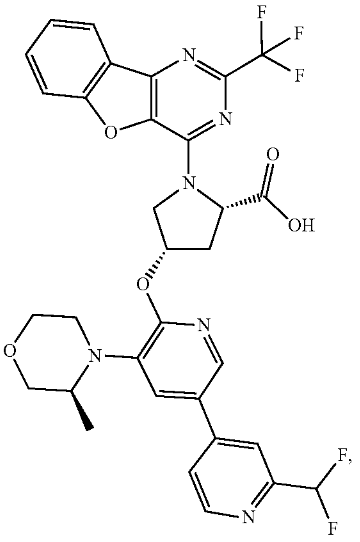
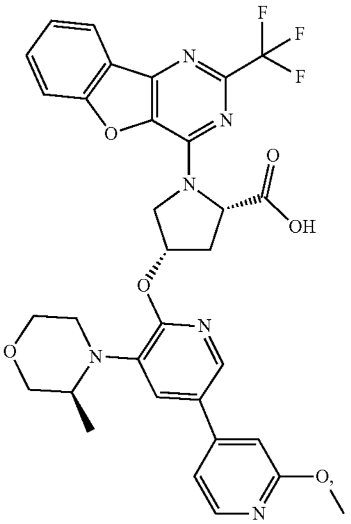
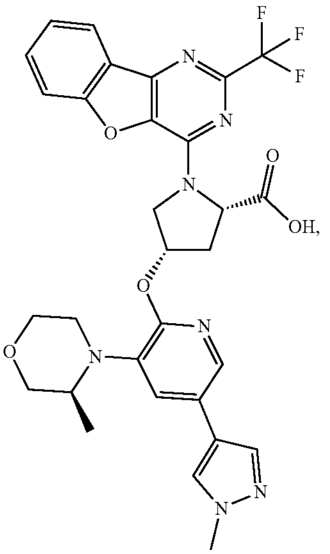

-continued
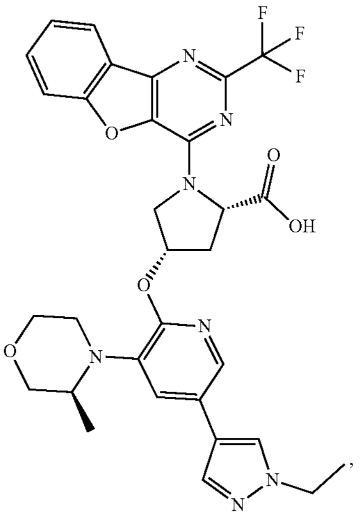
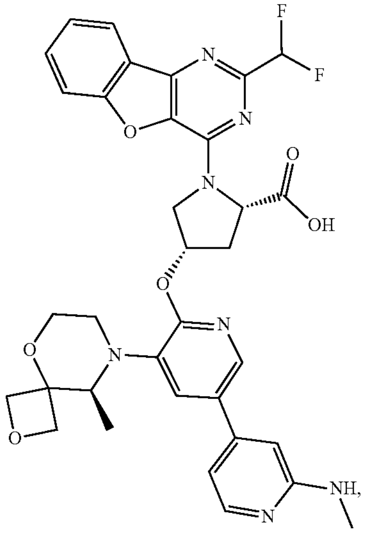
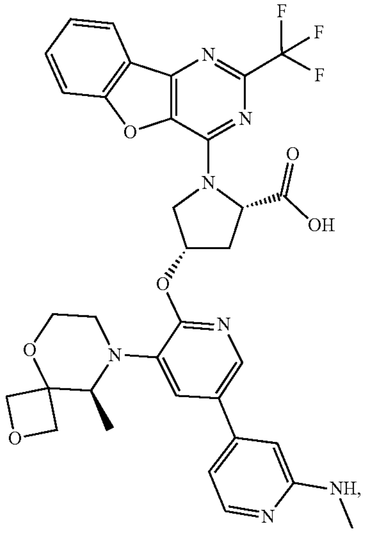
-continued
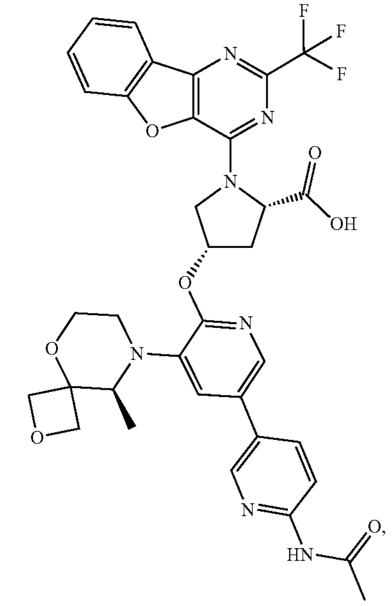
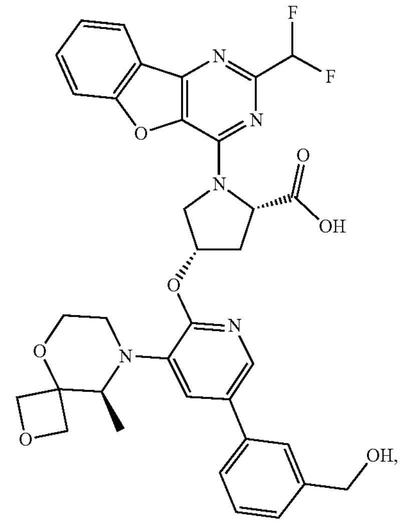
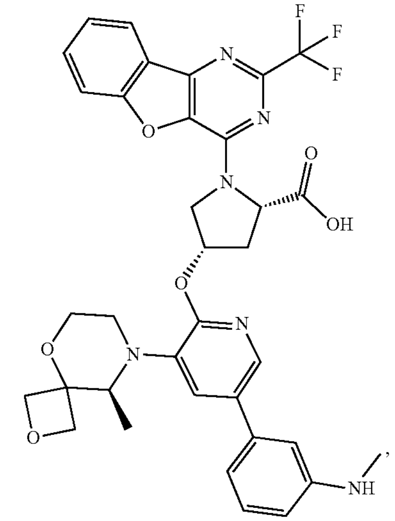

-continued
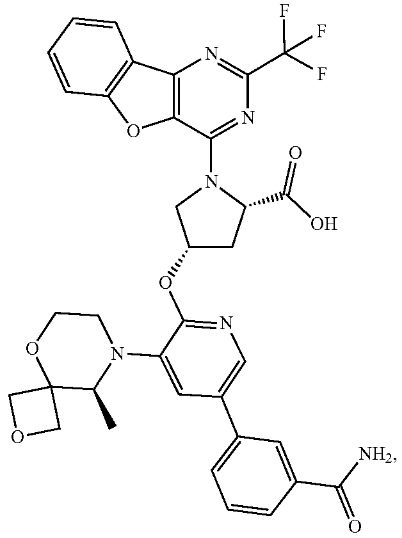
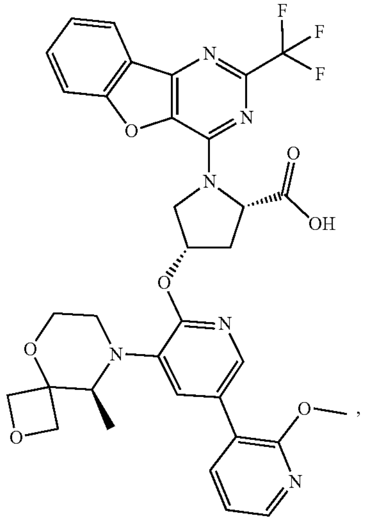
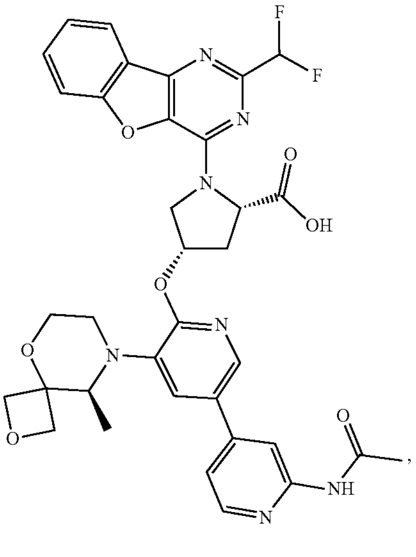
-continued
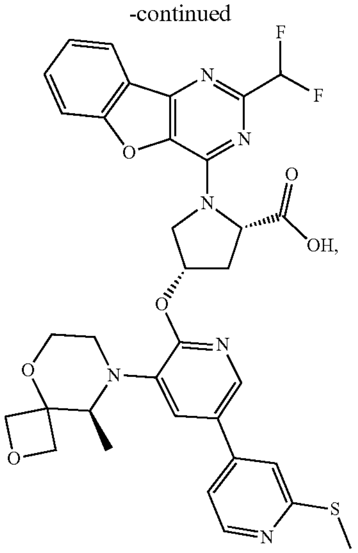
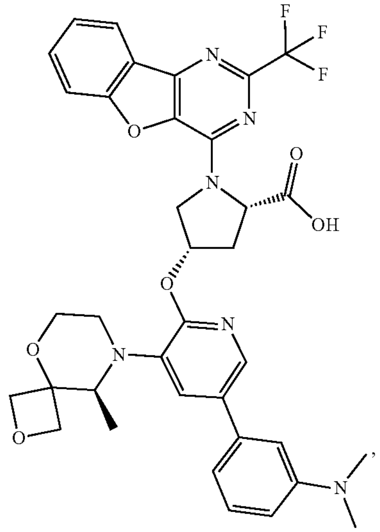
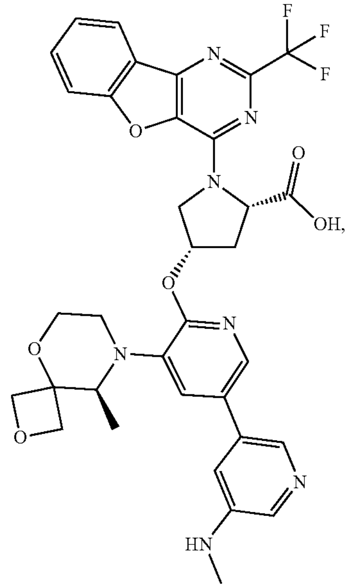

-continued
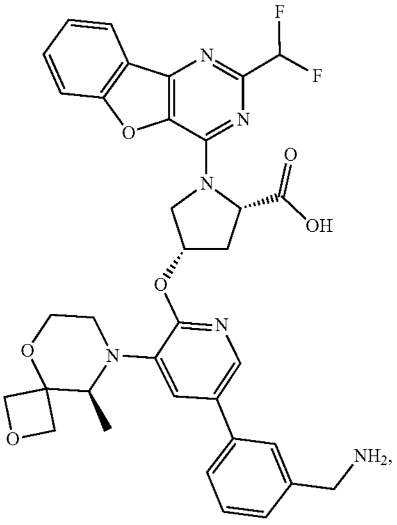
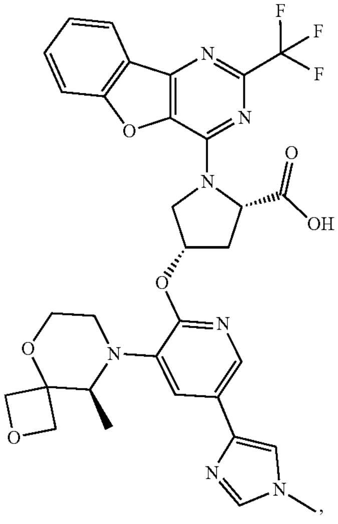
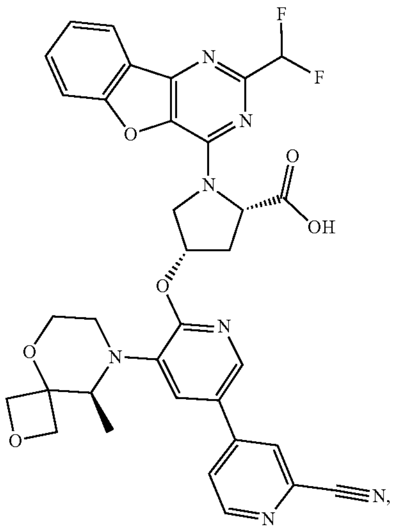
-continued
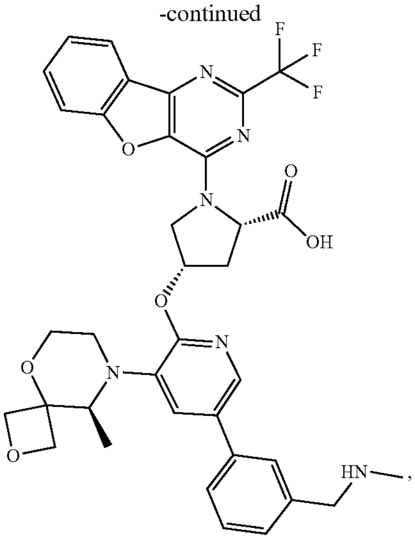
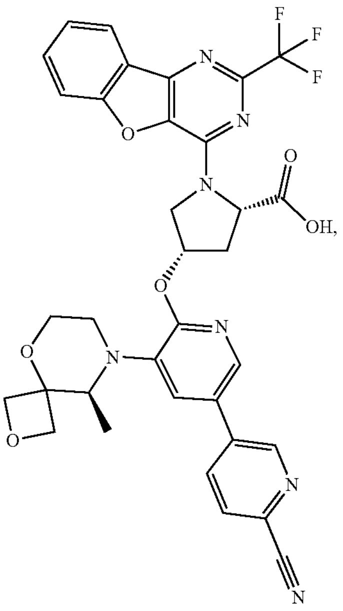
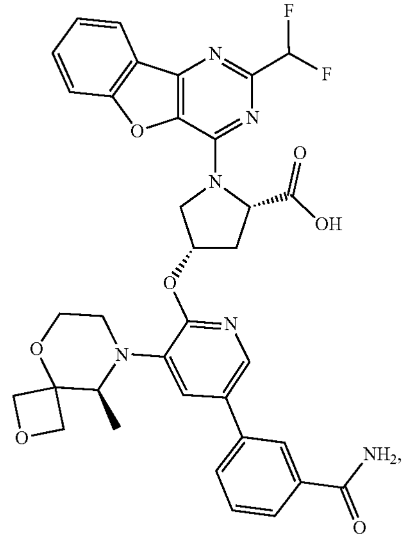

-continued
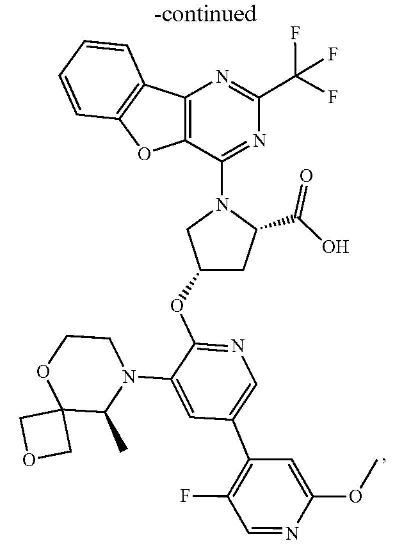
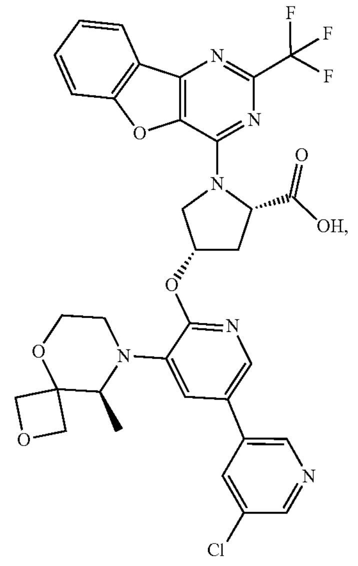
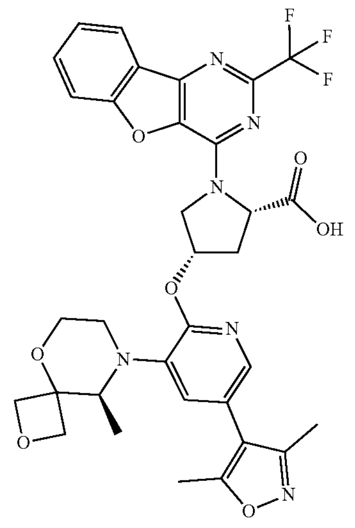
-continued
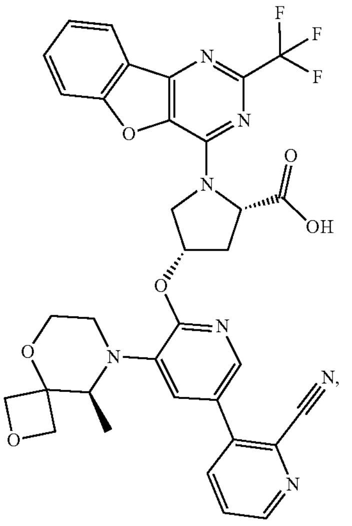
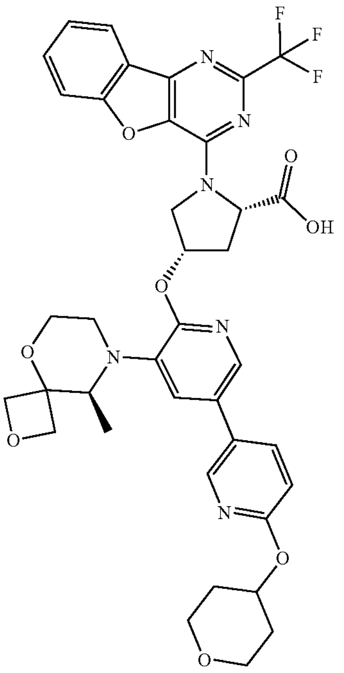
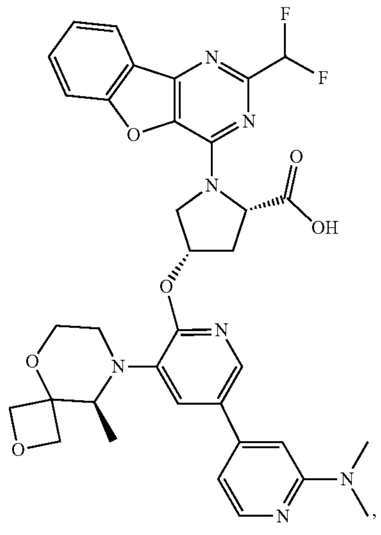

-continued
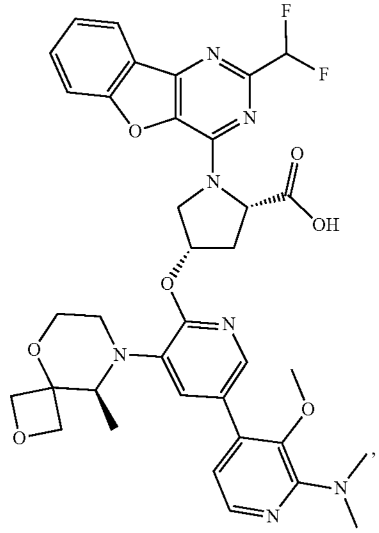
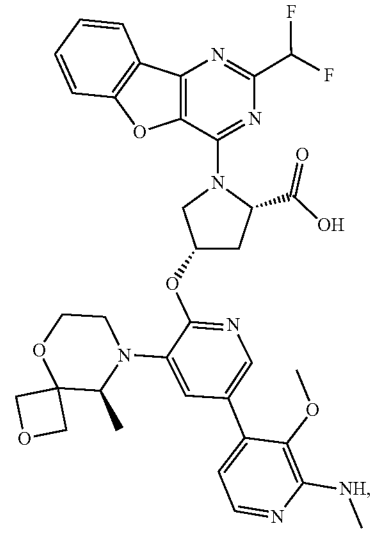
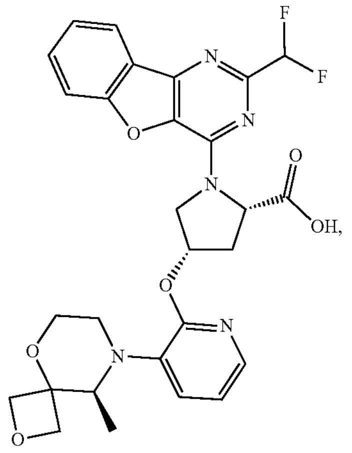
-continued
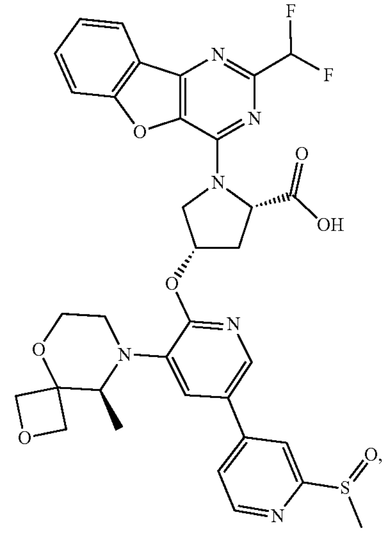
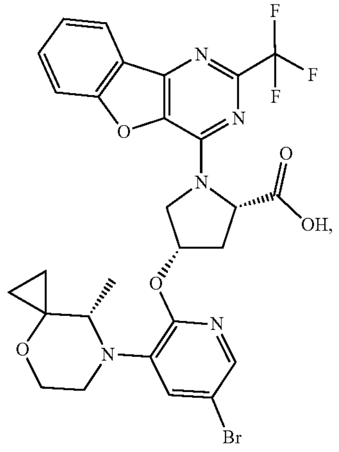
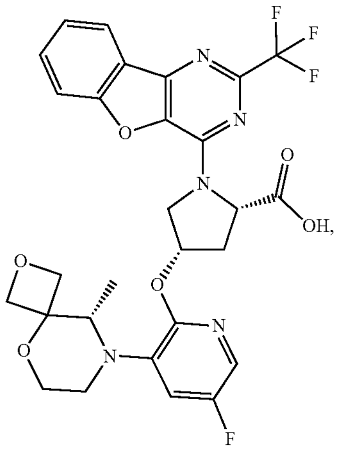

-continued
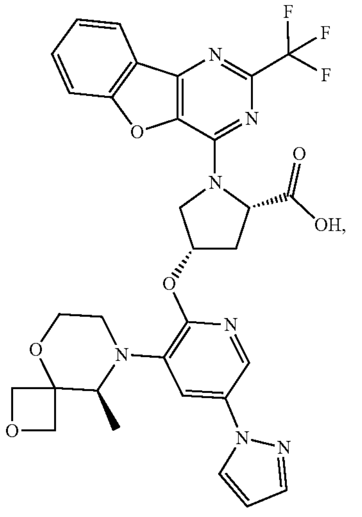
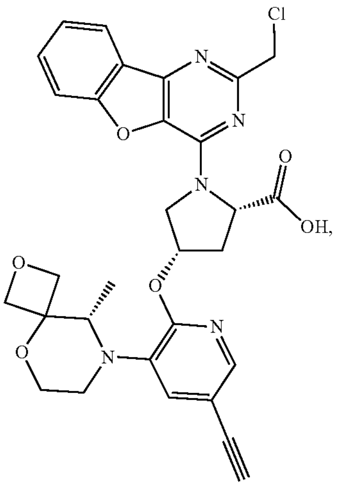
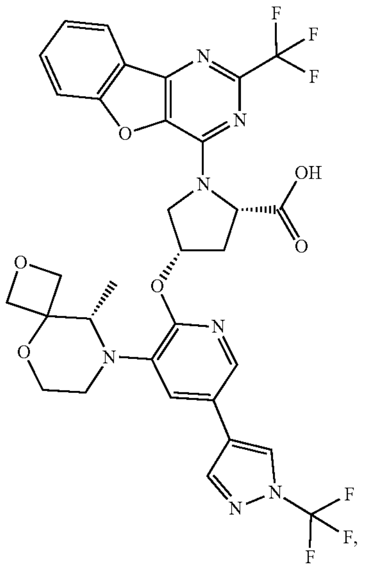
-continued
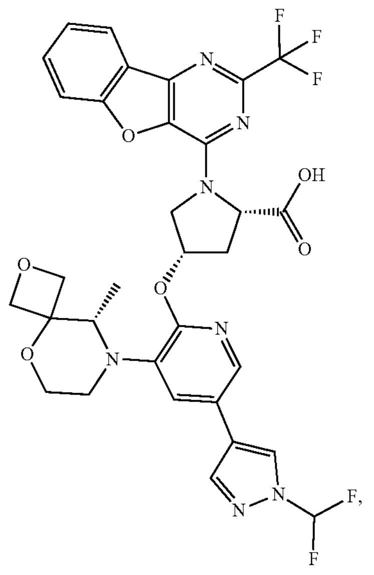
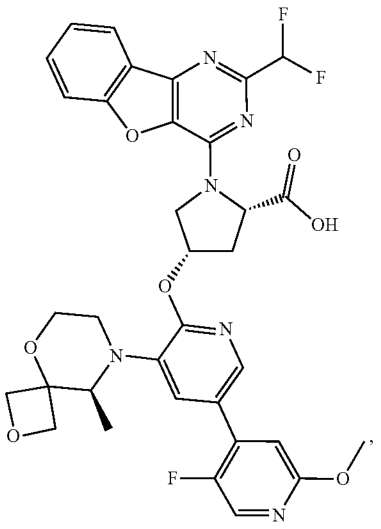
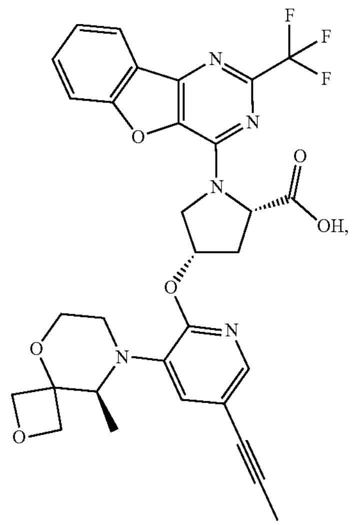

-continued
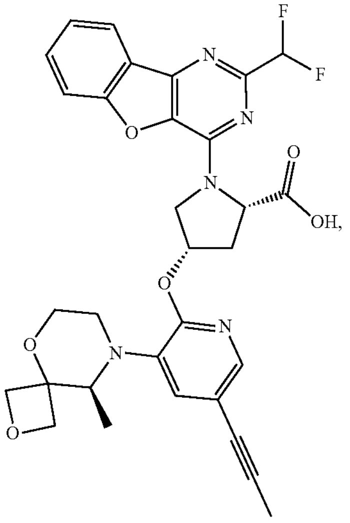
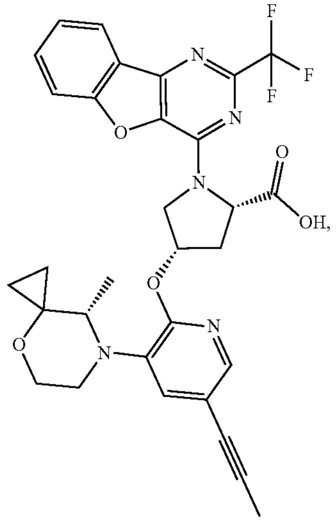
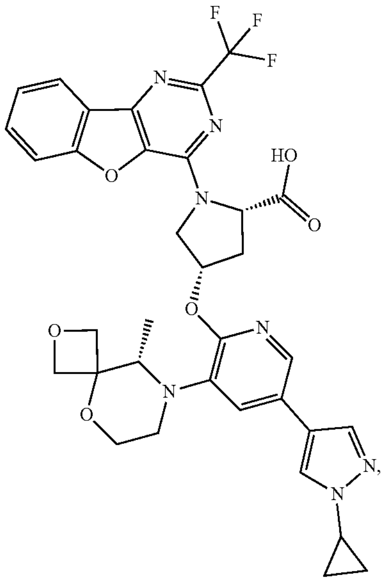
-continued
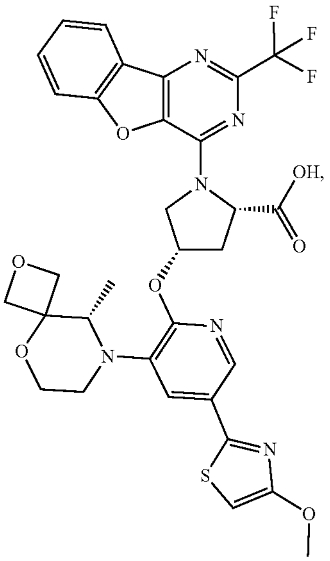
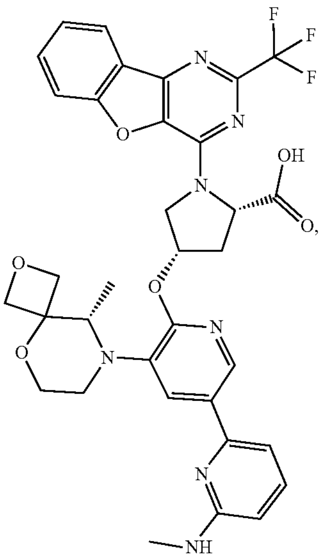
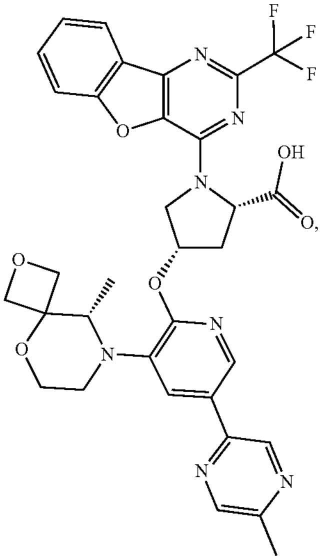

-continued

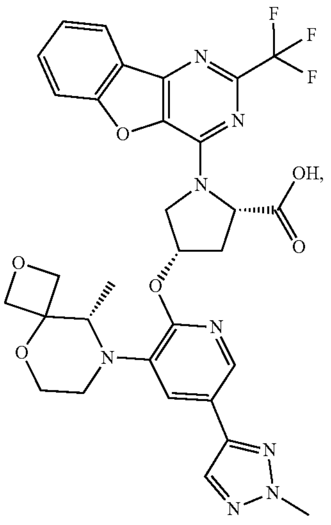

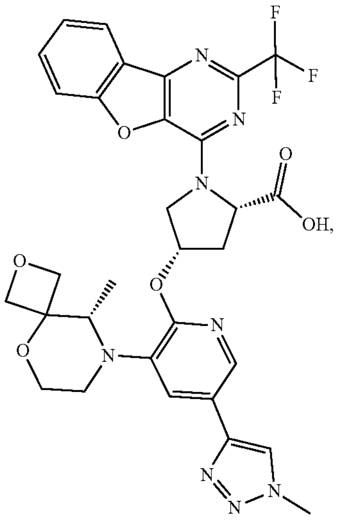

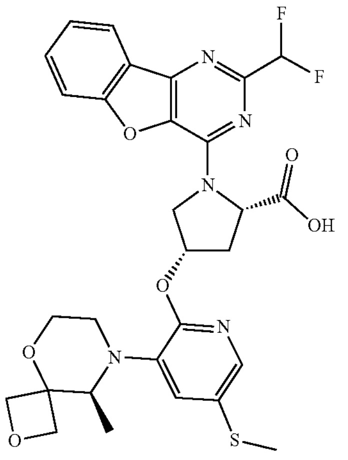

and

-continued

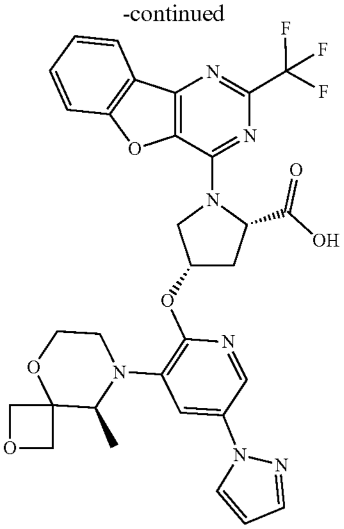

and prodrugs or pharmaceutically acceptable salts of these compounds.

In another embodiment the invention relates to the aforementioned compounds of formula (I) or of formula (I'), for use in the treatment of a disease that can be treated by the inhibition of cGAS.

In a preferred embodiment the invention refers to the above-mentioned compounds of formula (I) or of formula (I'), for use in the treatment of a disease selected from the group consisting of systemic lupus erythematosus (SLE), interferonopathies, Aicardi-Goutières syndrome, age-related macular degeneration (AMD), amyotrophic lateral sclerosis (ALS), inflammatory bowel disease (IBD), chronic obstructive pulmonary disease (COPD), Bloom's syndrome, Sjogren's syndrome, Parkinsons disease, heart failure and cancer, systemic sclerosis (SSc), non-alcoholic steatotic hepatitis (NASH), interstitial lung disease (ILD), preferably progressive fibrosing interstitial lung disease (PF-ILD), in particular idiopathic pulmonary fibrosis (IPF).

In a more preferred embodiment the invention relates to the aforementioned compounds of formula (I) or of formula (I'), for use in the treatment of a disease selected from the group consisting of systemic lupus erythematosus (SLE), interferonopathies, Aicardi-Goutières syndrome, age-related macular degeneration (AMD), amyotrophic lateral sclerosis (ALS), inflammatory bowel disease (IBD), chronic obstructive pulmonary disease (COPD), Bloom's syndrome, Sjogren's syndrome and Parkinsons disease.

In another more preferred embodiment the invention relates to the above-mentioned compounds of formula (I) or of formula (I'), for use in the treatment of a fibrosing disease selected from the group consisting of systemic sclerosis (SSc), interferonopathies, non-alcoholic steatotic hepatitis (NASH), interstitial lung disease (ILD), preferably progressive fibrosing interstitial lung disease (PF-ILD), in particular idiopathic pulmonary fibrosis (IPF).

In another more preferred embodiment the invention relates to the above-mentioned compounds of formula (I) or of formula (I'), for use in the treatment of a disease selected from the group consisting of age-related macular degeneration (AMD), heart failure, COVID-19/SARS-CoV-2 infection, renal inflammation, renal fibrosis, dysmetabolism, vascular diseases, cardiovascular diseases and cancer.

In another embodiment the invention relates to a pharmaceutical composition comprising at least one of the above-mentioned compounds of formula (I) or of formula (I'), and optionally one or more pharmaceutically acceptable carriers and/or excipients.

In another preferred embodiment the invention refers to an intermediate of formula (IV)

(IV)

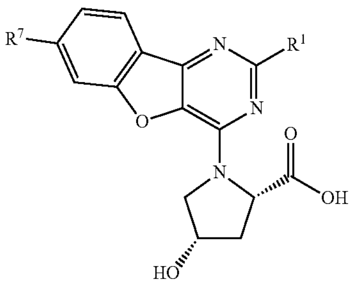

according to synthesis Scheme 1,
or formula (V)

(V)

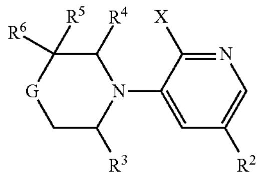

according to synthesis Scheme 1,
or formula (X)

(X)

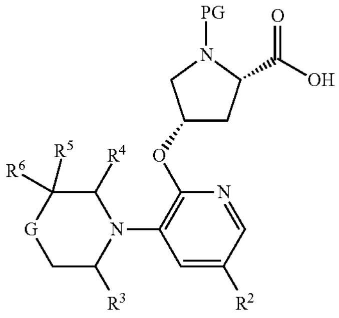

according to synthesis Scheme 2,
or formula (XI)

(XI)

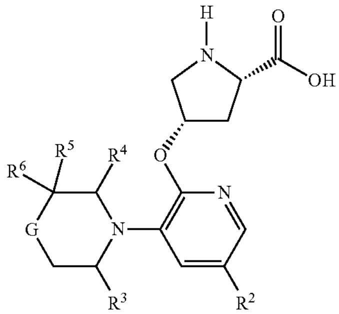

according to synthesis Scheme 2, wherein G, $R^1$, $R^2$, $R^3$, $R^4$, $R^5$, $R^6$ and $R^7$ are defined as described aforementioned and wherein X is F or $NO_2$, and wherein PG is a protecting group selected from the group consisting of tert-butoxycarbonyl (BOC), benzyloxy-carbonyl (Cbz), fluorenylmethylenoxycarbonyl (Fmoc), allyloxycarbonyl (Alloc), benzyl (Bn), p-methoxybenzyl (PMB), 3,4-methoxybenzyl (DMPM), p-methoxyphenyl (PMP), tosyl (Ts), trichloroethyl chloroformate (Troc), acetyl (Ac) or benzoyl (Bn).

In a further preferred embodiment, the invention relates to a prodrug of any of the aforementioned compounds of formula (I) or of formula (I'), wherein this prodrug falls within the scope of formula (A)

(A)

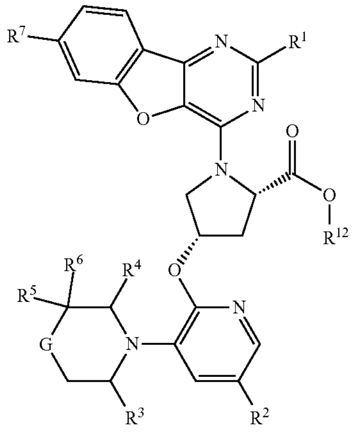

or within the scope of formula (A')

(A')

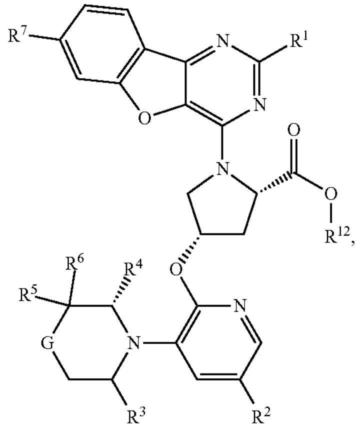

wherein G, $R^1$, $R^2$, $R^3$, $R^4$, $R^5$, $R^6$ and $R^7$ are defined as described aforementioned and wherein $R^{12}$ is $C_{1-4}$-alkyl, aryl, —$CH_2$-aryl, NH—$SO_2$—$C_{1-3}$-alkyl.

In particular the invention relates to the aforementioned prodrugs of formula (A) or of formula (A'), wherein $R^{12}$ is methyl.

In another preferred embodiment the invention relates to a combination of a compound of formula (I) or of formula (I') and one or more active agents selected from the group consisting of anti-inflammatory agents, anti-fibrotic agents, anti-allergic agents/anti-histamines, bronchodilators, beta 2 agonists/betamimetics, adrenergic agonists, anticholinergic agents, methotrexate, mycophenolate mofetil, leukotriene modulators, JAK inhibitors, anti-interleukin antibodies, non-specific immunotherapeutics such as interferons or other cytokines/chemokines, cytokine/chemokine receptor modulators, toll-like receptor agonists, immune checkpoint regulators, an anti-TNF antibody such as Humira™, an anti-BAFF antibody such as Belimumab and Etanercept.

In a further particularly preferred embodiment, the invention concerns a combination of a compound of formula (I) or of formula (I') and one or more anti-fibrotic agents selected from the group consisting of Pirfenidon and Nintedanib.

In a further particularly preferred embodiment the invention relates to a combination of a compound of formula (I) or of formula (I') with one or more anti-inflammatory agents selected from the group consisting of NSAIDs and corticosteroids.

In a further particularly preferred embodiment the invention concerns a combination of a compound of formula (I) or of formula (I') and one or more active agents selected from the group of bronchodilators, beta 2 agonists/betamimetics, adrenergic agonists and anticholinergic agents.

In a further particularly preferred embodiment the invention relates to a combination of a compound of formula (I) or of formula (I') and one or more anti-interleukin antibodies selected from the group consisting of anti-IL23 antibodies such as Risankizumab, anti-IL17 antibodies, anti-IL1 antibodies, anti-IL4 antibodies, anti-IL13 antibodies, anti-IL-5 antibodies, anti-IL-6 antibodies such as Actemra™, anti-IL-12 antibodies and anti-IL-15 antibodies.

In another preferred embodiment the invention concerns a pharmaceutical composition comprising a compound of formula (I) or of formula (I') combined with any of the above-mentioned active agents.

3 3 TERMS AND DEFINITIONS USED

Unless stated otherwise, all the substituents are independent of one another. If for example a number of $C_{1-6}$-alkyl groups are possible substituents at a group, in the case of three substituents, for example, $C_{1-6}$-alkyl could represent, independently of one another, a methyl, a n-propyl and a tert-butyl.

By the term "$C_{1-6}$-alkyl" (including those which are part of other groups) are meant branched and unbranched alkyl groups with 1 to 6 carbon atoms and by the term "$C_{1-3}$-alkyl" are meant branched and unbranched alkyl groups with 1 to 3 carbon atoms. "$C_{1-4}$-alkyl" accordingly denotes branched and unbranched alkyl groups with 1 to 4 carbon atoms. Alkyl groups with 1 to 4 carbon atoms are preferred. Examples of these include methyl, ethyl, n-propyl, iso-propyl, n-butyl, iso-butyl, sec-butyl, tert-butyl, n-pentyl, iso-pentyl, neo-pentyl and hexyl. The abbreviations Me, Et, n-Pr, i-Pr, n-Bu, i-Bu, t-Bu, etc., may also optionally be used for the above-mentioned groups. Unless stated otherwise, the definitions propyl, butyl, pentyl and hexyl include all the possible isomeric forms of the groups in question. Thus, for example, propyl includes n-propyl and iso-propyl, butyl includes iso-butyl, sec-butyl and tert-butyl etc.

By the term "$C_{1-6}$-alkylene" (including those which are part of other groups) are meant branched and unbranched alkylene groups with 1 to 6 carbon atoms and by the term "$C_{1-4}$-alkylene" are meant branched and unbranched alkylene groups with 1 to 4 carbon atoms. Alkylene groups with 1 to 4 carbon atoms are preferred. Examples of these include methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene and hexylene. Unless stated otherwise, the definitions propylene, butylene, pentylene and hexylene include all the possible isomeric forms of the groups in question with the same number of carbons. Thus, for example, propyl includes also 1-methylethylene and butylene includes 1-methylpropylene, 1,1-dimethylethylene, 1,2-dimethylethylene etc.

If the carbon chain is substituted by a group which together with one or two carbon atoms of the alkylene chain forms a carbocyclic ring with 3, 5 or 6 carbon atoms, this includes, inter alia, the following examples of the rings:

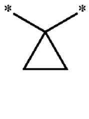 ; 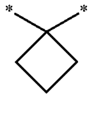 ; 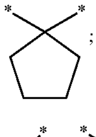 ; 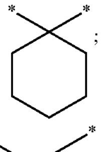 ;

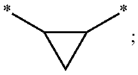 ; 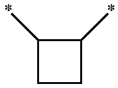 ; 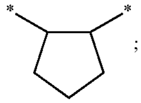 ;

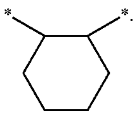.

By the term "$C_{2-6}$-alkenyl" (including those which are part of other groups) are meant branched and unbranched alkenyl groups with 2 to 6 carbon atoms and by the term "$C_{2-4}$-alkenyl" are meant branched and unbranched alkenyl groups with 2 to 4 carbon atoms, provided that they have at least one double bond. Alkenyl groups with 2 to 4 carbon atoms are preferred. Examples include: ethenyl or vinyl, propenyl, butenyl, pentenyl or hexenyl. Unless stated otherwise, the definitions propenyl, butenyl, pentenyl and hexenyl include all the possible isomeric forms of the groups in question. Thus, for example, propenyl includes 1-propenyl and 2-propenyl, butenyl includes 1-, 2- and 3-butenyl, 1-methyl-1-propenyl, 1-methyl-2-propenyl etc.

By the term "$C_{2-5}$-alkynyl" (including those which are part of other groups) are meant branched and unbranched alkynyl groups with 2 to 5 carbon atoms and by the term "$C_{2-4}$-alkynyl" are meant branched and unbranched alkynyl groups with 2 to 4 carbon atoms, provided that they have at least one triple bond. Alkynyl groups with 2 to 4 carbon atoms are preferred.

By the term "$C_{2-6}$-alkenylene" (including those which are part of other groups) are meant branched and unbranched alkenylene groups with 2 to 6 carbon atoms and by the term "$C_{2-4}$-alkenylene" are meant branched and unbranched alkylene groups with 2 to 4 carbon atoms. Alkenylene groups with 2 to 4 carbon atoms are preferred. Examples of these include: ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene and hexenylene. Unless stated otherwise, the definitions propenylene, butenylene, pentenylene and hexenylene include all the possible isomeric forms of the groups in question with the same number of carbons. Thus, for example, propenyl also includes 1-methylethenylene and butenylene includes 1-methylpropenylene, 1,1-dimethylethenylene, 1,2-dimethylethenylene.

By the term "aryl" (including those which are part of other groups) are meant aromatic ring systems with 6 or 10 carbon atoms. Examples include phenyl or naphthyl, the preferred aryl group being phenyl. Unless otherwise stated, the aromatic groups may be substituted by one or more groups selected from among methyl, ethyl, iso-propyl, tert-butyl, hydroxy, fluorine, chlorine, bromine and iodine.

By the term "aryl-$C_{1-6}$-alkylene" (including those which are part of other groups) are meant branched and unbranched alkylene groups with 1 to 6 carbon atoms, which are substituted by an aromatic ring system with 6 or 10 carbon atoms. Examples include benzyl, 1- or 2-phenylethyl and 1- or 2-naphthylethyl. Unless otherwise stated, the aromatic groups may be substituted by one or more groups selected from among methyl, ethyl, iso-propyl, tert-butyl, hydroxy, fluorine, chlorine, bromine and iodine.

By the term "heteroaryl-$C_{1-6}$-alkylene" (including those which are part of other groups) are meant—even though they are already included under "aryl-$C_{1-6}$-alkylene"—branched and unbranched alkylene groups with 1 to 6 carbon atoms, which are substituted by a heteroaryl.

If not specifically defined otherwise, a heteroaryl of this kind includes five- or six-membered heterocyclic aromatic groups or 5-10-membered, bicyclic heteroaryl rings which may contain one, two, three or four heteroatoms selected from among oxygen, sulfur and nitrogen, and contain so many conjugated double bonds that an aromatic system is formed. The following are examples of five- or six-membered heterocyclic aromatic groups and bicyclic heteroaryl rings:

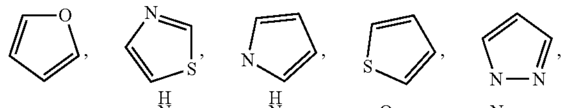

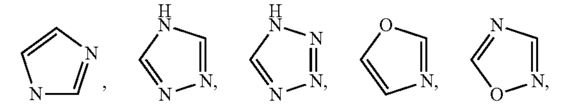

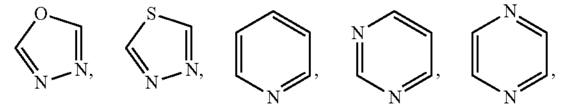

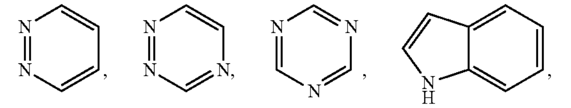

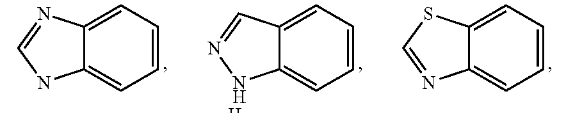

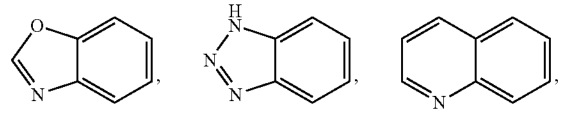

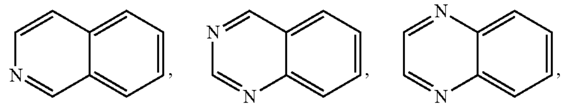

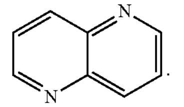

Unless otherwise stated, these heteroaryls may be substituted by one or more groups selected from among methyl, ethyl, iso-propyl, tert-butyl, hydroxy, amino, nitro, alkoxy, fluorine, chlorine, bromine and iodine.

The following are examples of heteroaryl-$C_{1-6}$-alkylenes:

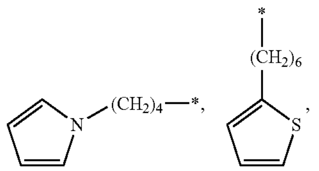

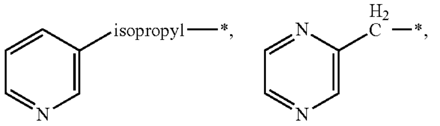

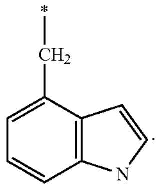

By the term "$C_{1-6}$-haloalkyl" (including those which are part of other groups) are meant branched and unbranched alkyl groups with 1 to 6 carbon atoms, which are substituted by one or more halogen atoms. By the term "$C_{1-4}$-haloalkyl" are meant branched and unbranched alkyl groups with 1 to 4 carbon atoms, which are substituted by one or more halogen atoms. Alkyl groups with 1 to 4 carbon atoms are preferred. Examples include: $CF_3$, $CHF_2$, $CH_2F$, $CH_2CF_3$.

By the term "$C_{3-7}$-cycloalkyl" (including those which are part of other groups) are meant cyclic alkyl groups with 3 to 7 carbon atoms, if not specifically defined otherwise. Examples include: cyclopropyl, cyclobutyl, cyclopentyl, cyclohexyl and cycloheptyl. Unless otherwise stated, the cyclic alkyl groups may be substituted by one or more groups selected from among methyl, ethyl, iso-propyl, tert-butyl, hydroxy, fluorine, chlorine, bromine and iodine.

If not specifically defined otherwise, by the term "$C_{3-10}$-cycloalkyl" are also meant monocyclic alkyl groups with 3 to 7 carbon atoms and also bicyclic alkyl groups with 7 to 10 carbon atoms, or monocyclic alkyl groups which are bridged by at least one $C_{1-3}$-carbon bridge.

By the term "heterocyclic rings" or "heterocycle" are meant, unless stated otherwise, five-, six- or seven-membered, saturated, partially saturated or unsaturated heterocyclic rings which may contain one, two or three heteroatoms selected from among oxygen, sulfur and nitrogen, while the ring may be linked to the molecule through a carbon atom or through a nitrogen atom, if there is one. Although included by the term "heterocyclic rings" or "heterocycles", the term "saturated heterocyclic ring" refers to five-, six- or seven-membered saturated rings. Examples include:

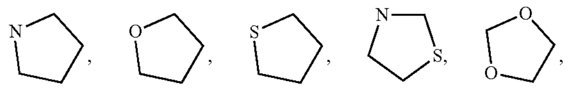

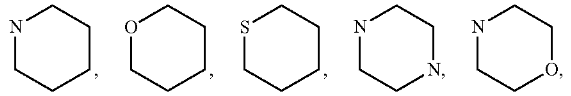

-continued

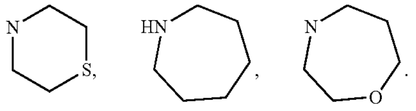

Although included by the term "heterocyclic rings" or "heterocyclic group", the term "partially saturated heterocyclic group" refers to five-, six- or seven-membered partially saturated rings which contain one or two double bonds, without so many double bonds being produced that an aromatic system is formed, unless specifically defined otherwise. Examples include:

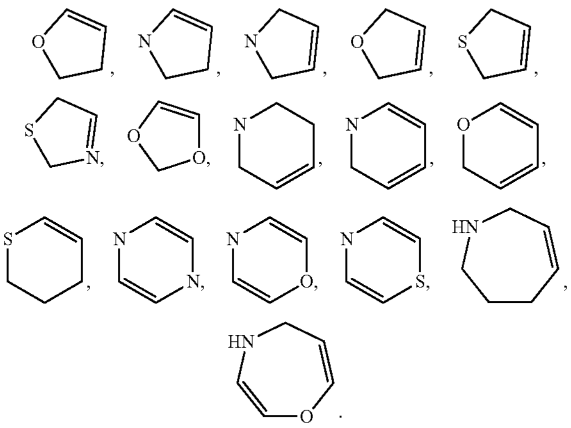

Although included by the term "heterocyclic rings" or "heterocycles", the term "heterocyclic aromatic rings", "unsaturated heterocyclic group" or "heteroaryl" refers to five- or six-membered heterocyclic aromatic groups or 5-10-membered, bicyclic heteroaryl rings which may contain one, two, three or four heteroatoms selected from among oxygen, sulfur and nitrogen, and contain so many conjugated double bonds that an aromatic system is formed, unless not specifically defined otherwise. Examples of five- or six-membered heterocyclic aromatic groups include:

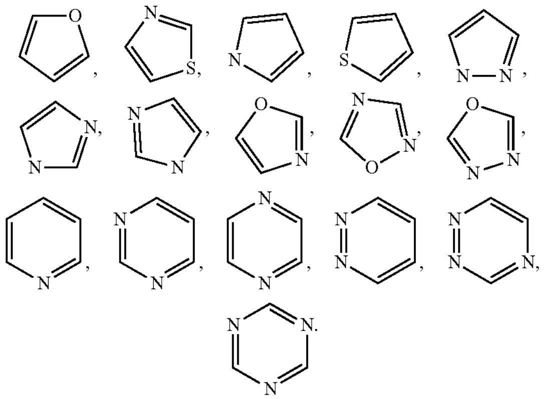

Unless otherwise mentioned, a heterocyclic ring (or heterocycle) may be provided with a keto group. Examples include:

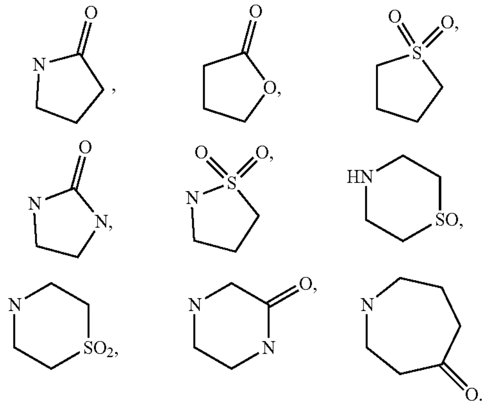

Although covered by the term "cycloalkyl", the term "bicyclic cycloalkyls" generally denotes eight-, nine- or ten-membered bicyclic carbon rings. Examples include:

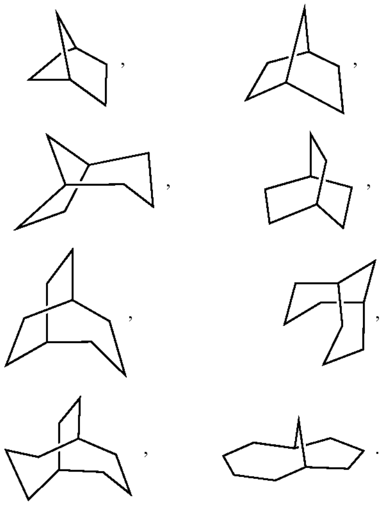

Although already included by the term "heterocycle", the term "bicyclic heterocycles" generally denotes eight-, nine- or ten-membered bicyclic rings which may contain one or more heteroatoms, preferably 1-4, more preferably 1-3, even more preferably 1-2, particularly one heteroatom, selected from among oxygen, sulfur and nitrogen, unless not specifically defined otherwise. The ring may be linked to the molecule through a carbon atom of the ring or through a nitrogen atom of the ring, if there is one. Examples include:

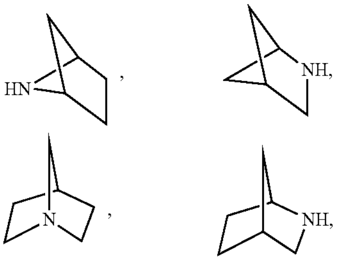

-continued

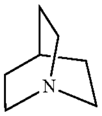 , 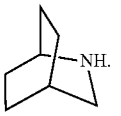

Although already included by the term "aryl", the term "bicyclic aryl" denotes a 5-10 membered, bicyclic aryl ring which contains sufficient conjugated double bonds to form an aromatic system. One example of a bicyclic aryl is naphthyl.

Although already included under "heteroaryl", the term "bicyclic heteroaryl" denotes a 5-10 membered, bicyclic heteroaryl ring which may contain one, two, three or four heteroatoms, selected from among oxygen, sulfur and nitrogen, and contains sufficient conjugated double bonds to form an aromatic system, unless specifically defined otherwise.

Although included by the term "bicyclic cycloalkyls" or "bicyclic aryl", the term "fused cycloalkyl" or "fused aryl" denotes bicyclic rings wherein the bridge separating the rings denotes a direct single bond. The following are examples of a fused, bicyclic cycloalkyl:

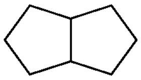 , 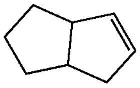 ,

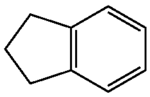 , 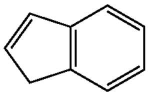 ,

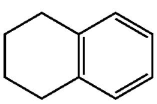 , 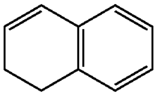 .

Although included by the term "bicyclic heterocycles" or "bicyclic heteroaryls", the term "fused bicyclic heterocycles" or "fused bicyclic heteroaryls" denotes bicyclic 5-10 membered heterorings which contain one, two, three or four heteroatoms, selected from among oxygen, sulfur and nitrogen and wherein the bridge separating the rings denotes a direct single bond. The "fused bicyclic heteroaryls" moreover contain sufficient conjugated double bonds to form an aromatic system. Examples include pyrrolizine, indole, indolizine, isoindole, indazole, purine, quinoline, isoquinoline, benzimidazole, benzofuran, benzopyran, benzothiazole, benzothiazole, benzoisothiazole, pyridopyrimidine, pteridine, pyrimidopyrimidine,

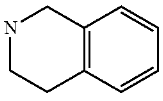 , 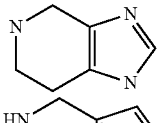 ,

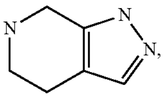 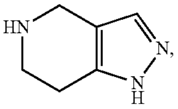

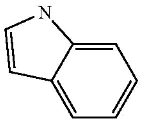 , 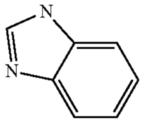 ,

-continued

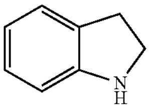 , 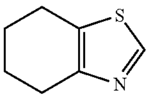 ,

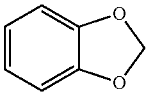 .

"Halogen" within the scope of the present invention denotes fluorine, chlorine, bromine or iodine. Unless stated to the contrary, fluorine, chlorine and bromine are regarded as preferred halogens.

As mentioned previously, the compounds of formulas (I) or (I') may be converted into the salts thereof, particularly for pharmaceutical use into the physiologically and pharmacologically acceptable salts thereof. The phrase "pharmaceutically acceptable" is employed herein to refer to those compounds, materials, compositions, and/or dosage forms which are, within the scope of sound medical judgement, suitable for use in contact with the tissue of human beings and animals without excessive toxicity, irritation, allergic response, or other problem or complication, and commensurate with a reasonable benefit/risk ratio. These salts may be present on the one hand as physiologically and pharmacologically acceptable acid addition salts of the compounds of formulas (I) or (I') with inorganic or organic acids. On the other hand, the compound of formulas (I) or (I') may be converted by reaction with inorganic bases into physiologically and pharmacologically acceptable salts with alkali or alkaline earth metal cations as counter-ion. The acid addition salts may be prepared for example using hydrochloric acid, hydrobromic acid, sulfuric acid, phosphoric acid, methanesulphonic acid, p-toluenesulfonic acid, acetic acid, fumaric acid, succinic acid, lactic acid, citric acid, tartaric acid or maleic acid. It is also possible to use mixtures of the above-mentioned acids. To prepare the alkali and alkaline earth metal salts of the compounds of formulas (I) or (I') it is preferable to use the alkali and alkaline earth metal hydroxides and hydrides, of which the hydroxides and hydrides of the alkali metals, particularly sodium, potassium, magnesium, calcium, zinc and diethanolamine, are preferred, while sodium and potassium hydroxide are particularly preferred.

The invention relates to the compounds in question, optionally in the form of the individual optical isomers, diastereomers, mixtures of diastereomers, mixtures of the individual enantiomers or racemates, in the form of the tautomers as well as in the form of the free bases or the corresponding acid addition salts with pharmacologically acceptable acids—such as for example acid addition salts with hydrohalic acids—for example hydrochloric or hydrobromic acid—or organic acids—such as for example oxalic, fumaric, diglycolic or methanesulfonic acid.

The compounds of formula (I) or (I') according to the invention may optionally be present as mixtures of diastereomeric isomers but may also be obtained as pure diastereoisomers. Preferred are the compounds with the specific stereochemistry of formula (I').

4 METHODS OF SYNTHESIS

The compounds according to the invention and their intermediates may be obtained using the methods of synthesis which are known to the one skilled in the art and described in the literature of organic synthesis, for example.

Moreover, the invention provides processes for making a compound of formula (I) or of formula (I').

Optimal reaction conditions and reaction times may vary depending on the particular reactants used. Unless otherwise specified, solvents, temperature, pressures and other reaction conditions, may be readily selected by one of ordinary skill in the art. Specific procedures are provided in the Synthetic Examples section. Typically, reaction progress may be monitored by thin layer chromatography (TLC) or liquid chromatography mass spectrometry (LC-MS), if desired, and intermediates and products may be purified by chromatography on silica gel, HPLC and/or by recrystallization. The examples which follow are illustrative and, as one skilled in the art will recognize, particular reagents or conditions could be modified as needed for individual compounds without undue experimentation. Starting materials and intermediates used in the methods below are either commercially available or easily prepared from commercially available materials by those skilled in the art.

A compound of Formula (I) may be prepared by the methods outlined in Schemes 1-4, wherein $R^1$, $R^2$, $R^3$, $R^4$, $R^5$, $R^6$, $R^7$, $R^8$, $R^9$, $R^{10}$, $R^{11}$ and G are defined aforementioned and wherein PG is a protecting group preferably selected from the group consisting of tert-butoxycarbonyl (BOC), benzyloxycarbonyl (Cbz), fluorenylmethylenoxycarbonyl (Fmoc) and allyloxycarbonyl (Alloc):

Scheme 1

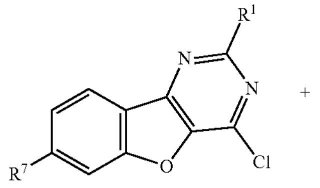

(II)

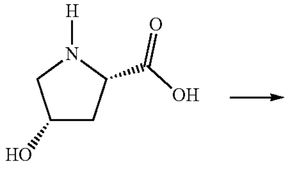

(III)

-continued

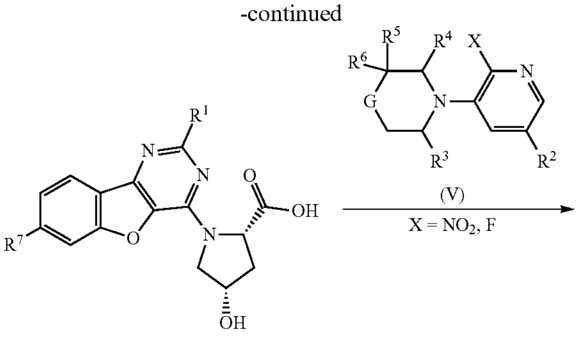

(IV) (V)

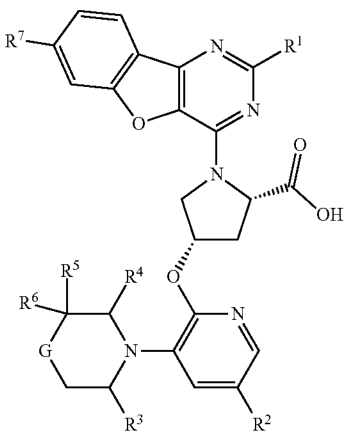

(I)

As illustrated in Scheme 1, the reaction of (2S,4S)-4-hydroxypyrrolidine-2-carboxylic acid (III) with chloro-pyrimidine (II) in the presence of a suitable base such as diisopropylethylamine, potassium carbonate or sodium hydride in a suitable solvent such as DMSO provides a hydroxyproline derivative of formula (IV). Reaction of the hydroxyproline (IV) with a pyridine of formula (V) (in which X is F or $NO_2$) in the presence of a suitable base such as NaH in a suitable solvent such as DMA, DMF or NMP provides a compound of formula (I).

Scheme 2

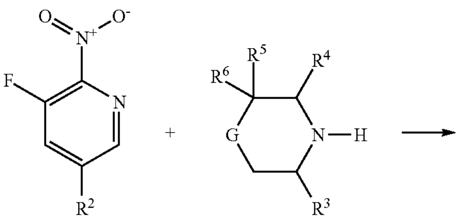

(VI) (VII)

-continued

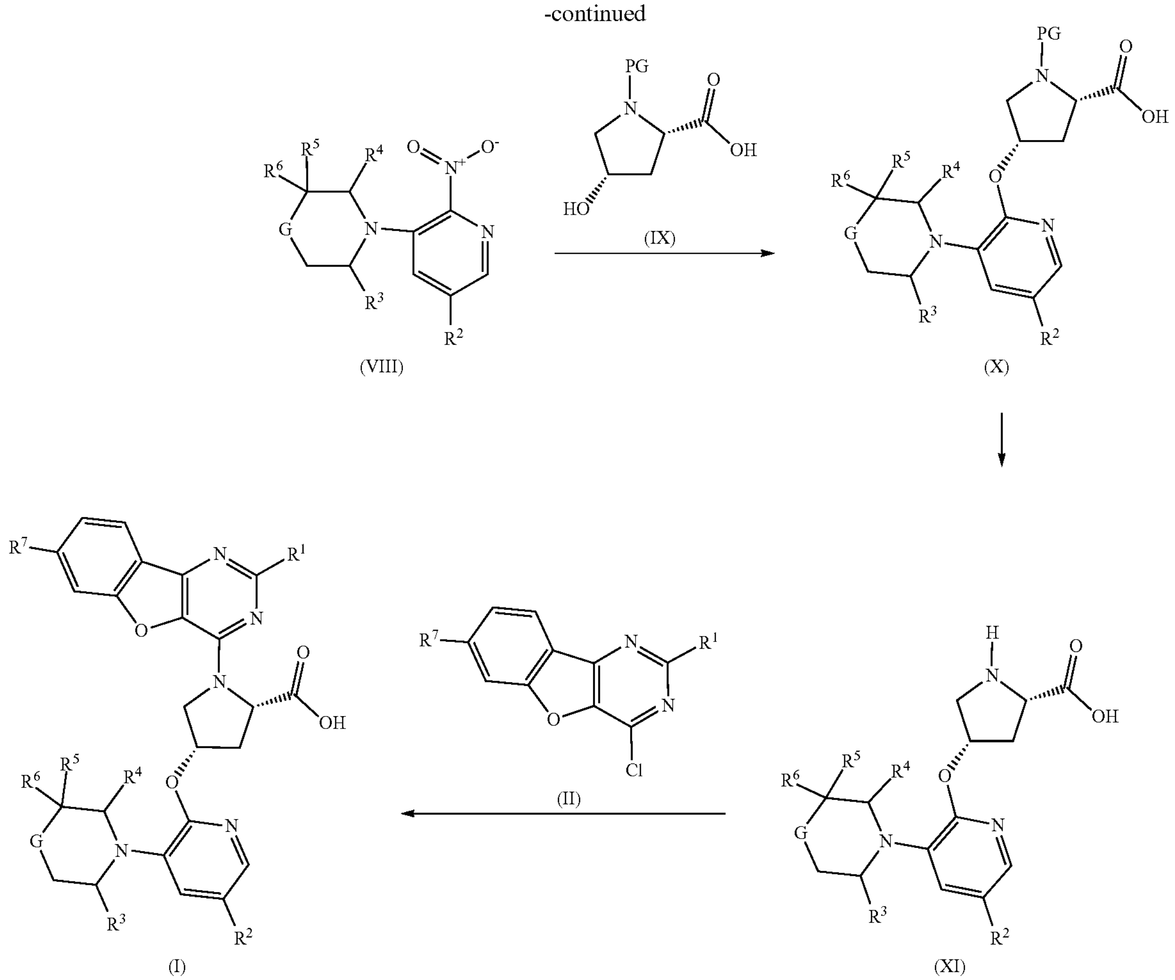

(VIII) (X) (I) (XI)

As illustrated in Scheme 2, the reaction of fluoronitropyridine (VI) with a cyclic amine (VII) in the presence of a suitable base such as $K_2CO_3$ in a suitable solvent such as acetonitrile provides a nitropyridine of formula (VIII). This nitropyridine (VIII) can react with a hydroxyproline of formula (IX), wherein the protecting group PG can be for example tert-butoxycarbonyl (BOC), in the presence of a suitable base such as NaH in a suitable solvent such as DMF, NMP or DMA to provide a compound of formula (X). Removal of the protecting group PG of (X) under standard conditions provides a proline derivative of formula (XI), i.e. if PG is BOC, the deprotection can be carried out using TFA in a suitable solvent such as acetonitrile. Reaction of compound (XI) with a chloro-pyrimidine of formula (II) in the presence of a suitable base such as diisopropylethylamine, potassium carbonate or sodium hydride in a suitable solvent such as DMSO or DMF provides a compound of formula (I).

Following this general reaction Scheme 2, the substituent $R^2$ can either be in place from the beginning of the reaction sequence in compound (VI) and remain unchanged until compound (I) is obtained (i.e. if $R^2$ is H, Br, Cl, aryl or alkynyl), or it can be introduced at a later stage during the synthesis via Suzuki coupling or other arylation reactions known to someone skilled in the art. For example, a compound of formula (VI), (VIII), (X) or (I) where $R^2$ is Br, I or OTf can be reacted with a suitable aryl boronate (ester/acid) in the presence of a suitable base such as $Na_2CO_3$, $K_3PO_4$ or KOH and a suitable catalyst such as $Pd(dppf)Cl_2$ or $Pd(PPh_3)_4$ (using a suitable ligand such as Xphos) in a suitable solvent such as dioxane or DMF to afford the respective compound wherein $R^2$ is aryl.

Alternatively, a compound of formula (VI), (VIII), (X) or (I) wherein $R^2$ is halogen or OTf can react with a borylating reagent such as bis(pinacolato)diboron in the presence of a suitable catalyst such as $Pd(dppf)Cl_2$ and a suitable base such as potassium acetate to provide a boronic ester. This boronic ester can react with a suitable aryl-halogenide in a Suzuki coupling in the presence of a suitable base such as $Na_2CO_3$, $K_3PO_4$ or KOH and a suitable catalyst such as $Pd(dppf)Cl_2$ or $Pd(PPh_3)_4$ (using a suitable ligand such as Xphos) in a suitable solvent such as dioxane or DMF to afford the respective compound wherein $R_2$ is aryl.

Alternatively, a compound of formula (VI), (VIII), (X) or (I) where $R^2$ is halogen can react with a suitable alkyne such as ethynyltris(propan-2-yl)silane in the presence of a suitable catalyst such as $PdCl_2(PPh_3)_2$ and copper (I) iodide and in the presence of a suitable base such as DIPEA in a suitable solvent such as THE to provide the respective compound wherein $R^2$ is alkyne.

The carboxylic acid functionality of the proline motif (i.e. in a compound of formula (X) or (I)) may be protected with a suitable protecting group such as an alkyl ester during specific reactions in this sequence, i.e. a tert-butyl ester is a suitable protecting group to introduce an aryl moiety at $R^2$.

Scheme 3

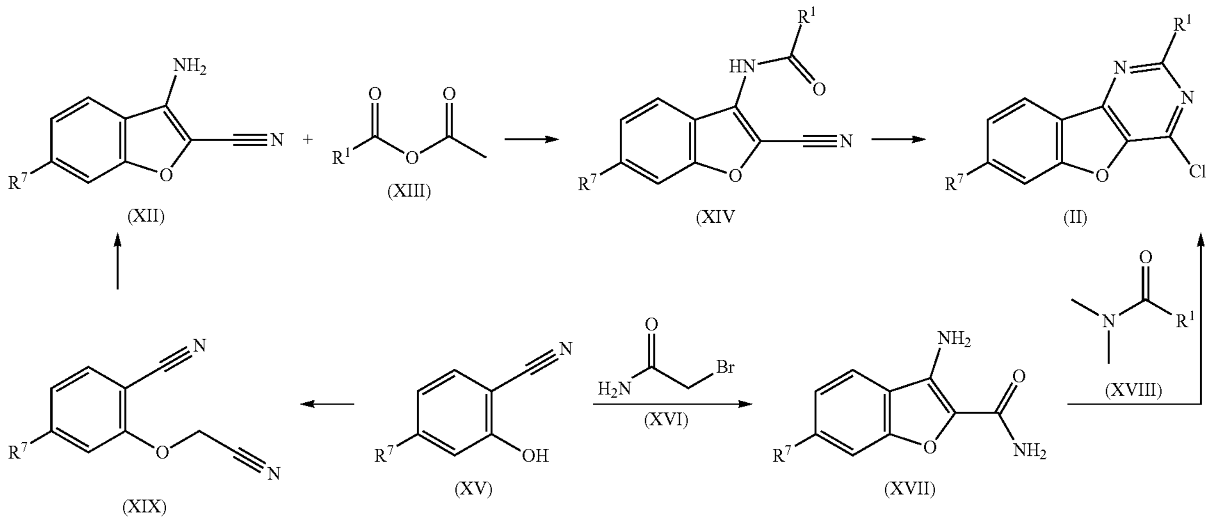

A compound of formula (II) can be prepared as illustrated in Scheme 3.

The reaction of a carbonitrile of formula (XII) with an anhydride of formula (XIII) or the corresponding acid in a suitable solvent such as pyridine provides amide (XIV). Upon reaction with a suitable chlorination reagent such as phosphorus pentachloride in a suitable solvent such as sulfolane, amide (XIV) cyclizes to form a compound of formula (II).

In an alternative synthetic sequence, a compound of formula (XV) reacts with 2-bromoacetamide in the presence of a suitable base such as $K_2CO_3$ or KOH in a suitable solvent such as ethanol to provide a compound of formula (XVII). Compound (XVII) reacts with a dimethylamide of formula (XVIII) in the presence of a suitable chlorination reagent such as phosphorus oxychloride and forms a compound of formula (II).

In another alternative synthetic sequence, a compound of formula (XV) reacts with bromoacteonitrilein the presence of a suitable base such as $K_2CO_3$ in a suitable solvent such as DMF to yield a compound of formula (XIX). This compound cyclizes in the presence of a suitable base such as tert-butoxide in a suitable solvent such as THE to form carbonitrile (XII), and can be converted into a compound of formula (XIV) and subsequently into a compound of formula (II) as described above.

Compounds of formula (VII) are either commercially available or can be prepared according to literature procedures or are described as exemplified in the experimental section. A compound of formula (VII), exemplified by a compound of formula (XXIII), can be prepared as illustrated in Scheme 4:

Scheme 4

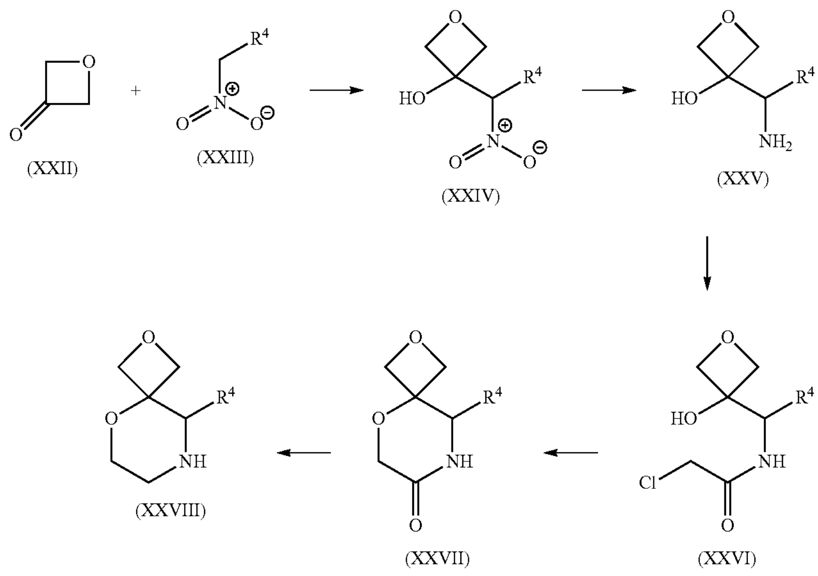

Oxetan-3-one (XXII) reacts with a nitroalkane of formula (XXIII) in a suitable solvent such as methanol and forms a compound of formula (XXIV). Hydrogenation of compound (XXIV) in the presence of hydrogen and a suitable catalyst such as $Pd(OH)_2/C$ in a suitable solvent such as ethanol provides a compound of formula (XXV). Reaction of compound (XXV) with chloroacetyl chloride and in the presence of a suitable base such as triethylamine in a suitable solvent such as acetonitrile provides compound (XXVI) which cyclizes under treatment with a suitable base such as tert-butoxide in a suitable solvent such as tert-amyl alcohol to form a lactam of formula (XXVII). Reduction of compound (XXVII) with a suitable reducing reagent such as lithium aluminium hydride in a suitable solvent such as diethylether provides a morpholine compound of formula (XXVIII).

Further modifications of compounds of Formula (I) by methods known to persons skilled in the art and illustrated in the Examples below, may be used to prepare additional compounds of this invention.

The synthetic routes presented may rely on the use of protecting groups. For example, potentially reactive groups present, such as hydroxyl, carbonyl, carboxy, amino, alkylamino, or imino, may be protected during the reaction by conventional protecting groups which are cleaved again after the reaction. Suitable protecting groups for the respective functionalities and their removal are well known to those skilled in the art and are described in the literature of organic synthesis for example in "Protecting Groups, 3$^{rd}$ Edition", Philip J. Kocienski, Thieme, 2005 or "Protective Groups in Organic Synthesis, 4$^{th}$ Edition", Peter G. M. Wuts, Theodora W. Greene, John Wiley and Sons, 2007.

The compounds of general Formula (I) may be resolved into their diastereoisomers (ds) as mentioned below. Thus, for example, cis/trans mixtures may resolved into their cis and trans isomers.

The cis/trans mixtures may be resolved, for example, by chromatography into the cis and the trans isomer thereof. Diastereomeric mixtures of compounds of the general formula (I) may be resolved into their diastereoisomers by taking advantage of their different physico-chemical properties using methods known per se, e.g. chromatography and/or fractional crystallization.

Racemic intermediates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds. Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids commonly used for such a purpose as well as optically active alcohols applicable as auxiliary residues are known to those skilled in the art.

As mentioned above, the compounds of Formula (I) may be converted into salts, particularly for pharmaceutical use into the pharmaceutically acceptable salts. As used herein, "pharmaceutically acceptable salts" refer to derivatives of the disclosed compounds wherein the parent compound is modified by forming pharmaceutically acceptable acid or base salts thereof, The phrase "pharmaceutically acceptable" is employed herein to refer to those compounds, materials, compositions, and/or dosage forms which are, within the scope of sound medical judgement, suitable for use in contact with the tissue of human beings and animals without excessive toxicity, irritation, allergic response, or other problem or complication, and commensurate with a reasonable benefit/risk ratio. Examples of pharmaceutically acceptable salts include, but are not limited to, mineral or organic acid salts of basic residues such as amines; alkali or organic salts of acidic residues such as carboxylic acids; and the like.

For examples, such salts include salts from benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid and tartraric acid.

Further pharmaceutically acceptable salts can be formed with cations from ammonia, L-arginine, calcium, 2,2'-iminobisethanol, L-lysine, magnesium, N-methyl-D-glucamine, potassium, sodium and tris(hydroxymethyl)-aminoethane.

The pharmaceutical acceptable salts of the present invention can be synthesized from the parent compound which contains a basic or acidic moiety by conventional chemical methods. Generally, such salts can be prepared by reacting the free acid or base form of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

The compounds according to the invention are advantageously also obtainable using the methods described in the examples that follow, which may also be combined for this purpose with methods known to those skilled in the art from literature.

General Technical Remarks

The terms "ambient temperature" and "room temperature" are used interchangeably and designate a temperature of about 20° C., e.g. 15 to 25° C.

As a rule, $^1$H NMR spectra and/or mass spectra have been obtained of the compounds prepared. Unless otherwise stated, all chromatographic operations were performed at room temperature.

SYNTHESES OF INTERMEDIATES

Intermediate 1.1.I

N-(2-Cyano-1-benzofuran-3-yl)-2,2,2-trifluoroacetamide

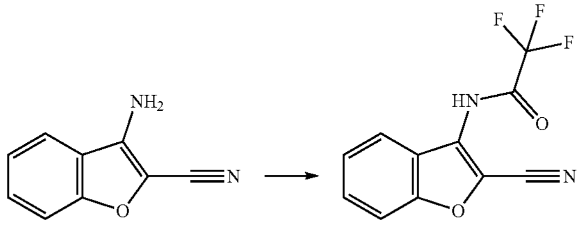

Int 1.1.I

TFAA (5.31 g, 25.3 mmol) was added to a mixture of 3-amino-1-benzofuran-2-carbonitrile (4.00 g, 25.3 mmol) in pyridine (40.0 mL) at RT. The mixture was stirred at 25° C. for 12 h, then concentrated under reduced pressure, diluted with 20 mL water and extracted with EtOAc. The combined organic layers were washed with brine, dried over $Na_2SO_4$, filtered and concentrated under reduced pressure. The residue was purified by column chromatography (silica gel; PE/EtOAc=20/1 to 5/1).

ESI-MS: 254.9 $[M+H]^+$ $R_t$ (HFPLC): 0.56 min (method A)

The following intermediates were prepared according to the general procedure (INTERMEDIATE 1.1.I ) described above:

Intermediate 1.1.III

N-(2-Cyano-1-benzofuran-3-yl)-2,2-difluoropropanamide

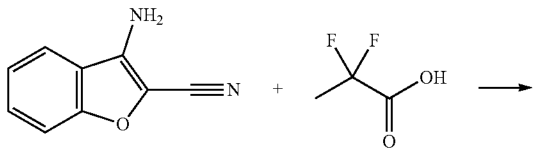

| Int. | Starting materials | | Structure | ESI-MS | $R_t$ (HPLC) or $R_f$ (TLC): | Reaction conditions |
|---|---|---|---|---|---|---|
| 1.1.II | 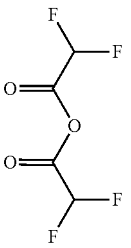 [SMILES: O=C(OC(=O)C(F)F)C(F)F] | 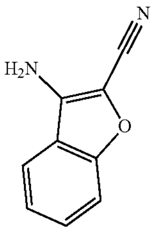 [SMILES: N#Cc1oc2ccccc2c1N] | 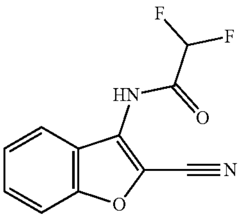 [SMILES: N#Cc1oc2ccccc2c1NC(=O)C(F)F] | 237 $[M + H]^+$ | $R_f$ (TLC): 0.6 (PE/EtOAc = 2/1) | |
| 1.1.IV | 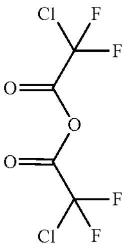 [SMILES: O=C(OC(=O)C(F)(F)Cl)C(F)(F)Cl] | 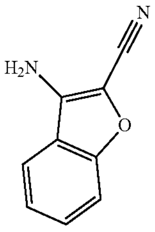 [SMILES: N#Cc1oc2ccccc2c1N] | 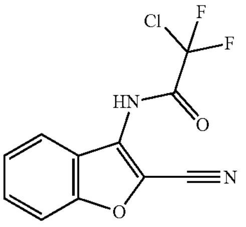 [SMILES: N#Cc1oc2ccccc2c1NC(=O)C(F)(F)Cl] | 271 $[M + H]^+$ | $R_f$ (TLC): 0.6 (PE/EtOAc = 3/1) | |
| 1.1.V | 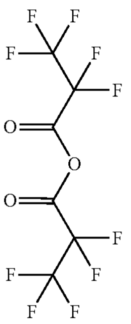 [SMILES: O=C(OC(=O)C(F)(F)C(F)(F)F)C(F)(F)C(F)(F)F] | 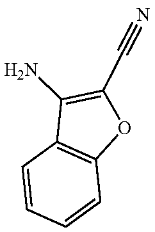 [SMILES: N#Cc1oc2ccccc2c1N] | 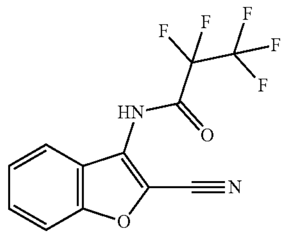 [SMILES: N#Cc1oc2ccccc2c1NC(=O)C(F)(F)C(F)(F)F] | 323 $[M + H]^+$ | $R_t$ (HPLC): 1.02 min method (C) | no pyridine 70° C., 15 h |
| 1.1.VI | 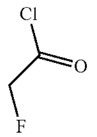 | 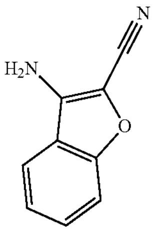 [SMILES: N#Cc1oc2ccccc2c1N] | 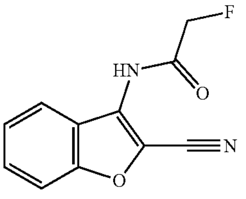 [SMILES: N#Cc1oc2ccccc2c1NC(=O)CF] | 217 $[M + H]^+$ | $R_t$ (HPLC): 1.19 min method O | solvent: DCM |

-continued

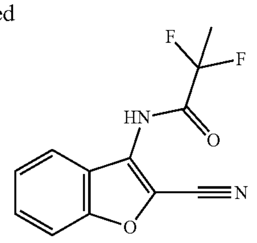

Int. 1.1.III

To a mixture of 2,2-difluoropropionic acid (300 mg, 2.73 mmol) and DIPEA (1.41 mL, 8.18 mmol) in 2.00 mL DMF at RT was added HATU (1.04 g, 2.73 mmol), followed by 3-amino-1-benzofuran-2-carbonitrile (474 mg, 3.00 mmol). After stirring the reaction at RT for 1.5 h, a mixture of 2,2-difluoropropionic acid (300 mg, 2.73 mmol) DIPEA (1.41 mL, 8.18 mmol) and HATU (1.04 g, 2.73 mmol) in 2.0 mL was added to the reaction mixture and stirring was continued. DCM and water were added to the reaction mixture and the product was extracted. The phases were separated and concentrated in vacuo, and the crude product was purified by RP-HPLC (X-Bridge C18, ACN/H2O/TFA).

ESI-MS: 249 $[M-H]^-$ $R_t$ (H PLC): 0.53 min (method A)

Intermediate 1.2.I

6-Chloro-4-(trifluoromethyl)-8-oxa-3,5-diazatricyclo [7.4.0.0$^{2,7}$]trideca-1(9),2(7),3,5,10,12-hexaene

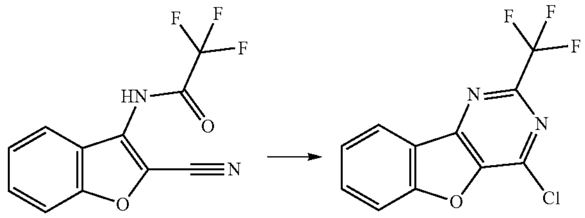

Int. 1.1.I

Int. 1.2.I

To a solution of N-(2-cyano-1-benzofuran-3-yl)-2,2,2-trifluoroacetamide (INTERMEDIATE 1.1.I, 4.00 g, 15.7 mmol) in sulfolane (10.0 mL) was added phosphorus pentachloride (13.1 g, 63.0 mmol). The mixture was stirred at 110° C. for 16 h. The reaction mixture was poured into ice water and extracted with EtOAc. The combined organic layers were washed with brine, dried over $Na_2SO_4$, filtered and concentrated under reduce pressure. The residue was purified by column chromatography (silica gel; PE/EtOAc=20/1 to 10/1).

ESI-MS: 273 $[M+H]^+$ $R_t$ (HPLC): 0.71 min (method A)

The following compounds were prepared according to the general procedure (INTERMEDIATE 1.2.I) described above:

| Int. | Starting material | Structure | ESI-MS | $R_t$ (HPLC) or $R_f$ (TLC): |
|---|---|---|---|---|
| 1.2.II | 1.1.II | 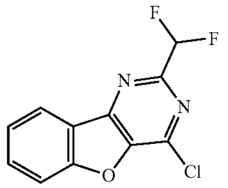 [SMILES: FC(F)c1nc(Cl)c2oc3ccccc3c2n1] | 255/257 $[M + H]^+$ | $R_f$ (TLC): 0.6 (PE/ EtOAc = 5/1) |
| 1.2.III | 1.1.III | 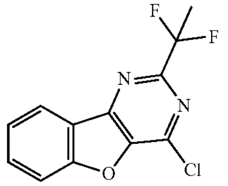 [SMILES: CC(F)(F)c1nc(Cl)c2oc3ccccc3c2n1] | 269/271 $[M + H]^+$ | $R_f$ (TLC): 0.6 (PE/ EtOAc = 5/1) |
| 1.2.IV | 1.1.IV | 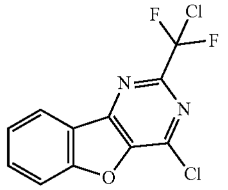 [SMILES: FC(F)(Cl)c1nc(Cl)c2oc3ccccc3c2n1] | 289/291 $[M + H]^+$ | $R_f$ (TLC): 0.6 (PE/ EtOAc = 5/1) |
| 1.2.V | 1.1.V | 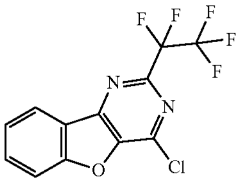 [SMILES: FC(F)(F)C(F)(F)c1nc(Cl)c2oc3ccccc3c2n1] | 323/325 $[M + H]^+$ | $R_t$ (HPLC): 1.20 min method (C) |
| 1.2.VI | 1.1.VI | 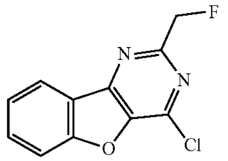 [SMILES: FCc1nc(Cl)c2oc3ccccc3c2n1] | 237/239 $[M + H]^+$ | $R_t$ (HPLC): 3.20 min Method (A) |

Intermediate 1.3.I (2S,4S)-4-hydroxy-1-[4-(trifluoromethyl)-8-oxa-3,5-diazatricyclo[7.4.0.0$^{2,7}$]-trideca-1(9),2(7),3,5,10,12-hexaen-6-yl]pyrrolidine-2-carboxylic acid

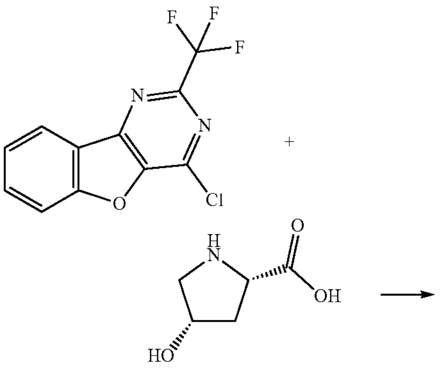

-continued

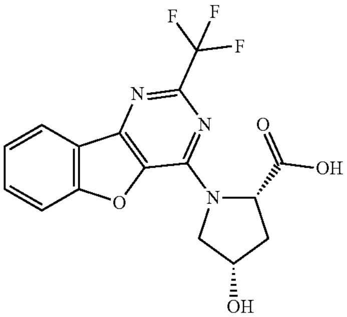

Int. 1.2.I Int. 1.3.I

To a preheated mixture of (2S,4S)-4-hydroxypyrrolidine-2-carboxylic acid (1.44 g, 11.0 mmol) in DMSO (25.0 mL) at 110° C. was added DIPEA (3.90 g, 30.0 mmol) and 6-chloro-4-(trifluoromethyl)-8-oxa-3,5-diazatricyclo [7.4.0.$0^{2,7}$]trideca-1(9),2(7),3,5,10,12-hexaene (INTERMEDIATE 1.2.I, 2.73 g, 10.0 mmol). Stirring was continued at 110° C. for 10 min, before the reaction mixture was added dropwise into water and acidified with 4 M HCl. The precipitate was filtered and dried.

ESI-MS: 368 $[M+H]^+$ $R_t$ (HPLC): 0.50 min (method A)

The following compounds were prepared according to the general procedure (INTERMEDIATE 1.3.1) described above:

| Int. | Starting material | Structure | ESI-MS | $R_t$ (HPLC) [min] (method) | Reaction conditions |
|---|---|---|---|---|---|
| 1.3.II | Int. 1.2.II | 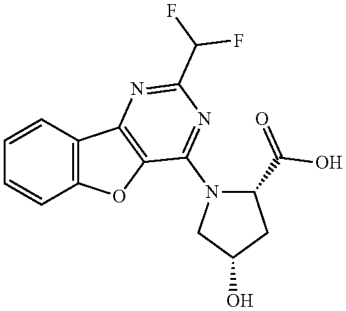 [SMILES: O=C(O)[C@@H]1C[C@H](O)CN1c1nc(C(F)F)nc2c1oc1ccccc12] | 350 $[M + H]^+$ | 0.26 (F) | |
| 1.3.III | Int.1.2.III | 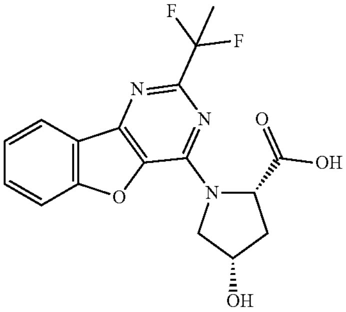 [SMILES: CC(F)(F)c1nc(N2C[C@@H](O)C[C@H]2C(=O)O)c2oc3ccccc3c2n1] | 364 $[M + H]^+$ | 0.46 (A) | time: 1 h HPLC Purification |
| 1.3.IV | Int.1.2.IV | 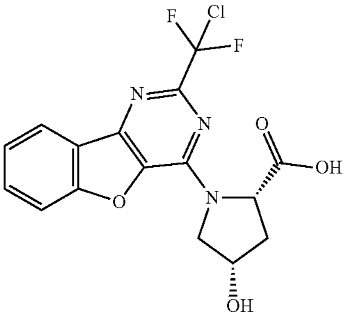 [SMILES: O=C(O)[C@@H]1C[C@H](O)CN1c1nc(C(F)(F)Cl)nc2c1oc1ccccc12] | 384/ 386 $[M + H]^+$ | 0.53 (A) | time: 1 h HPLC Purification |

-continued
| Int. | Starting material | Structure | ESI-MS | $R_t$ (HPLC) [min] (method) | Reaction conditions |
|---|---|---|---|---|---|
| 1.3.V | Int.1.2.V | 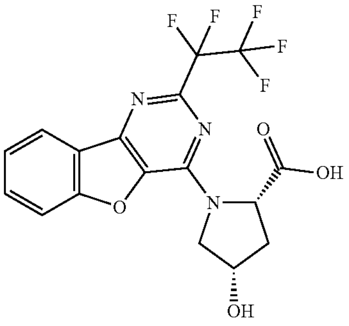 [SMILES: O=C(O)[C@@H]1C[C@H](O)CN1c1nc(C(F)(F)C(F)(F)F)nc2c1oc1ccccc12] | 418 $[M + H]^+$ | 0.85 (C) | HPLC Purification |
| 1.3.VI | 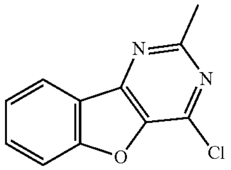 | 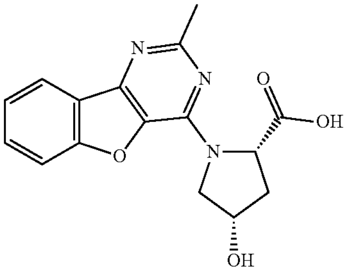 [SMILES: Cc1nc(N2C[C@@H](O)C[C@H]2C(=O)O)c2oc3ccccc3c2n1] | 314 $[M + H]^+$ | 0.27 (A) | time: 35 min |
| 1.3.VII | 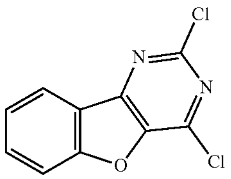 [SMILES: Clc1nc(Cl)c2oc3ccccc3c2n1] | 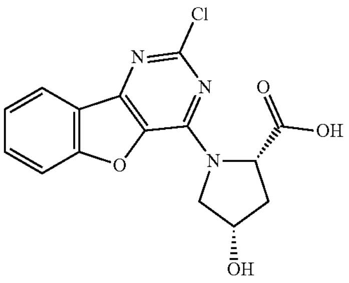 [SMILES: O=C(O)[C@@H]1C[C@H](O)CN1c1nc(Cl)nc2c1oc1ccccc12] | 334/ 336 $[M + H]^+$ | 0.86 (M) | 100° C., 1 h |

Intermediate 2.1

3-(1-Nitroethyl)oxetan-3-ol

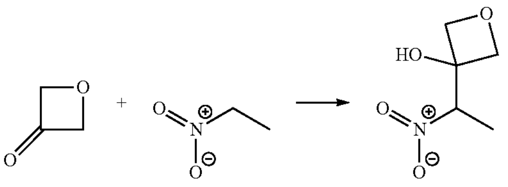

Int. 2.1

A mixture of nitroethane (27.3 g, 364 mmol) in 50 mL methanol was cooled to 0° C. TEA (9.74 mL, 69.4 mmol) was added dropwise under cooling followed by dropwise addition of oxetan-3-one (25.0 g, 347 mmol). The cooling was removed, the reaction mixture was stirred at RT for 1 h and then concentrated. The residue was purified by column chromatography (silica gel; CH/EtOAc=75/25 to 50/50).

ESI-MS: r 146 $[M-H]^-$ $R_t$ (EI): 3.38 min

Intermediate 2.2

3-(1-Aminoethyl)oxetan-3-ol

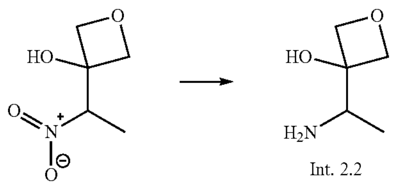

Int. 2.2

Int. 2.1

A mixture of 3-(1-nitroethyl)oxetan-3-ol (INTERMEDIATE 2.1, 24.5 g, 157 mmol), 280 mL ethanol and $Pd(OH)_2/C$ 5 mol % (5.52 g, 7.87 mmol) was placed under hydrogen pressure (50 psi) in a Parr apparatus for 16 h. The reaction mixture was filtered and concentrated under reduced pressure and used for the next step without further purification.

ESI-MS: 118 $[M+H]^+$ $R_f$ (TLC): 0.20 (PE/EtOAc=0/1)

Intermediate 2.3

2-Chloro-N-[1-(3-hydroxyoxetan-3-yl)ethyl]acetamide

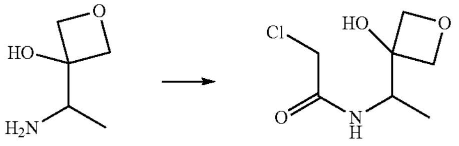

Int. 2.2 Int. 2.3

A mixture of 3-(1-aminoethyl)oxetan-3-ol (INTERMEDIATE 2.2, 32.4 g, 262 mmol) in 500 mL ACN was cooled to 0° C. and TEA (44.2 mL, 315 mmol) was added, followed by dropwise addition of chloroacetyl chloride (23.0 mL, 289 mmol). The mixture was allowed to reach RT and stirred for 3 h. The precipitate was removed by filtration and the filtrate was diluted with 50 mL methanol and concentrated in vacuo. The residue was purified by column chromatography (silica gel; DCM/methanol=97/3 to 85/15).

ESI-MS: 194 $[M+H]^+$ $R_t$ (H PLC): 0.27 min (method E)

The following compound was prepared according to the general procedure (INTERMEDIATE 2.3) described above:

| Int. | Starting material | Structure | ESI-MS | $R_t$ (HPLC) [min] (method) | Reaction conditions |
|---|---|---|---|---|---|
| 2.3.I | 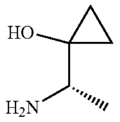 (US2014/66453) | 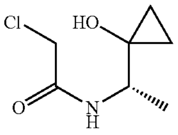 | 178 $[M+H]^+$ | 0.33 (E) | like Intermediate 2.3 |

Intermediate 2.4

9-Methyl-2,5-dioxa-8-azaspiro[3.5]nonan-7-one

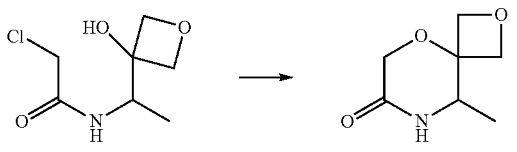

Int. 2.3 Int. 2.4

Under argon at RT, a degassed solution of 2-chloro-N-[1-(3-hydroxyoxetan-3-yl)ethyl]acetamide (INTERMEDIATE 2.3, 1.24 g, 6.02 mmol) in 24.0 mL tert-amyl alcohol was added dropwise to a stirred, degassed solution of potassium tert-butoxide (1.01 g, 9.03 mmol) in 12.0 mL tert-amyl alcohol within 30 min. After completed addition, the reaction mixture was stirred for an additional 1 h at RT. Then, MeOH (5.0 mL) and water (0.5 mL) were added and the mixture was stirred for 20 min at RT. After evaporation of the volatiles, the residue was taken up in in DCM and purified by column chromatography (silica gel; DCM/methanol=99/1 to 90/10).

ESI-MS: 158 $[M+H]^+$ $R_t$ (H PLC): 0.24 min (method E)

The following compound was prepared according to the general procedure (INTERMEDIATE 2.4) described above:

| Int. | Starting material | Structure | ESI-MS | $R_t$ (HPLC) [min] (method) | Reaction conditions |
|---|---|---|---|---|---|
| 2.4.I | 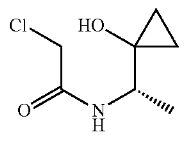 Int.2.3.I | 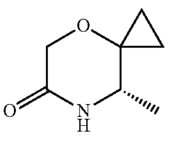 | 142 [M + H]$^+$ | 0.34 (E) | like Intermediate 2.4 |

Intermediate 2.5

9-Methyl-2,5-dioxa-8-azaspiro[3.5]nonane

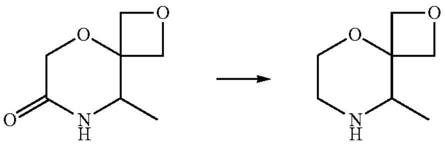

Int. 2.4 Int. 2.5

Under argon, a 1.0 M solution of $LiAlH_4$ in diethyl ether was added dropwise to a degassed mixture of 9-methyl-2,5-dioxa-8-azaspiro[3.5]nonan-7-one (INTERMEDIATE 2.4, 3.80 g, 23.0 mmol) in 90.0 mL THE while the temperature was kept below 0° C. After addition was complete, the reaction mixture was allowed to warm to RT and stirred for an additional 16 h at this temperature.

The reaction mixture was cooled to 0° C., diluted with 60 mL anhydrous diethylether and treated successively with 1.33 mL water, 1.33 mL 4N aqueous NaOH solution and finally with 4 mL water. The reaction mixture was allowed to reach room temperature and stirred for an additional 15 min. The mixture was dried over sodium sulfate, then filtered and the solvent evaporated in vacuo. The remaining residue was coevaporated with ACN twice to remove residual water.

ESI-MS: 144 [M+H]$^+$ $R_t$ (H PLC): 0.17 min (method E)

The following compound was prepared according to the general procedure (INTERMEDIATE 2.5) described above:

| Int. | Starting material | Structure | ESI-MS | $R_t$ (HPLC) [min] (method) | Reaction con-ditions |
|---|---|---|---|---|---|
| 2.5.I | 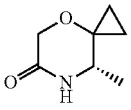 2.4.I | 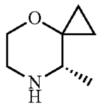 | 128 [M + H]$^+$ | 0.14 (E) | like Int. 2.5 |

Intermediate 2.6.I

8-(5-Bromo-2-nitropyridin-3-yl)-9-methyl-2,5-dioxa-8-azaspiro[3.5]nonane

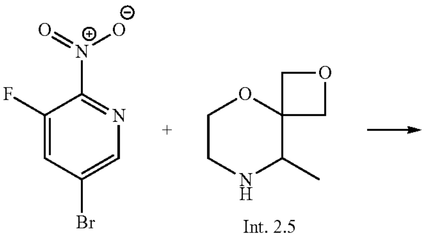

Int. 2.5

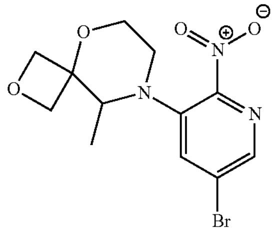

Int. 2.6.I

To a mixture of 5-bromo-3-fluoro-2-nitropyridine (1.00 g, 4.53 mmol) in 20.0 mL ACN was added $K_2CO_3$ (1.88 g, 13.58 mmol) and 9-methyl-2,5-dioxa-8-azaspiro[3.5]-nonane (INTERMEDIATE 2.5, 777 mg, 5.43 mmol). The mixture was heated to 60° C. and stirred for 16.5 h. The reaction was diluted with EtOAc and water was added. The phases were separated, and the aqueous phase was extracted with EtOAc. The combined organic phases were dried over $Na_2SO_4$ and concentrated.

ESI-MS: 344/346 [M+H]$^+$ $R_t$ (H PLC): 0.85 min (method B)

The following compounds were prepared according to the general procedure (INTERMEDIATE 2.6.1) as described above:

| Int. | Starting materials | | Structure | ESI-MS | $R_t$ (HPLC) [min] (method) | Reaction conditions |
|---|---|---|---|---|---|---|
| 2.6.II | 5-chloro-3-fluoro-2-nitropyridine | Int. 2.5 | 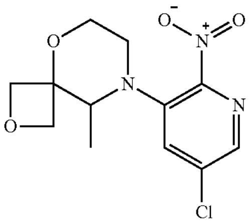 [SMILES: CC1N(c2cc(Cl)cnc2[N+](=O)[O-])CCOC12COC2] | 300/302 $[M + H]^+$ | 0.51 (A) | solvent: ACN, $K_2CO_3$: 3.0 eq, 60° C., 2 h |
| 2.6.III | 5-chloro-3-fluoro-2-nitropyridine | 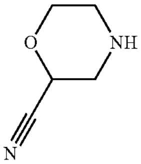 | 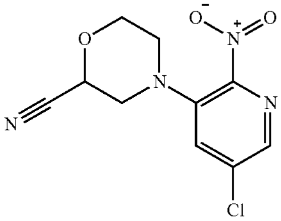 [SMILES: N#CC1CN(c2cc(Cl)cnc2[N+](=O)[O-])CCO1] | 269 $[M + H]^+$ | 0.71 (E) | solvent: DMF, DIPEA: 10 eq, RT, 2 days |
| 2.6.IV | 5-chloro-3-fluoro-2-nitropyridine | 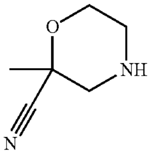 | 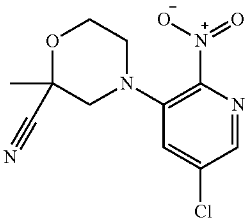 [SMILES: CC1(C#N)CN(c2cc(Cl)cnc2[N+](=O)[O-])CCO1] | 283 $[M + H]^+$ | 0.79 (E) | DIPEA: 3.0 eq solvent: DMF, RT, 2 days |
| 2.6.V | 5-chloro-3-fluoro-2-nitropyridine | 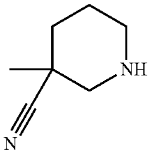 | 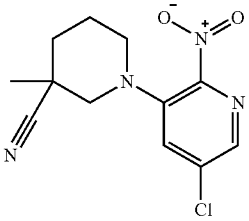 [SMILES: CC1(C#N)CCCN(c2cc(Cl)cnc2[N+](=O)[O-])C1] | 281/283 $[M + H]^+$ | 0.90 (E) | DIPEA: 3.0 eq solvent: DMF, RT, overnight |
| 2.6.VI | 5-chloro-3-fluoro-2-nitropyridine | 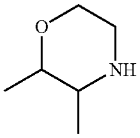 | 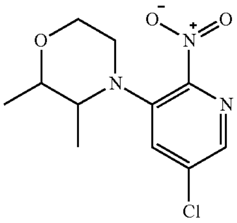 [SMILES: CC1OCCN(c2cc(Cl)cnc2[N+](=O)[O-])C1C] | 272/274 $[M + H]^+$ | 1.01 (C) | solvent: ACN, $K_2CO_3$: 3.0 eq, 60° C., 1 h Purification: HPLC: Sunfire $ACN/H_2O/TFA$ |
| 2.6.VII | 5-chloro-3-fluoro-2-nitropyridine | 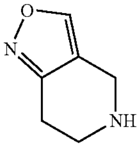 | 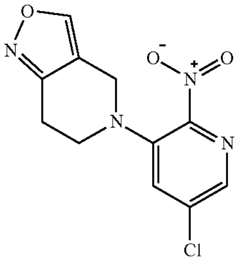 [SMILES: O=[N+]([O-])c1ncc(Cl)cc1N1CCc2nocc2C1] | 281/283 $[M + H]^+$ | 0.50 (A) | solvent: ACN, $K_2CO_3$: 1.5 eq, 60° C., 16 h |

-continued

| Int. | Starting materials | | Structure | ESI-MS | $R_t$ (HPLC) [min] (method) | Reaction conditions |
|---|---|---|---|---|---|---|
| 2.6.VIII | 5-bromo-3-fluoro-2-nitropyridine | morpholine | 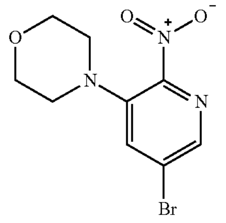 [SMILES: O=[N+]([O-])c1ncc(Br)cc1N1CCOCC1] | 288/290 $[M + H]^+$ | 0.94 (C) | solvent: ACN, no $K_2CO_3$, RT, 30 min |
| 2.6.IX | 5-bromo-3-fluoro-2-nitropyridine | 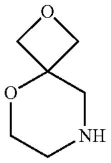 | 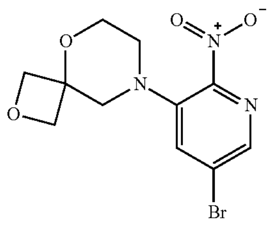 [SMILES: O=[N+]([O-])c1ncc(Br)cc1N1CCOC2(COC2)C1] | 330/332 $[M + H]^+$ | 0.48 (A) | solvent: ACN, $K_2CO_3$: 1.5 eq, 60° C., 1.5 h |
| 2.6.X | 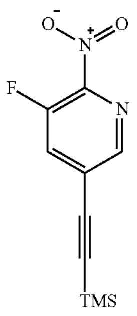 [SMILES: C[Si](C)(C)C#Cc1cnc([N+](=O)[O-])c(F)c1] Int 2.7.III | 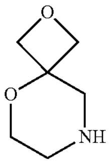 | 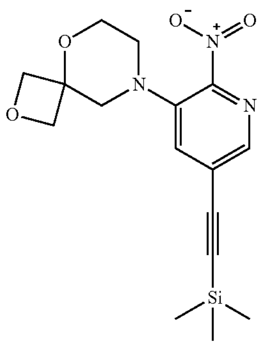 [SMILES: C[Si](C)(C)C#Cc1cnc([N+](=O)[O-])c(N2CCOC3(COC3)C2)c1] | 348 $[M + H]^+$ | 0.70 (A) | solvent: ACN, $K_2CO_3$: 1.5 eq, 60° C., 1.5 h |
| 2.6.XI | 5-bromo-3-fluoro-2-nitropyridine | 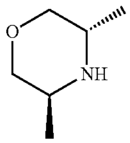 | 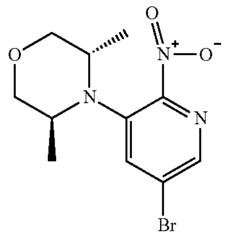 [SMILES: C[C@H]1COC[C@H](C)N1c1cc(Br)cnc1[N+](=O)[O-]] | 316/318 $[M + H]^+$ | 1.02 (C) | TEA: 5.0 eq solvent: ACN, 2 days, 80° C. |
| 2.6.XII | 5-chloro-3-fluoro-2-nitropyridine | 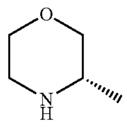 | 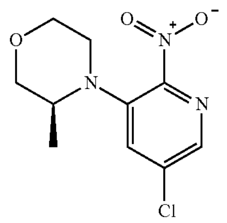 [SMILES: C[C@H]1COCCN1c1cc(Cl)cnc1[N+](=O)[O-]] | 258/260 $[M + H]^+$ | 0.56 (A) | solvent: ACN, $K_2CO_3$: 1.5 eq, 60° C., 1.5 h |
| 2.6.XIII | 5-bromo-3-fluoro-2-nitropyridine | 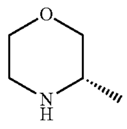 | 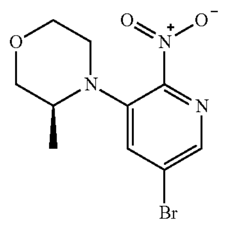 [SMILES: C[C@H]1COCCN1c1cc(Br)cnc1[N+](=O)[O-]] | 302/304 $[M + H]^+$ | 0.57 (A) | solvent: ACN, $K_2CO_3$: 1.5 eq, 60° C., 1.5 h |

-continued

| Int. | Starting materials | | Structure | ESI-MS | $R_t$ (HPLC) [min] (method) | Reaction conditions |
|---|---|---|---|---|---|---|
| 2.6.XIV | Int. 2.7.III | 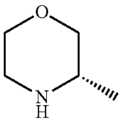 | 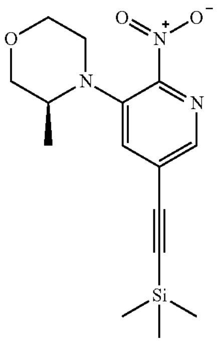 [SMILES: C[C@H]1COCCN1c1cc(C#C[Si](C)(C)C)cnc1[N+](=O)[O-]] | 320 [M + H]$^+$ | 1.21 (C) | solvent: ACN, DIPEA: 2.0 eq 90° C., 30 min |
| 2.6.XV | 5-bromo-3-fluoro-2-nitropyridine | 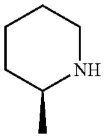 | 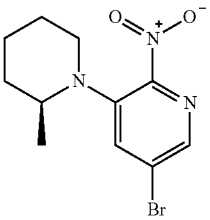 [SMILES: C[C@H]1CCCCN1c1cc(Br)cnc1[N+](=O)[O-]] | 300/302 [M + H]$^+$ | 0.72 (C) | solvent: ACN, $K_2CO_3$: 1.5 eq, 60° C., 1.5 h |
| 2.6.XVI | 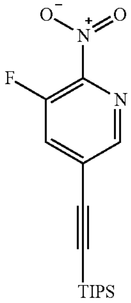<br>Int.2.7.V | 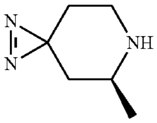<br>Int.12.2 | 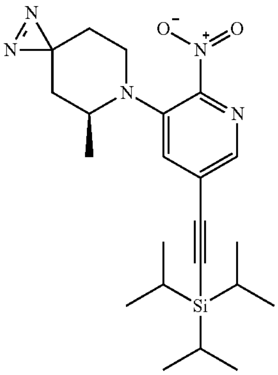 [SMILES: CC(C)[Si](C#Cc1cnc([N+](=O)[O-])c(N2CCC3(C[C@@H]2C)N=N3)c1)(C(C)C)C(C)C] | 428 [M + H]$^+$ | 1.39 (C) | solvent: ACN, TEA: 4.0 eq, 70° C., 5 h, Purification RP-HPLC, ACN/$H_2O$/TFA |
| 2.6.XVII | 5-chloro-3-fluoro-2-nitropyridine | 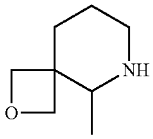<br>Int.13.6 | 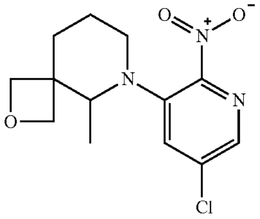 [SMILES: CC1N(c2cc(Cl)cnc2[N+](=O)[O-])CCCC12COC2] | 298/300 [M + H]$^+$ | 0.57 (A) | solvent: ACN, $K_2CO_3$: 3.0 eq, 60° C., 1.5 h |
| 2.6.XVIII | 5-bromo-3-fluoro-2-nitropyridine | 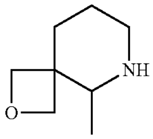<br>Int.13.6 | 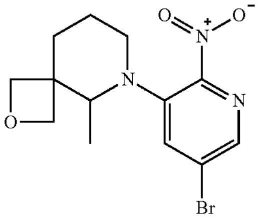 | 342/344 [M + H]$^+$ | 0.60 (A) | solvent: ACN, $K_2CO_3$: 3.0 eq, 60° C., 1.5 h |

-continued

| Int. | Starting materials | | Structure | ESI-MS | $R_t$ (HPLC) [min] (method) | Reaction conditions |
|---|---|---|---|---|---|---|
| 2.6.XIX | 5-bromo-3-fluoro-2-nitropyridine | 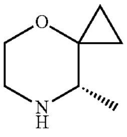 Int.2.5.I | 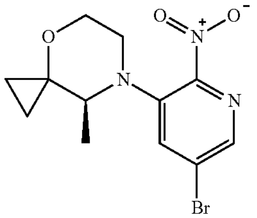 [SMILES: C[C@@H]1N(c2cc(Br)cnc2[N+](=O)[O-])CCOC12CC2] | 328/330 [M + H]+ | 0.63 (A) | solvent: ACN, $K_2CO_3$: 3.0 eq, 60° C., 1.5 h |

Intermediate 2.7.I

9-Methyl-8-(2-nitro-5-{2-[tris(propan-2-yl)silyl]ethynyl}pyridin-3-yl)-2,5-dioxa-8-azaspiro[3.5]nonane

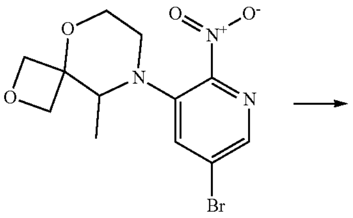

Int. 2.6.I

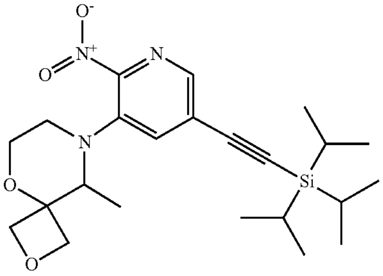

Int. 2.7.I

To a degassed solution of 8-(5-bromo-2-nitropyridin-3-yl)-9-methyl-2,5-dioxa-8-azaspiro[3.5]nonane (INTERMEDIATE 2.6.I, 584 mg, 1.70 mmol) in 6.80 mL THE under argon was added DIPEA (2.31 mL, 12.8 mmol), followed by (triisopropylsilyl)-acetylene (0.780 mL, 3.40 mmol), $PdCl_2(PPh_3)_2$ (60 mg, 0.085 mmol) and copper (I) iodide (49 mg, 0.25 mmol). The mixture was stirred at 80° C. for 1 h. The reaction mixture was diluted with ACN, filtered and concentrated under reduced pressure. The residue was purified by column chromatography (silica gel; CH/EtOAc=50/50 to 60/40).

ESI-MS: 446 $[M+H]^+$ $R_t$ (HPLC): 0.66 min (method G)

The following compounds were prepared according to the general procedure (INTERMEDIATE 2.7.1) described above:

| Int. | Starting materials | | Structure | ESI-MS | $R_t$ (HPLC) [min] (method) | Reaction conditions |
|---|---|---|---|---|---|---|
| 2.7.II | 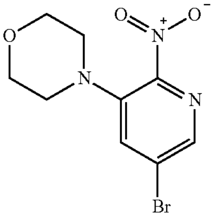 [SMILES: O=[N+]([O-])c1ncc(Br)cc1N1CCOCC1] Int.2.6.VIII | 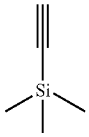 1.2 eq | 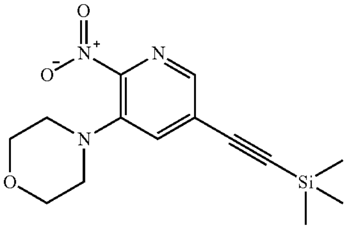 [SMILES: C[Si](C)(C)C#Cc1cnc([N+](=O)[O-])c(N2CCOCC2)c1] | 306 [M + H]+ | 1.91 (C) | RT, overnight, Purification: RP-HPLC, ACN/$H_2O$/TFA |

-continued

| Int. | Starting materials | | Structure | ESI-MS | $R_t$ (HPLC) [min] (method) | Reaction conditions |
|---|---|---|---|---|---|---|
| 2.7.III | 5-bromo-3-fluoro-2-nitropyridine | 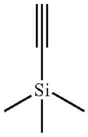 1.2 eq | 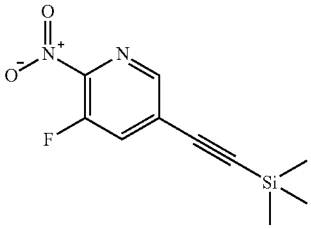 [SMILES: C[Si](C)(C)C#Cc1cnc([N+](=O)[O-])c(F)c1] | 239 $[M + H]^+$ | 1.16 (C) | RT, 1 h, Purification: RP-HPLC, ACN/$H_2O$/TFA |
| 2.7.IV | 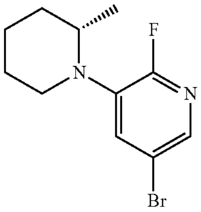 Int.7.1.II | 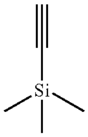 1.2 eq | 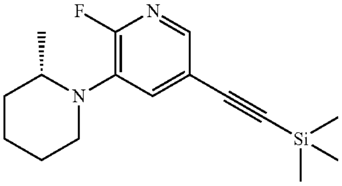 [SMILES: C[C@H]1CCCCN1c1cc(C#C[Si](C)(C)C)cnc1F] | 291 $[M + H]^+$ | 0.88 (A) | 80° C., 2 h, Purification: RP-HPLC, ACN/$H_2O$/TFA |
| 2.7.V | 5-bromo-3-fluoro-2-nitropyridine | 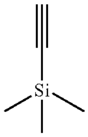 | 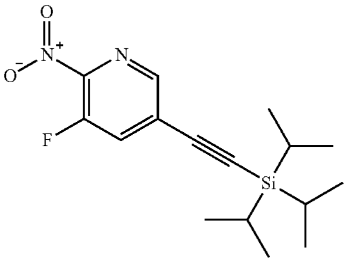 [SMILES: CC(C)[Si](C#Cc1cnc([N+](=O)[O-])c(F)c1)(C(C)C)C(C)C] | 323 $[M + H]^+$ | 1.33 (A) | RT, 3 h Purification: silica gel, CH/EtOAc = 99/1-90/10 |
| 2.7.VI | 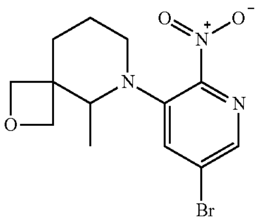 Int.2.6.XVIII | 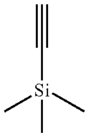 2.0 eq | 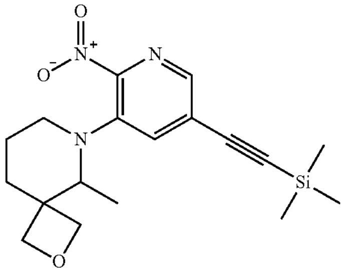 [SMILES: CC1N(c2cc(C#C[Si](C)(C)C)cnc2[N+](=O)[O-])CCCC12COC2] | 360 $[M + H]^+$ | 0.79 (A) | 80° C., 1 h, Purification: RP-HPLC, ACN/$H_2O$/TFA |

Intermediate 3.1.I (a)

(a): (2S,4S)-4-({5-Bromo-3-[(9S)-9-methyl-2,5-dioxa-8-azaspiro[3.5]nonan-8-yl]pyridin-2-yl}oxy)-1-[4-(difluoromethyl)-8-oxa-3,5-diazatricyclo [7.4.0.02,7]-trideca-1(9),2(7),3,5,10,12-hexaen-6-yl] pyrrolidine-2-carboxylic acid

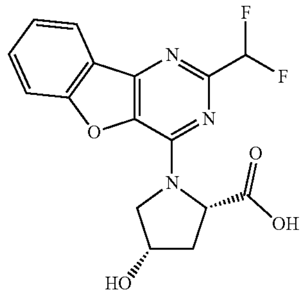

Int. 1.3.II

+

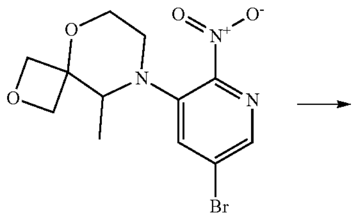

Int. 2.6.I

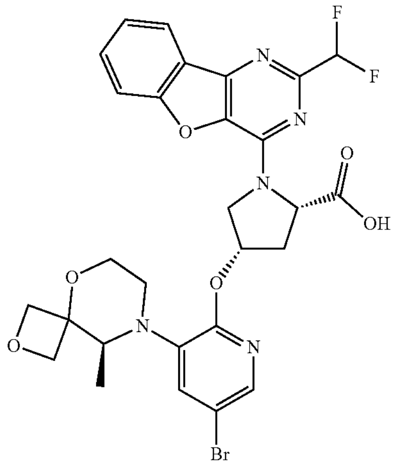

+

Int. 3.1.I (a)

-continued

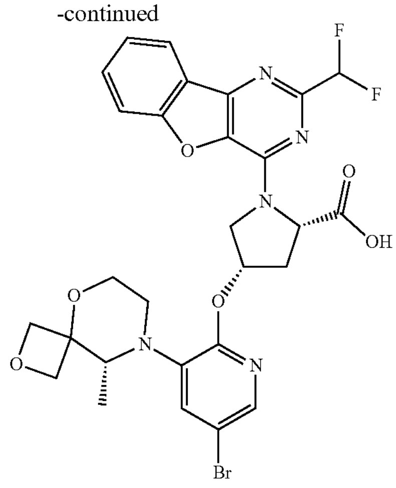

Int. 3.1.I (b)

To a mixture of (2S,4S)-1-[4-(difluoromethyl)-8-oxa-3,5-diazatricyclo[7.4.0.$0^{2,7}$]-trideca-1(9),2(7),3,5,10,12-hexaen-6-yl]-4-hydroxypyrrolidine-2-carboxylic acid (INTERMEDIATE 1.3.11, 1.00 g, 2.72 mmol) and 8-(5-bromo-2-nitropyridin-3-yl)-9-methyl-2,5-dioxa-8-azaspiro[3.5] nonane (INTERMEDIATE 2.6.I, 2.00 g, 5.44 mmol) in 20 mL DMA at RT was added NaH (326 mg, 8.16 mmol).

The mixture was stirred at RT overnight. Water was added and the mixture was acidified with TFA.

The precipitate was collected by filtration and dried in vacuo. The crude product was purified by RP-HPLC (Sunfire C18, ACN/$H_2O$/TFA) to provide two diastereomers (a) and (b). Diastereomer (a) was carried on to the next step.

ESI-MS: 646/648 $[M+H]^+$ $R_t$ (HPLC): 1.03 min (method C)—diastereomer (a)

1.08 min (method C)—diastereomer (b)

The following compound was prepared according to the general procedure (INTERMEDIATE 3.1.I) described above:

| Int. | Starting materials | Structure | ESI-MS | $R_t$ (HPLC) [min] (method) | Reaction conditions |
|---|---|---|---|---|---|
| 3.1.II | Int. 1.3.I 1.0 eq; Int. 2.6.XIII 1.5 eq | 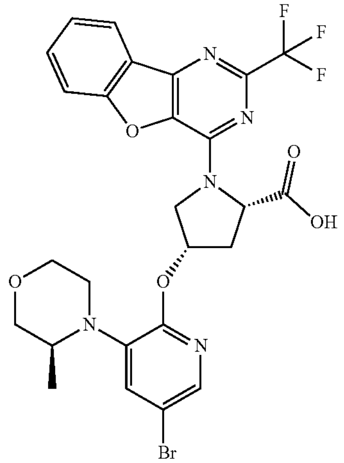 [SMILES: C[C@H]1COCCN1c1cc(Br)cnc1O[C@H]1C[C@@H](C(=O)O)N(c2nc(C(F)(F)F)nc3c2oc2ccccc23)C1] | 622/624 $[M + H]^+$ | 1.163 (B) | solvent: DMA, NaH: 3.0 eq 80° C. 10 min, RT overnight |

Intermediate 3.2 tert-Butyl (2S,4S)-4-({5-bromo-3-[(9S)-9-methyl-2,5-dioxa-8-azaspiro[3.5]nonan-8-yl]pyridin-2-yl}oxy)-1-[4-(difluoromethyl)-8-oxa-3,5-diazatricyclo[7.4.0.0$^{2,7}$]-trideca-1(9),2(7),3,5,10,12-hexaen-6-yl]pyrrolidine-2-carboxylate

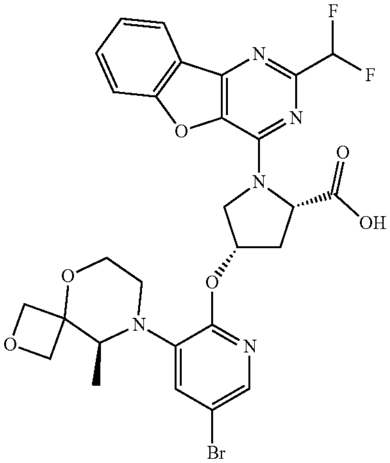

+

Int. 3.1.I (a)

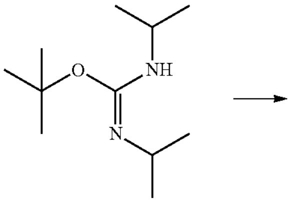

-continued

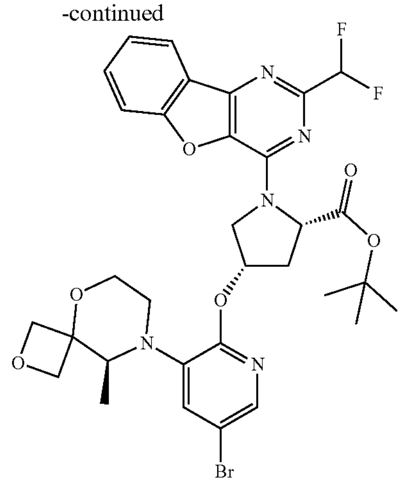

Int. 3.2

To (2S,4S)-4-({5-bromo-3-[(9S)-9-methyl-2,5-dioxa-8-azaspiro[3.5]nonan-8-yl]pyridin-2-yl}oxy)-1-[4-(difluoromethyl)-8-oxa-3,5-diazatricyclo[7.4.0.0$^{2,7}$]trideca-1(9),2(7),3,5,10,12-hexaen-6-yl]pyrrolidine-2-carboxylic acid (INTERMEDIATE 3.1.I(a), 110 mg, 0.170 mmol) in 2.30 mL THE was added 2-tert-butyl-1,3-diisopropylisourea (162 μL, 0.68 mmol). The reaction mixture was stirred at 70° C. for 1 h in a microwave oven. The precipitate was filtered and the filtrate was concentrated under reduced pressure. The residue was purified by column chromatography (silica gel; CH/EtOAc=93/7 to 60/40).

ESI-MS: 702/704 $[M+H]^+$ $R^t$ (H PLC): 0.87 min (method A)

Intermediate 3.3 tert-Butyl (2S,4S)-1-[4-(difluoromethyl)-8-oxa-3,5-diazatricyclo[7.4.0.$0^{2,7}$]-trideca-1(9),2(7),3,5,10,12-hexaen-6-yl]-4-({3-[(9S)-9-methyl-2,5-dioxa-8-azaspiro[3.5]nonan-8-yl]-5-(4,4,5,5-tetramethyl-1,3,2-dioxaborolan-2-yl)pyridin-2-yl}oxy)pyrrolidine-2-carboxylate

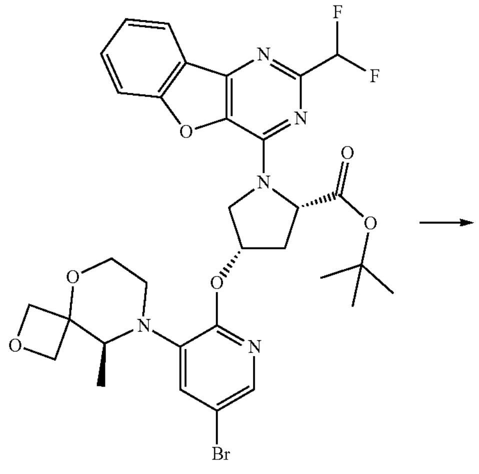

Int. 3.2

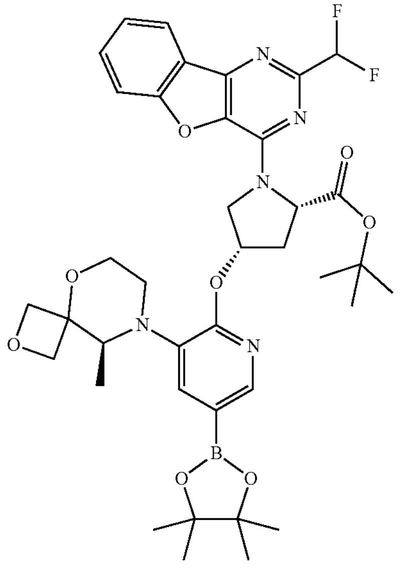

Int. 3.3

To tert-butyl (2S,4S)-4-({5-bromo-3-[(9S)-9-methyl-2,5-dioxa-8-azaspiro[3.5]nonan-8-yl]pyridin-2-yl}oxy)-1-[4-(difluoromethyl)-8-oxa-3,5-diazatricyclo[7.4.0.$0^{2}$,]trideca-1(9),2(7),3,5,10,12-hexaen-6-yl]pyrrolidine-2-carboxylate (INTERMEDIATE 3.2, 132 mg, 0.150 mmol) in 2.00 mL dioxane under argon was added bis(pinacolato)-diboron (113 mg, 0.445 mmol), Pd(dppf)$Cl_2$ (12.0 mg, 0.0160 mmol) and potassium acetate (58.0 mg, 0.591 mmol). The reaction mixture was stirred at 90° C. overnight. The reaction mixture was diluted with water and extracted with DCM/methanol. The organic phases were treated using an ISOLUTE® phase separator and concentrated under reduced pressure.

ESI-MS: 750 $[M+H]^+$ $R_t$ (HPLC): 0.90 min (method A)

Intermediate 3.4.I tert-Butyl(2S,4S)-1-[4-(difluoromethyl)-8-oxa-3,5-diazatricyclo[7.4.0.$0^{2,7}$]trideca-1(9),2(7),3,5,10,12-hexaen-6-yl]-4-({N,N-dimethyl-5-[(9S)-9-methyl-2,5-dioxa-8-azaspiro[3.5]nonan-8-yl]-[3,4'-bipyridin]-2'-yl}oxy)pyrrolidine-2-carboxylate

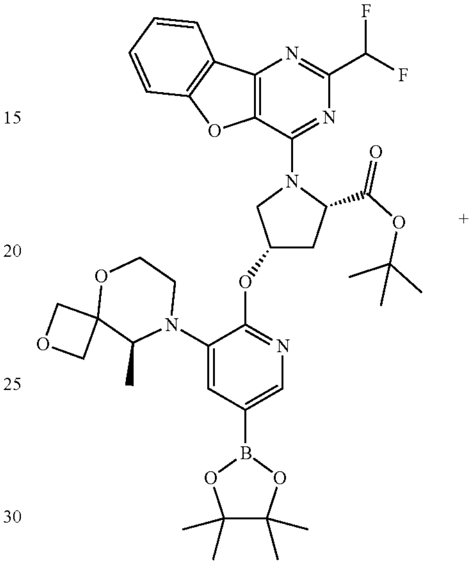

Int. 3.3

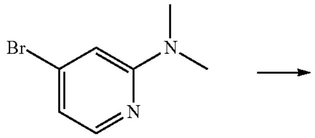

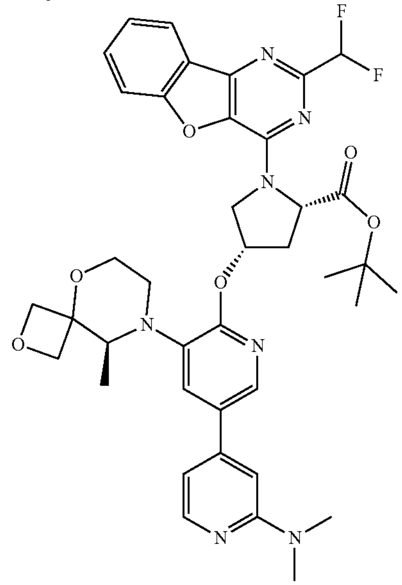

Int. 3.4.I

To tert-butyl (2S,4S)-1-[4-(difluoromethyl)-8-oxa-3,5-diazatricyclo[7.4.0.$0^{2,7}$]trideca-1(9),2(7),3,5,10,12-hexaen-6-yl]-4-({3-[(9S)-9-methyl-2,5-dioxa-8-azaspiro[3.5]nonan-8-yl]-5-(4,4,5,5-tetramethyl-1,3,2-dioxaborolan-2-yl)

pyridin-2-yl}oxy)pyrrolidine-2-carboxylate (INTERMEDIATE 3.3, 105 mg, 0.0700 mmol) in 2.00 mL dioxane under argon was added 4-bromo-N,N-dimethylpyridin-2-amine (22.0 mg, 0.109 mmol), $Pd(PPh_3)_4$ (9.7 mg, 0.0080 mmol), Xphos $3^{rd}$ gen (6.0 mg, 0.0070 mmol) and sodium carbonate solution 2 mol/L (105 μL, 0.210 mmol). The reaction mixture was stirred at 100° C. for 1.5 h. The reaction mixture was diluted with ACN/water, filtered and purified by RP-HPLC (Xbridge-C18, ACN/$H_2O$/0.1% $NH_4OH$).

ESI-MS: 744 $[M+H]^+$ $R_t$ (H PLC): 0.64 min (method A)

The following compounds were prepared according to the general procedure (INTERMEDIATE 3.4.1) described above:

| Int. | Starting materials | | Structure | ESI-MS | $R_t$ (HPLC) [min] (method) | Reaction conditions |
|---|---|---|---|---|---|---|
| 3.4.II | Int.3.3 | Int.4.1 | 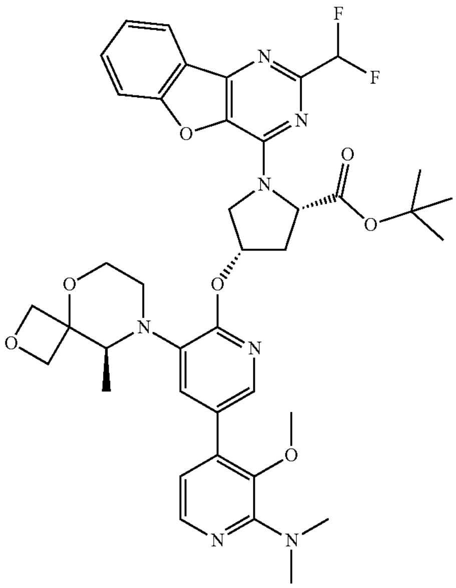 [SMILES: COc1c(-c2cnc(O[C@H]3C[C@@H](C(=O)OC(C)(C)C)N(c4nc(C(F)F)nc5c4oc4ccccc45)C3)c(N3CCOC4(COC4)[C@@H]3C)c2)ccnc1N(C)C] | 774 $[M + H]^+$ | 0.65 (A) | solvent: dioxane, 100° C., 3 h |
| 3.4.III | Int.3.3 | Int.5.1 | 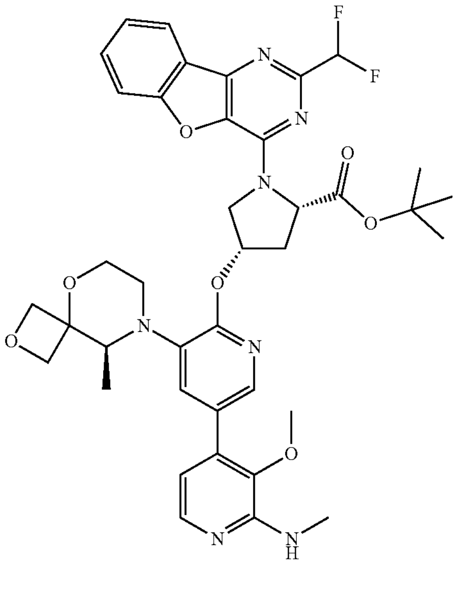 [SMILES: CNc1nccc(-c2cnc(O[C@H]3C[C@@H](C(=O)OC(C)(C)C)N(c4nc(C(F)F)nc5c4oc4ccccc45)C3)c(N3CCOC4(COC4)[C@@H]3C)c2)c1OC] | 760 $[M + H]^+$ | 0.62 (A) | solvent: dioxane, 70° C., 30 min |

-continued

| Int. | Starting materials | | Structure | ESI-MS | $R_t$ (HPLC) [min] (method) | Reaction conditions |
|---|---|---|---|---|---|---|
| 3.4.IV | Int.3.3 | 5.1 | 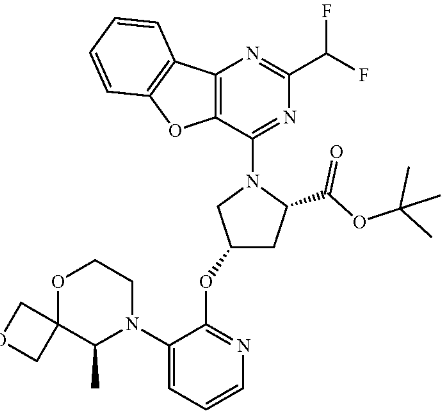 | 624 [M + H]$^+$ | 0.87 (F) | solvent: dioxane, 5 eq. $Na_2CO_3$ 0.2 eq. Xphos 0.24 eq $Pd(PPh_3)_4$, 100° C., 5.5 h, 90° C., 3.5 h |

Intermediate 4.1

4-Bromo-3-methoxy-N,N-dimethylpyridin-2-amine

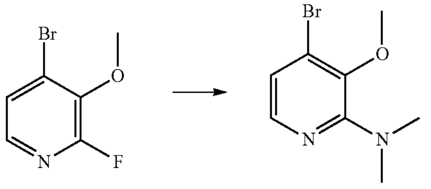

Int. 4.1

To 4-bromo-2-fluoro-3-methoxypyridine (200 mg, 0.97 mmol) in 3.00 mL THE was added dimethylamine (3.64 mL, 7.28 mmol). The reaction mixture was stirred at 50° C. overnight and then concentrated under reduced pressure to afford the title compound.

ESI-MS: 231/233 [M+H]$^+$ $R_t$ (HPLC): 0.30 min (method A)

Intermediate 5.1

4-Bromo-3-methoxy-N-methylpyridin-2-amine

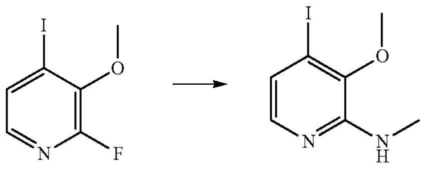

Int. 5.1

To 2-fluoro-4-iodo-3-methoxypyridine (500 mg, 1.98 mmol) in 8.00 mLTHF was added a 2.0 M solution of methylamine in THE (7.90 mL, 15.8 mmol). The reaction mixture was stirred at 55° C. for 48 h, then concentrated under reduced pressure.

ESI-MS: 265 [M+H]$^+$ $R_t$ (HPLC): 0.26 min (method A)

Intermediate 6.1

8-(2,5-difluoropyridin-3-yl)-9-methyl-2,5-dioxa-8-azaspiro[3.5]nonane

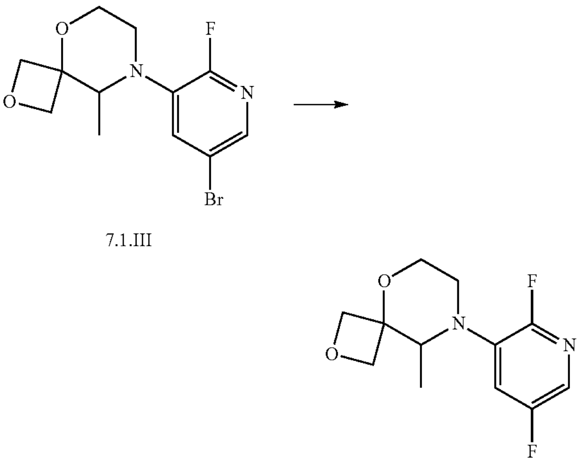

7.1.III

Int. 6.1

Under an argon atmosphere, a degassed solution of 8-(5-bromo-2-fluoropyridin-3-yl)-9-methyl-2,5-dioxa-8-azaspiro[3.5]nonane (INTERMEDIATE 7.1.III, 668 mg; 2.00 mmol) in THE (13.4 mL) was cooled to 0° C. Then, a solution of isopropylmagnesium chloride lithium chloride complex in THE (1.92 mL; 2.5 mmol) was added dropwise. The reaction mixture was allowed to reach room temperature and stirred for 2.5 h. Additional isopropylmagnesium chloride lithium chloride complex in THE (0.45 mL; 0.59 mmol) was added and stirring was continued for an additional 1.5 h. The mixture was concentrated in vacuo, then taken up in DCM (5.00 mL) and cooled to −78° C. A solution of N-fluorobenzenesulfonamide (863 mg, 2.60 mmol) in a mixture of DCM (7.50 mL) and perfluorodecalin (2.50 mL) was added dropwise under stirring at −78° C. After completed addition, the reaction mixture was warmed to 0° C., stirred for 30 min, then warmed to RT and stirred for an additional 1 h. The reaction mixture was poured into saturated $NH_4Cl$ solution and stirred for 5 min. The mixture was filtered through celite and after phase separation, the aqueous phase was extracted with DCM and the combined organic phase was dried with sodium sulfate, filtered and evaporated. The residue was dissolved in $ACN/H_2O$, filtered and purified by RP-HPLC.

ESI-MS: 257 $[M+H]^+$ $R_t$ (HPLC): 0.45 min (method A)

Intermediate 7.1.I

5-Chloro-2-fluoro-3-{4H,5H,6H,7H-[1,2]oxazolo[4,3-c]pyridin-5-yl}pyridine

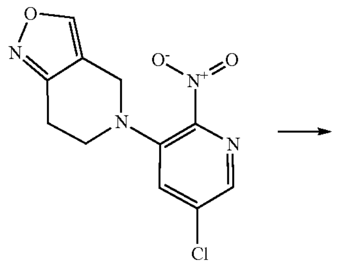

Int. 2.6.VII

-continued

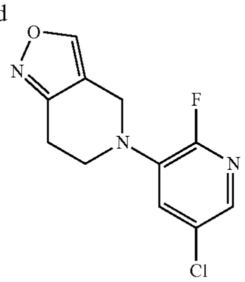

Int. 7.1.I

To 5-chloro-2-nitro-3-{4H,5H,6H,7H-[1,2]oxazolo[4,3-c]pyridin-5-yl}pyridine (INTERMEDIATE 2.6.VII, 210 mg, 0.750 mmol) in 2.00 mL DMF was added a 1.0 M solution of TBAF in THE (1.50 mL, 1.50 mmol). The reaction mixture was stirred for 30 min at RT, then for 3 h at 50° C. Again, TBAF was added (1.50 mL, 1.50 mmol) and the reaction mixture was stirred for 5 h at 50° C. ACN/water was added to the reaction mixture, the precipitate was collected by filtration and purified by RP-HPLC (Xbridge C18, $ACN/H_2O/TFA$).

ESI-MS: 254/256 $[M+H]^+$ $R_t$ (H PLC): 0.77 min (method E)

The following compounds were prepared according to the general procedure (INTERMEDIATE 7.1.I) described above:

| Int. | Starting material | Structure | ESI-MS | $R_t$ (HPLC) [min] (method) | Reaction conditions |
|---|---|---|---|---|---|
| 7.1.II | Int.2.6.XV | 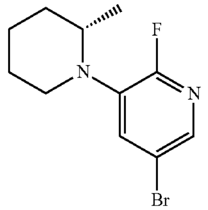 | 273/275 $[M+H]^+$ | 0.72 (A) | 3 eq. TBAF, RT 16 h; 3 eq. TBAF, 50° C., 20 h |
| 7.1.III | Int.2.6.I | 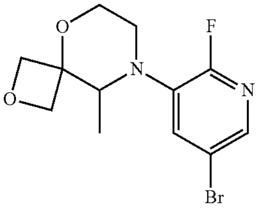 [SMILES: CC1N(c2cc(Br)cnc2F)CCOC12COC2] | 317/319 $[M+H]^+$ | 0.55 (A) | 2 eq. TBAF, DMF, 50° C., 3 h |

INTERMEDIATE 8.1

(2S,4S)-4-{[5-ethynyl-3-(morpholin-4-yl)pyridin-2-yl]oxy}pyrrolidine-2-carboxylic acid

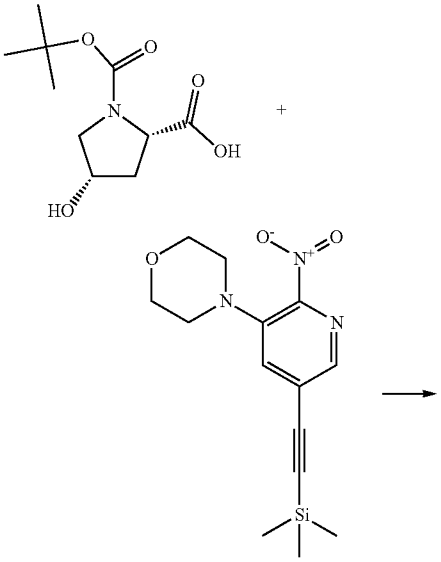

Int. 2.7.II

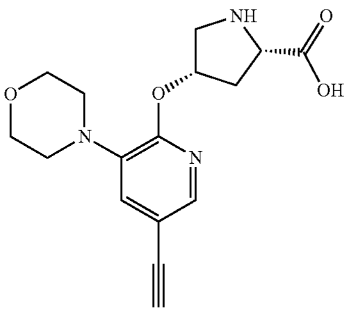

Int. 8.1

To (2S,4S)-1-(tert-butoxycarbonyl)-4-hydroxypyrrolidine-2-carboxylic acid (202 mg, 0.83 mmol) in 3.00 mL DMA was added NaH (99.8 mg, 2.50 mmol). This mixture was stirred at RT for 30 min, before a solution of 4-{2-nitro-5-[2-(trimethylsilyl)ethynyl]-pyridin-3-yl}morpholine (INTERMEDIATE 2.7.II, 127 mg, 0.42 mmol) in 2.00 mL DMA was added. After stirring the reaction mixture at RT for 2 h, it was diluted with ACN and acidified with TFA. The precipitate was collected by filtration and purified by RP-HPLC (Sunfire, ACN/$H_2O$/TFA). The residue was diluted in 10.0 mL DCM and 1.00 ml TFA was added. The reaction mixture was stirred overnight at RT and concentrated to afford the title compound.

ESI-MS: 318 $[M+H]^+$ $R_t$ (H PLC): 0.67 min (method C)

Intermediate 9.1(a)

(2S,4S)-1-[(tert-Butoxy)carbonyl]-4-({5-ethynyl-3-[(9S)-9-methyl-2,5-dioxa-8-azaspiro[3.5]nonan-8-yl]pyridin-2-yl}oxy)pyrrolidine-2-carboxylic acid

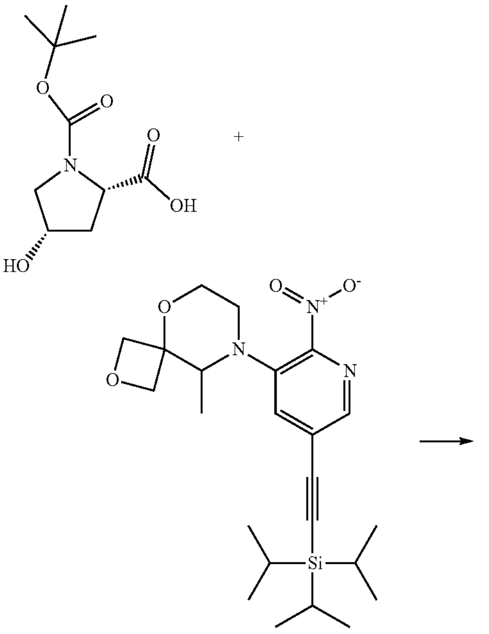

Int. 2.7.I

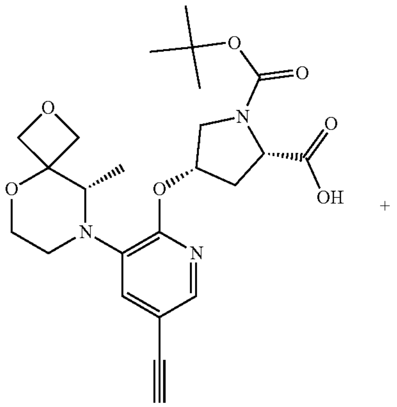

Int. 9.1 (a)

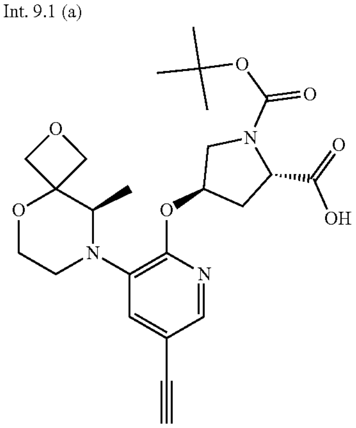

Int. 9.1 (b)

To a mixture of (2S,4S)-1-[(tert-butoxy)carbonyl]-4-hydroxypyrrolidine-2-carboxylic acid (800 mg, 3.30 mmol) and 9-methyl-8-(2-nitro-5-{2-[tris(propan-2-yl)silyl]ethynyl}pyridin-3-yl)-2,5-dioxa-8-azaspiro[3.5]nonane (INTERMEDIATE 2.7.I, 1.55 g, 3.30 mmol) in 31.0 mL NMP was added NaH (660 mg, 16.5 mmol). The reaction mixture was stirred for 1 h 20 min at RT. The reaction mixture was quenched with water, acidified with 1N HCl, filtered and extracted with EtOAc thrice. The organic phases were combined and dried over sodium sulfate, filtered and evaporated. The crude product was dissolved in 10 mL THF, 2 mL TBAF solution (1.0 M in THF) was added and the reaction mixture was stirred for 1 h at 50° C. The reaction mixture was diluted with EtOAc and extracted with sat. $NH_4Cl$ solution twice. The organic phases were combined and dried over sodium sulfate, filtered and evaporated. The residue was purified by HPLC (Xbridge, ACN/$H_2O$/TFA).

ESI-MS: 474 $[M+H]^+$ $R_t$ (H PLC): 0.63 min (method A)—diastereomer (a)

0.66 min (method A)—diastereomer (b)

Intermediate 9.2

(2S,4S)-4-({5-Ethynyl-3-[(9S)-9-methyl-2,5-dioxa-8-azaspiro[3.5]nonan-8-yl]pyridin-2-yl}oxy)pyrrolidine-2-carboxylic acid

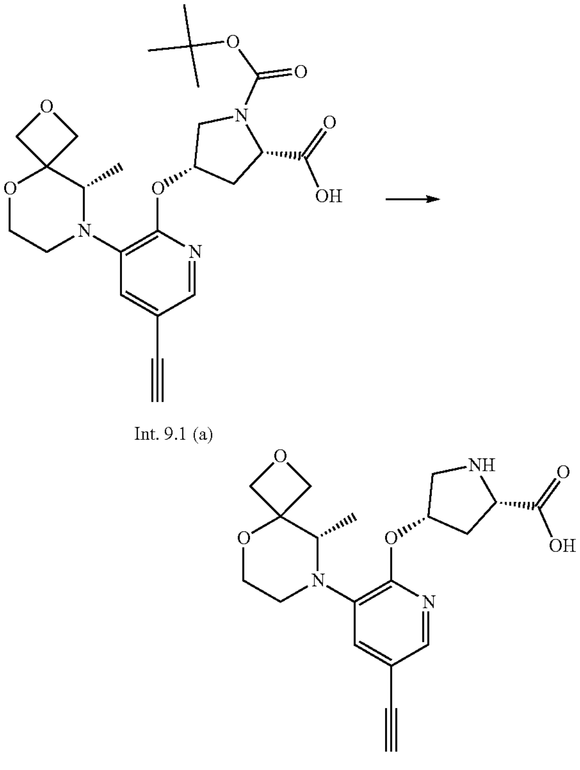

Int. 9.1 (a)

Int. 9.2

To (2S,4S)-1-[(tert-butoxy)carbonyl]-4-({5-ethynyl-3-[(9S)-9-methyl-2,5-dioxa-8-azaspiro[3.5]nonan-8-yl]pyridin-2-yl}oxy)pyrrolidine-2-carboxylic acid (INTERMEDIATE 9.1 (a), 40 mg, 0.080 mmol) in 3.00 mL ACN was added TosOH (35 mg, 0.18 mmol). The reaction mixture was stirred at RT for 48 h. The reaction mixture was evaporated and used without further purification for the next step.

ESI-MS: 374 $[M+H]^+$ $R_t$ (H PLC): 0.36 min (method A)

Intermediate 10.1

4-(Difluoromethyl)-2-methoxybenzonitrile

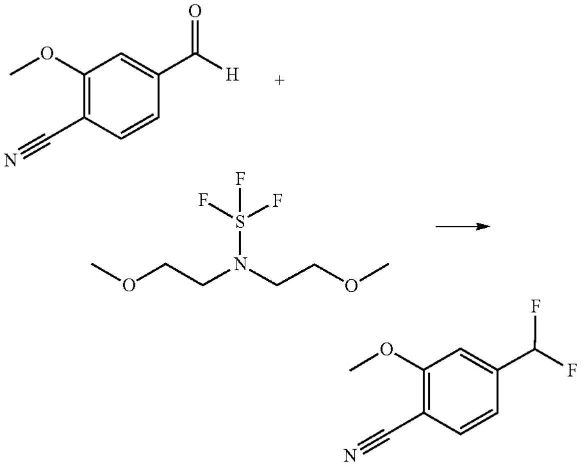

Int. 10.1

To 4-formyl-2-methoxybenzonitrile (806 mg, 5.00 mmol) in 3.00 mL DCM was added slowly bis(2-methoxyethyl)aminosulfur trifluoride (50% solution in toluene, 3.13 mL, 8.50 mmol) and ethanol (1.00 mmol, 57.6 μL). The reaction mixture was stirred at RT overnight. Again, bis(2-methoxyethyl)aminosulfur trifluoride (920 μL, 2.5 mmol) were added followed by ethanol (20.0 μL, 0.5 mmol). After stirring this mixture at RT for 1 h, it was poured onto a saturated aqueous $NaHCO_3$-solution and stirred for 5 min. The phases were separated, and the aqueous phase was extracted with DCM. The organic phases were combined, washed with water, dried and evaporated. The crude product was used as such for the next step.

$R_t$ (HPLC): 0.49 min (method A)

Intermediate 10.2

4-(Difluoromethyl)-2-hydroxybenzonitrile

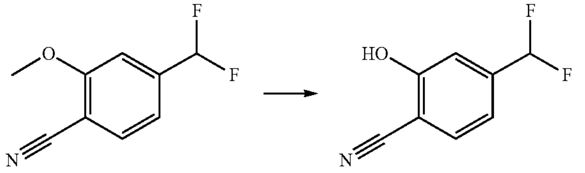

Int. 10.1 Int. 10.2

A mixture of 2-(diethylamino)ethanethiol (300 mg, 1.77 mmol) in 3.00 mL DMF was cooled to O ° C. and sodium tert-butoxide (340 mg, 3.54 mmol) was added. The reaction mixture was stirred at 0° C. for 5 min. Then the cooling bath was removed and the mixture was allowed to reach RT. A solution of 4-(difluoromethyl)-2-methoxybenzonitrile (INTERMEDIATE 10.1, 50.0 mg, 0.270 mmol) in 2.00 mL DMF was added at RT and the resulting mixture was heated under stirring to 160° C. for 1.5 h. Then, the reaction mixture was cooled to 0° C. and acidified with 1N aqueous HCl. The reaction mixture was extracted with EtOAc, the combined organic layers were dried and evaporated. The crude product was purified by RP-HPLC (Xbridge, ACN/$H_2O$/TFA).

ESI-MS: 170 $[M+H]^+$ $R_t$ (HPLC): 0.41 min (method A)

Intermediate 10.3.1

3-Amino-6-(difluoromethyl)-1-benzofuran-2-carboxamide

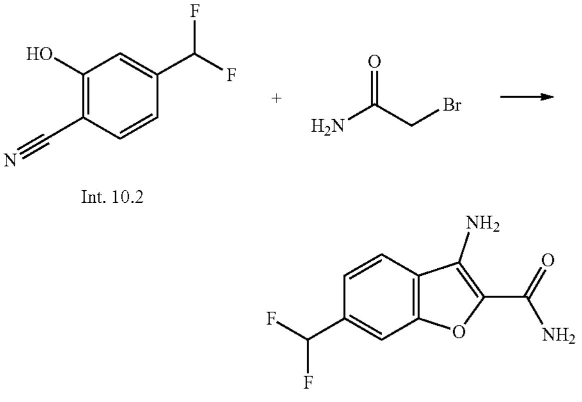

Int. 10.2

Int. 10.3.1

To 4-(difluoromethyl)-2-hydroxybenzonitrile (120 mg, 0.71 mmol) in 5.00 mL ethanol was added $K_2CO_3$ (INTERMEDIATE 10.2, 150 mg, 1.09 mmol) and 2-bromoacetamide (119 mg, 0.87 mmol). The reaction mixture was heated to reflux for 2 h. The reaction mixture was allowed to reach RT and KOH (95.1 mg, 1.44 mmol) was added. Then, the mixture was heated to reflux for 2 h. After cooling to RT, the reaction mixture was diluted with water. The ethanol was evaporated in vacuo, the precipitate was collected by filtration washed with water and dried.

ESI-MS: 227 $[M+H]^+$ $R_t$ (H PLC): 0.39 min (method A)

The following compounds were prepared according to the general procedure (INTERMEDIATE 10.3.I) described above:

Intermediate 10.4.I

6-Chloro-11-(difluoromethyl)-4-methyl-8-oxa-3,5-diazatricyclo[7.4.0.0$^{2,7}$]trideca-1(9),2(7),3,5,10,12-hexaene

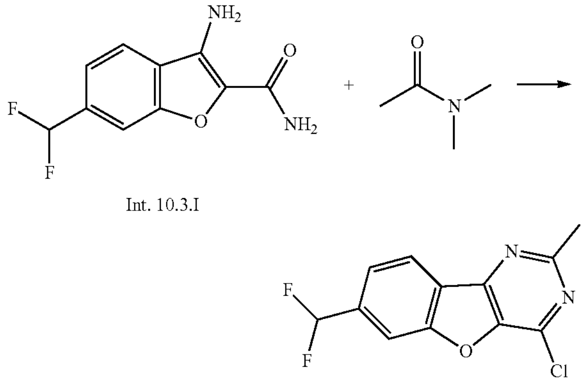

Int. 10.3.I

Int. 10.4.I

Under an argon atmosphere at 0° C., a mixture of phosphorus oxychloride (92.0 IL, 1.01 mmol) and DMA (39.0 μL, 0.40 mmol) was stirred for 30 min. This mixture was diluted with 0.5 mL phosphorus oxychloride and then added dropwise to 3-amino-6-(difluoromethyl)-1-benzofuran-2-carboxamide (INTERMEDIATE 10.3.I, 76.0 mg, 0.34 mmol). Upon completed addition, the mixture was heated to 50° C. and stirred for 3 h. Again, phosphorus oxychloride (184 μL, 2.02 mmol) was added and the reaction mixture was stirred at 50° C. overnight. The reaction mixture was cooled to RT, diluted with ice water and neutralized with aqueous $NaHCO_3$ solution. The mixture was extracted with DCM, the organic phase was dried, filtered and evaporated.

ESI-MS: 269 $[M+H]^+$ $R_t$ (H PLC): 0.62 min (method A)

| Int. | Starting material (carbonitrile) | Structure | ESI-MS | $R_t$ (HPLC) [min] (method) | Reaction conditions |
|---|---|---|---|---|---|
| 10.3.II | 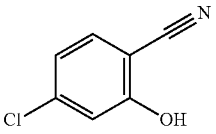 | 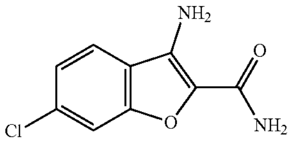 [SMILES: NC(=O)c1oc2cc(Cl)ccc2c1N] | 211/213 $[M + H]^+$ | 0.42 (A) | solvent: EtOH reflux: 2 h, 16 h |
| 10.3.III | 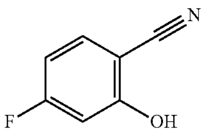 | 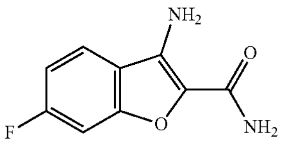 [SMILES: NC(=O)c1oc2cc(F)ccc2c1N] | 195 $[M + H]^+$ | 0.51 (E) | solvent: EtOH, reflux: 2 h, 2 h |

The following compounds were prepared according to the general procedure (INTERMEDIATE 10.4.I) described above:

| Int. | Starting material (carboxamide) | Structure | ESI-MS | $R_t$ (HPLC) [min] (method) |
|---|---|---|---|---|
| 10.4.II | 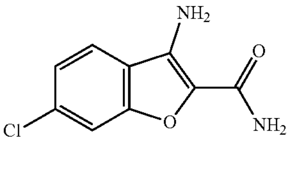 [SMILES: NC(=O)c1oc2cc(Cl)ccc2c1N] | 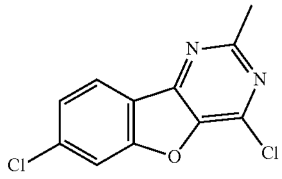 [SMILES: Cc1nc(Cl)c2oc3cc(Cl)ccc3c2n1] | 253/255 $[M + H]^+$ | 0.67 (A) |
| 10.4.III | 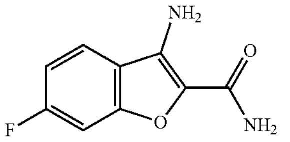 [SMILES: NC(=O)c1oc2cc(F)ccc2c1N] | 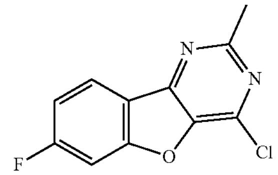 [SMILES: Cc1nc(Cl)c2oc3cc(F)ccc3c2n1] | 237/239 $[M + H]^+$ | 0.60 (A) |

Intermediate 11.1

(2S)-1-(5-Bromo-2-nitropyridin-3-yl)-2-methylpiperazine

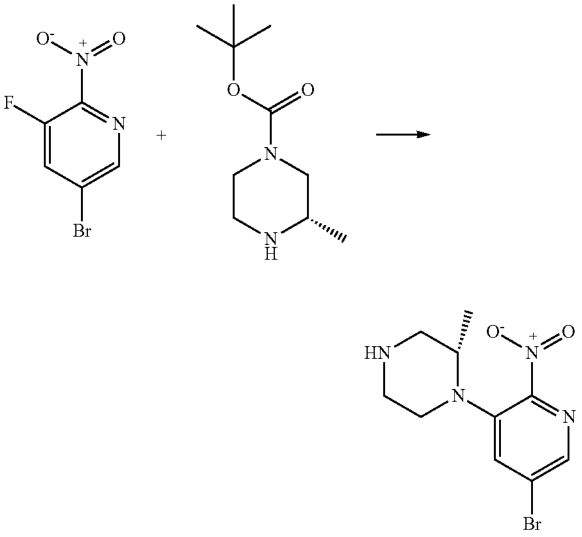

Int. 11.1

To 5-bromo-3-fluoro-2-nitropyridine (200 mg, 0.91 mmol) in 4.00 mL ACN was added tert-butyl (3S)-3-methylpiperazine-1-carboxylate (272 mg, 1.36 mmol) and TEA (635 µL, 4.53 mmol). The reaction mixture was stirred at 80° C. for 2.75 h. The reaction mixture was quenched with EtOAc and extracted with half sat. $NH_4Cl$ solution, half sat. $NaHCO_3$ solution and sat. NaCl solution. The organic phase was dried, filtered and concentrated. The residue was diluted in 4N HCl in dioxane, stirred at RT for 45 min and concentrated to afford the title compound as salt.

ESI-MS: 301/303 $[M+H]^+$ $R_t$ (HPLC): 0.70 min (method C)

Intermediate 11.2

(3S)-4-(5-Bromo-2-nitropyridin-3-yl)-3-methylpiperazine-1-carbonitrile

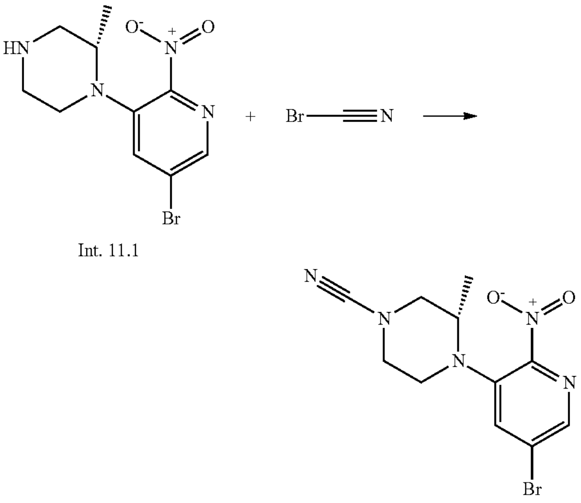

Int. 11.2

To (2S)-1-(5-bromo-2-nitropyridin-3-yl)-2-methylpiperazine hydrochloride (INTERMEDIATE 11.1, 80.0 mg, 0.24 mmol) in 2.00 mL DCM was added DIPEA (103 µL, 0.592 mmol) and cyanogen bromide (3 mol/L in DCM, 86.9 µL, 0.261 mmol). The reaction mixture was stirred at RT overnight. Again, cyanogen bromide (3 mol/L in DCM, 86.9 µL, 0.261 mmol) was added to the reaction mixture and stirring was continued at RT for 1 h. The reaction mixture was quenched with half sat. aqueous $NaHCO_3$ solution.

The phases were separated and extracted with DCM. The combined organic phases were dried over ISOLUTE® phase separator and evaporated.

ESI-MS: 326/328 $[M+H]^+$ $R_t$ (H PLC): 0.83 min (method C)

Intermediate 12.1 tert-Butyl (5S)-5-methyl-1,2,6-triazaspiro[2.5]oct-1-ene-6-carboxylate

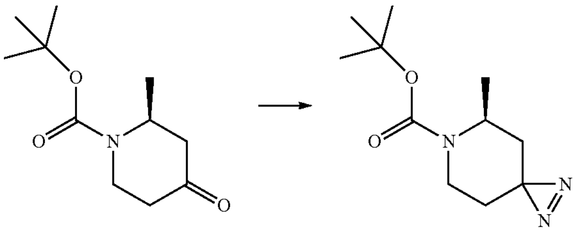

Int. 12.1

At 0° C., 6.70 mL ammonia (7N in methanol) was added to tert-butyl (2S)-2-methyl-4-oxopiperidine-1-carboxylate (1.00 g, 4.69 mmol). The reaction mixture was stirred and allowed to reach RT overnight. The mixture was then cooled to −20° C. and hydroxylamine-O-sulfonic acid (1.33 g, 11.7 mmol) was added portion wise. The reaction mixture was allowed to reach RT and stirred for 1 h. The precipitate was filtered off, washed with methanol and the filtrate was concentrated in vacuo. The concentrate was taken up in EtOAc/TEA (20 mL72 mL) and extracted with 10% aq. $Na_2CO_3$ (15 mL). The organic phase was extracted with water and dried over ISOLUTE® phase separator.

The organic layer was diluted with 10 mL methanol and subsequently cooled to −10° C. Iodine (1.31 g, 5.16 mmol) was added and the reaction mixture was allowed to reach RT. The reaction mixture was quenched with 5% sodium sulfite solution and extracted with 10% aqueous NaCl solution. The organic phase was dried over $Na_2SO_4$, filtered and evaporated. The product was purified by HPLC (Sunfire, ACN/$H_2O$/TFA)

ESI-MS: 248 $[M+Na]^+$ $R_t$ (H PLC): 1.09 min (method C)

Intermediate 12.2

(5S)-5-Methyl-1,2,6-triazaspiro[2.5]oct-1-ene

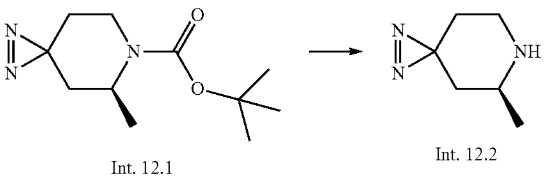

Int. 12.1

Int. 12.2

To tert-butyl (5S)-5-methyl-1,2,6-triazaspiro[2.5]oct-1-ene-6-carboxylate (INTERMEDIATE 12.1, 440 mg, 1.95 mmol) in 5.00 mL DCM was added TFA (0.50 mL 3.00 mmol). The reaction mixture was stirred at RT for 6 h, then concentrated and used for the next step without further purification.

ESI-MS: 126 $[M+H]^+$ $R_t$ (HPLC): 0.11 min (method C)

Intermediate 13.1

Methyl 2-methylpiperidine-3-carboxylate acetate

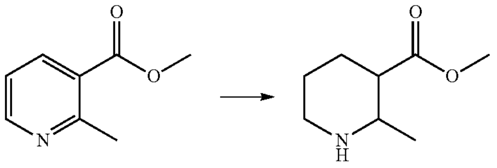

Int. 13.1

To methyl 2-methylpyridine-3-carboxylate (10.0 g, 66.2 mmol) in 80.0 mL acetic acid was added $Pd(OH)_2/C$ (1.00 g) and the mixture was hydrogenated under 3 bar at 80° C. for 12 h. The reaction mixture was filtered and concentrated under reduced pressure and used for the next step without further purification.

ESI-MS: 158 $[M+H]^+$ $R_t$ (H PLC): 0.27 min (method N)

Intermediate 13.2

1-tert-Butyl 3-methyl 2-methylpiperidine-1,3-dicarboxylate

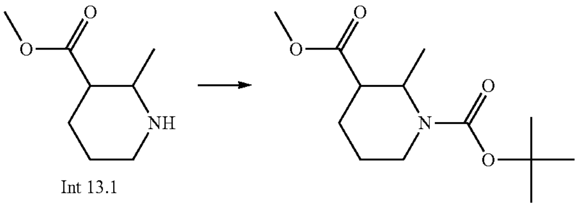

Int 13.1

Int. 13.2

To methyl 2-methylpiperidine-3-carboxylate (INTERMEDIATE 13.1, 15.0 g, 60.4 mmol) in 90.0 mLTHF was added TEA (8.49 mL, 60.4 mmol) and di-tert-butyl dicarbonate (13.2 g, 60.4 mmol) and the reaction mixture was stirred at RT for 1.5 h. The reaction mixture was diluted with EtOAc and extracted with half sat. $NaHCO_3$ solution. The organic phase was dried over $Na_2SO_4$, filtered and evaporated. The crude product was purified by column chromatography (silica gel; CH/EtOAc=99/1 to 1/99).

ESI-MS: 258 $[M+H]^+$ $R_t$ (H PLC): 0.65 min (method F)

Intermediate 13.3

1-tert-Butyl 3,3-dimethyl 2-methylpiperidine-1,3,3-tricarboxylate

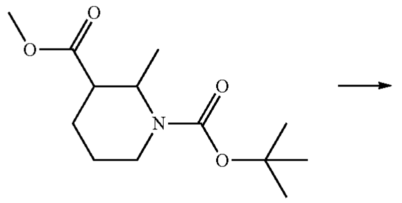

Int. 13.2

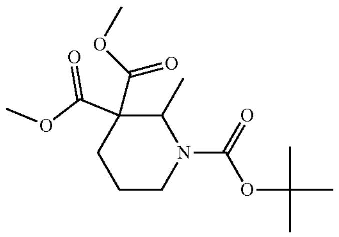

Int. 13.3

A solution of 1-tert-butyl 3-methyl 2-methylpiperidine-1,3-dicarboxylate (INTERMEDIATE 13.2, 5.00 g, 18.5 mmol) in 20.0 mL THF was added at −78° C. under argon to a solution of lithium diisopropylamide (2 mol/L, 11.1 mL, 22.2 mmol) in 32.5 mL THF. The reaction mixture was allowed to reach −20° C. and was stirred for 30 min. Then the reaction mixture was cooled to −78° C. and a solution of methyl chloroformate (2.25 mL, 27.7 mmol) in 10.0 mL THE was added dropwise to the reaction mixture. During the addition the temperature was kept below −65° C. After complete addition, the reaction mixture was allowed to reach RT and was stirred at RT for 2 h. The reaction mixture was quenched with sat. $NH_4Cl$ solution and stirred for 10 min at RT. The mixture was diluted with water and extracted with DCM. The organic layers were combined and dried over sodium sulfate, filtered and concentrated in vacuo. The residue was purified by column chromatography (silica gel; CH/EtOAc=95/5 to 60/40).

ESI-MS: 316 $[M+H]^+$ $R_f$ (TLC): 0.29 (CH/EtOAc=20/80)

Intermediate 13.4 tert-Butyl 3,3-bis(hydroxymethyl)-2-methylpiperidine-1-carboxylate

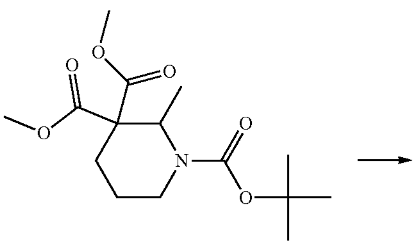

Int. 13.3

-continued

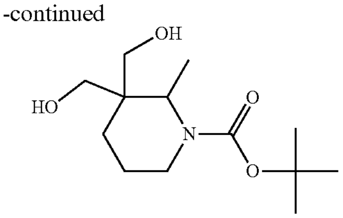

Int. 13.4

To a degassed solution of 1-tert-butyl 3,3-dimethyl 2-methylpiperidine-1,3,3-tricarboxylate (INTERMEDIATE 13.3, 5.60 g, 16.9 mmol) in 44.8 mLTHF at RT was added dropwise under argon $LiAlH_4$ (2.3 mol/L in 2-methyltetrahydrofurane, 14.6 mL, 33.7 mmol) and this mixture was stirred for 1.5 h at RT. The reaction mixture was cooled to 0° C., diluted with 80.0 mL diethylether and carefully treated with 1.25 mL water, then 1.25 mL 4 N NaOH and finally with 3.75 mL water. The reaction mixture was allowed to reach RT and was stirred for 15 min. The mixture was dried over $Na_2SO_4$, filtered and evaporated. The residue was purified by column chromatography (silica gel; CH/EtOAc=75/25 to 0/100).

ESI-MS: 260 $[M+H]^+$ $R_f$ (TLC): 0.14 (CH/EtOAc=50/50)

Intermediate 13.5 tert-Butyl 5-methyl-2-oxa-6-azaspiro[3.5]nonane-6-carboxylate

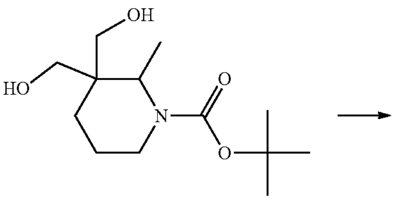

Int. 13.4

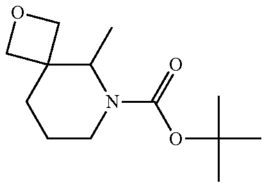

Int. 13.5

To tert-butyl 3,3-bis(hydroxymethyl)-2-methylpiperidine-1-carboxylate (INTERMEDIATE 13.4, 259 mg, 1.00 mmol) in 6.00 mLTHF was added triphenylphosphine (525 mg, 2.00 mmol). The reaction mixture was stirred for 5 min at RT. Then Ziram (483 mg, 1.50 mmol) and diisopropyl azodicarboxylate (413 µL, 2.00 mmol) were added and the mixture was stirred at 70° C. for 16 h. The reaction mixture was diluted with EtOAc, filtered through a pad of celite and washed with EtOAc. The filtrate was washed with 5% aq. $NH_3$ solution. The organic phase was dried, filtered and evaporated. The residue was purified by column chromatography (silica gel; DCM/EtOAc=95/5 to 70/30). The residue was purified by HPLC (Sunfire, ACN/$H_2O$/TFA).

ESI-MS: 242 $[M+H]^+$ $R_t$ (H PLC): 0.80 min (method E)

Intermediate 13.6

5-methyl-2-oxa-6-azaspiro[3.5]nonane

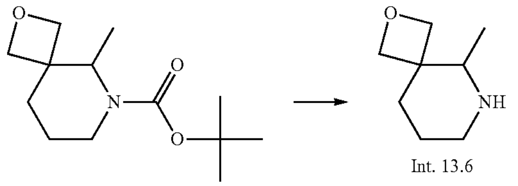

Int. 13.5

Int. 13.6

To tert-butyl 5-methyl-2-oxa-6-azaspiro[3.5]nonane-6-carboxylate (INTERMEDIATE 13.5, 134 mg, 0.56 mmol) in 2.00 mL DCM was added TFA (500 mL, 6.48 mmol). The reaction mixture was stirred for at RT for 30 min, then concentrated under reduced pressure and used for the next step without further purification.

ESI-MS: 142 $[M+H]^+$ $R_t$ (H PLC): 0.17 min (method E)

Intermediate 14.1

2-(Cyanomethoxy)-4-ethylbenzonitrile

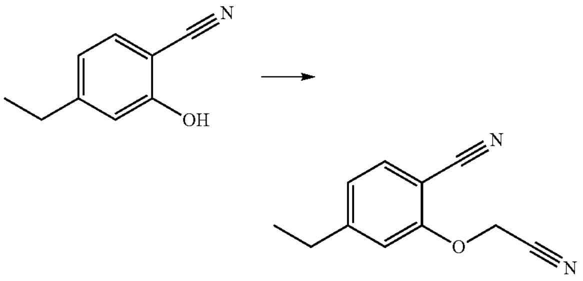

Int. 14.1

Bromoacetonitrile (1.22 mL, 17.5 mmol) was added to a mixture of 4-ethyl-2-hydroxy-benzonitrile (2.34 g, 16.2 mmol) and potassium carbonate (4.83 g, 35.0 mmol) in 40.0 mL DMF and the reaction mixture was stirred at 50° C. overnight. The reaction mixture was poured into water and extracted with DCM. The organic phase was concentrated in vacuo and the crude product used for the next step without further purification.

Intermediate 14.2

3-Amino-6-ethyl-1-benzofuran-2-carbonitrile

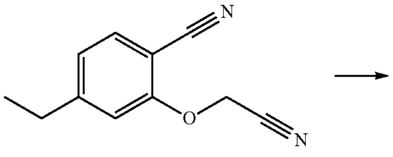

Int 14.1

-continued

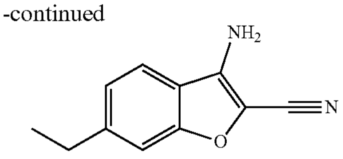

Int 14.2

To a mixture of 2-(cyanomethoxy)-4-ethylbenzonitrile (INTERMEDIATE 14.1, 1.79 g, 10.0 mmol) in 40.0 mL THF was added potassium tert-butoxide (108 mg, 0.964 mmol), and the mixture was stirred at RT overnight. The solvent was evaporated in vacuo and the product was purified by column chromatography and used as such for the next step.

Intermediate 14.3

N-(2-Cyano-6-ethyl-1-benzofuran-3-yl)-2,2,2-trifluoroacetamide

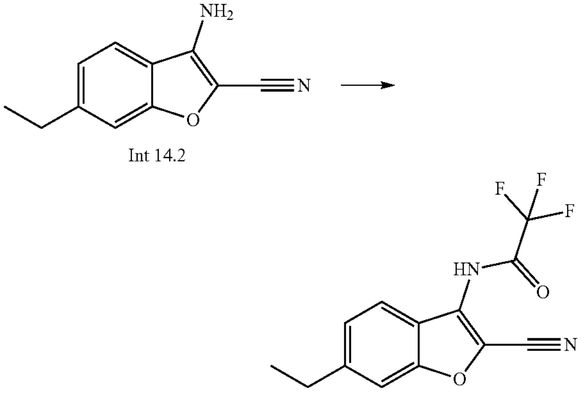

Int 14.2

Int. 14.3

A mixture of 3-amino-6-ethyl-1-benzofuran-2-carbonitrile (INTERMEDIATE 14.2, 1.40 g, 7.51 mmol) in 20 mL TFAA was stirred at 50° C. for 3 h. The solvent was evaporated to dryness under reduced pressure. The residue was taken up in ethyl acetate and the organic phase was washed with water and concentrated in vacuo. The crude product was used for the next step without further purification.

Intermediate 14.4

6-Chloro-11-ethyl-4-(trifluoromethyl)-8-oxa-3,5-diazatricyclo[$7.4.0.0^{2,7}$]trideca-1(13),2,4,6,9,11-hexaene

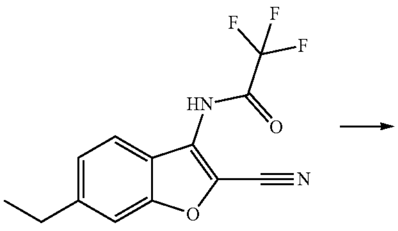

Int. 14.3

-continued

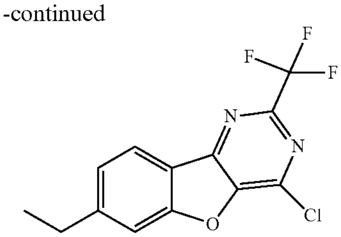

Int.14.4

To a mixture of N-(2-cyano-6-ethyl-1-benzofuran-3-yl)-2,2,2-trifluoroacetamide (INTERMEDIATE 14.3, 2.00 g, 7.09 mmol) in 5.0 mL sulfolane was added phosphorus pentachloride (5.90 g, 28.3 mmol) at 45° C. The mixture was stirred at 110° C. for 16 h, then poured onto ice water and extracted with EtOAc. The combined organic layers were washed with brine and evaporated. The residue was purified by column chromatography (silica gel; CH/EtOAc=100/0 to 95/5).

ESI-MS: 301/303 $[M+H]^+$ $R_t$ (H PLC): 0.79 min (method A)

Intermediate 15.1

3-(2-Chloroacetamido)-1-benzofuran-2-carboxamide

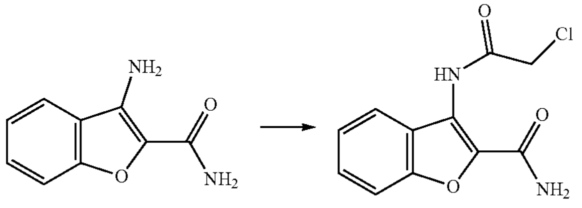

Int. 15.1

A mixture of 3-aminobenzofurane-2-carboxamide (3.52 g, 176 mmol) in chloroacetylchloride (6.00 mL, 75 mmol) was stirred at 60° C. for 10 min. Chloroacetylchloride (4.00 mL, 50 mmol) was added and stirring continued for 20 min at 60° C. The reaction mixture was poured onto ice water, the precipitate was collected by filtration, resuspended in water, filtered and washed with water. The crude product was used as such for the next step without further purification.

ESI-MS: 253 $[M+H]^+$ $R_t$ (HPLC): 0.41 min (method A)

Intermediate 15.2

4-(Hydroxymethyl)-8-oxa-3,5-diazatricyclo [7.4.0.02,7]trideca-1(9),2(7),3,10,12-pentaen-6-one

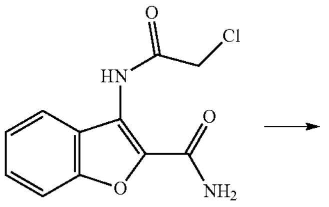

Int. 15.1

-continued

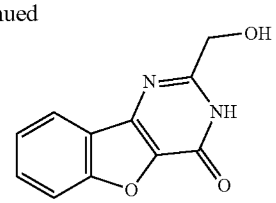

Int. 15.2

A mixture of 3-(2-chloroacetamido)-1-benzofuran-2-carboxamide (INTERMEDIATE 15.1, 5.80 g, 23.0 mmol) in aqueous 2M NaOH solution was stirred at 60° C. for 10 min. After cooling to RT, stirring was continued for 10 h, then the pH was adjusted to 1 by addition of conc. hydrochloric acid. The precipitate is collected by filtration and washed with water and dried.

ESI-MS: 217 $[M+H]^+$ $R_t$ (H PLC): 0.59 min (method C)

Intermediate 15.3

6-Chloro-4-(chloromethyl)-8-oxa-3,5-diazatricyclo [7.4.0.0$^{2,7}$]trideca-1(9),2(7),3,5,10,12-hexaene

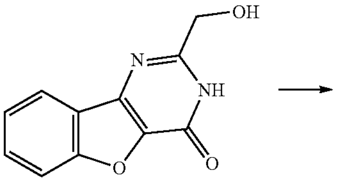

Int. 15.2

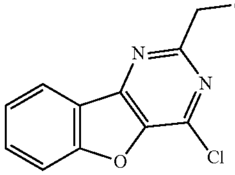

Int. 15.3

Phosphorus oxychloride (30 mL, 328 mmol) was added under stirring to 4-(hydroxymethyl)-8-oxa-3,5-diazatricyclo [7.4.0.02,7]trideca-1(9),2(7),3,10,12-pentaen-6-one (INTERMEDIATE 15.2, 5.00 g, 17.3 mmol) and the resulting mixture was heated under reflux for 1.5 h. The reaction mixture was cooled to RT and concentrated in vacuo. Ethyl acetate was added to the residues, and the mixture was neutralized by addition of an aqueous saturated solution of sodium bicarbonate. The mixture was filtered over celite, phases were separated and the organic phase was dried over magnesium sulfate and evaporated. The crude product was purified by flash column chromatography (cyclohexane/EtOAc=88/12→0/100).

ESI-MS: 253 $[M+H]^+$ $R_t$ (H PLC): 1.07 min (method C)

Intermediate 16.1

(2S,4S)-4-({3-[(9S)-9-methyl-2,5-dioxa-8-azaspiro[3.5]nonan-8-yl]-5-(4,4,5,5-tetramethyl-1,3,2-dioxaborolan-2-yl)pyridin-2-yl}oxy)-1-[4-(trifluoromethyl)-8-oxa-3,5-diazatricyclo[7.4.0.0$^{2,7}$]-trideca-1(9),2(7),3,5,10,12-hexaen-6-yl]pyrrolidine-2-carboxylic acid

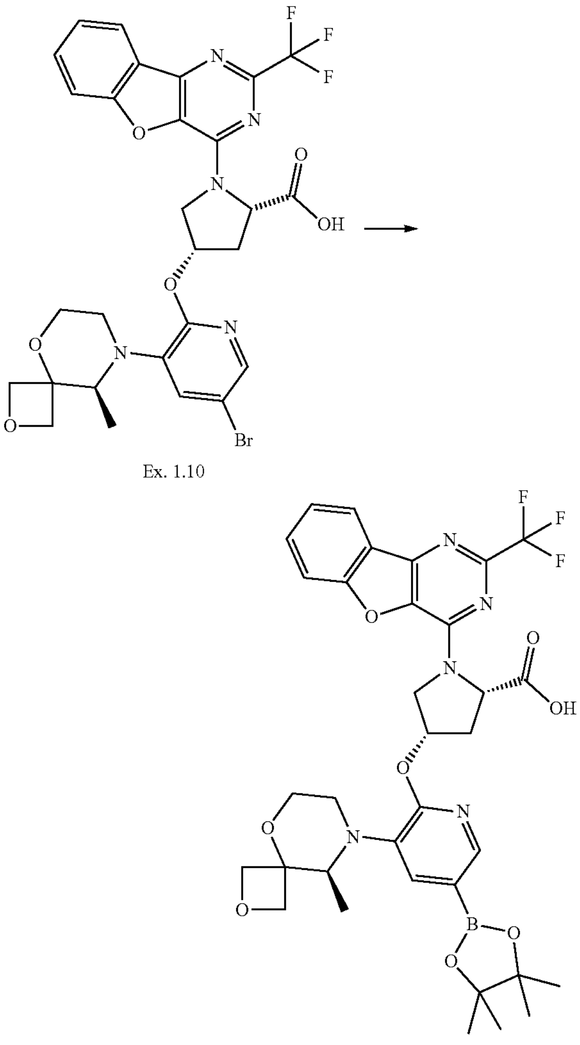

Ex. 1.10

Int. 16.1

To a degassed mixture of mixture of Ex. 1.10 (1.50 g, 2.26 mmol), bis-(pinacolato)-diboron (630 mg, 2.48 mmol) and potassium acetate (670 mg, 6.93 mmol) in 30 mL dioxane under an argon atmosphere was added Pd(dppf)$Cl_2$ (165 mg, 0.226 mmol). The reaction mixture was heated to 90° C. for 3 h, then cooled to RT, poured onto ice water and extracted with diethyl ether/THF. The organic phases were combined, dried over sodium sulfate and concentrated under reduced pressure. The crude product was purified by flash column chromatography (EtOAc/MeOH=10:1).

ESI-MS: 712 $[M+H]^+$ $R_t$ (H PLC): 1.05 min (method A)

PREPARATION OF FINAL COMPOUNDS

Example 1.01 (General Route)

(2S,4S)-4-{[5-Chloro-3-(2-cyanomorpholin-4-yl)pyridin-2-yl]oxy}-1-[4-(trifluoromethyl)-8-oxa-3,5-diazatricyclo[7.4.0.0$^{2,7}$]trideca-1(13),2,4,6,9,11-hexaen-6-yl]pyrrolidine-2-carboxylic acid

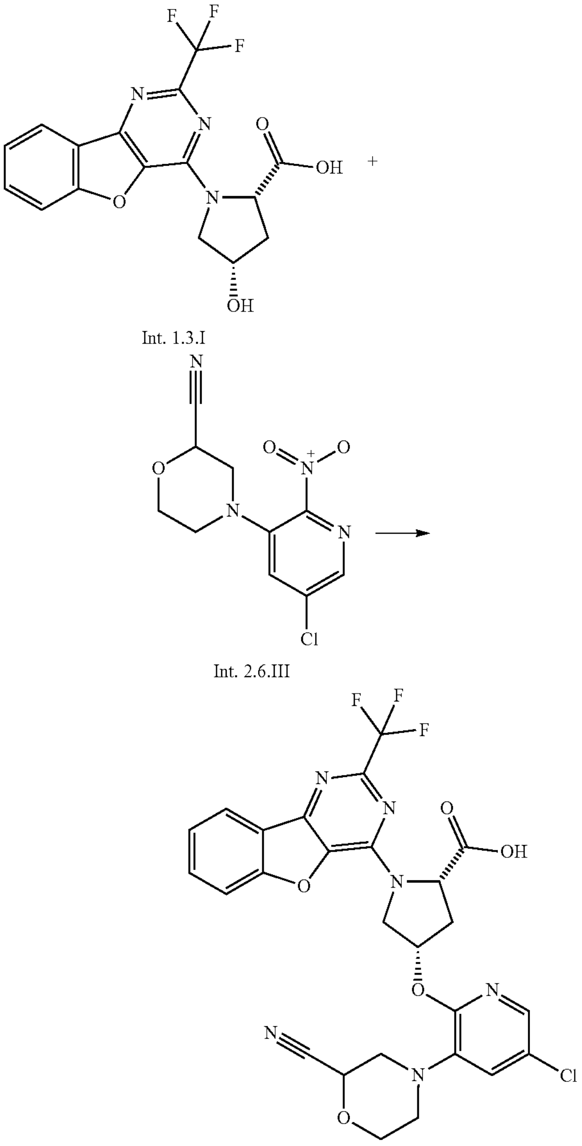

Int. 1.3.I

Int. 2.6.III

Ex. 1.01

To (2S,4S)-4-hydroxy-1-[4-(trifluoromethyl)-8-oxa-3,5-diazatricyclo[7.4.0.0$^{2,7}$]trideca-1(9),2(7),3,5,10,12-hexaen-6-yl]pyrrolidine-2-carboxylic acid (INTERMEDIATE 1.3.I, 58.0 mg, 0.15 mmol) in 2.00 mL DMA were added 4-(5-chloro-2-nitropyridin-3-yl)morpholine-2-carbonitrile (INTERMEDIATE 2.6.111, 80.6 mg, 0.30 mmol, 2.0 eq) and NaH (18.0 mg, 0.45 mmol, 3.0 eq). The reaction mixture was stirred for 20 min at 80° C. The reaction mixture was diluted with ACN/water, acidified with TFA, filtered and purified by HPLC (ACN/H2O/TFA). The product was obtained as a mixture of two diastereoisomers.

ESI-MS: 589 $[M+H]^+$ $R_t$ (H PLC): 1.05 min (method H)

The compounds listed in the table below were prepared according to the general procedure (EXAMPLE 1.01) described above. Where indicated in the table, the EXAMPLE compounds were either isolated as diastereomeric mixtures (ds-mix) or pure diasteroisomers ($R_t$ are given for both isolated diastereoisomers (EXAMPLE and 2nd diasteroisomer (2nd ds)).

| Ex. | Starting materials | Structure | Reaction conditions | ESI-MS | $R_t$ (HPLC) [min] (method) Example | 2nd ds |
|---|---|---|---|---|---|---|
| 1.02 | Int.1.3.II + Int.2.6.IV (2.0 eq) | 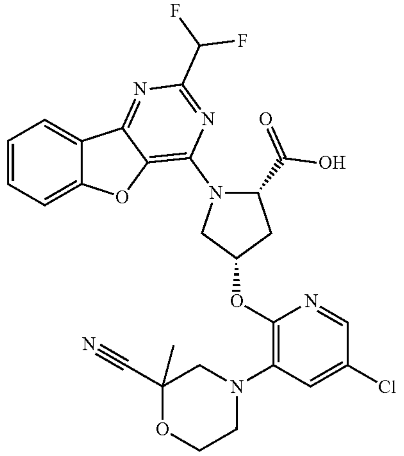 [SMILES: CC1(C#N)CN(c2cc(Cl)cnc2O[C@H]2C[C@@H](C(=O)O)N(c3nc(C(F)F)nc4c3oc3ccccc34)C2)CCO1] | solvent: DMA, NaH: 2.0 eq, RT, 1 h | 585 $[M + H]^+$ | 0.52 (D) ds-mix | — |
| 1.03 | Int.1.3.I + Int.2.6.IV (2.0 eq) | 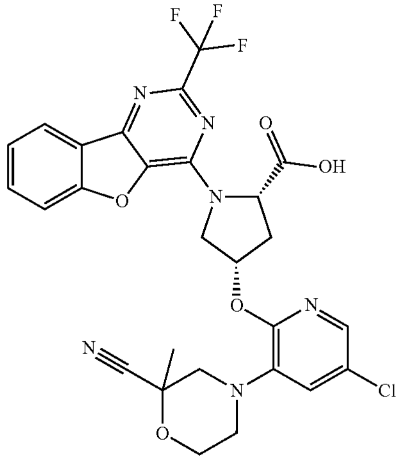 [SMILES: CC1(C#N)CN(c2cc(Cl)cnc2O[C@H]2C[C@@H](C(=O)O)N(c3nc(C(F)(F)F)nc4c3oc3ccccc34)C2)CCO1] | solvent: DMA, NaH: 2.0 eq, RT, 1 h | 603 $[M + H]^+$ | 0.57 (D) ds-mix | — |
| 1.04 | Int.1.3.II + Int.2.6.V (2.0 eq) | 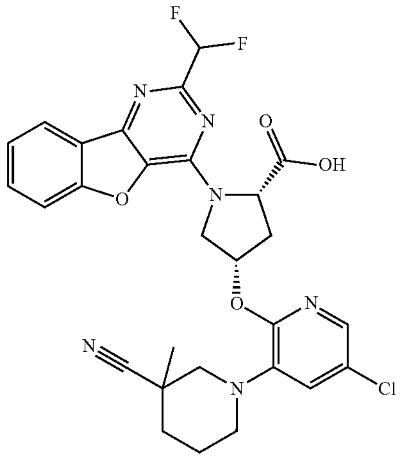 [SMILES: CC1(C#N)CCCN(c2cc(Cl)cnc2O[C@H]2C[C@@H](C(=O)O)N(c3nc(C(F)F)nc4c3oc3ccccc34)C2)C1] | solvent: DMA, NaH: 2.0 eq, RT, 1 h | 583 $[M + H]^+$ | 0.63 (D) ds-mix | — |

-continued
| Ex. | Starting materials | Structure | Reaction conditions | ESI-MS | $R_t$ (HPLC) [min] (method) Example | $2^{nd}$ ds |
|---|---|---|---|---|---|---|
| 1.05 | Int.1.3.I + Int.2.6.V (2.0 eq) | 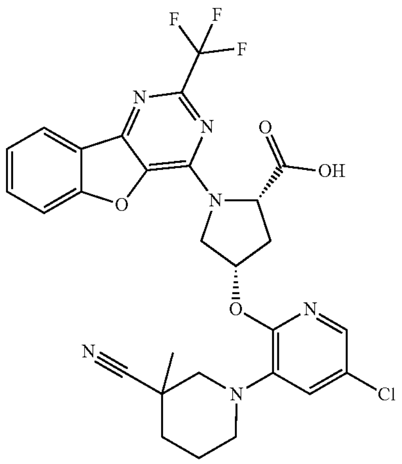 [SMILES: CC1(C#N)CCCN(c2cc(Cl)cnc2O[C@H]2C[C@@H](C(=O)O)N(c3nc(C(F)(F)F)nc4c3oc3ccccc34)C2)C1] | solvent: DMA, NaH: 2.0 eq, RT 1 h | 601 $[M + H]^+$ | 0.67 (D) ds-mix | — |
| 1.06 | Int.1.3.I + Int.2.6.VI (1.0 eq) | 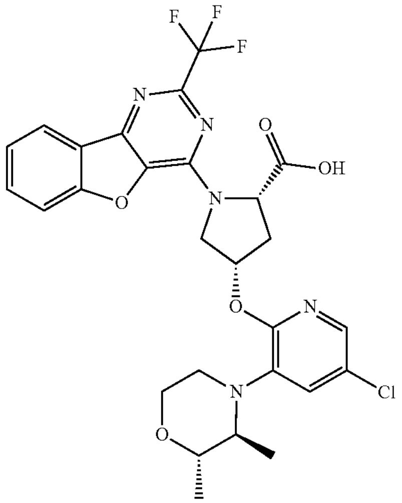 [SMILES: C[C@@H]1OCCN(c2cc(Cl)cnc2O[C@H]2C[C@@H](C(=O)O)N(c3nc(C(F)(F)F)nc4c3oc3ccccc34)C2)[C@H]1C] | solvent: DMA, NaH: 3.0 eq, 85° C., 45 min | 592/ 594 $[M + H]^+$ | 2.72 (L) | 2.81 (L) |
| 1.07 | Int.1.3.I + Int.7.1.I (1.3 eq) | 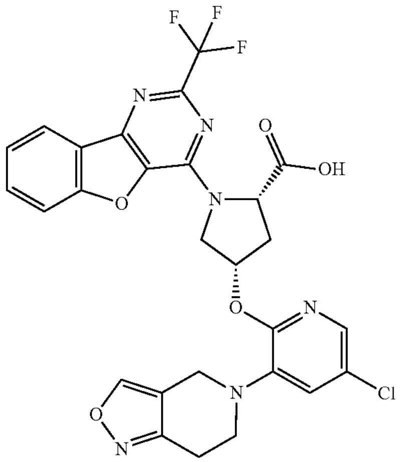 [SMILES: O=C(O)[C@@H]1C[C@H](Oc2ncc(Cl)cc2N2CCc3nocc3C2)CN1c1nc(C(F)(F)F)nc2c1oc1ccccc12] | solvent: NMP, NaH: 5.0 eq, RT, 1 h | 601 $[M + H]^+$ | 0.74 (A) | — |

-continued
| Ex. | Starting materials | Structure | Reaction conditions | ESI-MS | $R_t$ (HPLC) [min] (method) Example | $2^{nd}$ ds |
|---|---|---|---|---|---|---|
| 1.08 | Int.1.3.II + Int.7.1.I (1.3 eq) | 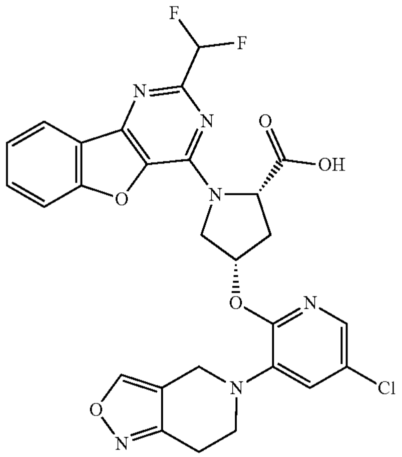 [SMILES: O=C(O)[C@@H]1C[C@H](Oc2ncc(Cl)cc2N2CCc3nocc3C2)CN1c1nc(C(F)F)nc2c1oc1ccccc12] | solvent: NMP, NaH: 5.0 eq, RT 1 h | 583 $[M + H]^+$ | 0.69 (A) | — |
| 1.09 | Int.1.3.II + Int.2.6.II | 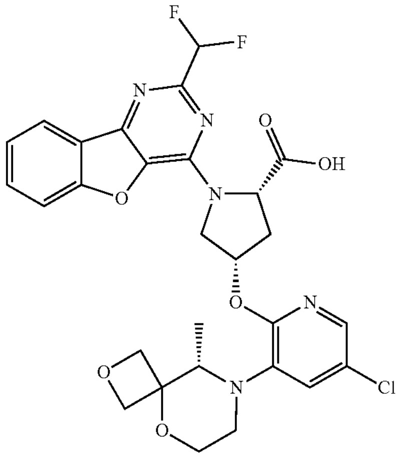 [SMILES: C[C@@H]1N(c2cc(Cl)cnc2O[C@H]2C[C@@H](C(=O)O)N(c3nc(C(F)F)nc4c3oc3ccccc34)C2)CCOC12COC2] | solvent: NMP, NaH: 5.0 eq, 80° C. 1 h | 602/ 604 $[M + H]^+$ | 0.70 (A) | 0.74 (A) |
| 1.10 | Int.1.3.I + Int.2.6.I (1.3 eq) | 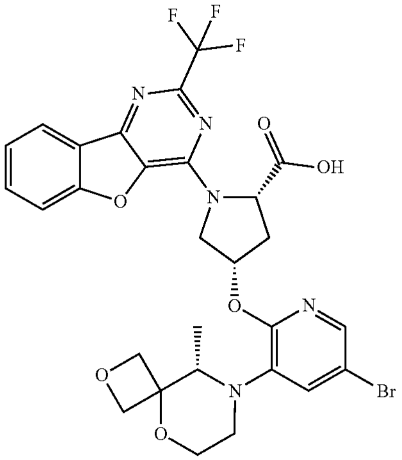 [SMILES: C[C@@H]1N(c2cc(Br)cnc2O[C@H]2C[C@@H](C(=O)O)N(c3nc(C(F)(F)F)nc4c3oc3ccccc34)C2)CCOC12COC2] | solvent: DMA, NaH: 3.0 eq, 80° C. 10 min, RT overnight | 664/ 666 $[M + H]^+$ | 1.07 (B) | 1.13 (B) |

-continued
| Ex. | Starting materials | Structure | Reaction conditions | ESI-MS | $R_t$ (HPLC) [min] (method) Example | $2^{nd}$ ds |
|---|---|---|---|---|---|---|
| 1.11 | Int.1.3.II + Int.2.7.I (1.0 eq) | 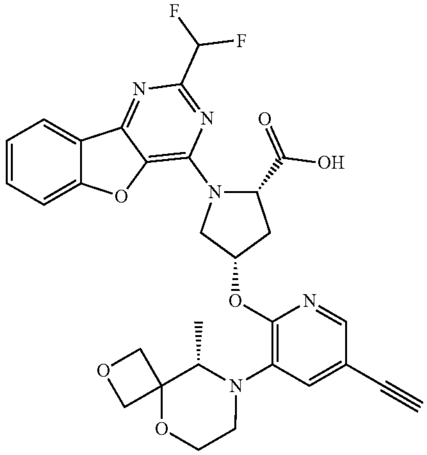 [SMILES: C#Cc1cnc(O[C@H]2C[C@@H](C(=O)O)N(c3nc(C(F)F)nc4c3oc3ccccc34)C2)c(N2CCOC3(COC3)[C@@H]2C)c1] | solvent: NMP, NaH: 5.0 eq, RT, 10 min | 592 $[M + H]^+$ | 0.67 (A) | 0.71 (A) |
| 1.12 | Int.1.3.I + Int.2.7.I (1.0 eq) | 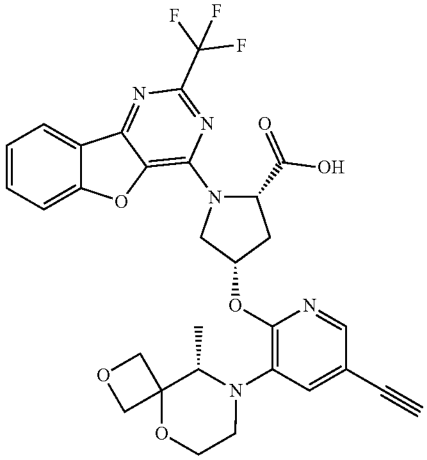 [SMILES: C#Cc1cnc(O[C@H]2C[C@@H](C(=O)O)N(c3nc(C(F)(F)F)nc4c3oc3ccccc34)C2)c(N2CCOC3(COC3)[C@@H]2C)c1] | solvent: NMP, NaH: 5.0 eq, RT 15 min | 610 $[M + H]^+$ | 0.74 (A) | 0.79 (A) |
| 1.13 | Int.1.3.I + Int.2.6.II (2.0 eq) | 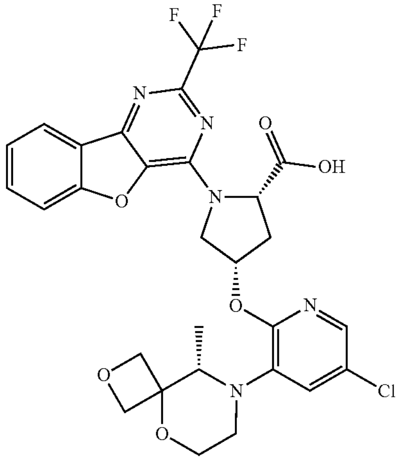 [SMILES: C[C@@H]1N(c2cc(Cl)cnc2O[C@H]2C[C@@H](C(=O)O)N(c3nc(C(F)(F)F)nc4c3oc3ccccc34)C2)CCOC12COC2] | solvent: NMP, NaH: 5.0 eq 80° C., 1 h | 620/622 $[M + H]^+$ | 0.75 (A) | 0.79 (A) |

-continued
| Ex. | Starting materials | Structure | Reaction conditions | ESI-MS | $R_t$ (HPLC) [min] (method) Example | $2^{nd}$ ds |
|---|---|---|---|---|---|---|
| 1.14 | Int.1.3.III + Int.2.7.I (1.0 eq) | 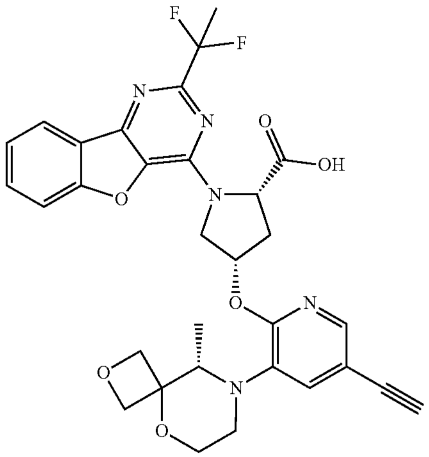 [SMILES: C#Cc1cnc(O[C@H]2C[C@@H](C(=O)O)N(c3nc(C(C)(F)F)nc4c3oc3ccccc34)C2)c(N2CCOC3(COC3)[C@@H]2C)c1] | solvent: NMP, NaH: 5.0 eq, RT, 25 min, | 606 $[M + H]^+$ | 0.69 (A) | 0.73 (A)- |
| 1.15 | Int.1.3.III + Int.2.7.I (1.0 eq) | 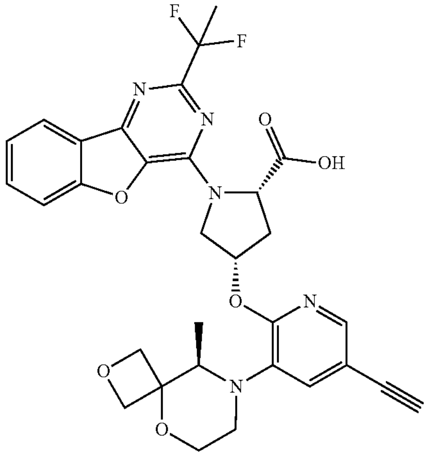 [SMILES: C#Cc1cnc(O[C@H]2C[C@@H](C(=O)O)N(c3nc(C(C)(F)F)nc4c3oc3ccccc34)C2)c(N2CCOC3(COC3)[C@H]2C)c1] | solvent: NMP, NaH: 5.0 eq, RT 25 min, | 606 $[M + H]^+$ | 0.73 (A) | 0.69 (A) |
| 1.16 | Int.1.3.IV + 2.7.I (1.0 eq) | 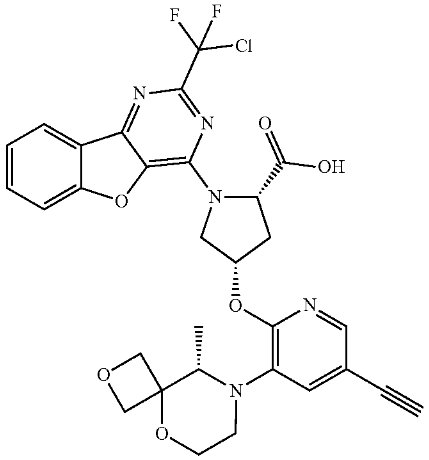 [SMILES: C#Cc1cnc(O[C@H]2C[C@@H](C(=O)O)N(c3nc(C(F)(F)Cl)nc4c3oc3ccccc34)C2)c(N2CCOC3(COC3)[C@@H]2C)c1] | solvent: NMP, NaH: 5.0 eq, RT, 20 min | 626 $[M + H]^+$ | 1.14 (B) | 1.65 (B) |

-continued
| Ex. | Starting materials | Structure | Reaction conditions | ESI-MS | $R_t$ (HPLC) [min] (method) Example | $2^{nd}$ ds |
|---|---|---|---|---|---|---|
| 1.17 | Int.1.3.V + Int.2.7.I (1.0 eq) | 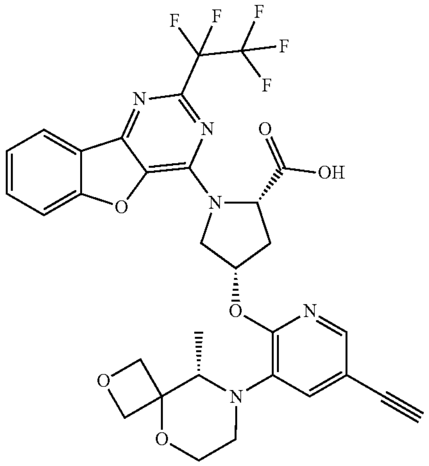 [SMILES: C#Cc1cnc(O[C@H]2C[C@@H](C(=O)O)N(c3nc(C(F)(F)C(F)(F)F)nc4c3oc3ccccc34)C2)c(N2CCOC3(COC3)[C@@H]2C)c1] | solvent: NMP, NaH: 5.0 eq, RT, 30 min | 660 $[M + H]^+$ | 1.04 (C) | 1.09 (C) |
| 1.18 | Int.1.3.II + Int.11.2 (1.3 eq) | 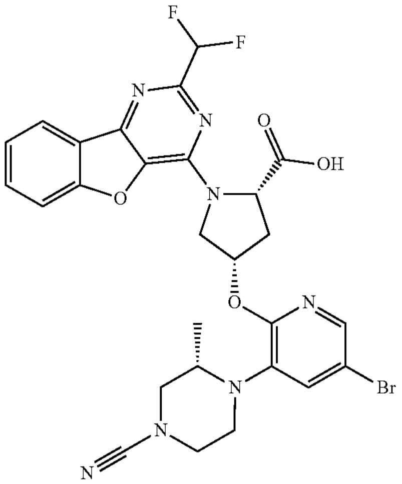 [SMILES: C[C@H]1CN(C#N)CCN1c1cc(Br)cnc1O[C@H]1C[C@@H](C(=O)O)N(c2nc(C(F)F)nc3c2oc2ccccc23)C1] | solvent: DMF, NaH: 3.0 eq, RT, 1.25 h | 628 $[M + H]^+$ | 1.12 (C) | — |
| 1.19 | 1.3.II + 2.7.IV (1.5 eq) | 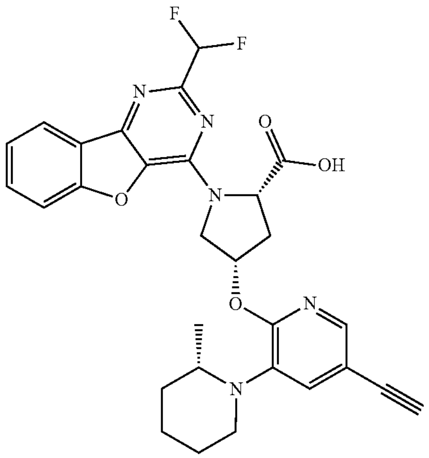 [SMILES: C#Cc1cnc(O[C@H]2C[C@@H](C(=O)O)N(c3nc(C(F)F)nc4c3oc3ccccc34)C2)c(N2CCCC[C@@H]2C)c1] | solvent: DMA, NaH: 3.0 eq, RT, 30 min | 548 $[M + H]^+$ | 0.71 (H) | — |

-continued
| Ex. | Starting materials | Structure | Reaction conditions | ESI-MS | $R_t$ (HPLC) [min] (method) Example | $2^{nd}$ ds |
|---|---|---|---|---|---|---|
| 1.20 | Int.1.3.II + Int.2.6.XVI (1.0 eq) | 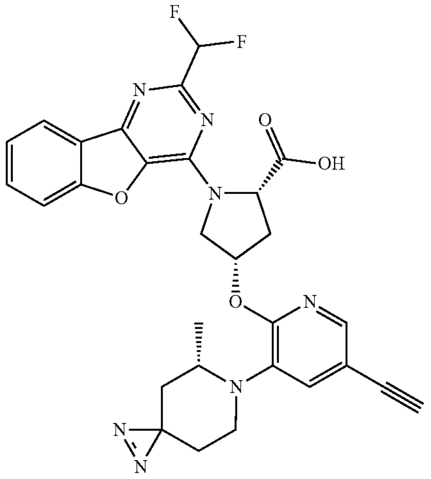 [SMILES: C#Cc1cnc(O[C@H]2C[C@@H](C(=O)O)N(c3nc(C(F)F)nc4c3oc3ccccc34)C2)c(N2CCC3(C[C@@H]2C)N=N3)c1] | solvent: DMF, NaH: 3.0 eq, RT, 15 min | 574 $[M + H]^+$ | 1.13 (C) | — |
| 1.21 | Int.1.3.II + Int. 2.6.XVII (2.0 eq) | 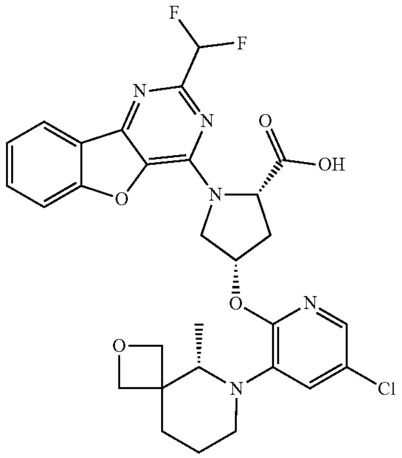 [SMILES: C[C@@H]1N(c2cc(Cl)cnc2O[C@H]2C[C@@H](C(=O)O)N(c3nc(C(F)F)nc4c3oc3ccccc34)C2)CCCC12COC2] | solvent: NMP, NaH: 5.0 eq, 80° C., 1 h | 600/ 602 $[M + H]^+$ | 0.74 (A) | 0.80 (A) |
| 1.22 | Int.1.3.I + Int.2.7.VI (1.0 eq) | 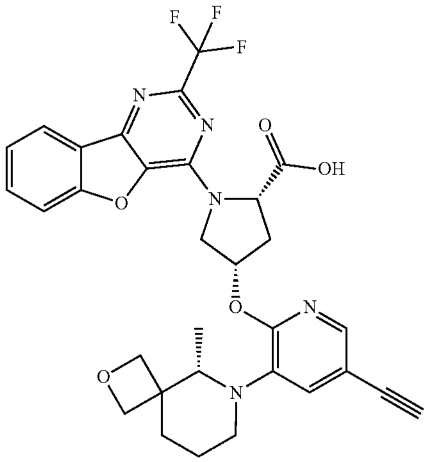 [SMILES: C#Cc1cnc(O[C@H]2C[C@@H](C(=O)O)N(c3nc(C(F)(F)F)nc4c3oc3ccccc34)C2)c(N2CCCC3(COC3)[C@@H]2C)c1] | solvent: NMP, NaH: 5.0 eq, 80° C., 1 h | 608 $[M + H]^+$ | 0.78 (A) | 0.85 (A) |

-continued
| Ex. | Starting materials | Structure | Reaction conditions | ESI-MS | $R_t$ (HPLC) [min] (method) Example | $2^{nd}$ ds |
|---|---|---|---|---|---|---|
| 1.23 | Int.1.3.II + Int.2.7.VI (1.0 eq) | 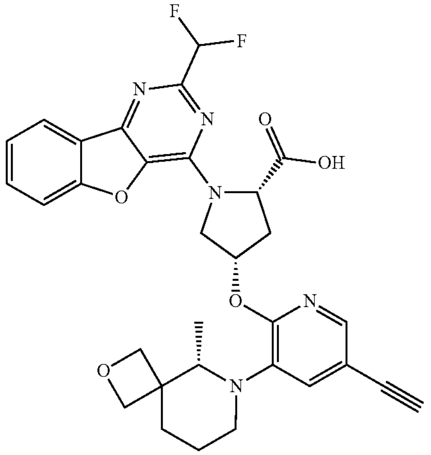 [SMILES: C#Cc1cnc(O[C@H]2C[C@@H](C(=O)O)N(c3nc(C(F)F)nc4c3oc3ccccc34)C2)c(N2CCCC3(COC3)[C@@H]2C)c1] | solvent: NMP, NaH: 5.0 eq, 80° C.1 h | 590 $[M + H]^+$ | 0.73 (A) | 0.80 (A) |
| 1.24 | Int.1.3.II + Int.2.6.IX (2.0 eq) | 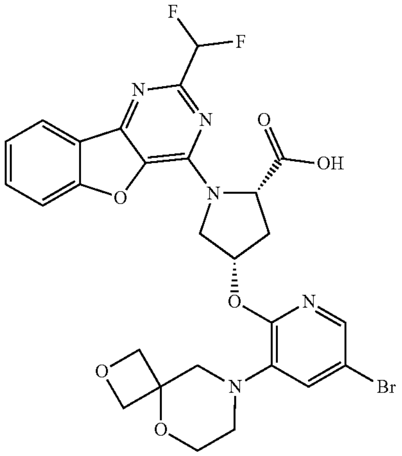 [SMILES: O=C(O)[C@@H]1C[C@H](Oc2ncc(Br)cc2N2CCOC3(COC3)C2)CN1c1nc(C(F)F)nc2c1oc1ccccc12] | solvent: DMA NaH: 3.0 eq 80° C., 10 min | 632 $[M + H]^+$ | 1.03 min (H) | — |
| 1.25 | Int.1.3.II + Int.2.6.X | 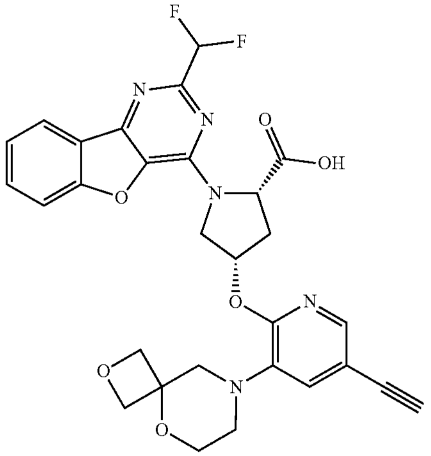 [SMILES: C#Cc1cnc(O[C@H]2C[C@@H](C(=O)O)N(c3nc(C(F)F)nc4c3oc3ccccc34)C2)c(N2CCOC3(COC3)C2)c1] | solvent: DMA, 80° C. 10 min | 578 $[M + H]^+$ | 0.96 (H) | — |

-continued
| Ex. | Starting materials | Structure | Reaction conditions | ESI-MS | $R_t$ (HPLC) [min] (method) Example | $2^{nd}$ ds |
|---|---|---|---|---|---|---|
| 1.26 | Int.1.3.II + Int.2.6.XI | 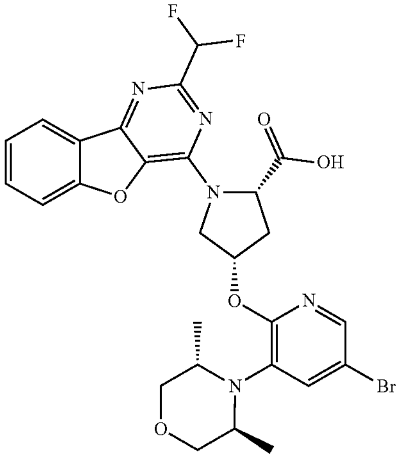 [SMILES: C[C@H]1COC[C@H](C)N1c1cc(Br)cnc1O[C@H]1C[C@@H](C(=O)O)N(c2nc(C(F)F)nc3c2oc2ccccc23)C1] | solvent: DMA, RT overnight | 618 $[M + H]^+$ | 1.028 (C) | — |
| 1.27 | Int.1.3.II + Int.2.6.XII | 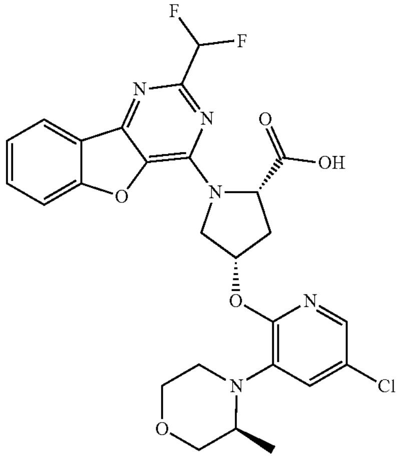 [SMILES: C[C@H]1COCCN1c1cc(Cl)cnc1O[C@H]1C[C@@H](C(=O)O)N(c2nc(C(F)F)nc3c2oc2ccccc23)C1] | solvent: DMA, 10 min 80° C. | 560 $[M + H]^+$ | 0.53 (D) | — |
| 1.28 | Int.1.3.II + Int.2.6.XIII | 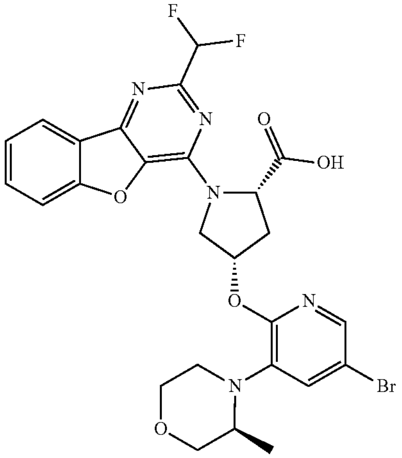 [SMILES: C[C@H]1COCCN1c1cc(Br)cnc1O[C@H]1C[C@@H](C(=O)O)N(c2nc(C(F)F)nc3c2oc2ccccc23)C1] | solvent: DMA, 10 min 80° C. | 604 $[M + H]^+$ | 1.05 (H) | — |

-continued
| Ex. | Starting materials | Structure | Reaction conditions | ESI-MS | $R_t$ (HPLC) [min] (method) Example | 2nd ds |
|---|---|---|---|---|---|---|
| 1.29 | Int.1.3.VI + Int.2.6.XIV | 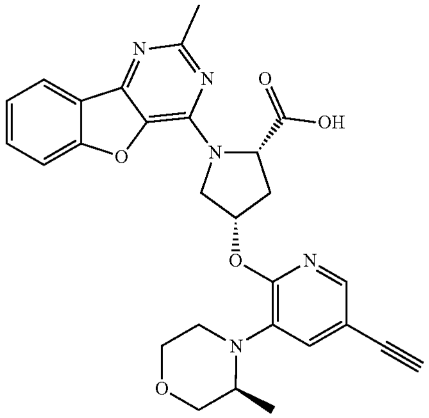 [SMILES: C#Cc1cnc(O[C@H]2C[C@@H](C(=O)O)N(c3nc(C)nc4c3oc3ccccc34)C2)c(N2CCOC[C@@H]2C)c1] | solvent: DMF, 30 min RT | 514 $[M + H]^+$ | 0.86 (C) | — |
| 1.30 | Int.1.3.I + Int.2.6.XIV | 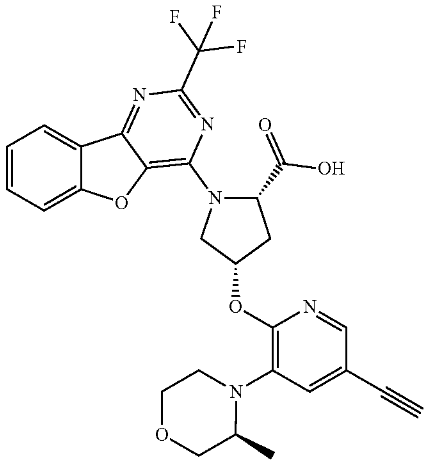 [SMILES: C#Cc1cnc(O[C@H]2C[C@@H](C(=O)O)N(c3nc(C(F)(F)F)nc4c3oc3ccccc34)C2)c(N2CCOC[C@@H]2C)c1] | solvent: DMF, 30 min RT | 568 $[M + H]^+$ | 1.16 (C) | — |
| 1.31 | Int.1.3.II + Int.2.6.XIV | 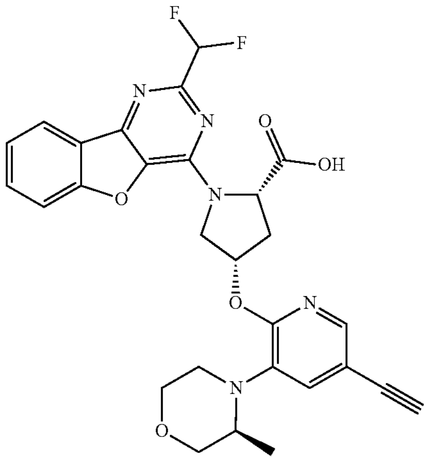 [SMILES: C#Cc1cnc(O[C@H]2C[C@@H](C(=O)O)N(c3nc(C(F)F)nc4c3oc3ccccc34)C2)c(N2CCOC[C@@H]2C)c1] | solvent: DMA, 45 min RT | 550 $[M + H]^+$ | 1.18 (C) | — |

-continued
| Ex. | Starting materials | Structure | Reaction conditions | ESI-MS | $R_t$ (HPLC) [min] (method) Example | 2nd ds |
|---|---|---|---|---|---|---|
| 1.32 | Int.1.3.VII + Int.2.6.XIV | 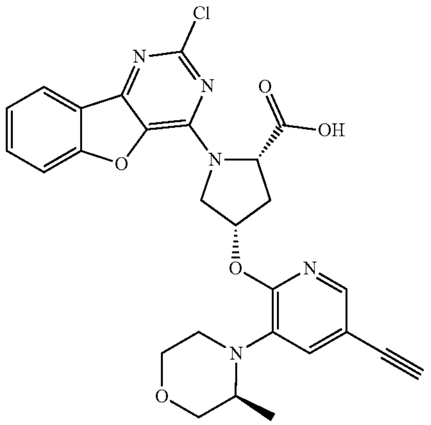 [SMILES: C#Cc1cnc(O[C@H]2C[C@@H](C(=O)O)N(c3nc(Cl)nc4c3oc3ccccc34)C2)c(N2CCOC[C@@H]2C)c1] | solvent: DMA, 45 min RT | 534 $[M + H]^+$ | 1.11 (C) | — |
| 1.33 | Int.1.3.I + Int.2.6.XIX (1.1 eq) | 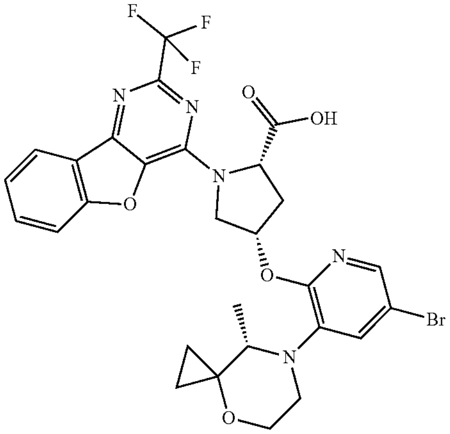 [SMILES: C[C@@H]1N(c2cc(Br)cnc2O[C@H]2C[C@@H](C(=O)O)N(c3nc(C(F)(F)F)nc4c3oc3ccccc34)C2)CCOC12CC2] | solvent: NMP 1.5 h, RT | 648/ 650 $[M + H]^+$ | 0.79 (A) | |
| 1.34 | Int.1.3.I + Int.6.1 (1.2 eq) | 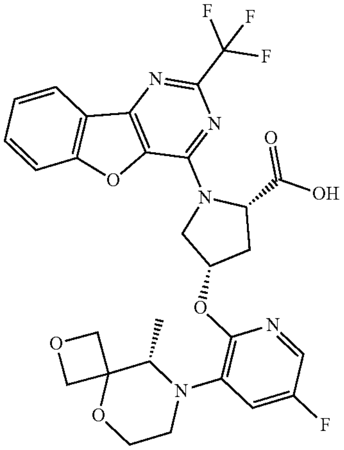 [SMILES: C[C@@H]1N(c2cc(F)cnc2O[C@H]2C[C@@H](C(=O)O)N(c3nc(C(F)(F)F)nc4c3oc3ccccc34)C2)CCOC12COC2] | solvent: NMP 30 min, RT | 604 $[M + H]^+$ | 0.70 (A) | 0.75 (A) |

The absolute stereochemistry of Example 1.10 was confirmed via small molecule X-ray as illustrated below:

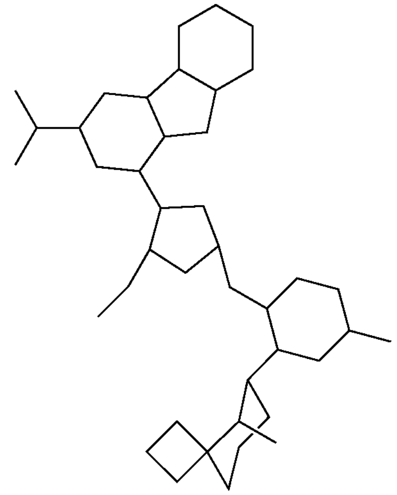 [SMILES: CCC1CC(CC2CCC(C)CC2C2CCCC3(CCC3)C2C)CC1C1CC(C(C)C)CC2C3CCCCC3CC21]

The absolute stereochemistry of Example 1.28 was confirmed via small molecule X-ray as illustrated below:

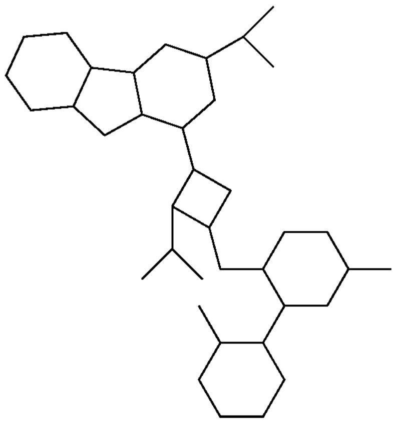 [SMILES: CC1CCC(CC2CC(C3CC(C(C)C)CC4C5CCCCC5CC43)C2C(C)C)C(C2CCCCC2C)C1]

Example 2.01 (General Route)

(2S,4S)-1-[4-(Difluoromethyl)-8-oxa-3,5-diazatricyclo[7.4.0.0$^{2,7}$]trideca-1(13),2,4,6,9,11-hexaen-6-yl]-4-{[5-ethynyl-3-(morpholin-4-yl)pyridin-2yl]oxy}-pyrrolidine-2-carboxylic acid

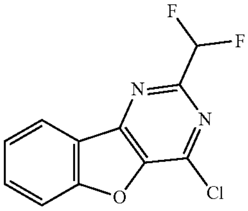

Int. 1.2.II

+

-continued

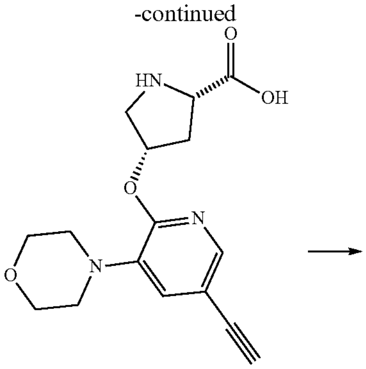

Int. 8.1

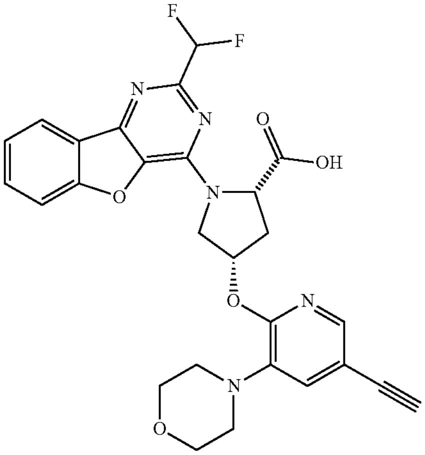

Ex. 2.01

To 6-chloro-4-(difluoromethyl)-8-oxa-3,5-diazatricyclo [7.4.0.0$^{2,7}$]trideca-1(9),2(7),3,5,10,12-hexaene (INTERMEDIATE 1.2.11, 30.0 mg, 0.12 mmol) in 1.50 mL DMSO were added (2S,4S)-4-{[5-ethynyl-3-(morpholin-4-yl)pyridin-2-yl]oxy}pyrrolidine-2-carboxylic acid (INTERMEDIATE 8.1, 55.9 mg, 0.13 mmol) and DI PEA (60.8 μL, 0.35 mmol). The reaction mixture was stirred for 1 h at 110° C. The reaction mixture was diluted with ACN, acidified with TEA, filtered and purified by HPLC (ACN/H2O/TFA).

ESI-MS: 536 [M+H]$^+$ $R_t$ (H PLC): 1.08 min (method C)

The following EXAMPLES were prepared according to the general procedure (EXAMPLE 2.1) described above:

| Ex. | Starting materials | Structure | Reaction conditions | ESI-MS | $R_t$ (HPLC) [min] (method) |
|---|---|---|---|---|---|
| 2.02 | Int. 1.2.I + Int. 8.1 (1.1 eq) | 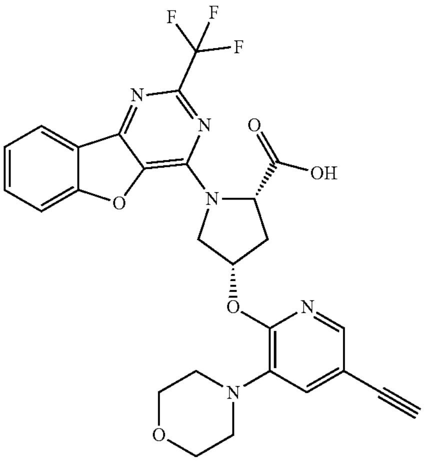 [SMILES: C#Cc1cnc(O[C@H]2C[C@@H](C(=O)O)N(c3nc(C(F)(F)F)nc4c3oc3ccccc34)C2)c(N2CCOCC2)c1] | solvent: DMSO, DIPEA: 3.0 eq, 110° C., 1 h | 554 $[M + H]^+$ | 1.14 (C) |
| 2.03 | 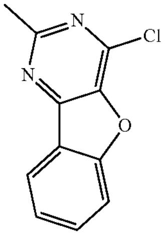 + Int. 9.2 (1.0 eq) | 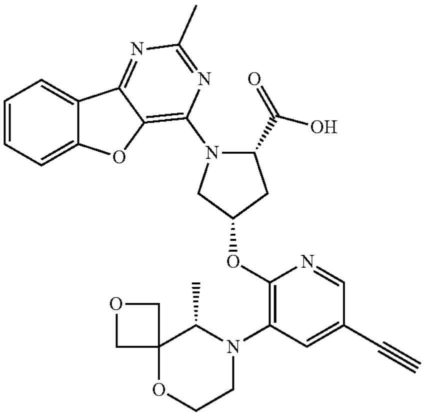 [SMILES: C#Cc1cnc(O[C@H]2C[C@@H](C(=O)O)N(c3nc(C)nc4c3oc3ccccc34)C2)c(N2CCOC3(COC3)[C@@H]2C)c1] | 4 eq. $K_2CO_3$ solvent: DMF, RT, 1 h, 50° C. 30 min | 556 $[M + H]^+$ | 0.50 (A) |
| 2.04 | 1.2.VI + Int. 9.2 | 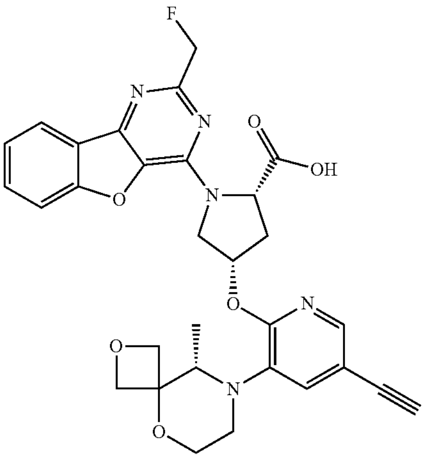 [SMILES: C#Cc1cnc(O[C@H]2C[C@@H](C(=O)O)N(c3nc(CF)nc4c3oc3ccccc34)C2)c(N2CCOC3(COC3)[C@@H]2C)c1] | 4 eq. $K_2CO_3$ solvent: DMF, RT, 45 min, 50° C., 30 min | 574 $[M + H]^+$ | 0.58 (A) |

-continued
| Ex. | Starting materials | Structure | Reaction conditions | ESI-MS | $R_t$ (HPLC) [min] (method) |
|---|---|---|---|---|---|
| 2.05 | Int. 1.3.VII + Int. 9.2 | 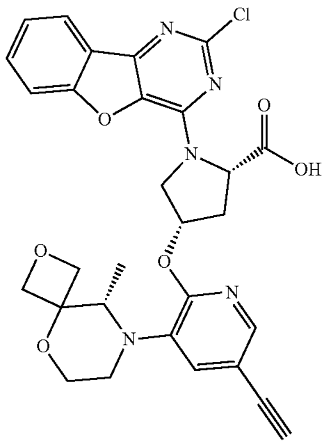 [SMILES: C#Cc1cnc(O[C@H]2C[C@@H](C(=O)O)N(c3nc(Cl)nc4c3oc3ccccc34)C2)c(N2CCOC3(COC3)[C@@H]2C)c1] | 4 eq. $K_2CO_3$ solvent: DMF, RT 2 h | 576 $[M + H]^+$ | 0.66 (A) |
| 2.06 | Int. 10.4.I + Int. 9.2 | 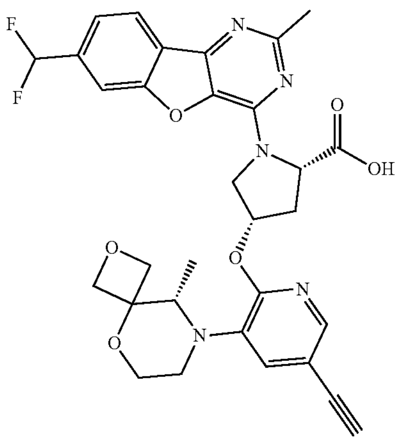 [SMILES: C#Cc1cnc(O[C@H]2C[C@@H](C(=O)O)N(c3nc(C)nc4c3oc3cc(C(F)F)ccc34)C2)c(N2CCOC3(COC3)[C@@H]2C)c1] | 4 eq. $K_2CO_3$ solvent: DMF, RT 2 h, 50° C. 1 h | 606 $[M + H]^+$ | 0.53 (A) |
| 2.07 | Int. 10.4.II + Int. 9.2 | 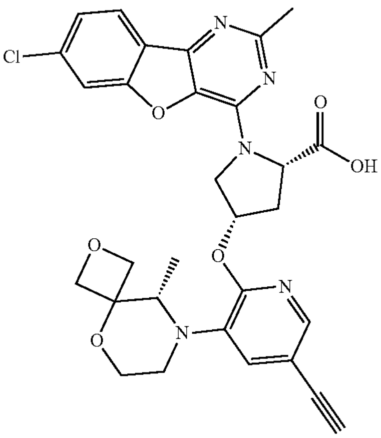 [SMILES: C#Cc1cnc(O[C@H]2C[C@@H](C(=O)O)N(c3nc(C)nc4c3oc3cc(Cl)ccc34)C2)c(N2CCOC3(COC3)[C@@H]2C)c1] | 4 eq. $K_2CO_3$ solvent: DMF, RT 2 h, 50° C. 1 h | 590 $[M + H]^+$ | 0.54 (A) |

-continued
| Ex. | Starting materials | Structure | Reaction conditions | ESI-MS | $R_t$ (HPLC) [min] (method) |
|---|---|---|---|---|---|
| 2.08 | Int. 10.4.III + Int. 9.2 | 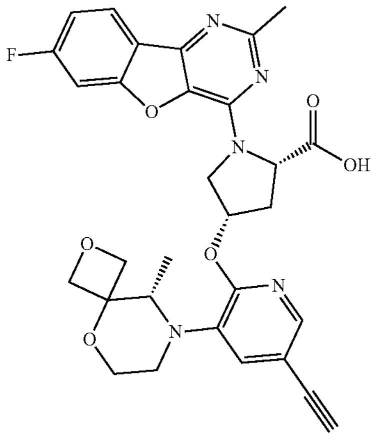 [SMILES: C#Cc1cnc(O[C@H]2C[C@@H](C(=O)O)N(c3nc(C)nc4c3oc3cc(F)ccc34)C2)c(N2CCOC3(COC3)[C@@H]2C)c1] | 4 eq. $K_2CO_3$ solvent: DMF, RT 1 h, 50° C. 1 h | 574 $[M + H]^+$ | 0.51 (A) |
| 2.09 | Int. 14.4 + Int. 9.2 | 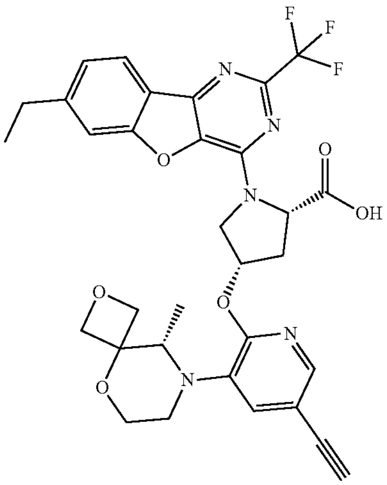 [SMILES: C#Cc1cnc(O[C@H]2C[C@@H](C(=O)O)N(c3nc(C(F)(F)F)nc4c3oc3cc(CC)ccc34)C2)c(N2CCOC3(COC3)[C@@H]2C)c1] | 4 eq. $K_2CO_3$ solvent: DMF, RT 2 h, 50° C. 4.5 h | 638 $[M + H]^+$ | 0.78 (A) |
| 2.10 | Int. 15.3 + Int. 9.2 | 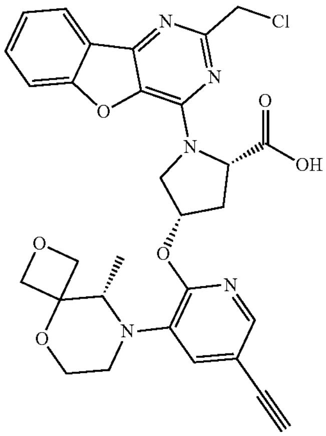 [SMILES: C#Cc1cnc(O[C@H]2C[C@@H](C(=O)O)N(c3nc(CCl)nc4c3oc3ccccc34)C2)c(N2CCOC3(COC3)[C@@H]2C)c1] | 2.3 eq. $K_2CO_3$, DMF, RT 6 h | 590/592 $[M + H]^+$ | 0.68 (A) |

Example 3.01 (General Route)

(2S,4S)-4-({5-[(35)-3-methylmorpholin-4-yl]-[3,4'-bipyridin]-6-yl}oxy)-1-[4-(trifluoromethyl)-8-oxa-3,5-diazatricyclo[7.4.0.0$^{2,7}$]trideca-1(9),2(7),3,5,10,12-hexaen-6-yl]pyrrolidine-2-carboxylic acid

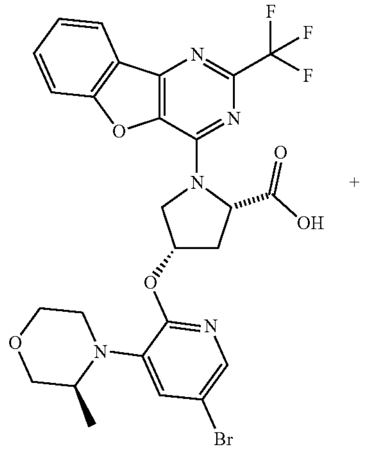

Int. 3.1.II

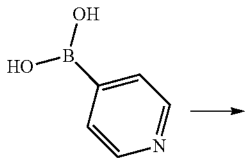

-continued

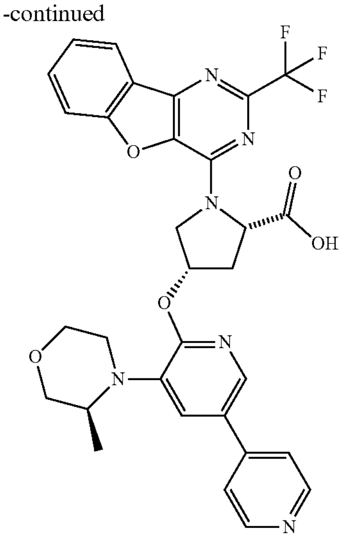

Ex. 3.01

To a mixture of (2S,4S)-4-({5-bromo-3-[(3S)-3-methylmorpholin-4-yl]pyridin-2-yl}oxy)-1-[4-(trifluoromethyl)-8-oxa-3,5-diazatricyclo[7.4.0.0$^{2,7}$]trideca-1(9),2(7),3,5,10,12-hexaen-6-yl]pyrrolidine-2-carboxylic acid (INTERMEDIATE 3.1.II, 50.0 mg, 0.08 mmol), (pyridin-4-yl)boronic acid (24.7 mg, 0.20 mmol), $Na_2CO_3$ solution (2.0M, 100 μL, 0.20 mmol), Xphos 3$^{rd}$ gen (3.40 mg) and $Pd(PPh_3)_4$ (4.64 mg) was added under argon 2.00 mL dioxane. The reaction mixture was stirred for 2 h at 100° C. The reaction mixture was filtered, diluted with ACN/methanol and purified by HPLC (Xbridge, ACN/$H_2O$/TFA).

ESI-MS: 621 $[M+H]^+$ $R_t$ (H PLC): 0.818 min (method B)

The following EXAMPLES were prepared according to the general procedure (EXAMPLE 3.01) described above. The boronates or boronic acids used are either commercially available or can be easily prepared as described in the literature (Boronic Acids: Preparation and Applications in Organic Synthesis, Medicine and Materials, 1&2, 2$^{nd}$ Edition, ISBN 9783527325986).

| Ex. | Starting materials | Structure | Reaction conditions | ESI-MS | $R_t$ (HPLC) [min] (method) |
|---|---|---|---|---|---|
| 3.02 | Int. 3.1.II + 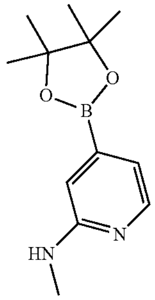 | 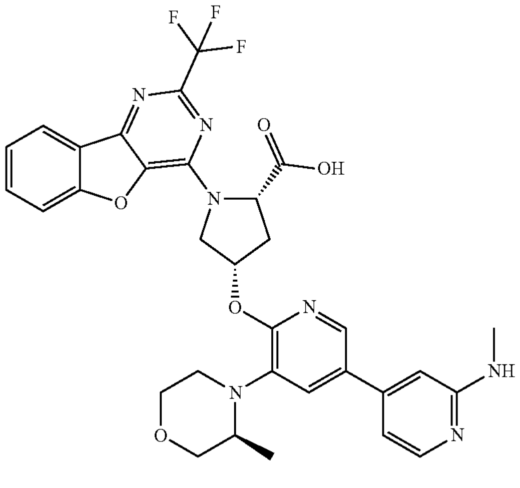 [SMILES: CNc1cc(-c2cnc(O[C@H]3C[C@@H](C(=O)O)N(c4nc(C(F)(F)F)nc5c4oc4ccccc45)C3)c(N3CCOC[C@@H]3C)c2)ccn1] | solvent: dioxane, 2 h 100° C., RT overnight | 650 $[M + H]^+$ | 0.81 (B) |

-continued
| Ex. | Starting materials | Structure | Reaction conditions | ESI-MS | $R_t$ (HPLC) [min] (method) |
|---|---|---|---|---|---|
| 3.03 | Int. 3.1.II + 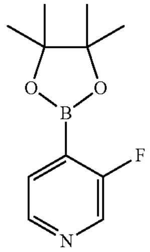 | 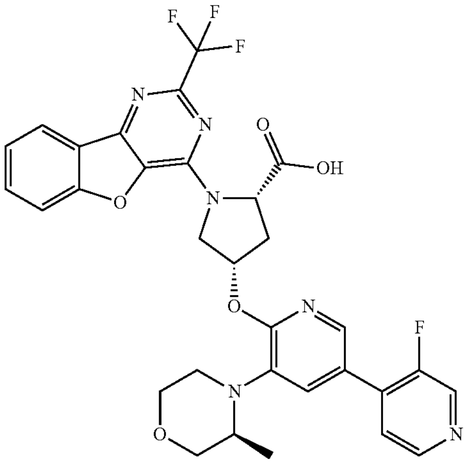 [SMILES: C[C@H]1COCCN1c1cc(-c2ccncc2F)cnc1O[C@H]1C[C@@H](C(=O)O)N(c2nc(C(F)(F)F)nc3c2oc2ccccc23)C1] | solvent: dioxane, 2 h 100° C. | 639 $[M + H]^+$ | 0.56 (K) |
| 3.04 | Int. 3.1.II + 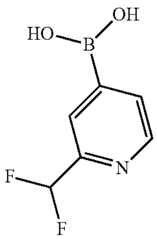 [SMILES: OB(O)c1ccnc(C(F)F)c1] | 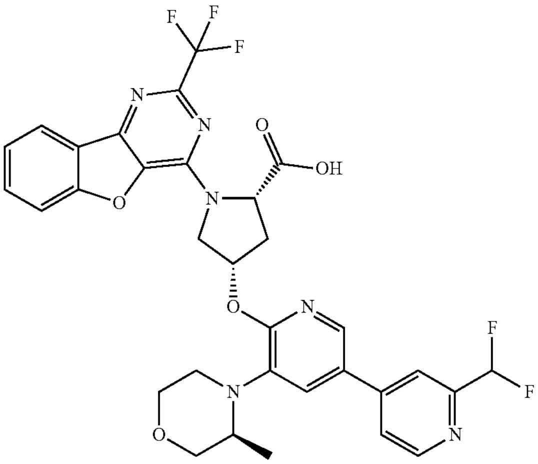 [SMILES: C[C@H]1COCCN1c1cc(-c2ccnc(C(F)F)c2)cnc1O[C@H]1C[C@@H](C(=O)O)N(c2nc(C(F)(F)F)nc3c2oc2ccccc23)C1] | solvent: dioxane, 2 h 100° C. | 671 $[M + H]^+$ | 0.59 (K) |
| 3.05 | Int. 3.1.II + 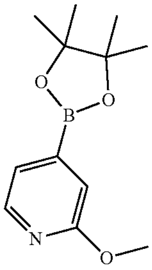 | 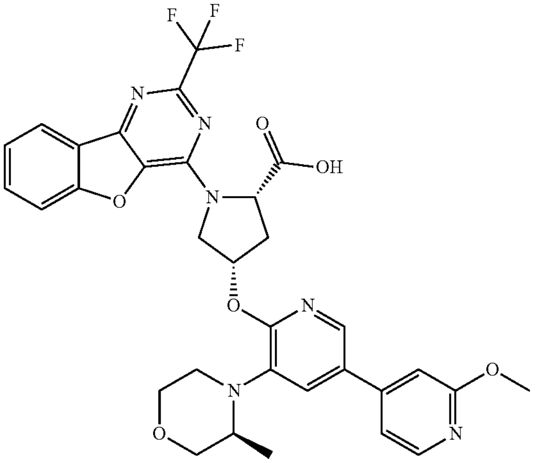 [SMILES: COc1cc(-c2cnc(O[C@H]3C[C@@H](C(=O)O)N(c4nc(C(F)(F)F)nc5c4oc4ccccc45)C3)c(N3CCOC[C@@H]3C)c2)ccn1] | solvent: dioxane, 2 h 100° C. | 651 $[M + H]^+$ | 1.11 (B) |

-continued
| Ex. | Starting materials | Structure | Reaction conditions | ESI-MS | $R_t$ (HPLC) [min] (method) |
|---|---|---|---|---|---|
| 3.06 | Int. 3.1.II + 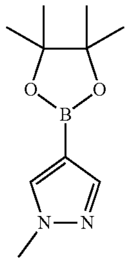 | 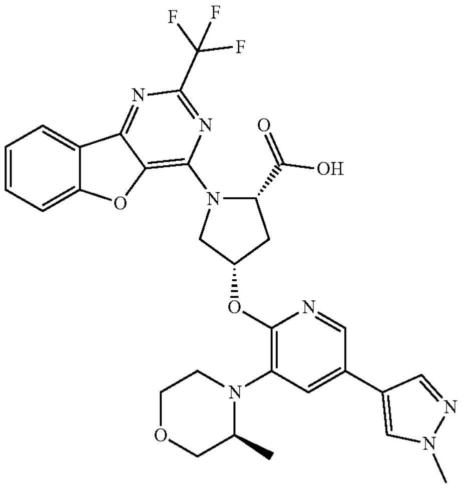 [SMILES: C[C@H]1COCCN1c1cc(-c2cnn(C)c2)cnc1O[C@H]1C[C@@H](C(=O)O)N(c2nc(C(F)(F)F)nc3c2oc2ccccc23)C1] | solvent: dioxane, 2 h 100° C., RT overnight | 624 $[M + H]^+$ | 0.91 (B) |
| 3.07 | Int. 3.1.II + 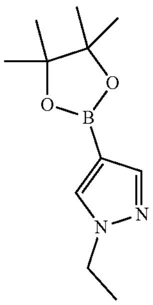 | 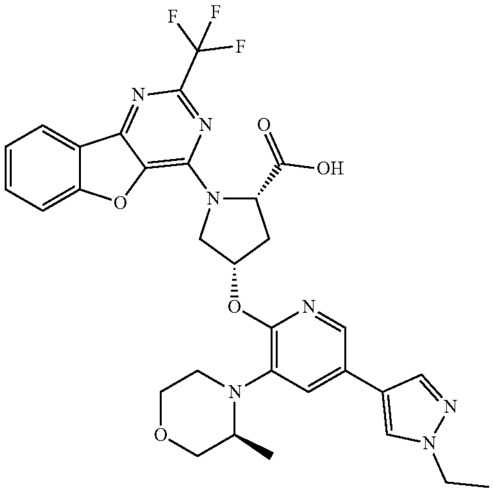 [SMILES: CCn1cc(-c2cnc(O[C@H]3C[C@@H](C(=O)O)N(c4nc(C(F)(F)F)nc5c4oc4ccccc45)C3)c(N3CCOC[C@@H]3C)c2)cn1] | solvent: dioxane, 2 h 100° C., RT overnight | 638 $[M + H]^+$ | 0.94 (B) |
| 3.08 | Int. 3.1.I + 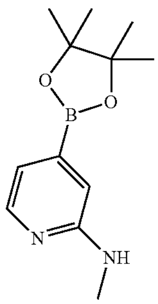 | 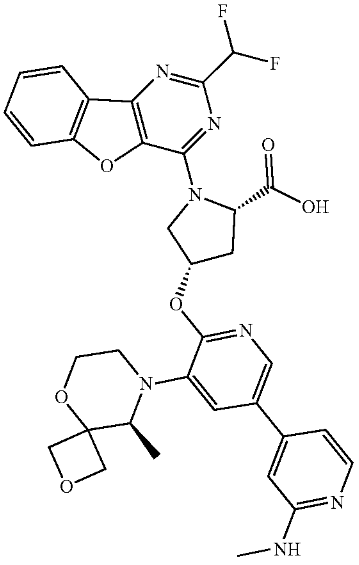 [SMILES: CNc1cc(-c2cnc(O[C@H]3C[C@@H](C(=O)O)N(c4nc(C(F)F)nc5c4oc4ccccc45)C3)c(N3CCOC4(COC4)[C@@H]3C)c2)ccn1] | solvent: dioxane, 1.5 h 100° C. | 674 $[M + H]^+$ | 0.76 (I) |

-continued
| Ex. | Starting materials | Structure | Reaction conditions | ESI-MS | $R_t$ (HPLC) [min] (method) |
|---|---|---|---|---|---|
| 3.09 | Ex. 1.10 + 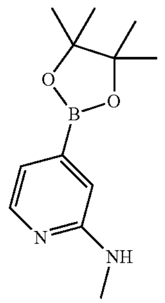 | 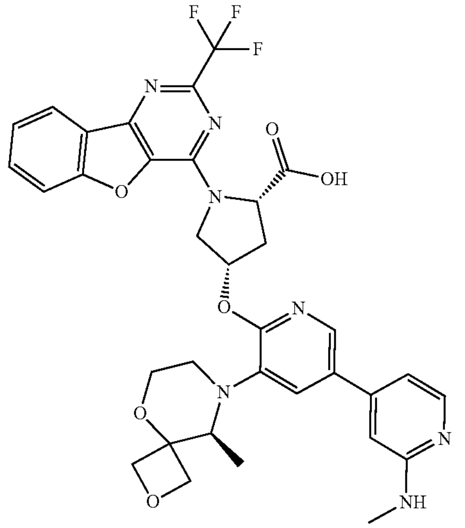 [SMILES: CNc1cc(-c2cnc(O[C@H]3C[C@@H](C(=O)O)N(c4nc(C(F)(F)F)nc5c4oc4ccccc45)C3)c(N3CCOC4(COC4)[C@@H]3C)c2)ccn1] | solvent: dioxane, 100° C., 1.5 h | 692 $[M + H]^+$ | 0.72 (J) |
| 3.10 | Ex. 1.10 + 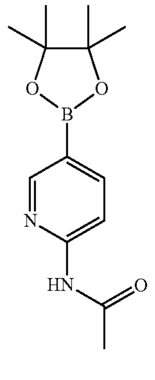 | 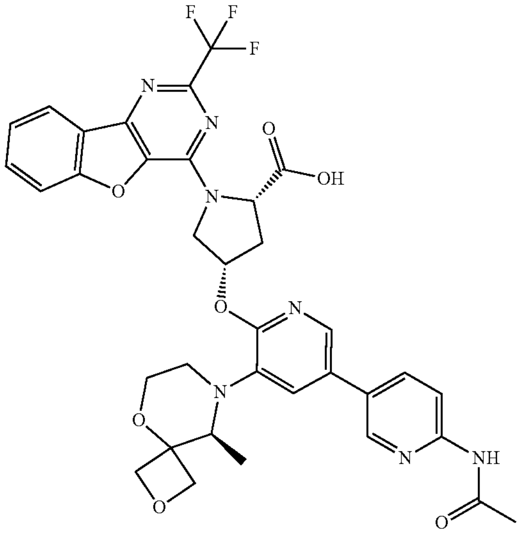 [SMILES: CC(=O)Nc1ccc(-c2cnc(O[C@H]3C[C@@H](C(=O)O)N(c4nc(C(F)(F)F)nc5c4oc4ccccc45)C3)c(N3CCOC4(COC4)[C@@H]3C)c2)cn1] | solvent: dioxane, 100° C., 1.5 h | 720 $[M + H]^+$ | 0.50 (K) |

-continued
| Ex. | Starting materials | Structure | Reaction conditions | ESI-MS | $R_t$ (HPLC) [min] (method) |
|---|---|---|---|---|---|
| 3.11 | Ex. 1.10 + 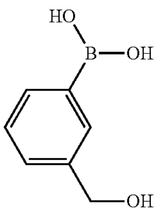 [SMILES: OCc1cccc(B(O)O)c1] | 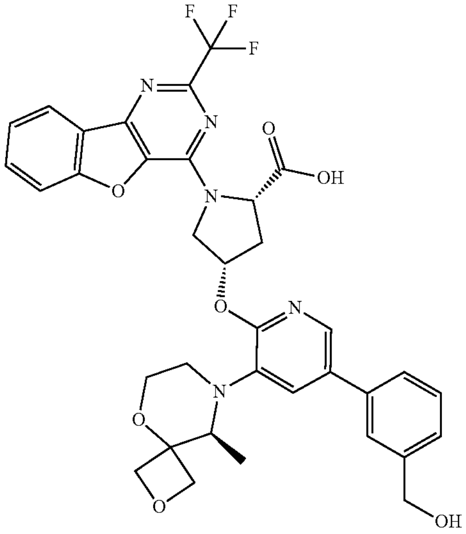 [SMILES: C[C@@H]1N(c2cc(-c3cccc(CO)c3)cnc2O[C@H]2C[C@@H](C(=O)O)N(c3nc(C(F)(F)F)nc4c3oc3ccccc34)C2)CCOC12COC2] | solvent: dioxane, 100° C., 4 h | 674 $[M + H]^+$ | 0.92 (J) |
| 3.12 | Ex. 1.10 + 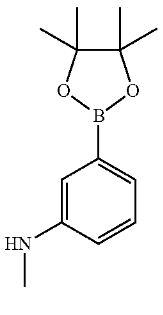 | 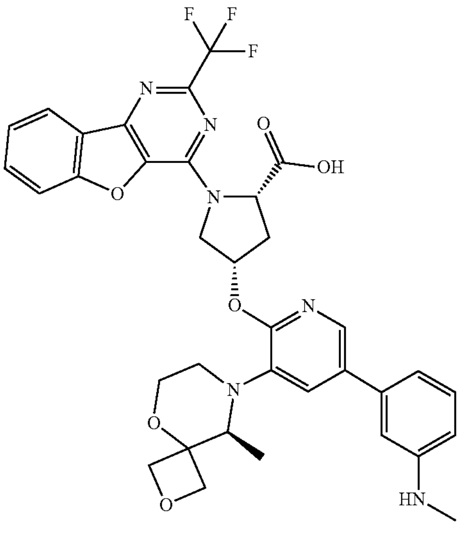 [SMILES: CNc1cccc(-c2cnc(O[C@H]3C[C@@H](C(=O)O)N(c4nc(C(F)(F)F)nc5c4oc4ccccc45)C3)c(N3CCOC4(COC4)[C@@H]3C)c2)c1] | solvent: dioxane, 100° C. 2 h | 691 $[M + H]^+$ | 0.58 (D) |

-continued
| Ex. | Starting materials | Structure | Reaction conditions | ESI-MS | $R_t$ (HPLC) [min] (method) |
|---|---|---|---|---|---|
| 3.13 | Ex. 1.10 + 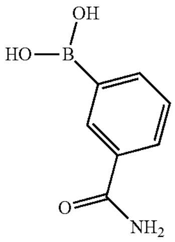 [SMILES: NC(=O)c1cccc(B(O)O)c1] | 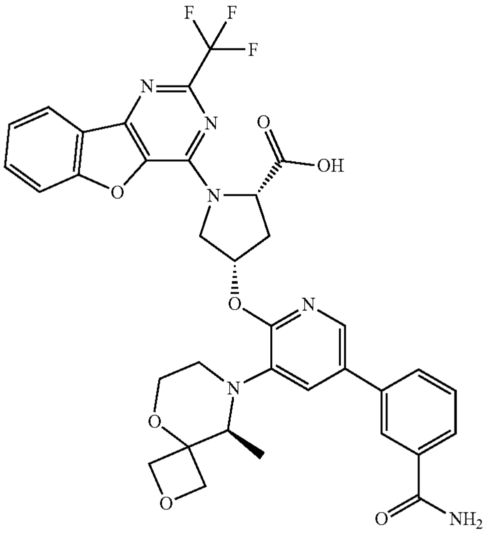 [SMILES: C[C@@H]1N(c2cc(-c3cccc(C(N)=O)c3)cnc2O[C@H]2C[C@@H](C(=O)O)N(c3nc(C(F)(F)F)nc4c3oc3ccccc34)C2)CCOC12COC2] | solvent: dioxane, 100° C. 1 h | 705 $[M + H]^+$ | 0.64 (A) |
| 3.14 | Ex. 1.10 + 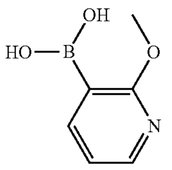 | 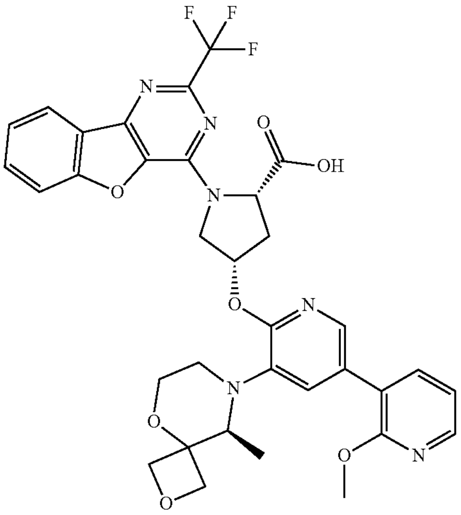 [SMILES: COc1ncccc1-c1cnc(O[C@H]2C[C@@H](C(=O)O)N(c3nc(C(F)(F)F)nc4c3oc3ccccc34)C2)c(N2CCOC3(COC3)[C@@H]2C)c1] | solvent: dioxane, 100° C. 1.5 h | 693 $[M + H]^+$ | 0.57 (K) |

-continued
| Ex. | Starting materials | Structure | Reaction conditions | ESI-MS | $R_t$ (HPLC) [min] (method) |
|---|---|---|---|---|---|
| 3.15 | Int. 3.1.I + 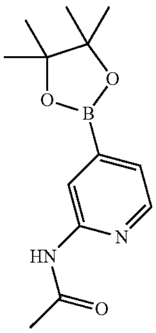 | 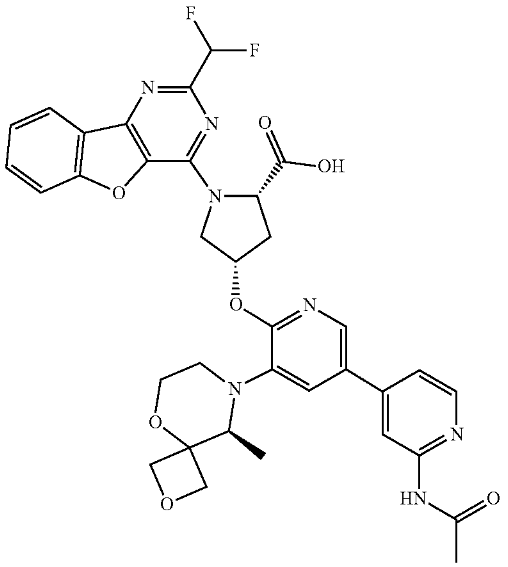 [SMILES: CC(=O)Nc1cc(-c2cnc(O[C@H]3C[C@@H](C(=O)O)N(c4nc(C(F)F)nc5c4oc4ccccc45)C3)c(N3CCOC4(COC4)[C@@H]3C)c2)ccn1] | solvent: dioxane, 100° C. 1.5 h | 702 [M + H]$^+$ | 0.69 (H) |
| 3.16 | Int. 3.1.I + 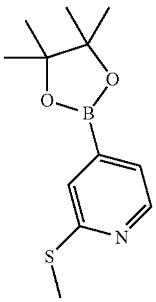 | 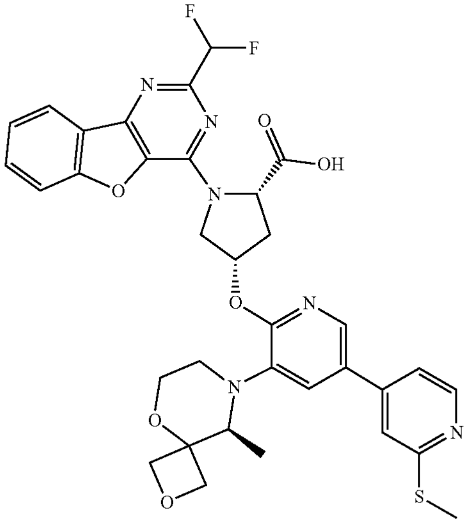 [SMILES: CSc1cc(-c2cnc(O[C@H]3C[C@@H](C(=O)O)N(c4nc(C(F)F)nc5c4oc4ccccc45)C3)c(N3CCOC4(COC4)[C@@H]3C)c2)ccn1] | solvent: dioxane, 100° C. 1.5 h | 691 [M + H]$^+$ | 0.54 (D) |
| 3.17 | Ex. 1.10 + 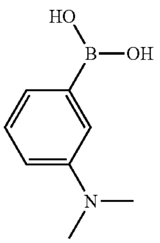 | 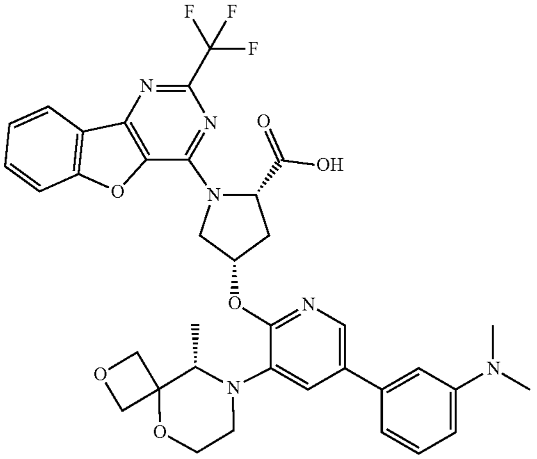 [SMILES: C[C@@H]1N(c2cc(-c3cccc(N(C)C)c3)cnc2O[C@H]2C[C@@H](C(=O)O)N(c3nc(C(F)(F)F)nc4c3oc3ccccc34)C2)CCOC12COC2] | solvent: dioxane, 100° C. 6 h | 705 [M + H]$^+$ | 0.83 (H) |

-continued
| Ex. | Starting materials | Structure | Reaction conditions | ESI-MS | $R_t$ (HPLC) [min] (method) |
|---|---|---|---|---|---|
| 3.18 | Ex. 1.10 + 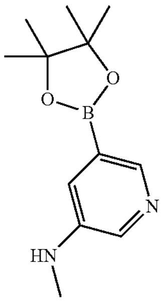 | 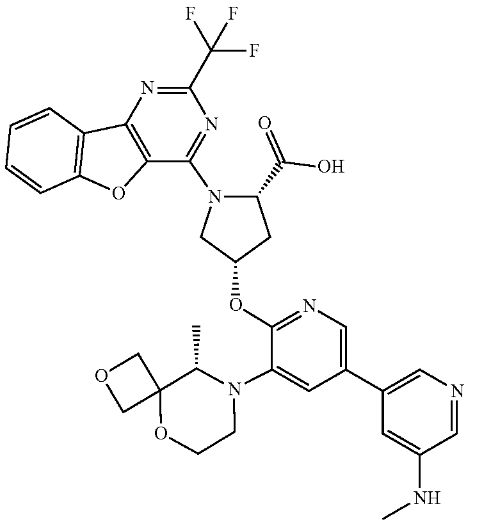 [SMILES: CNc1cncc(-c2cnc(O[C@H]3C[C@@H](C(=O)O)N(c4nc(C(F)(F)F)nc5c4oc4ccccc45)C3)c(N3CCOC4(COC4)[C@@H]3C)c2)c1] | solvent: dioxane, 100° C. 1.5 h | 692 $[M + H]^+$ | 0.73 (H) |
| 3.19 | Int. 3.1.I + 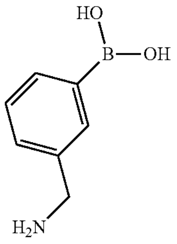 [SMILES: NCc1cccc(B(O)O)c1] | 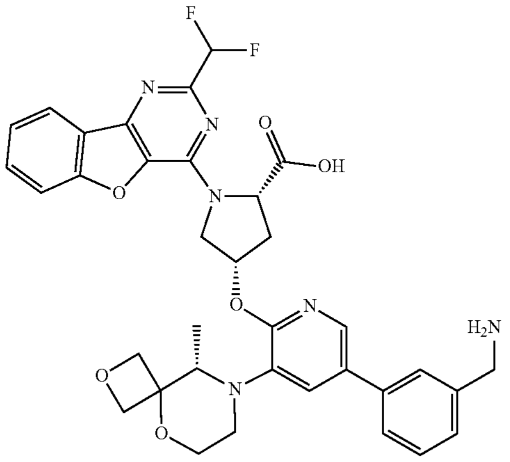 [SMILES: C[C@@H]1N(c2cc(-c3cccc(CN)c3)cnc2O[C@H]2C[C@@H](C(=O)O)N(c3nc(C(F)F)nc4c3oc3ccccc34)C2)CCOC12COC2] | solvent: dioxane, 100° C. overnight | 673 $[M + H]^+$ | 0.68 (H) |
| 3.20 | Ex. 1.10 + 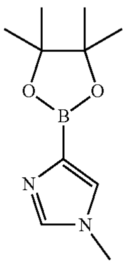 | 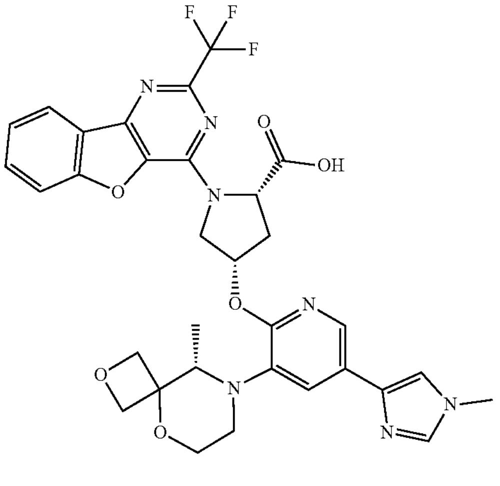 [SMILES: C[C@@H]1N(c2cc(-c3cn(C)cn3)cnc2O[C@H]2C[C@@H](C(=O)O)N(c3nc(C(F)(F)F)nc4c3oc3ccccc34)C2)CCOC12COC2] | solvent: dioxane, 100° C., 1.5 h | 666 $[M + H]^+$ | 0.69 (H) |

-continued
| Ex. | Starting materials | Structure | Reaction conditions | ESI-MS | $R_t$ (HPLC) [min] (method) |
|---|---|---|---|---|---|
| 3.21 | Int. 3.1.I + 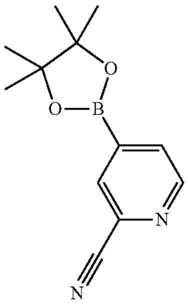 | 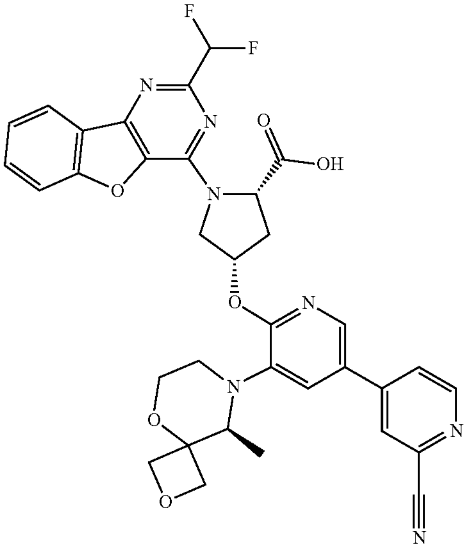 [SMILES: C[C@@H]1N(c2cc(-c3ccnc(C#N)c3)cnc2O[C@H]2C[C@@H](C(=O)O)N(c3nc(C(F)F)nc4c3oc3ccccc34)C2)CCOC12COC2] | solvent: dioxane, 100° C., 2.5 h, RT overnight | 670 $[M + H]^+$ | 0.50 (D) |
| 3.22 | Ex. 1.10 + 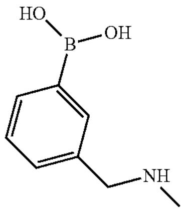 | 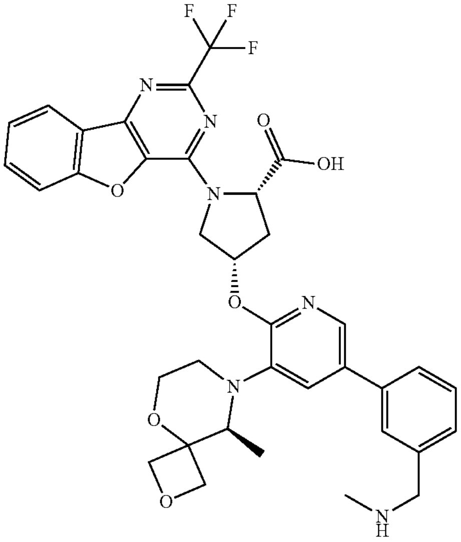 [SMILES: CNCc1cccc(-c2cnc(O[C@H]3C[C@@H](C(=O)O)N(c4nc(C(F)(F)F)nc5c4oc4ccccc45)C3)c(N3CCOC4(COC4)[C@@H]3C)c2)c1] | solvent: dioxane, 100° C. 3 h | 705 $[M + H]^+$ | 0.75 (H) |

-continued
| Ex. | Starting materials | Structure | Reaction conditions | ESI-MS | $R_t$ (HPLC) [min] (method) |
| --- | --- | --- | --- | --- | --- |
| 3.23 | Ex. 1.10 + 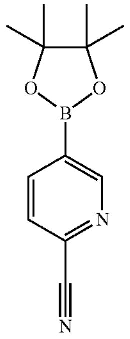 | 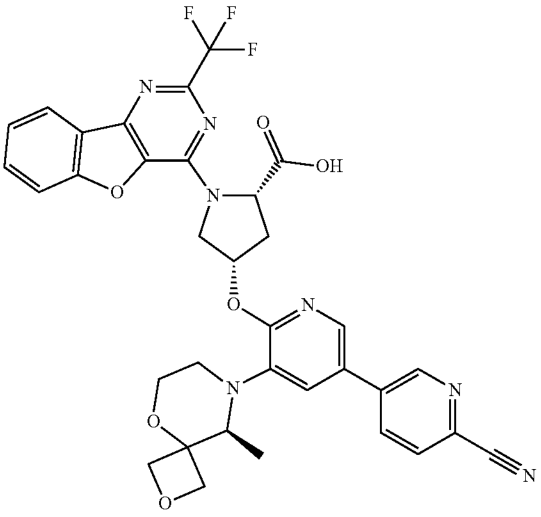 [SMILES: C[C@@H]1N(c2cc(-c3ccc(C#N)nc3)cnc2O[C@H]2C[C@@H](C(=O)O)N(c3nc(C(F)(F)F)nc4c3oc3ccccc34)C2)CCOC12COC2] | solvent: dioxane, 100° C. 1.5 h | 688 $[M + H]^+$ | 1.01 (B) |
| 3.24 | Int. 3.1.I 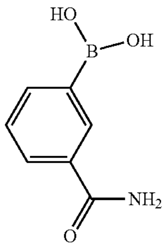 [SMILES: NC(=O)c1cccc(B(O)O)c1] | 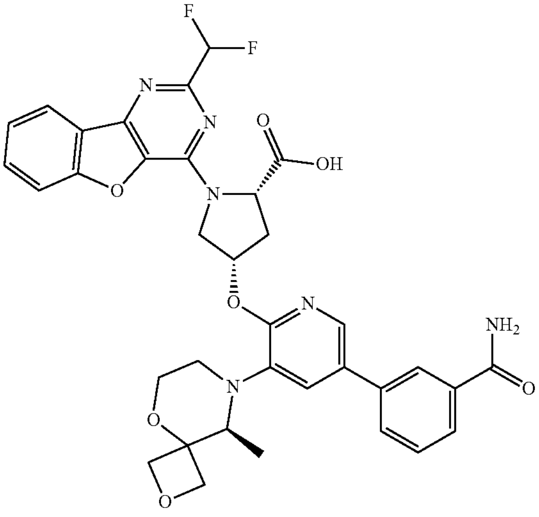 [SMILES: C[C@@H]1N(c2cc(-c3cccc(C(N)=O)c3)cnc2O[C@H]2C[C@@H](C(=O)O)N(c3nc(C(F)F)nc4c3oc3ccccc34)C2)CCOC12COC2] | solvent: dioxane, 100° C. 2.5 h | 687 $[M + H]^+$ | 0.85 (J) |
| 3.25 | Ex. 1.10 + 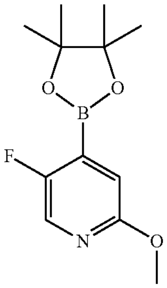 | 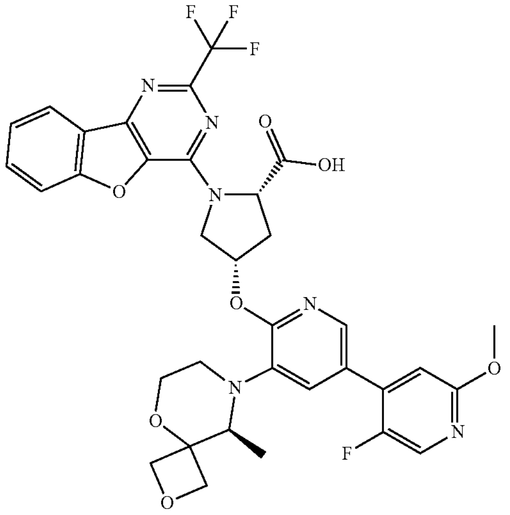 [SMILES: COc1cc(-c2cnc(O[C@H]3C[C@@H](C(=O)O)N(c4nc(C(F)(F)F)nc5c4oc4ccccc45)C3)c(N3CCOC4(COC4)[C@@H]3C)c2)c(F)cn1] | solvent: dioxane, 100° C. 1.5 h, RT overnight | 711 $[M + H]^+$ | 0.60 (D) |

-continued
| Ex. | Starting materials | Structure | Reaction conditions | ESI-MS | $R_t$ (HPLC) [min] (method) |
|---|---|---|---|---|---|
| 3.26 | Ex. 1.10 + 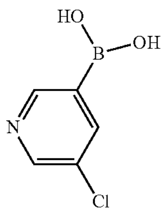 | 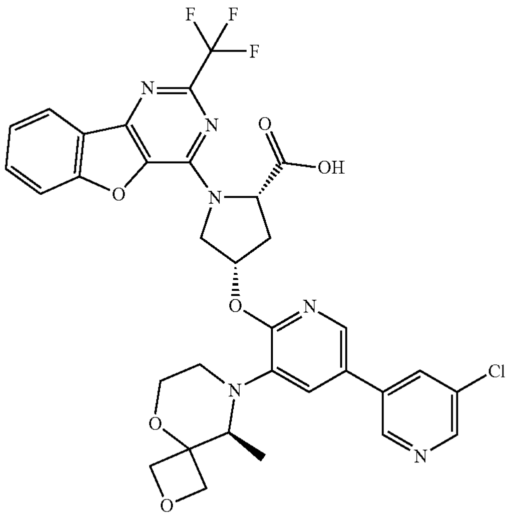 [SMILES: C[C@@H]1N(c2cc(-c3cncc(Cl)c3)cnc2O[C@H]2C[C@@H](C(=O)O)N(c3nc(C(F)(F)F)nc4c3oc3ccccc34)C2)CCOC12COC2] | solvent: dioxane, 100° C. 1.5 h, RT overnight | 697 $[M + H]^+$ | 1.07 (J) |
| 3.27 | Ex. 1.10 + 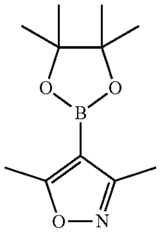 | 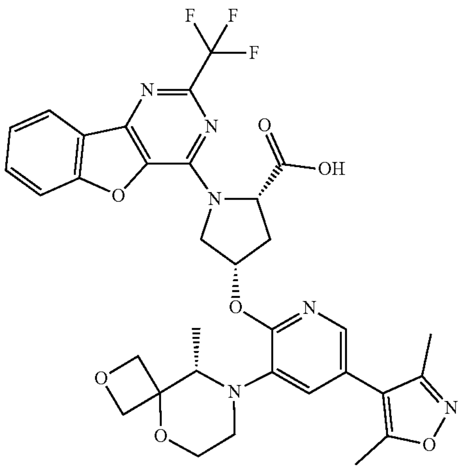 [SMILES: Cc1noc(C)c1-c1cnc(O[C@H]2C[C@@H](C(=O)O)N(c3nc(C(F)(F)F)nc4c3oc3ccccc34)C2)c(N2CCOC3(COC3)[C@@H]2C)c1] | solvent: dioxane, 100° C. 1.5 h, RT overnight | 681 $[M + H]^+$ | 1.04 (J) |
| 3.28 | Ex. 1.10 + 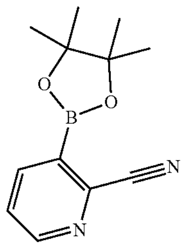 | 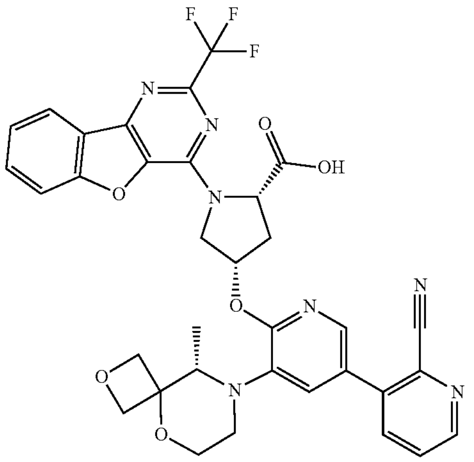 [SMILES: C[C@@H]1N(c2cc(-c3cccnc3C#N)cnc2O[C@H]2C[C@@H](C(=O)O)N(c3nc(C(F)(F)F)nc4c3oc3ccccc34)C2)CCOC12COC2] | solvent: dioxane, 100° C. 1.5 h, RT overnight | 688 $[M + H]^+$ | 1.00 (J) |

-continued
| Ex. | Starting materials | Structure | Reaction conditions | ESI-MS | $R_t$ (HPLC) [min] (method) |
|---|---|---|---|---|---|
| 3.29 | Ex. 1.10 + 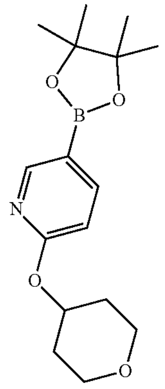 | 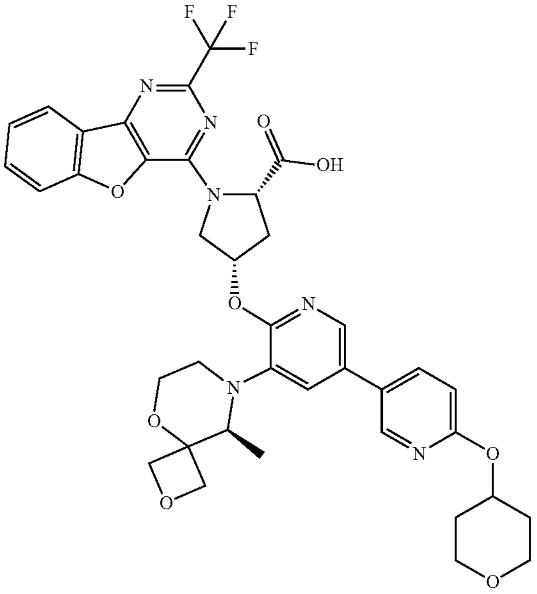 [SMILES: C[C@@H]1N(c2cc(-c3ccc(OC4CCOCC4)nc3)cnc2O[C@H]2C[C@@H](C(=O)O)N(c3nc(C(F)(F)F)nc4c3oc3ccccc34)C2)CCOC12COC2] | solvent: dioxane, 100° C. 1.5 h | 763 $[M + H]^+$ | 0.59 (K) |
| 3.30 | Ex. 1.10 + 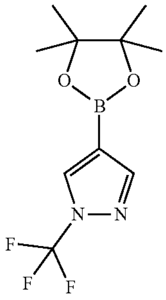 | 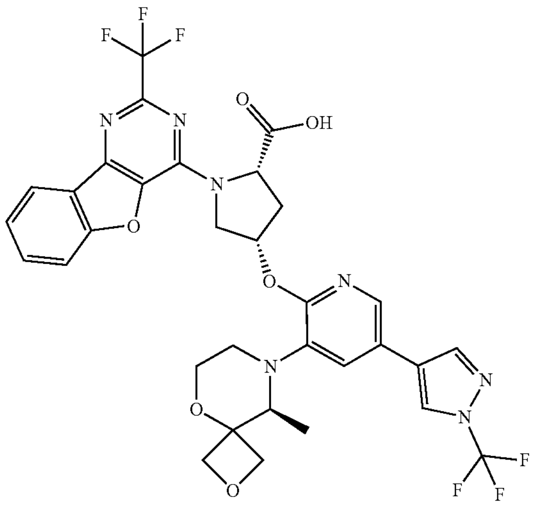 [SMILES: C[C@@H]1N(c2cc(-c3cnn(C(F)(F)F)c3)cnc2O[C@H]2C[C@@H](C(=O)O)N(c3nc(C(F)(F)F)nc4c3oc3ccccc34)C2)CCOC12COC2] | solvent: dioxane, 100° C. 2 h | 720 $[M + H]^+$ | 0.53 (A) |

-continued
| Ex. | Starting materials | Structure | Reaction conditions | ESI-MS | $R_t$ (HPLC) [min] (method) |
|---|---|---|---|---|---|
| 3.31 | Ex. 110 + 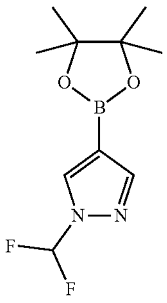 | 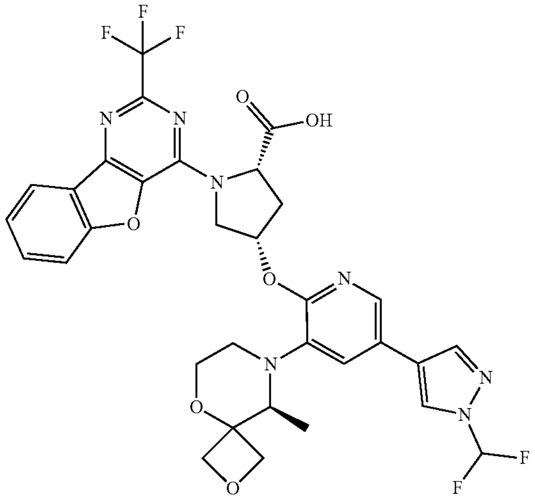 [SMILES: C[C@@H]1N(c2cc(-c3cnn(C(F)F)c3)cnc2O[C@H]2C[C@@H](C(=O)O)N(c3nc(C(F)(F)F)nc4c3oc3ccccc34)C2)CCOC12COC2] | solvent: dioxane, 100° C., 2 h | 702 $[M + H]^+$ | 0.55 (D) |
| 3.32 | Int. 3.1.I 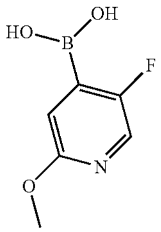 | 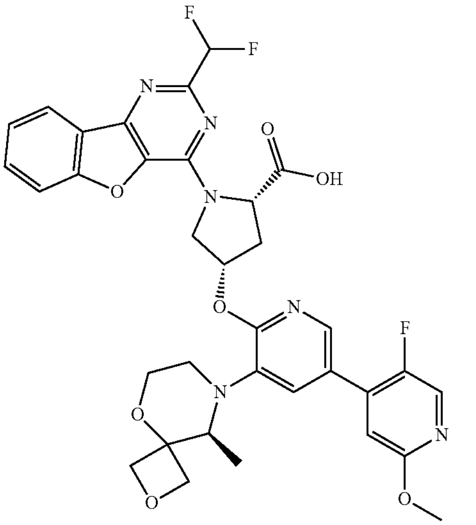 [SMILES: COc1cc(-c2cnc(O[C@H]3C[C@@H](C(=O)O)N(c4nc(C(F)F)nc5c4oc4ccccc45)C3)c(N3CCOC4(COC4)[C@@H]3C)c2)c(F)cn1] | solvent: dioxane, 90° C. 1 h | 693 $[M + H]^+$ | 1.05 (E) |

Example 4.01 (General Route)

(2S,4S)-1-[(Difluoromethyl)-8-oxa-3,5-diazatricyclo[7.4.0.0$^{2,7}$]trideca-1(9),2(7),3,5,10,12-hexaen-6-yl]-4-({N,N-dimethyl-5-[(9S)-9-methyl-2,5-dioxa-8-azaspiro[3.5]nonan-8-yl]-[3,4'-bipyridin]-2'-yl}oxy)pyrrolidine-2-carboxylic acid

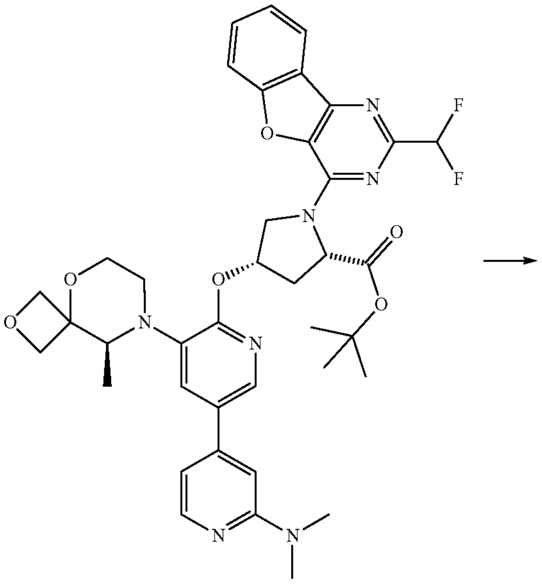

Int. 3.4.I

-continued

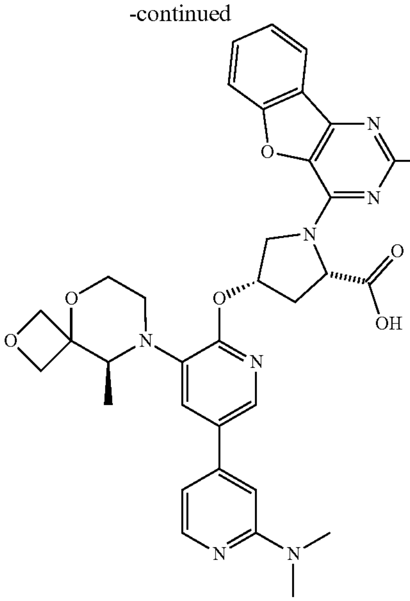

Ex. 4.01

To tert-butyl (2S,4S)-1-[4-(difluoromethyl)-8-oxa-3,5-diazatricyclo[7.4.0.0$^{2,7}$]trideca-1(9),2(7),3,5,10,12-hexaen-6-yl]-4-({N,N-dimethyl-5-[(9S)-9-methyl-2,5-dioxa-8-aza-spiro[3.5]nonan-8-yl]-[3,4'-bipyridin]-2'-yl}oxy)pyrrolidine-2-carboxylate (INTERMEDIATE 3.4.I, 13 mg, 0.020 mmol) in 2.00 mL DCM was added over a period of 1 day trifluoroacetic acid (650 μL, 8.49 mmol). The reaction mixture was stirred overnight at RT and then concentrated under reduced pressure. The crude product was purified by HPLC (Xbridge, ACN/$H_2O$/TFA).

ESI-MS: 688 $[M+H]^+$ $R_t$ (HPLC): 0.51 min (method A)

The following EXAMPLES were prepared according to the general procedure (EXAMPLE 4.1) described above:

| Ex. | Starting material | Structure | Reaction conditions | ESI-MS | $R_t$ (HPLC) [min] (method) |
|---|---|---|---|---|---|
| 4.02 | Int. 3.4.II | 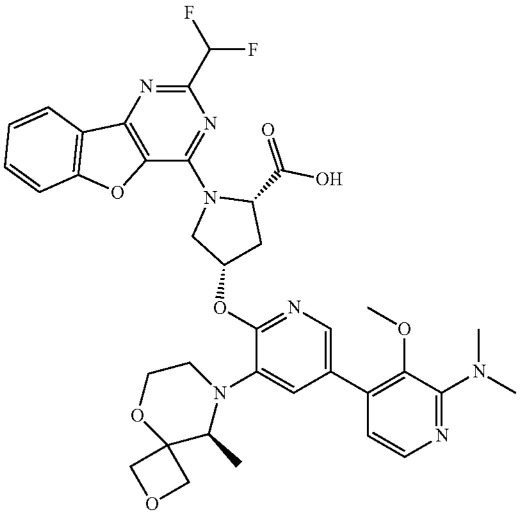 [SMILES: COc1c(-c2cnc(O[C@H]3C[C@@H](C(=O)O)N(c4nc(C(F)F)nc5c4oc4ccccc45)C3)c(N3CCOC4(COC4)[C@@H]3C)c2)ccnc1N(C)C] | solvent: DCM, RT overnight | 718 $[M + H]^+$ | 0.53 (A) |

-continued
| Ex. | Starting material | Structure | Reaction conditions | ESI-MS | $R_t$ (HPLC) [min] (method) |
|---|---|---|---|---|---|
| 4.03 | Int.3.4.III | 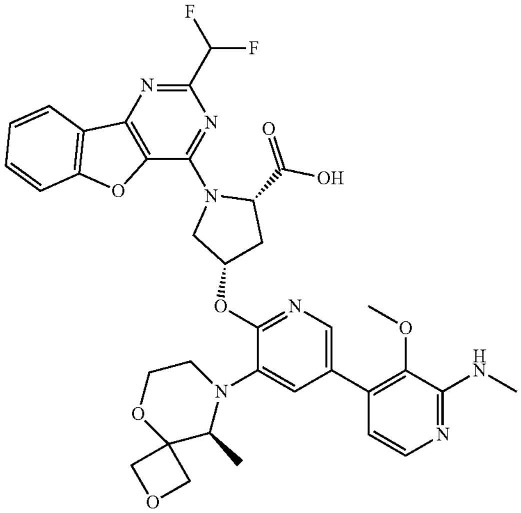 [SMILES: CNc1nccc(-c2cnc(O[C@H]3C[C@@H](C(=O)O)N(c4nc(C(F)F)nc5c4oc4ccccc45)C3)c(N3CCOC4(COC4)[C@@H]3C)c2)c1OC] | solvent: DCM, RT overnight | 704 $[M + H]^+$ | 0.51 (A) |
| 4.04 | Int.3.4.IV | 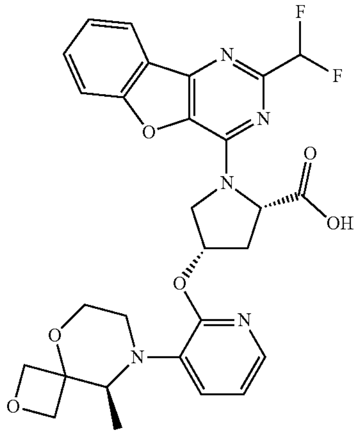 [SMILES: C[C@@H]1N(c2cccnc2O[C@H]2C[C@@H](C(=O)O)N(c3nc(C(F)F)nc4c3oc3ccccc34)C2)CCOC12COC2] | solvent: DCM, RT overnight | 568 $[M + H]^+$ | 0.63 (A) |

Example 5.01

(2S,4S)-1-[4-(Difluoromethyl)-8-oxa-3,5-diazatricyclo[7.4.0.0$^{2,7}$]trideca-1(9),2(7),3,5,10,12-hexaen-6-yl]-4-({2'-methanesulfinyl-5-[(9S)-9-methyl-2,5-dioxa-8-azaspiro[3.5]nonan-8-yl]-[3,4'-bipyridin]-6-yl}oxy)pyrrolidine-2-carboxylic acid

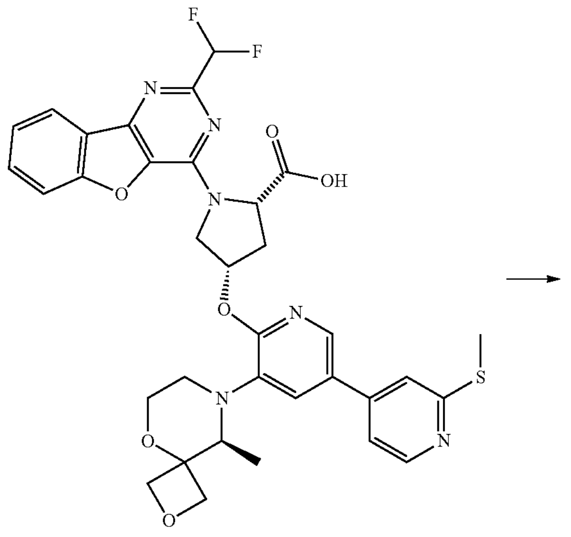

Ex. 3.16

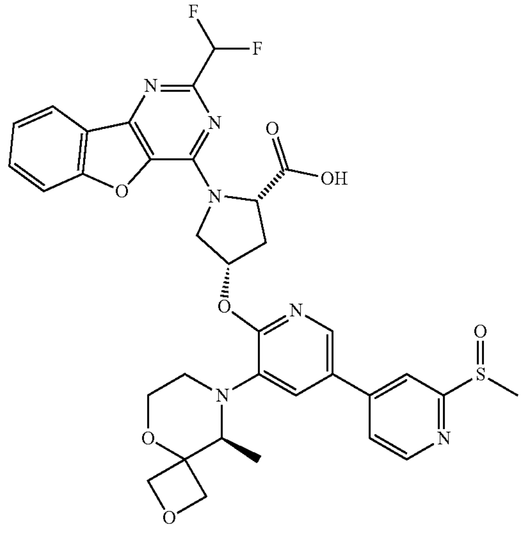

Ex. 5.01

To a cooled solution of (2S,4S)-1-[4-(difluoromethyl)-8-oxa-3,5-diazatricyclo-[7.4.0.0$^{2,7}$]trideca-1(9),2(7),3,5,10,12-hexaen-6-yl]-4-({5-[(9S)-9-methyl-2,5-dioxa-8-azaspiro[3.5]nonan-8-yl]-2'-(methylsulfanyl)-[3,4'-bipyridin]-6-yl}oxy)-pyrrolidine-2-carboxylic acid (EXAMPLE 3.16, 25.0 mg, 0.04 mmol) in 1.00 mL DCM was added at −15° C. meta-chloroperoxybenzoic acid (7.30 mg, 0.03 mmol). The reaction mixture was stirred at −15° C. for 10 min and subsequently purified by HPLC (Xbridge, ACN/$H_2O$/TFA).

ESI-MS: 707 $[M+H]^+$ $R_t$ (H PLC): 0.85 min (method H)

Example 6.01

(2S,4S)-4-({3-[(9S)-9-Methyl-2,5-dioxa-8-azaspiro[3.5]nonan-8-yl]-5-(prop-1-yn-1-yl)pyridin-2- yl}-oxy)-1-[4-(trifluoromethyl)-8-oxa-3,5-diazatricyclo[7.4.0.0$^{2,7}$]trideca-1(9),2(7),3,5,10,12hexaen-6-yl]pyrrolidine-2-carboxylic acid

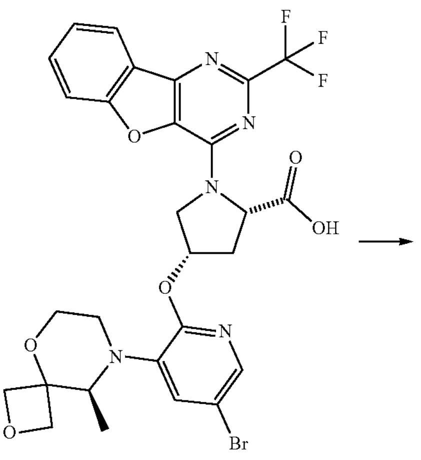

Ex. 1.10

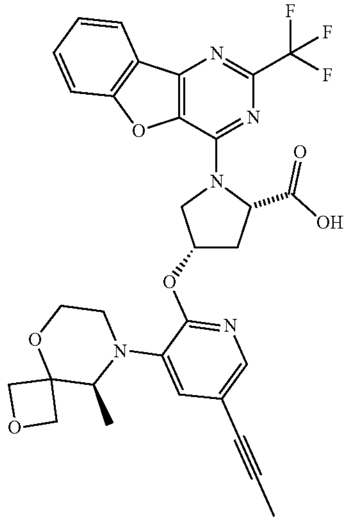

Ex. 6.01

To a degassed solution of (2S,4S)-4-({5-bromo-3-[(9S)-9-methyl-2,5-dioxa-8-azaspiro[3.5]nonan-8-yl]pyridin-2-yl}oxy)-1-[4-(trifluoromethyl)-8-oxa-3,5-diazatricyclo[7.4.0.0$^{2,7}$]trideca-1(9),2(7),3,5,10,12-hexaen-6-yl]pyrrolidine-2-carboxylic acid (EXAMPLE 1.10, 150 mg, 0.230 mmol) in 5.00 mL THE was added copper(I) iodide (4.3 mg, 0.023 mmol) followed by Pd(dppf)$Cl_2$ (33 mg, 0.050 mmol)). After stirring for a few minutes, a 1M solution of methylacetylene in THE (1.35 mL, 1.35 mmol) was added and the mixture was heated to 75° C. for 4 h. The reaction mixture was diluted with ACN, acidified with acetic acid, filtered and purified by HPLC (Xbridge, ACN/$H_2O$/TFA).

ESI-MS: 624 $[M+H]^+$ $R_t$ (H PLC): 1.08 min (method E)

The following EXAMPLES were prepared according to the general procedure (EXAMPLE 6.01) described above:

| Ex. | Starting material | Structure | Reaction conditions | ESI-MS | $R_t$ (HPLC) [min] (method) |
|---|---|---|---|---|---|
| 6.02 | Ex 1.10 | 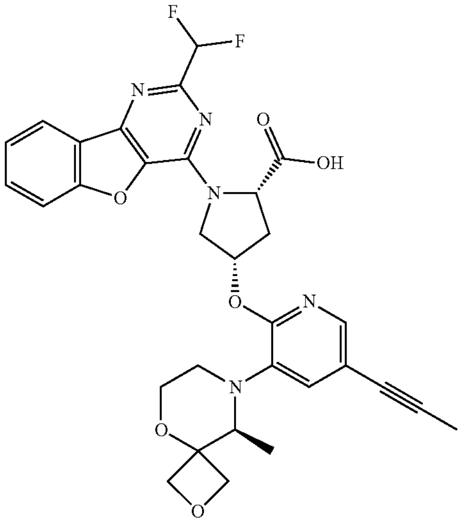 [SMILES: CC#Cc1cnc(O[C@H]2C[C@@H](C(=O)O)N(c3nc(C(F)F)nc4c3oc3ccccc34)C2)c(N2CCOC3(COC3)[C@@H]2C)c1] | like Ex. 6.01 | 606 $[M + H]^+$ | 1.01 (E) |
| 6.03 | Ex 1.33 | 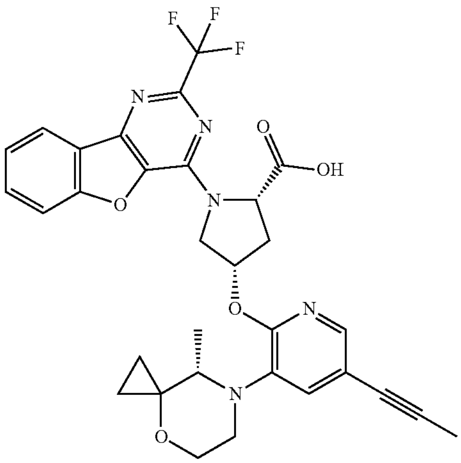 [SMILES: CC#Cc1cnc(O[C@H]2C[C@@H](C(=O)O)N(c3nc(C(F)(F)F)nc4c3oc3ccccc34)C2)c(N2CCOC3(CC3)[C@@H]2C)c1] | like Ex. 6.01 | 608 $[M + H]^+$ | 1.13 (P) |

Example 7.01

(2S,4S)-4-({3-[(9S)-9-Methyl-2,5-dioxa-8-azaspiro[3.5]nonan-8-yl]-5-(pyrimidin-5-yl)pyridin-2-yl}oxy)-1-[4-(trifluoromethyl)-8-oxa-3,5-diazatricyclo[7.4.0.0$^{2,7}$]trideca-1(9),2(7),3,5,10,12-hexaen-6-yl]pyrrolidine-2-carboxylic acid

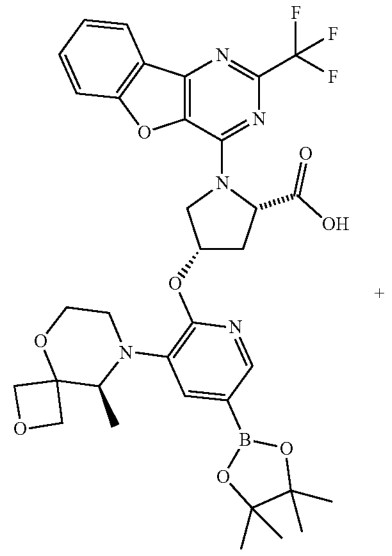

Int. 16.1

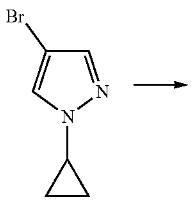

-continued

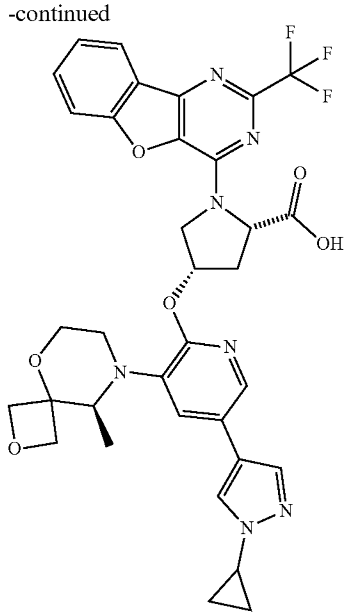

Ex. 7.01

To a degassed mixture of (2S,4S)-4-({3-[(9S)-9-methyl-2,5-dioxa-8-azaspiro[3.5]nonan-8-yl]-5-(4,4,5,5-tetramethyl-1,3,2-dioxaborolan-2-yl)pyridin-2-yl}oxy)-1-[4-(trifluoromethyl)-8-oxa-3,5-diazatricyclo-[7.4.0.02,7]-trideca-1(9),2(7),3,5,10,12-hexaen-6-yl]pyrrolidine-2-carboxylic acid (INTERMEDIATE 16.1, 220 mg, 0.309 mmol), potassium carbonate solution (2.0 mol/L, 0.463 mL, 0.928 mmol) and 4-bromo-1-cyclopropyl-1H-pyrazole (119 mg, 618 mmol) in 5.00 mL dioxane was added Xphos 3rd gen (15 mg, 0.018 mmol). The reaction mixture was heated to 80° C. for 2 h, then cooled to RT and diluted with ethyl acetate. Saturated aqueous ammonium chloride solution was added and water. The phases were separated, and the aqueous layer extracted with ethyl acetate. The combined organic layers were washed with saturated ammonium chloride solution and dried over sodium sulfate, filtered, evaporated and purified by HPLC (Sunfire, ACN/$H_2O$/TFA).

ESI-MS: 692 $[M+H]^+$ $R_t$ (H PLC): 1.01 min (E)

The following EXAMPLES were prepared according to the general procedure (EXAMPLE 7.01) described above:

| Ex. | Starting material | Structure | Reaction conditions | ESI-MS | $R_t$ (HPLC) [min] (method) |
|---|---|---|---|---|---|
| 7.02 | Ex. 1.10 + 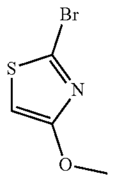 | 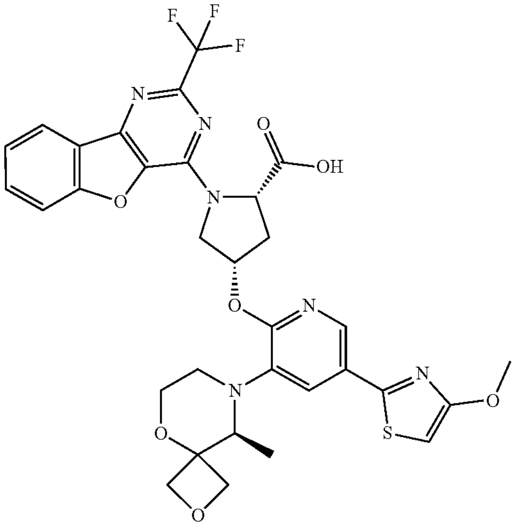 [SMILES: COc1csc(-c2cnc(O[C@H]3C[C@@H](C(=O)O)N(c4nc(C(F)(F)F)nc5c4oc4ccccc45)C3)c(N3CCOC4(COC4)[C@@H]3C)c2)n1] | Dioxane, $K_2CO_3$, 95° C., 30 min | 699 $[M + H]^+$ | 0.74 (A) |
| 7.03 | Ex. 1.10 + | 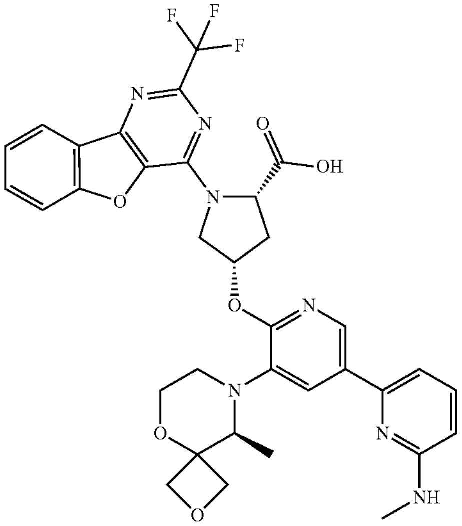 [SMILES: CNc1cccc(-c2cnc(O[C@H]3C[C@@H](C(=O)O)N(c4nc(C(F)(F)F)nc5c4oc4ccccc45)C3)c(N3CCOC4(COC4)[C@@H]3C)c2)n1] | Dioxane, $Cs_2CO_3$, 100° C., 2 h | 692 $[M + H]^+$ | 0.73 (P) |
| 7.04 | Ex. 1.10 + 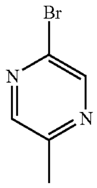 | 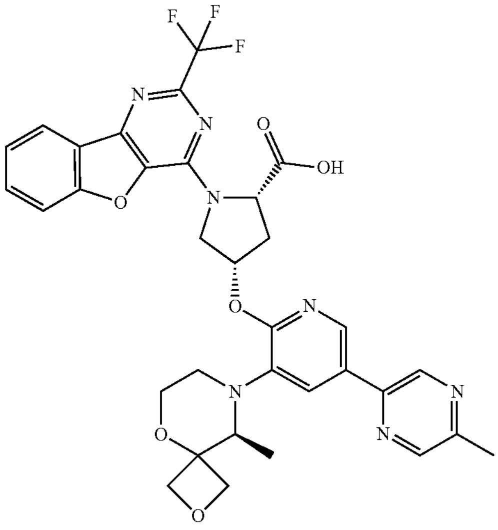 [SMILES: Cc1cnc(-c2cnc(O[C@H]3C[C@@H](C(=O)O)N(c4nc(C(F)(F)F)nc5c4oc4ccccc45)C3)c(N3CCOC4(COC4)[C@@H]3C)c2)cn1] | Dioxane, $Cs_2CO_3$, 100° C., 2 h | 678 $[M + H]^+$ | 1.02 (P) |

-continued

| Ex. | Starting material | Structure | Reaction conditions | ESI-MS | $R_t$ (HPLC) [min] (method) |
|---|---|---|---|---|---|
| 7.05 | Ex. 1.10 + 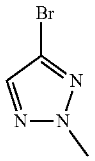 | 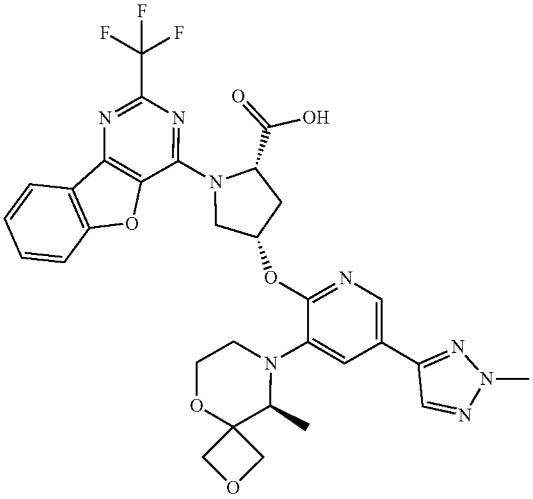 [SMILES: C[C@@H]1N(c2cc(-c3cnn(C)n3)cnc2O[C@H]2C[C@@H](C(=O)O)N(c3nc(C(F)(F)F)nc4c3oc3ccccc34)C2)CCOC12COC2] | Dioxane, $K_2CO_3$, 100° C., 2 h | 667 $[M + H]^+$ | 0.72 (A) |

Example 8.01

(2S,4S)-4-{[5-(1-methyl-1H-1,2,3-triazol-4-yl)-3-[(9S)-9-methyl-2,5-dioxa-8-azaspiro[3.5]nonan-8-yl]pyridin-2-yl]oxy}-1-[4-(trifluoromethyl)-8-oxa-3,5-diazatricyclo[$7.4.0.0^{2,7}$]trideca-1(9),2(7),3,5,10,12-hexaen-6-yl]pyrrolidine-2-carboxylic acid

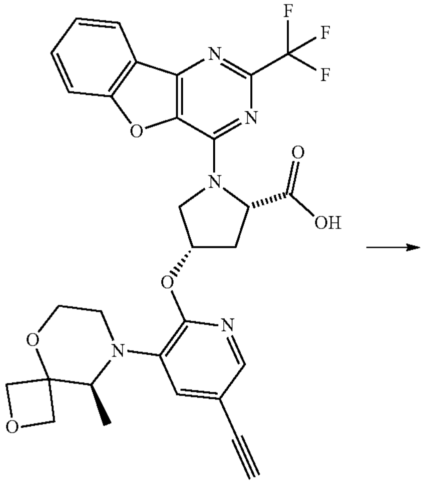

Ex. 1.12

-continued

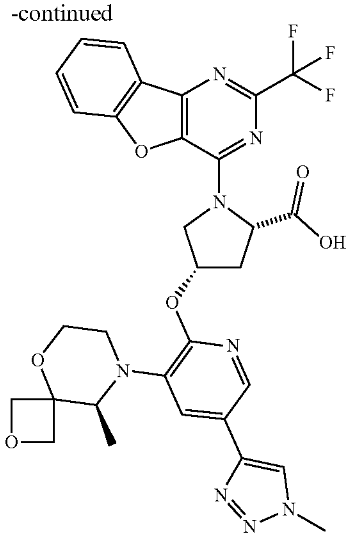

Ex. 8.01

A mixture of EXAMPLE 1.12 (75 mg, 0.12 mmol), trimethylsilylmethyl azide (16 mg, 0.012 mmol), copper(II)-sulfate (20 mg, 0.12 mmol) and L-ascorbic acid sodium salt (49 mg, 0.24 mmol) in a mixture if 1.00 mL DMSO and 0.10 mL water was stirred at RT for 1 h. Then, 1M TBAF solution (240 IL) was added and the reaction mixture was stirred for 1 h at room temperature. The reaction mixture was diluted with ACN/H2O, acidified with TFA, filtered and purified by HPLC.

ESI-MS: 667 $[M+H]^+$ $R_t$ (H PLC): 0.87 min (method P)

Example 9.01

(2S,4S)-1-[4-(difluoromethyl)-8-oxa-3,5-diazatricyclo[7.4.0.$0^{2,7}$]trideca-1(9),2(7),3,5,10,12-hexaen-6-yl]-4-({3-[(9S)-9-methyl-2,5-dioxa-8-azaspiro[3.5]nonan-8-yl]-5-(methylsulfanyl)pyridin-2-yl}oxy)pyrrolidine-2-carboxylic acid

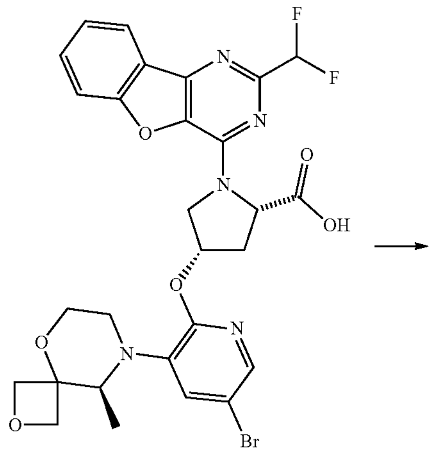

Int. 3.1.I (a)

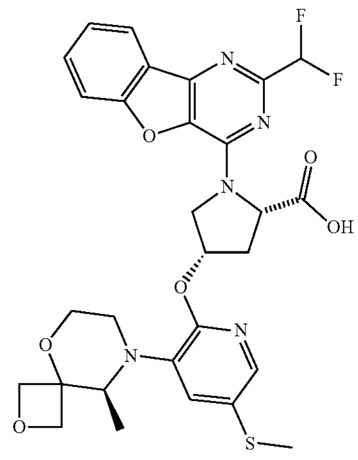

Ex. 9.01

A degassed mixture of (2S,4S)-4-({5-Bromo-3-[(9S)-9-methyl-2,5-dioxa-8-azaspiro[3.5]nonan-8-yl]pyridin-2-yl}oxy)-1-[4-(difluoromethyl)-8-oxa-3,5-diazatricyclo[7.4.0.02,7]-trideca-1(9),2(7),3,5,10,12-hexaen-6-yl]pyrrolidine-2-carboxylic acid (INTERMEDIATE 3.1.I (a), 160 mg, 0.25 mmol), XANTPHOS (20 mg, 0.035 mmol), sodium methanethiolate (0.25 mL, 0.59 mmol), DIPEA (0.100 mL, 0.58 mmol) and $Pd_2(dba)_3$ (16 mg, 0.017 mmol) in 8.00 mL dioxane was heated at 110° C. over night. After cooling to RT, ethyl acetate and water were added to the reaction mixture. The organic layer was separated, dried, concentrated in vacuo and purified by HPLC (Sunfire C-18, $H_2O$/ACN/TFA).

ESI-MS: 614 $[M+H]^+$ $R_t$ (HPLC): 1.01 min (method C)

Example 10.01

(2S,4S)-4-({3-[(9S)-9-methyl-2,5-dioxa-8-azaspiro[3.5]nonan-8-yl]-5-(1H-pyrazol-1-yl)pyridin-2-yl}oxy)-1-[4-(trifluoromethyl)-8-oxa-3,5-diazatricyclo[7.4.0.$0^{2,7}$]trideca-1(9),2(7),3,5,10,12-hexaen-6-yl]pyrrolidine-2-carboxylic acid

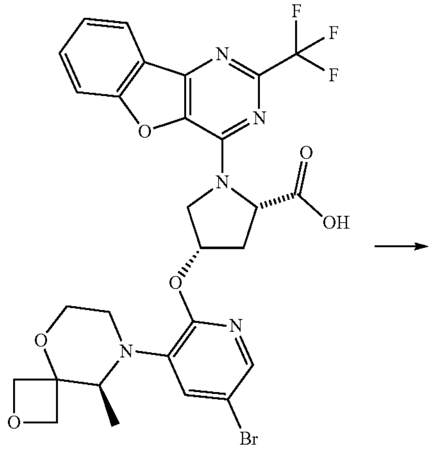

Ex. 1.10

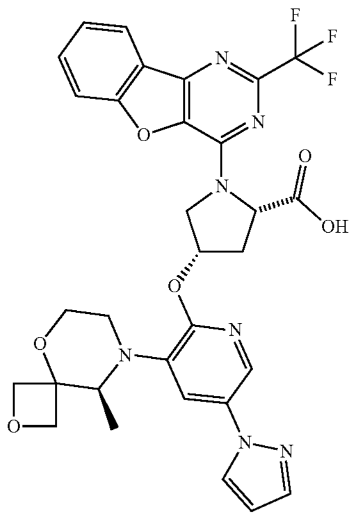

Ex. 10.01

To a degassed mixture of (2S,4S)-4-({5-bromo-3-[(9S)-9-methyl-2,5-dioxa-8-azaspiro[3.5]nonan-8-yl]pyridin-2-yl}oxy)-1-[4-(trifluoromethyl)-8-oxa-3,5-diazatricyclo[7.4.0.$0^{2,7}$]-trideca-1(9),2(7),3,5,10,12-hexaen-6-yl]pyrrolidine-2-carboxylic acid (Ex. 1.10, 30 mg, 0.045 mmol), LiHMDS (1M in THF, 0.120 mL, 0.120 mmol) and pyrazole (5.00 mg, 0.073 mmol) in 1.50 mL dioxane under an argon atmosphere was added tBuBrettPhos (5.00 mg, 0.006 mmol), and the mixture was heated at 80° C. for 5 h. After cooling to RT, the mixture was diluted with methanol, concentrated in vacuo and purified by HPLC.

ESI-MS: 652 $[M+H]^+$ $R_t$ (HPLC): 1.01 min (method P)

Peparation of Prodrugs:

Prodrug P01

Methyl (2S,4S)-4-({3-[(9S)-9-methyl-2,5-dioxa-8-azaspiro[3.5]nonan-8-yl]pyridin-2-yl}oxy)-1-[4-(difluoromethyl)-8-oxa-3,5-diazatricyclo[7.4.0.0$^{2,7}$]trideca-1(9),2(7),3,5,10,12-hexaen-6-yl]pyrrolidine-2-carboxylate

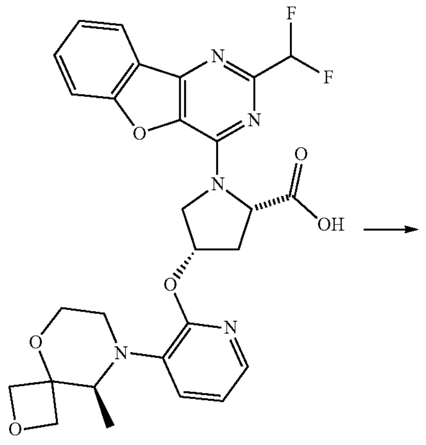

Ex. 4.04

-continued

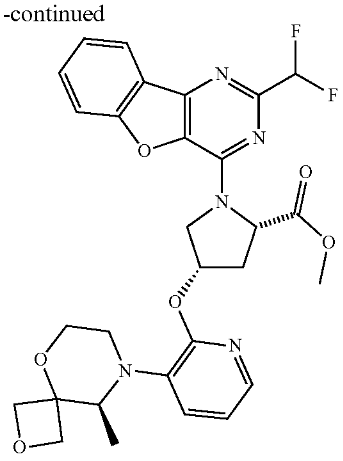

P01

To (2S,4S)-4-({3-[(9S)-9-methyl-2,5-dioxa-8-azaspiro[3.5]nonan-8-yl]-pyridin-2-yl}-oxy)$_1$-[4- (difluoro-methyl)-8-oxa-3,5-diazatricyclo[7.4.0.0$^{2,7}$]trideca-1(13),2,4,6,9,11-hexaen-6-yl]pyrrolidine-2-carboxylic acid (EXAMPLE 4.04, 15 mg, 0.020 mmol) in 1.0 mL THE was added O-methyl-N,N'-diisopropylurea (41 μL, 0.25 mmol). The reaction mixture was stirred at RT for 60 h, then diluted with ACN/water and purified by HPLC (ACN/H2O/TFA).

ESI-MS: 582 [M+H]$^+$ $R_t$ (H PLC): 0.69 min (method A)

The following compounds were prepared according to the general procedure (PRODRUG P01) described above:

| Pro-drug # | Starting material | Structure /name | Reaction conditions | ESI-MS | $R_t$ (HPLC) [min] (method) |
|---|---|---|---|---|---|
| P02 | Ex 1.10 | 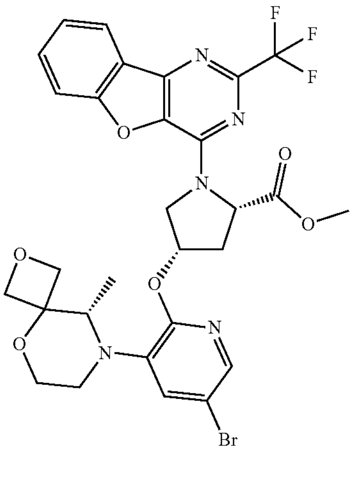 [SMILES: COC(=O)[C@@H]1C[C@H](Oc2ncc(Br)cc2N2CCOC3(COC3)[C@@H]2C)CN1c1nc(C(F)(F)F)nc2c1oc1ccccc12] | solvent: THF, RT, 3 days | 678 [M + H]$^+$ | 1.16 (D) |

-continued

| Pro-drug # | Starting material | Structure /name | Reaction conditions | ESI-MS | $R_t$ (HPLC) [min] (method) |
|---|---|---|---|---|---|
| P03 | Ex 1.12 | 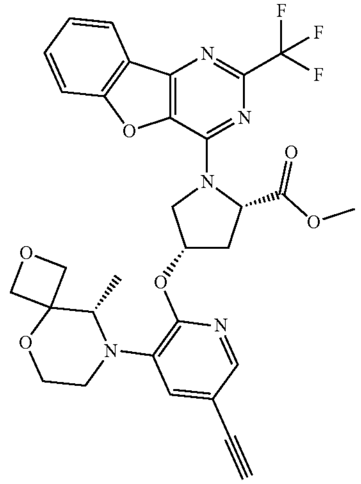 [SMILES: C#Cc1cnc(O[C@H]2C[C@@H](C(=O)OC)N(c3nc(C(F)(F)F)nc4c3oc3ccccc34)C2)c(N2CCOC3(COC3)[C@@H]2C)c1] | solvent: THF RT, 3 days | 624 [M + H]+ | 1.16 (H) |
| P04 | Ex 3.14 | 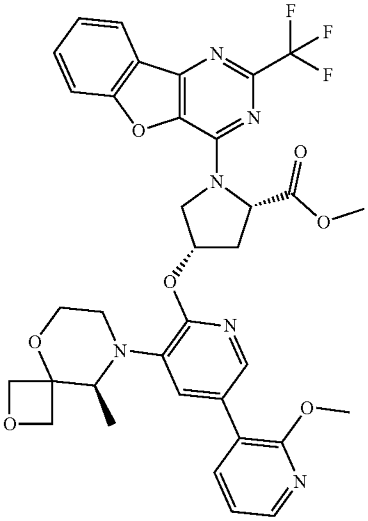 [SMILES: COC(=O)[C@@H]1C[C@H](Oc2ncc(-c3cccnc3OC)cc2N2CCOC3(COC3)[C@@H]2C)CN1c1nc(C(F)(F)F)nc2c1oc1ccccc12] | solvent: THF RT, 44 h | 707 [M + H]+ | 1.23 (J) |

LIST OF ABBREVIATIONS

ACN acetonitrile
aq. aqueous
° C. degree Celsius
CH cyclohexane
DBU diazabicyclo[5.4.0]undec-7-ene
DCM dichloromethane
DIPEA diisopropylethylamine
DMA dimethylacetamide
DMF N,N-dimethylformamide
ds diastereoisomer
ESI-MS electrospray ionisation mass spectrometry
EtOAc ethyl acetate
eq equivalent
FA formic acid
FC flash-chromatography, $SiO_2$ is used if no further details are given
h hour(s)
HCl hydrogenchloride
HATU [dimethylamino-(1,2,3-triazolo[4,5-b]pyridin-3-yloxy)-methylene]-dimethyl-ammonium hexafluorophosphate
HPLC high performance liquid chromatography
$K_2CO_3$ potassium carbonate
KOH potassium hydroxide
L liter
$LiAlH_4$ lithium aluminium hydride
LiHMDS lithium hexamethyldisilazide
MeOH methanol
min minute
mL milliliter
M molar
MS mass spectrum
n.d. not determined
$NH_4OH$ solution of $NH_3$ in water
$Pd_2(dba)_3$ Tris(dibenzylideneacetone)dipalladium(0)
$Pd(dppf)Cl_2$ (1,1'-bis-(diphenylphosphino)-ferrocene)-dichloropalladium (II)
$Pd(PPh_3)_4$ tetrakis(triphenylphosphine)palladium(0)
$Pd(OH)_2/C$ palladium hydroxide on carbon 20%
RT room temperature (about 20° C.)
Sol solvent
tBuBrettPhos (prop-2-en-1-yl)palladiumylium di-tert-butyl [3,6-dimethoxy-2',4',6'-tris(propan-2-yl)-[1,1'-biphenyl]-2-yl]phosphane trifluoromethanesulfonate TBS tert-butyl-dimethylsilyl
TBAF tetrabutylammoniumfluoride
TEA triethyl amine
TFA trifluoroacetic acid
TFAA trifluoroacetic acid anhydride
THE tetrahydrofurane
TIPS triisopropylsilyl
TMS trimethylsilyl
TosOH p-toluenesulfonic acid monohydrate
TLC thin layer chromatography
RP-HPLC reverse phase HPLC
$R_f$ retardation factor (TLC)
$R_t$ retention time in minutes
Vol % volume percent
Xphos 3rd gen (2-dicyclohexylphosphino-2',4',6'-triisopropyl-1,1'-biphenyl)[2-(2'-amino-1,1'-biphenyl)]palladium (II) methanesulfonate
Ziram dimethyldithiocarbamic acid zinc salt Analytical HPLC methods:

Method A

| time (min) | Vol % water (incl. 0.1% TFA) | Vol % ACN | Flow [mL/min] |
|---|---|---|---|
| 0.00 | 99 | 1 | 1.6 |
| 0.02 | 99 | 1 | 1.6 |
| 1.00 | 0 | 100 | 1.6 |
| 1.10 | 0 | 100 | 1.6 |

Analytical column: XBridge BEH C18_2.1×30 mm, 1.7 μm; column temperature: 60° C.

Method B

| time (min) | Vol % water (incl. 0.1% TFA) | Vol % ACN | Flow [mL/min] |
|---|---|---|---|
| 0.00 | 97 | 3 | 2.2 |
| 0.20 | 97 | 3 | 2.2 |
| 1.20 | 0 | 100 | 2.2 |
| 1.25 | 0 | 100 | 3.0 |
| 1.40 | 0 | 100 | 3.0 |

Analytical column: Stable Bond (Agilent) 1.8 μm; 3.0×30 mm; column temperature: 60° C.

Method C

| time (min) | Vol % water (incl. 0.1% TFA) | Vol % ACN | Flow [mL/min] |
|---|---|---|---|
| 0.00 | 97 | 3 | 2.2 |
| 0.20 | 97 | 3 | 2.2 |
| 1.20 | 0 | 100 | 2.2 |
| 1.25 | 0 | 100 | 3.0 |
| 1.40 | 0 | 100 | 3.0 |

Analytical column: Sunfire (Waters) 2.5.m; 3.0×30 mm; column temperature: 60° C.

Method D

| time (min) | Vol. % water (incl. 0.1% $NH_4OH$) | Vol. % ACN | Flow [mL/min] |
|---|---|---|---|
| 0.00 | 95 | 5 | 1.5 |
| 1.30 | 0 | 100 | 1.5 |
| 1.50 | 0 | 100 | 1.5 |
| 1.60 | 95 | 5 | 1.5 |

Analytical column: XBridge C18_3.0×30 mm-2.5 μm (Waters); column temperature: 60° C.

Method E

| time (min) | Vol. % water (incl. 0.1% TFA) | Vol. % ACN | Flow [mL/min] |
|---|---|---|---|
| 0.00 | 95 | 5 | 1.5 |
| 1.30 | 0 | 100 | 1.5 |
| 1.50 | 0 | 100 | 1.5 |

Analytical column: Sunfire C18 (Waters) 2.5 μm; 3.0×30 mm; column temperature: 60° C.

Method F

| time (min) | Vol % water (incl. 0.1% NH3) | Vol % ACN | Flow [mL/min] |
|---|---|---|---|
| 0.00 | 95 | 5 | 1.3 |
| 0.02 | 95 | 5 | 1.3 |
| 1.00 | 0 | 100 | 1.3 |
| 1.30 | 0 | 100 | 1.3 |

Analytical column: XBridge BEH (Waters) C18_2.1×30 mm, 2.5 μm; column temperature: 60° C.

Method G

| time (min) | Vol % water (incl. 0.1% TFA) | Vol % ACN | Flow [mL/min |
|---|---|---|---|
| 0.00 | 50 | 50 | 1.6 |
| 0.02 | 50 | 50 | 1.6 |
| 1.00 | 0 | 100 | 1.6 |
| 1.10 | 0 | 100 | 1.6 |

Analytical column: XBridge BEH (Waters) C18_2.1×30 mm, 1.7 μm; column temperature: 60° C.

Method H

| time (min) | Vol. % water (incl. 0.1% TFA) | Vol. % ACN | Flow [mL/min] |
|---|---|---|---|
| 0.00 | 95 | 5 | 1.5 |
| 1.30 | 0 | 100 | 1.5 |
| 1.50 | 0 | 100 | 1.5 |
| 1.60 | 95 | 5 | 1.5 |

Analytical column: Sunfire C18 (Waters) 2.5 μm; 3.0×30 mm; column temperature: 60° C.

Method I

| time (min) | Vol % water (incl. 0.1% NH3) | Vol % ACN | Flow [mL/min] |
|---|---|---|---|
| 0.00 | 97 | 3 | 2.2 |
| 0.20 | 97 | 3 | 2.2 |
| 1.20 | 0 | 100 | 2.2 |
| 1.25 | 0 | 100 | 3.0 |
| 1.40 | 0 | 100 | 3.0 |

Analytical column: XBridge (Waters) C18_3.0×30 mm, 2.5 μm; column temperature: 60° C.

| time (min) | Vol. % water (incl. 0.1% TFA) | Vol. % ACN | Flow [mL/min] |
|---|---|---|---|
| 0.00 | 95 | 5 | 1.5 |
| 1.30 | 0 | 100 | 1.5 |
| 1.50 | 0 | 100 | 1.5 |
| 1.60 | 95 | 5 | 1.5 |

Method J

Analytical column: Sunfire C18 (Waters) 2.5 μm; 3.0×30 mm; column temperature: 60° C.

Method K

| time (min) | Vol. % water (incl. 0.1% NH3) | Vol. % ACN | Flow [mL/min] |
|---|---|---|---|
| 0.00 | 95 | 5 | 1.5 |
| 1.30 | 0 | 100 | 1.5 |
| 1.50 | 0 | 100 | 1.5 |
| 1.60 | 95 | 5 | 1.5 |

Analytical column: Xbridge C18 (Waters) 2.5 μm; 3.0×30 mm; column temperature: 60 mC Method L

| time (min) | Vol. % carbon dioxide | Vol. % methanol | Flow [mL/min] |
|---|---|---|---|
| 0.00 | 97 | 3 | 1.3 |
| 2.50 | 55 | 45 | 1.3 |
| 3.50 | 55 | 45 | 1.3 |
| 3.51 | 97 | 3 | 1.3 |
| 4.00 | 97 | 3 | 1.3 |

Analytical column: Acquity UPC2 Torus 2-PIC (Waters) 1.7 μm; 3.0×100 mm; column temperature: 30° C.

Method M

| time (min) | Vol. % water (incl. 0.1% FA) | Vol. % ACN | Flow [mL/min] |
|---|---|---|---|
| 0.00 | 97 | 3 | 2.2 |
| 0.20 | 97 | 3 | 2.2 |
| 1.20 | 0 | 100 | 2.2 |
| 1.25 | 0 | 100 | 3.0 |
| 1.40 | 0 | 100 | 3.0 |

Analytical column: Sunfire C18 (Waters) 2.5 μm; 3.0×30 mm; column temperature: 60° C.

Method N

| time (min) | Vol. % water (incl. 0.1% TFA) | Vol. % ACN | Flow [mL/min] |
|---|---|---|---|
| 0.00 | 99 | 1 | 1.5 |
| 0.20 | 99 | 1 | 1.5 |
| 1.00 | 0 | 100 | 1.5 |
| 1.10 | 0 | 100 | 1.5 |

Analytical column: XSelect HSS PEP (Waters) 1.8 μm; 2.1×30 mm; column temperature: 60° C.

Method P

| time (min) | Vol. % water (incl. 0.1% formic acid) | Vol. % ACN | Flow [mL/min] |
|---|---|---|---|
| 0.00 | 80 | 20 | 0.5 |
| 0.10 | 80 | 20 | 0.5 |
| 1.10 | 0 | 100 | 0.5 |
| 2.50 | 80 | 20 | 0.5 |
| 3.00 | 80 | 20 | 0.5 |

Analytical column: Acquity UPLC BEH C18 (Waters) 1.7 μm; 2.1×100 mm; column temperature: 40

Method P

| time (min) | Vol. % water (incl. 0.1% TFA) | Vol. % ACN | Flow [mL/min] |
|---|---|---|---|
| 0.00 | 95 | 5 | 1.5 |
| 1.30 | 0 | 100 | 1.5 |
| 1.50 | 0 | 100 | 1.5 |
| 1.60 | 95 | 5 | 1.5 |

column: Sunfire C18 (Waters) 2.5 μm; 3.0×30 mm; CT: 60° C.

EXAMPLES

5.1 Example Compounds

The following Example compounds of formula (I) or of formula (I') as summarized in Table 1 have been synthesized and tested with respect to their pharmacological properties regarding their potency to inhibit cGAS activity.

In particular the "biochemical (in vitro) IC50-values" with regard to cGAS-inhibition (hcGAS IC50), the "IC50-value with regard to the inhibition of IFN induction in virus-stimulated THP1 cells" ($THP_{(vir)}$ IC50), the "IC50-value with regard to the inhibition of IFN induction in cGAMP-stimulated THP1 cells" ($THP_{(cGAMP)}$ IC50) and the "IC50-value with regard to inhibition of IFN induction in dsDNA-stimulated human whole blood" (hWB IC50) has been experimentally determined according to the assay methods as described in section 6 below. The results are summarized in Table 1.

The Example compounds of formula (I) or of formula (I') as summarized in Table 1 show at the same time the following three properties:

- a satisfying "biochemical (in vitro) IC50-value with regard to cGAS inhibition" (with a hcGAS IC50 of ≤100 nM, preferably of ≤50 nM, in particular of ≤10 nM),
- a satisfying "cellular IC50-value regarding cGAS inhibition" (with a $THP1_{(vir)}$ IC50 of 1 μM, preferably of 500 nM, more preferably of ≤100 nM, in particular of ≤50 nM) and
- a satisfying selectivity for cGAS-inhibition (with a ratio $THP1_{(CGAMP)}$IC50/$THP1_{(vir)}$ IC50 of ≥10, more preferably ≥50, more preferably ≥500, in particular ≥1000).

Additionally, the Example compounds of formula (I) or of formula (I') also show acceptable IC50-values with regard to inhibition of IFN induction in dsDNA-stimulated human whole blood (hWB IC50).

TABLE 1
Pharmacological properties of the Example compounds of the invention
| Exam. No. | Structure | hcGAS IC50 [nM] | $THP1_{(vir)}$ IC50 [nM] | $THP1_{(cGAMP)}$ IC50 [nM] | Ratio $THP1_{(cGAMP)}$ IC50/ $THP1_{(vir)}$ IC50 | hWB IC50 [nM] |
|---|---|---|---|---|---|---|
| 1.01 | 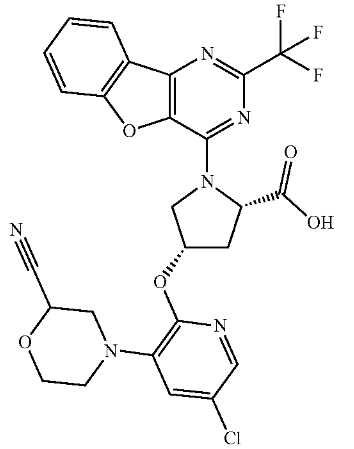 [SMILES: N#CC1CN(c2cc(Cl)cnc2O[C@H]2C[C@@H](C(=O)O)N(c3nc(C(F)(F)F)nc4c3oc3ccccc34)C2)CCO1] | 8 | 829 | 24551 | 30 | |
| 1.02 | 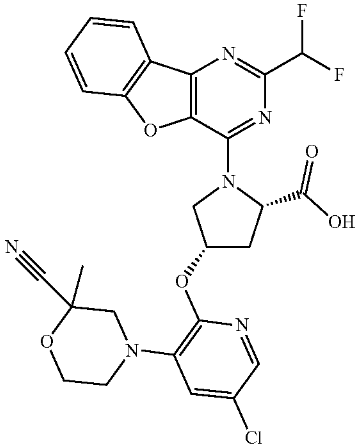 [SMILES: CC1(C#N)CN(c2cc(Cl)cnc2O[C@H]2C[C@@H](C(=O)O)N(c3nc(C(F)F)nc4c3oc3ccccc34)C2)CCO1] | 4 | 697 | 21869 | 31 | 3439 |
| 1.03 | 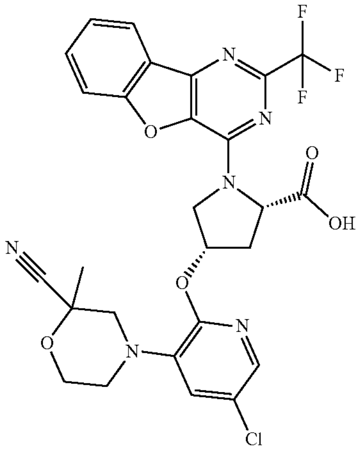 [SMILES: CC1(C#N)CN(c2cc(Cl)cnc2O[C@H]2C[C@@H](C(=O)O)N(c3nc(C(F)(F)F)nc4c3oc3ccccc34)C2)CCO1] | 7 | 399 | 15136 | 38 | 8453 |

TABLE 1-continued
| Pharmacological properties of the Example compounds of the invention | | | | | | |
|---|---|---|---|---|---|---|
| Exam. No. | Structure | hcGAS IC50 [nM] | $THP1_{(vir)}$ IC50 [nM] | $THP1_{(cGAMP)}$ IC50 [nM] | Ratio $THP1_{(cGAMP)}$ IC50/ $THP1_{(vir)}$ IC50 | hWB IC50 [nM] |
| 1.04 | 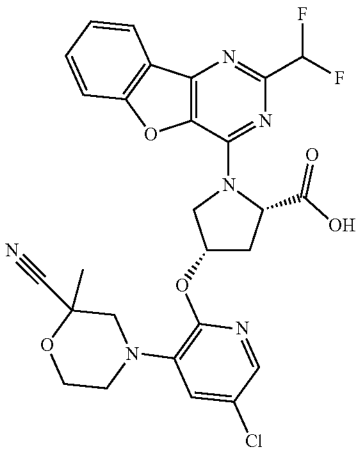 [SMILES: CC1(C#N)CN(c2cc(Cl)cnc2O[C@H]2C[C@@H](C(=O)O)N(c3nc(C(F)F)nc4c3oc3ccccc34)C2)CCO1] | 6 | 327 | 10029 | 31 | 3703 |
| 1.05 | 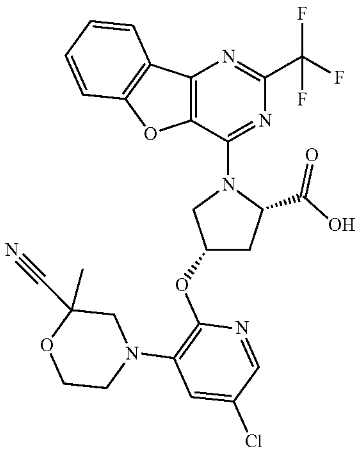 [SMILES: CC1(C#N)CN(c2cc(Cl)cnc2O[C@H]2C[C@@H](C(=O)O)N(c3nc(C(F)(F)F)nc4c3oc3ccccc34)C2)CCO1] | 14 | 775 | 12540 | 16 | 9506 |
| 1.06 | 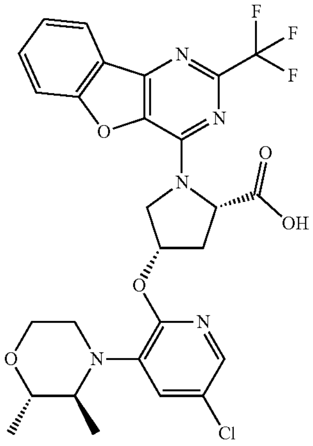 [SMILES: C[C@@H]1OCCN(c2cc(Cl)cnc2O[C@H]2C[C@@H](C(=O)O)N(c3nc(C(F)(F)F)nc4c3oc3ccccc34)C2)[C@H]1C] | 65 | 951 | 14283 | 15 | |

TABLE 1-continued
| Exam. No. | Structure | hcGAS IC50 [nM] | THP1$_{(vir)}$ IC50 [nM] | THP1$_{(cGAMP)}$ IC50 [nM] | Ratio THP1$_{(cGAMP)}$ IC50/ THP1$_{(vir)}$ IC50 | hWB IC50 [nM] |
|---|---|---|---|---|---|---|
| Pharmacological properties of the Example compounds of the invention | | | | | | |
| 1.07 | 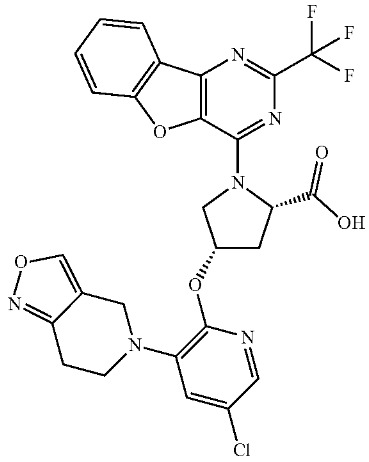 [SMILES: O=C(O)[C@@H]1C[C@H](Oc2ncc(Cl)cc2N2CCc3nocc3C2)CN1c1nc(C(F)(F)F)nc2c1oc1ccccc12] | 5 | 781 | 18722 | 24 | |
| 1.08 | 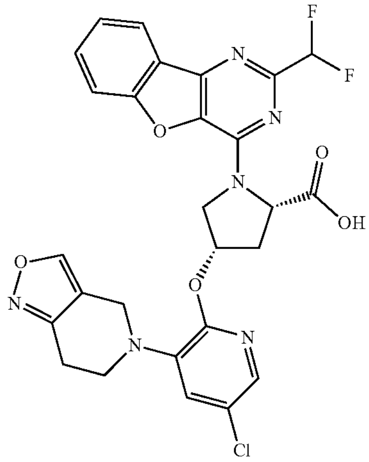 [SMILES: O=C(O)[C@@H]1C[C@H](Oc2ncc(Cl)cc2N2CCc3nocc3C2)CN1c1nc(C(F)F)nc2c1oc1ccccc12] | 4 | 831 | 18745 | 23 | |
| 1.09 | 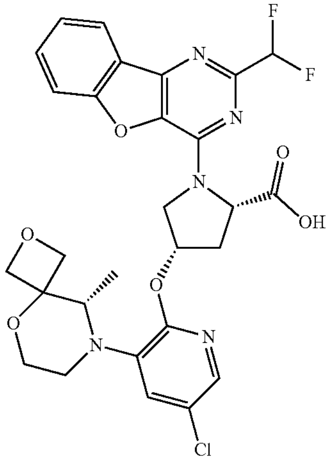 [SMILES: C[C@@H]1N(c2cc(Cl)cnc2O[C@H]2C[C@@H](C(=O)O)N(c3nc(C(F)F)nc4c3oc3ccccc34)C2)CCOC12COC2] | 2 | 19 | 22143 | 1169 | 19 |

TABLE 1-continued
Pharmacological properties of the Example compounds of the invention
| Exam. No. | Structure | hcGAS IC50 [nM] | $THP1_{(vir)}$ IC50 [nM] | $THP1_{(cGAMP)}$ IC50 [nM] | Ratio $THP1_{(cGAMP)}$ IC50/ $THP1_{(vir)}$ IC50 | hWB IC50 [nM] |
|---|---|---|---|---|---|---|
| 1.10 | 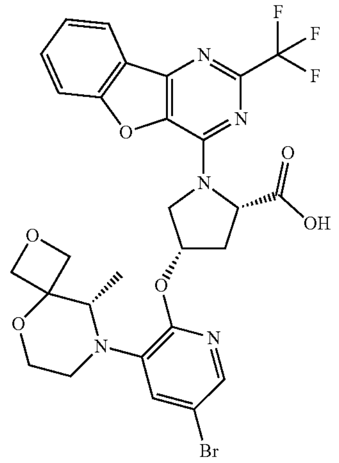 [SMILES: C[C@@H]1N(c2cc(Br)cnc2O[C@H]2C[C@@H](C(=O)O)N(c3nc(C(F)(F)F)nc4c3oc3ccccc34)C2)CCOC12COC2] | 5 | 91 | 16130 | 178 | 33 |
| 1.11 | 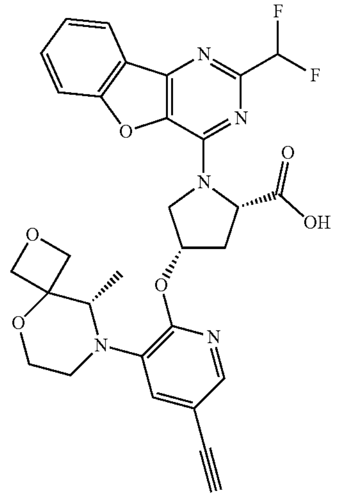 [SMILES: C#Cc1cnc(O[C@H]2C[C@@H](C(=O)O)N(c3nc(C(F)F)nc4c3oc3ccccc34)C2)c(N2CCOC3(COC3)[C@@H]2C)c1] | 2 | 6 | 18501 | 3095 | 5 |
| 1.12 | 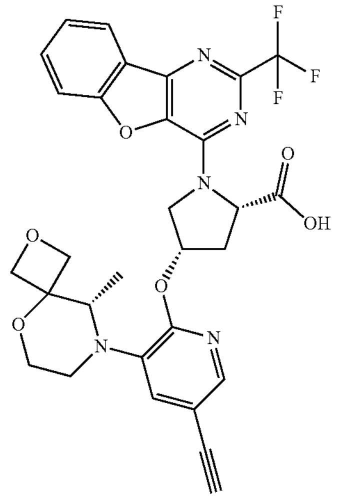 [SMILES: C#Cc1cnc(O[C@H]2C[C@@H](C(=O)O)N(c3nc(C(F)(F)F)nc4c3oc3ccccc34)C2)c(N2CCOC3(COC3)[C@@H]2C)c1] | 3 | 7 | 11892 | 1769 | 15 |

TABLE 1-continued
Pharmacological properties of the Example compounds of the invention
| Exam. No. | Structure | hcGAS IC50 [nM] | $THP1_{(vir)}$ IC50 [nM] | $THP1_{(cGAMP)}$ IC50 [nM] | Ratio $THP1_{(cGAMP)}$ IC50/ $THP1_{(vir)}$ IC50 | hWB IC50 [nM] |
|---|---|---|---|---|---|---|
| 1.13 | 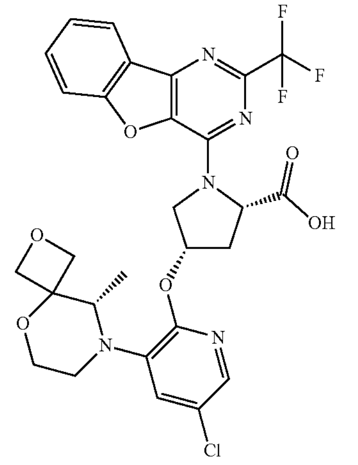 [SMILES: C[C@@H]1N(c2cc(Cl)cnc2O[C@H]2C[C@@H](C(=O)O)N(c3nc(C(F)(F)F)nc4c3oc3ccccc34)C2)CCOC12COC2] | 4 | 40 | 16406 | 413 | 102 |
| 1.14 | 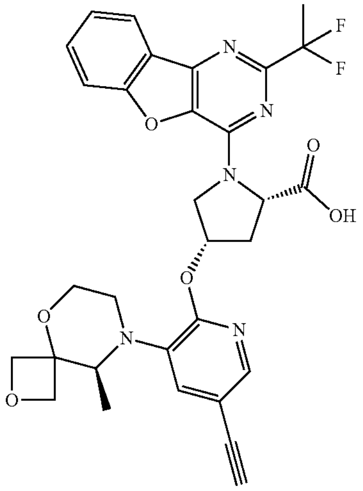 [SMILES: C#Cc1cnc(O[C@H]2C[C@@H](C(=O)O)N(c3nc(C(C)(F)F)nc4c3oc3ccccc34)C2)c(N2CCOC3(COC3)[C@@H]2C)c1] | 3 | 6 | >16591 | >2708 | 7 |
| 1.15 | 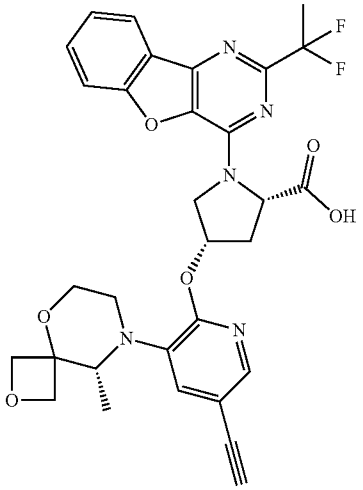 [SMILES: C#Cc1cnc(O[C@H]2C[C@@H](C(=O)O)N(c3nc(C(C)(F)F)nc4c3oc3ccccc34)C2)c(N2CCOC3(COC3)[C@H]2C)c1] | 75 | 332 | 26182 | 79 | 702 |

TABLE 1-continued
| Pharmacological properties of the Example compounds of the invention | | | | | | |
|---|---|---|---|---|---|---|
| Exam. No. | Structure | hcGAS IC50 [nM] | $THP1_{(vir)}$ IC50 [nM] | $THP1_{(cGAMP)}$ IC50 [nM] | Ratio $THP1_{(cGAMP)}$ IC50/ $THP1_{(vir)}$ IC50 | hWB IC50 [nM] |
| 1.16 | 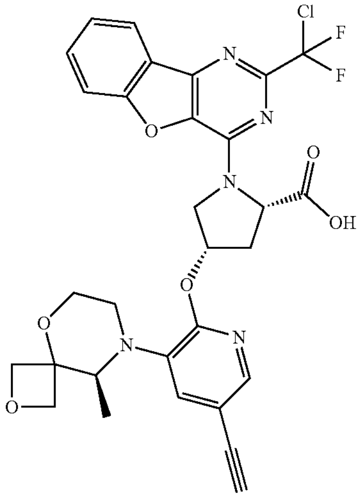 [SMILES: C#Cc1cnc(O[C@H]2C[C@@H](C(=O)O)N(c3nc(C(F)(F)Cl)nc4c3oc3ccccc34)C2)c(N2CCOC3(COC3)[C@@H]2C)c1] | 3 | 7 | 15012 | 2209 | 23 |
| 1.17 | 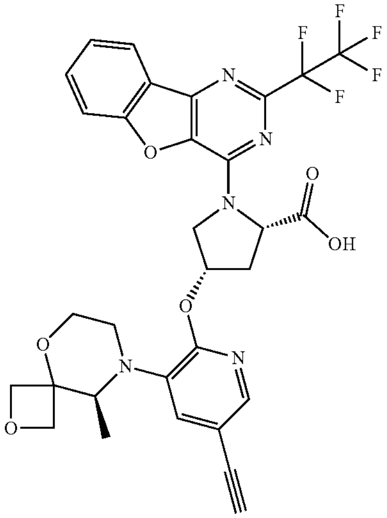 [SMILES: C#Cc1cnc(O[C@H]2C[C@@H](C(=O)O)N(c3nc(C(F)(F)C(F)(F)F)nc4c3oc3ccccc34)C2)c(N2CCOC3(COC3)[C@@H]2C)c1] | 17 | 154 | >16612 | >108 | 305 |
| 1.18 | 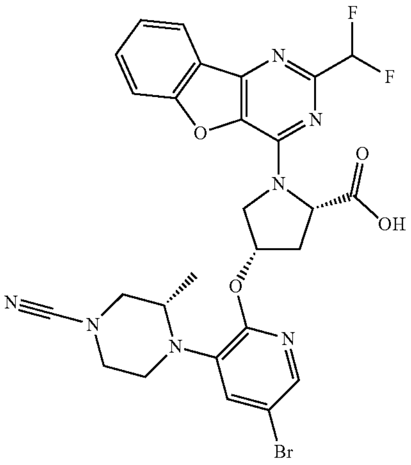 [SMILES: C[C@H]1CN(C#N)CCN1c1cc(Br)cnc1O[C@H]1C[C@@H](C(=O)O)N(c2nc(C(F)F)nc3c2oc2ccccc23)C1] | 4 | 239 | 6513 | 27 | 226 |

TABLE 1-continued
| Pharmacological properties of the Example compounds of the invention | | | | | | |
|---|---|---|---|---|---|---|
| Exam. No. | Structure | hcGAS IC50 [nM] | $THP1_{(vir)}$ IC50 [nM] | $THP1_{(cGAMP)}$ IC50 [nM] | Ratio $THP1_{(cGAMP)}$ IC50/ $THP1_{(vir)}$ IC50 | hWB IC50 [nM] |
| 1.19 | 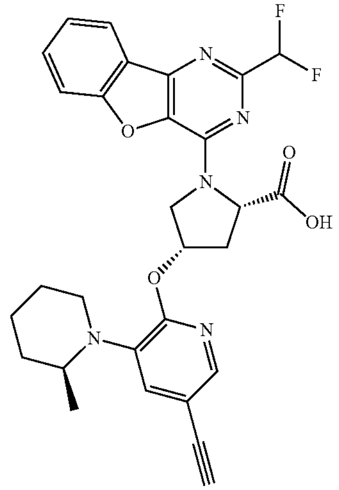 [SMILES: C#Cc1cnc(O[C@H]2C[C@@H](C(=O)O)N(c3nc(C(F)F)nc4c3oc3ccccc34)C2)c(N2CCCC[C@@H]2C)c1] | 4 | 699 | >16605 | >24 | 667 |
| 1.20 | 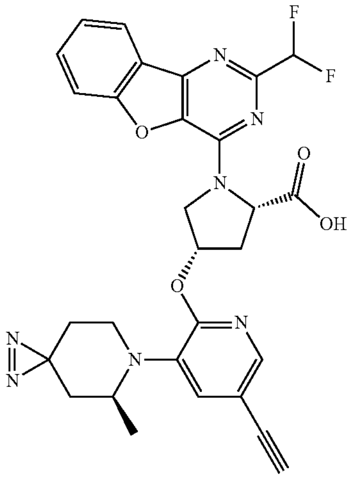 [SMILES: C#Cc1cnc(O[C@H]2C[C@@H](C(=O)O)N(c3nc(C(F)F)nc4c3oc3ccccc34)C2)c(N2CCC3(C[C@@H]2C)N=N3)c1] | 2 | 796 | >16608 | >21 | 670 |
| 1.21 | 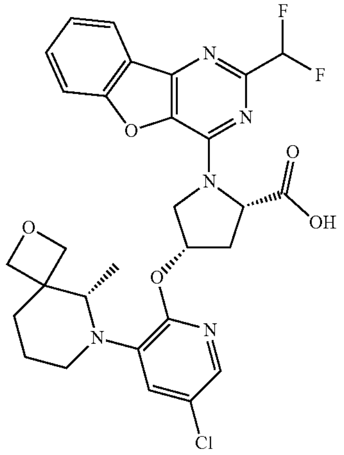 [SMILES: C[C@@H]1N(c2cc(Cl)cnc2O[C@H]2C[C@@H](C(=O)O)N(c3nc(C(F)F)nc4c3oc3ccccc34)C2)CCCC12COC2] | 4 | 85 | 14830 | 175 | 46 |

TABLE 1-continued
Pharmacological properties of the Example compounds of the invention
| Exam. No. | Structure | hcGAS IC50 [nM] | THP1$_{(vir)}$ IC50 [nM] | THP1$_{(cGAMP)}$ IC50 [nM] | Ratio THP1$_{(cGAMP)}$ IC50/ THP1$_{(vir)}$ IC50 | hWB IC50 [nM] |
|---|---|---|---|---|---|---|
| 1.22 | 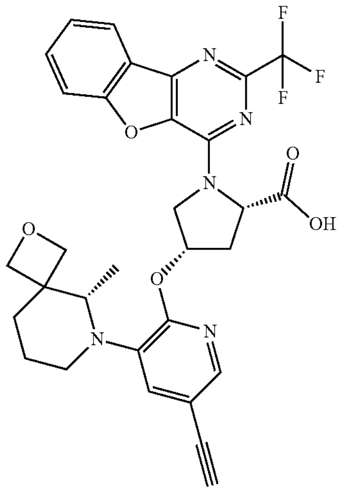 [SMILES: C#Cc1cnc(O[C@H]2C[C@@H](C(=O)O)N(c3nc(C(F)(F)F)nc4c3oc3ccccc34)C2)c(N2CCCC3(COC3)[C@@H]2C)c1] | 5 | 21 | 7637 | 355 | 29 |
| 1.23 | 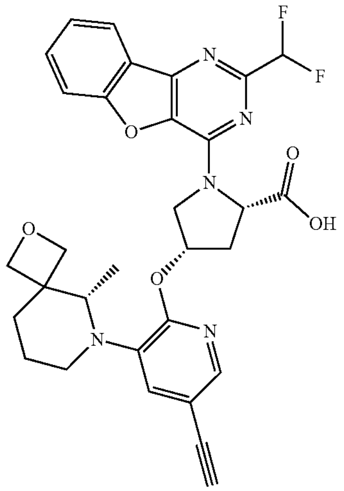 [SMILES: C#Cc1cnc(O[C@H]2C[C@@H](C(=O)O)N(c3nc(C(F)F)nc4c3oc3ccccc34)C2)c(N2CCCC3(COC3)[C@@H]2C)c1] | 4 | 10 | 10913 | 1134 | 12 |
| 1.24 | 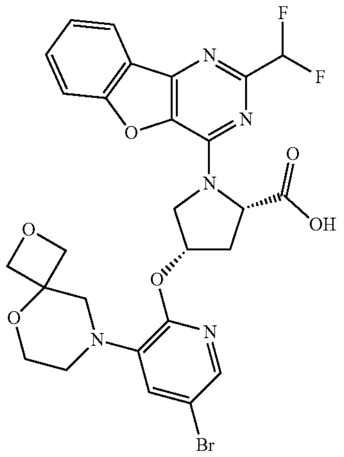 [SMILES: O=C(O)[C@@H]1C[C@H](Oc2ncc(Br)cc2N2CCOC3(COC3)C2)CN1c1nc(C(F)F)nc2c1oc1ccccc12] | 9 | 848 | >16597 | >20 | 850 |

TABLE 1-continued
Pharmacological properties of the Example compounds of the invention
| Exam. No. | Structure | hcGAS IC50 [nM] | $THP1_{(vir)}$ IC50 [nM] | $THP1_{(cGAMP)}$ IC50 [nM] | Ratio $THP1_{(cGAMP)}$ IC50/ $THP1_{(vir)}$ IC50 | hWB IC50 [nM] |
|---|---|---|---|---|---|---|
| 1.25 | 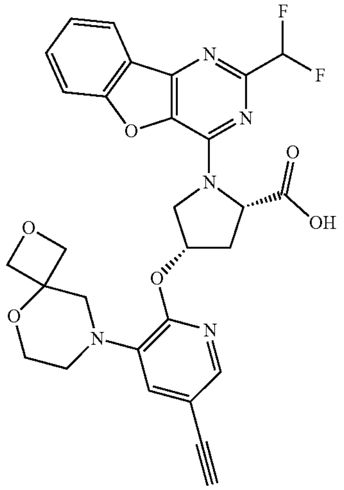 [SMILES: C#Cc1cnc(O[C@H]2C[C@@H](C(=O)O)N(c3nc(C(F)F)nc4c3oc3ccccc34)C2)c(N2CCOC3(COC3)C2)c1] | 4 | 517 | >16617 | >32 | 551 |
| 1.26 | 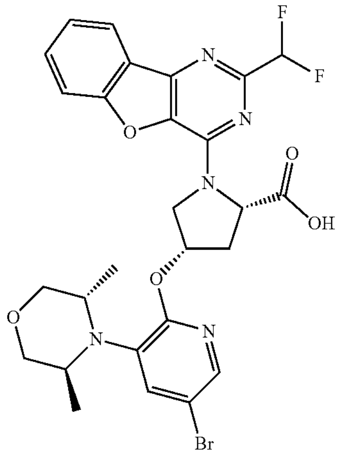 [SMILES: C[C@H]1COC[C@H](C)N1c1cc(Br)cnc1O[C@H]1C[C@@H](C(=O)O)N(c2nc(C(F)F)nc3c2oc2ccccc23)C1] | 10 | 583 | 9934 | 17 | 475 |
| 1.27 | 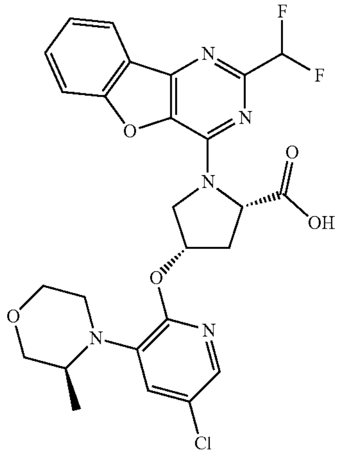 [SMILES: C[C@H]1COCCN1c1cc(Cl)cnc1O[C@H]1C[C@@H](C(=O)O)N(c2nc(C(F)F)nc3c2oc2ccccc23)C1] | 4 | 516 | >16604 | >32 | 221 |

TABLE 1-continued
Pharmacological properties of the Example compounds of the invention
| Exam. No. | Structure | hcGAS IC50 [nM] | $THP1_{(vir)}$ IC50 [nM] | $THP1_{(cGAMP)}$ IC50 [nM] | Ratio $THP1_{(cGAMP)}$ IC50/ $THP1_{(vir)}$ IC50 | hWB IC50 [nM] |
|---|---|---|---|---|---|---|
| 1.28 | 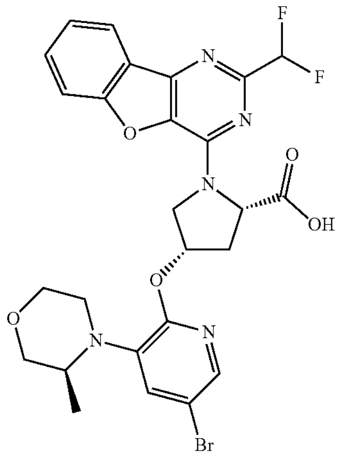 [SMILES: C[C@H]1COCCN1c1cc(Br)cnc1O[C@H]1C[C@@H](C(=O)O)N(c2nc(C(F)F)nc3c2oc2ccccc23)C1] | 3 | 500 | >16620 | >33 | 629 |
| 1.29 | 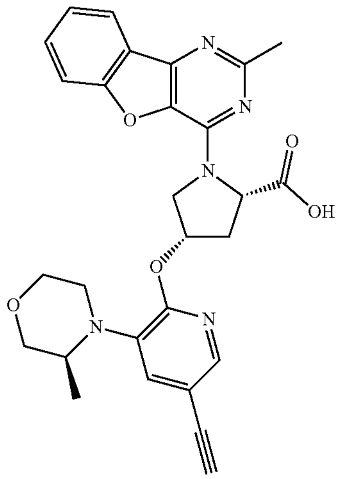 [SMILES: C#Cc1cnc(O[C@H]2C[C@@H](C(=O)O)N(c3nc(C)nc4c3oc3ccccc34)C2)c(N2CCOC[C@@H]2C)c1] | 4 | 296 | >16623 | >56 | 61 |
| 1.30 | 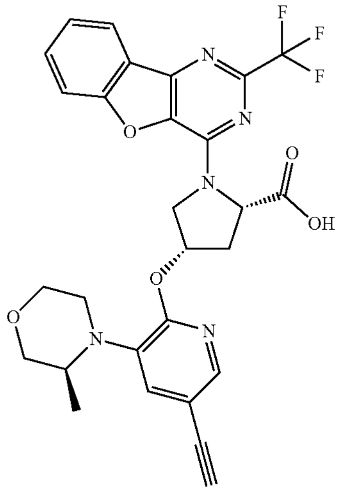 [SMILES: C#Cc1cnc(O[C@H]2C[C@@H](C(=O)O)N(c3nc(C(F)(F)F)nc4c3oc3ccccc34)C2)c(N2CCOC[C@@H]2C)c1] | 3 | 159 | 22053 | 139 | 80 |

TABLE 1-continued
| Pharmacological properties of the Example compounds of the invention | | | | | | |
|---|---|---|---|---|---|---|
| Exam. No. | Structure | hcGAS IC50 [nM] | $THP1_{(vir)}$ IC50 [nM] | $THP1_{(cGAMP)}$ IC50 [nM] | Ratio $THP1_{(cGAMP)}$ IC50/ $THP1_{(vir)}$ IC50 | hWB IC50 [nM] |
| 1.31 | 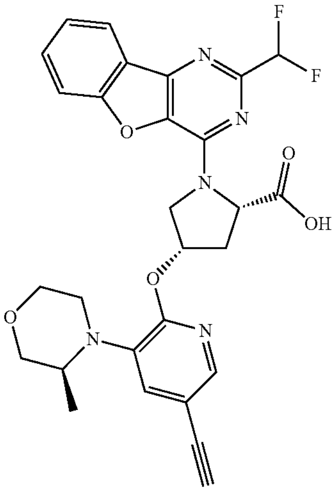 [SMILES: C#Cc1cnc(O[C@H]2C[C@@H](C(=O)O)N(c3nc(C(F)F)nc4c3oc3ccccc34)C2)c(N2CCOC[C@@H]2C)c1] | 3 | 232 | >16601 | >72 | 102 |
| 1.32 | 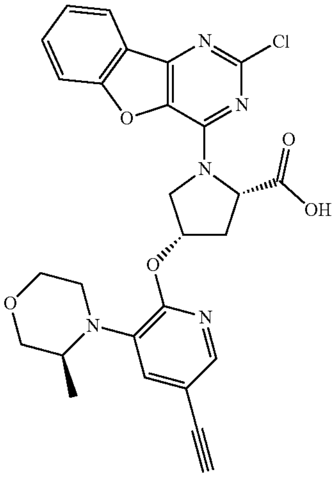 [SMILES: C#Cc1cnc(O[C@H]2C[C@@H](C(=O)O)N(c3nc(Cl)nc4c3oc3ccccc34)C2)c(N2CCOC[C@@H]2C)c1] | 4 | 487 | | | |
| 1.33 | 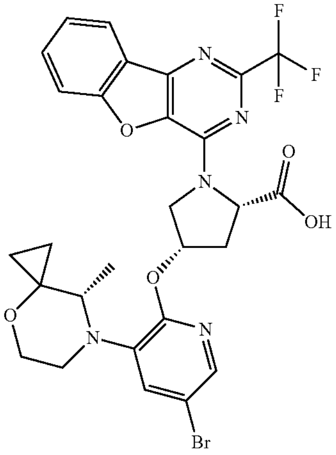 [SMILES: C[C@@H]1N(c2cc(Br)cnc2O[C@H]2C[C@@H](C(=O)O)N(c3nc(C(F)(F)F)nc4c3oc3ccccc34)C2)CCOC12CC2] | 3 | 15 | >10 000 | 677 | 252 |

TABLE 1-continued
| Pharmacological properties of the Example compounds of the invention | | | | | | |
|---|---|---|---|---|---|---|
| Exam. No. | Structure | hcGAS IC50 [nM] | $THP1_{(vir)}$ IC50 [nM] | $THP1_{(cGAMP)}$ IC50 [nM] | Ratio $THP1_{(cGAMP)}$ IC50/ $THP1_{(vir)}$ IC50 | hWB IC50 [nM] |
| 1.34 | 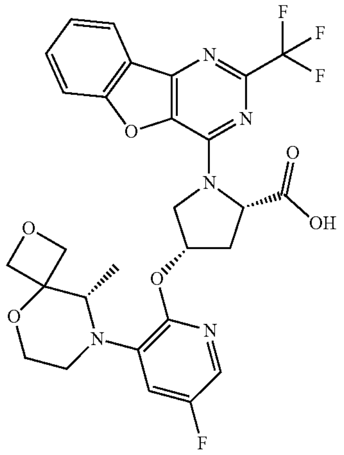 [SMILES: C[C@@H]1N(c2cc(F)cnc2O[C@H]2C[C@@H](C(=O)O)N(c3nc(C(F)(F)F)nc4c3oc3ccccc34)C2)CCOC12COC2] | 3 | 19 | >10 000 | 514 | 51 |
| 1.35 | 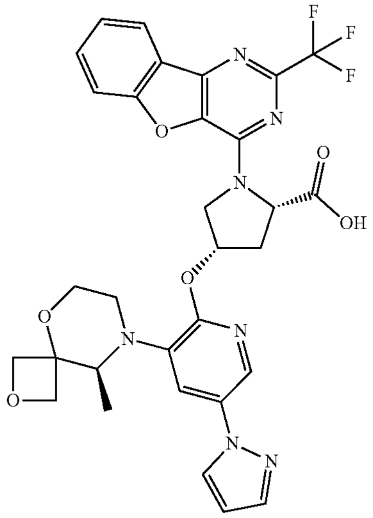 [SMILES: C[C@@H]1N(c2cc(-n3cccn3)cnc2O[C@H]2C[C@@H](C(=O)O)N(c3nc(C(F)(F)F)nc4c3oc3ccccc34)C2)CCOC12COC2] | 5 | 10 | >10 000 | >1000 | 47 |
| 2.01 | 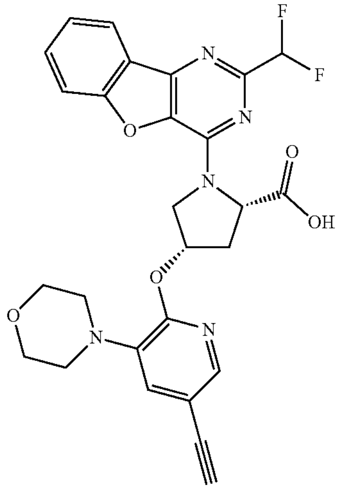 [SMILES: C#Cc1cnc(O[C@H]2C[C@@H](C(=O)O)N(c3nc(C(F)F)nc4c3oc3ccccc34)C2)c(N2CCOCC2)c1] | 8 | 858 | >16595 | >19 | 506 |

TABLE 1-continued
Pharmacological properties of the Example compounds of the invention
| Exam. No. | Structure | hcGAS IC50 [nM] | $THP1_{(vir)}$ IC50 [nM] | $THP1_{(cGAMP)}$ IC50 [nM] | Ratio $THP1_{(cGAMP)}$ IC50/ $THP1_{(vir)}$ IC50 | hWB IC50 [nM] |
|---|---|---|---|---|---|---|
| 2.02 | 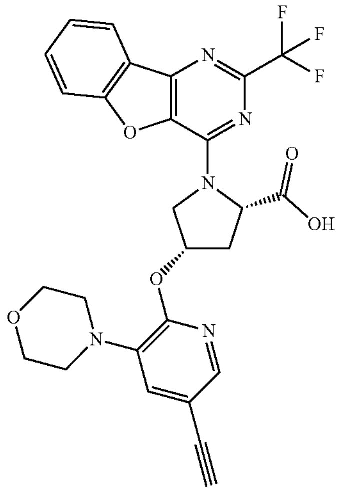 [SMILES: C#Cc1cnc(O[C@H]2C[C@@H](C(=O)O)N(c3nc(C(F)(F)F)nc4c3oc3ccccc34)C2)c(N2CCOCC2)c1] | 7 | 752 | >16602 | >22 | 1034 |
| 2.03 | 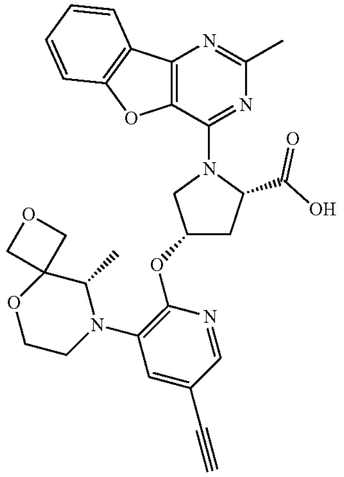 [SMILES: C#Cc1cnc(O[C@H]2C[C@@H](C(=O)O)N(c3nc(C)nc4c3oc3ccccc34)C2)c(N2CCOC3(COC3)[C@@H]2C)c1] | 3 | <5 | 16402 | 3043 | 9 |
| 2.04 | 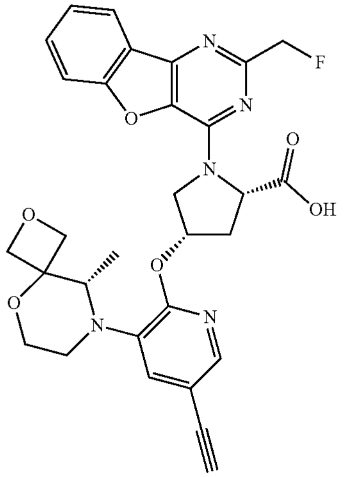 [SMILES: C#Cc1cnc(O[C@H]2C[C@@H](C(=O)O)N(c3nc(CF)nc4c3oc3ccccc34)C2)c(N2CCOC3(COC3)[C@@H]2C)c1] | 1 | 3 | 25412 | 8125 | 5 |

TABLE 1-continued
Pharmacological properties of the Example compounds of the invention
| Exam. No. | Structure | hcGAS IC50 [nM] | $THP1_{(vir)}$ IC50 [nM] | $THP1_{(cGAMP)}$ IC50 [nM] | Ratio $THP1_{(cGAMP)}$ IC50/ $THP1_{(vir)}$ IC50 | hWB IC50 [nM] |
|---|---|---|---|---|---|---|
| 2.05 | 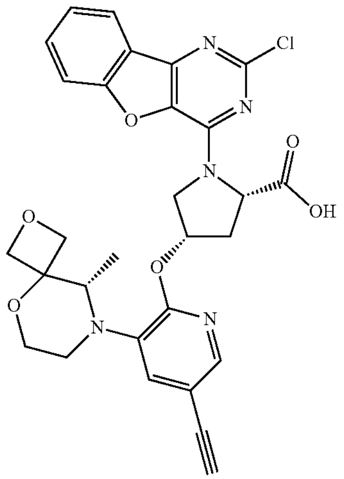 [SMILES: C#Cc1cnc(O[C@H]2C[C@@H](C(=O)O)N(c3nc(Cl)nc4c3oc3ccccc34)C2)c(N2CCOC3(COC3)[C@@H]2C)c1] | 2 | 4 | 10808 | 3018 | 8 |
| 2.06 | 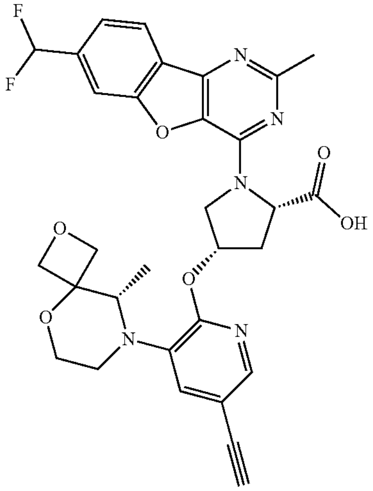 [SMILES: C#Cc1cnc(O[C@H]2C[C@@H](C(=O)O)N(c3nc(C)nc4c3oc3cc(C(F)F)ccc34)C2)c(N2CCOC3(COC3)[C@@H]2C)c1] | 4 | 63 | 11932 | 189 | 52 |
| 2.07 | 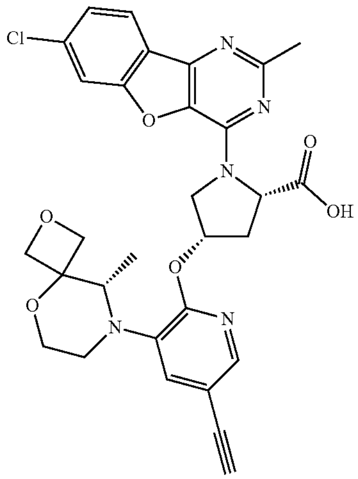 [SMILES: C#Cc1cnc(O[C@H]2C[C@@H](C(=O)O)N(c3nc(C)nc4c3oc3cc(Cl)ccc34)C2)c(N2CCOC3(COC3)[C@@H]2C)c1] | 3 | 14 | 14535 | 1005 | 28 |

TABLE 1-continued
| Pharmacological properties of the Example compounds of the invention | | | | | | |
|---|---|---|---|---|---|---|
| Exam. No. | Structure | hcGAS IC50 [nM] | $THP1_{(vir)}$ IC50 [nM] | $THP1_{(cGAMP)}$ IC50 [nM] | Ratio $THP1_{(cGAMP)}$ IC50/ $THP1_{(vir)}$ IC50 | hWB IC50 [nM] |
| 2.08 | 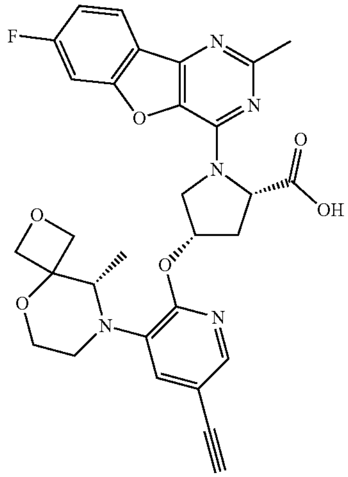 [SMILES: C#Cc1cnc(O[C@H]2C[C@@H](C(=O)O)N(c3nc(C)nc4c3oc3cc(F)ccc34)C2)c(N2CCOC3(COC3)[C@@H]2C)c1] | 3 | <5 | 18814 | 3490 | 6 |
| 2.09 | 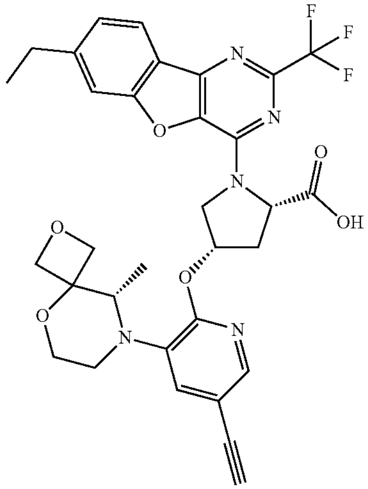 [SMILES: C#Cc1cnc(O[C@H]2C[C@@H](C(=O)O)N(c3nc(C(F)(F)F)nc4c3oc3cc(CC)ccc34)C2)c(N2CCOC3(COC3)[C@@H]2C)c1] | 6 | 31 | 5177 | 166 | 37 |
| 2.10 | 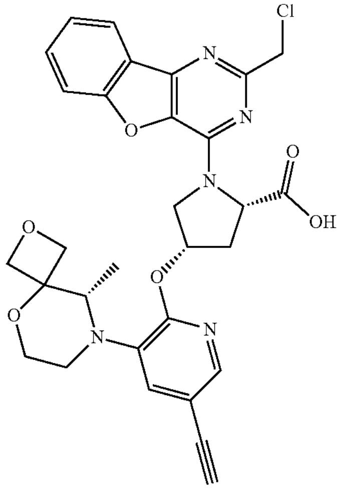 [SMILES: C#Cc1cnc(O[C@H]2C[C@@H](C(=O)O)N(c3nc(CCl)nc4c3oc3ccccc34)C2)c(N2CCOC3(COC3)[C@@H]2C)c1] | 3 | 5 | 2746 | 533 | 24 |

TABLE 1-continued
Pharmacological properties of the Example compounds of the invention
| Exam. No. | Structure | hcGAS IC50 [nM] | $THP1_{(vir)}$ IC50 [nM] | $THP1_{(cGAMP)}$ IC50 [nM] | Ratio $THP1_{(cGAMP)}$ IC50/ $THP1_{(vir)}$ IC50 | hWB IC50 [nM] |
|---|---|---|---|---|---|---|
| 3.01 | 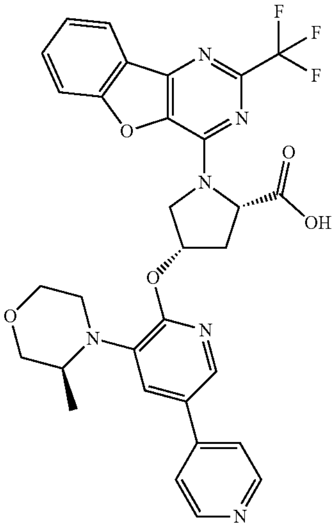 [SMILES: C[C@H]1COCCN1c1cc(-c2ccncc2)cnc1O[C@H]1C[C@@H](C(=O)O)N(c2nc(C(F)(F)F)nc3c2oc2ccccc23)C1] | 9 | 982 | >16604 | >17 | 1607 |
| 3.02 | 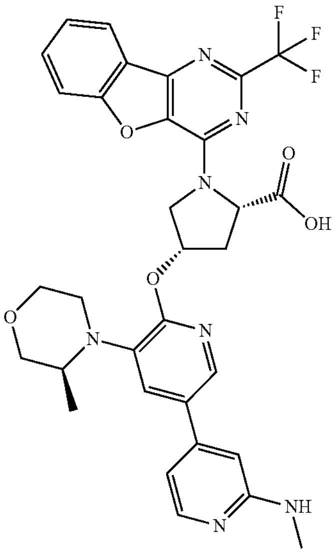 [SMILES: CNc1cc(-c2cnc(O[C@H]3C[C@@H](C(=O)O)N(c4nc(C(F)(F)F)nc5c4oc4ccccc45)C3)c(N3CCOC[C@@H]3C)c2)ccn1] | 13 | 306 | 4916 | 16 | 1538 |

TABLE 1-continued
Pharmacological properties of the Example compounds of the invention
| Exam. No. | Structure | hcGAS IC50 [nM] | $THP1_{(vir)}$ IC50 [nM] | $THP1_{(cGAMP)}$ IC50 [nM] | Ratio $THP1_{(cGAMP)}$ IC50/ $THP1_{(vir)}$ IC50 | hWB IC50 [nM] |
|---|---|---|---|---|---|---|
| 3.03 | 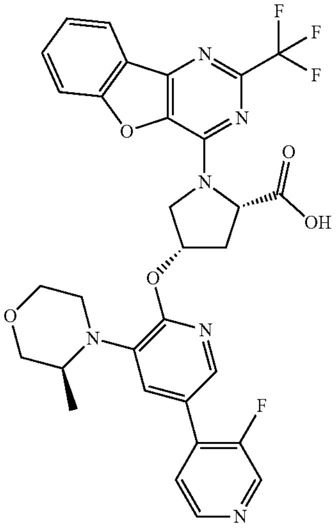 [SMILES: C[C@H]1COCCN1c1cc(-c2ccncc2F)cnc1O[C@H]1C[C@@H](C(=O)O)N(c2nc(C(F)(F)F)nc3c2oc2ccccc23)C1] | 7 | 899 | 12838 | 14 | 2125 |
| 3.04 | 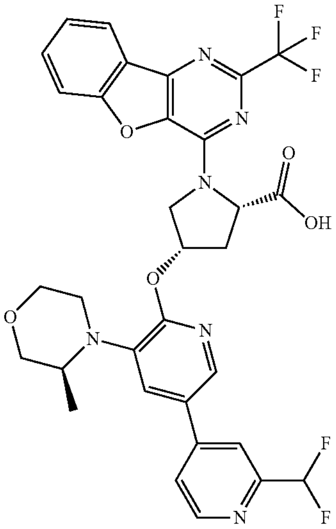 [SMILES: C[C@H]1COCCN1c1cc(-c2ccnc(C(F)F)c2)cnc1O[C@H]1C[C@@H](C(=O)O)N(c2nc(C(F)(F)F)nc3c2oc2ccccc23)C1] | 12 | 757 | 7779 | 10 | 2420 |

TABLE 1-continued
Pharmacological properties of the Example compounds of the invention
| Exam. No. | Structure | hcGAS IC50 [nM] | THP1$_{(vir)}$ IC50 [nM] | THP1$_{(cGAMP)}$ IC50 [nM] | Ratio THP1$_{(cGAMP)}$ IC50/ THP1$_{(vir)}$ IC50 | hWB IC50 [nM] |
|---|---|---|---|---|---|---|
| 3.05 | 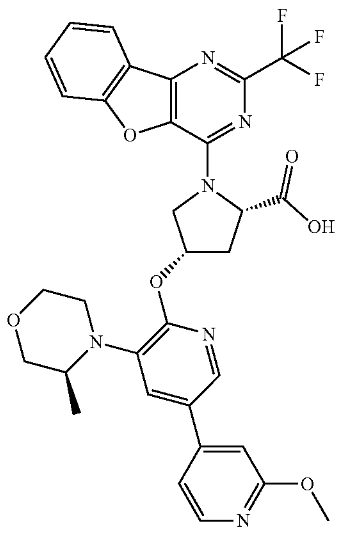 [SMILES: COc1cc(-c2cnc(O[C@H]3C[C@@H](C(=O)O)N(c4nc(C(F)(F)F)nc5c4oc4ccccc45)C3)c(N3CCOC[C@@H]3C)c2)ccn1] | 14 | 523 | 6710 | 13 | 1831 |
| 3.06 | 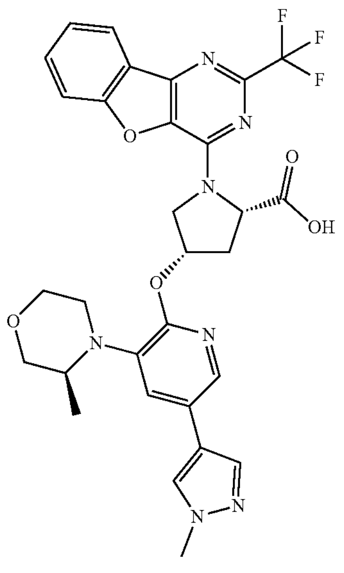 [SMILES: C[C@H]1COCCN1c1cc(-c2cnn(C)c2)cnc1O[C@H]1C[C@@H](C(=O)O)N(c2nc(C(F)(F)F)nc3c2oc2ccccc23)C1] | 9 | 525 | 21357 | 41 | 1988 |

TABLE 1-continued
Pharmacological properties of the Example compounds of the invention
| Exam. No. | Structure | hcGAS IC50 [nM] | THP1$_{(vir)}$ IC50 [nM] | THP1$_{(cGAMP)}$ IC50 [nM] | Ratio THP1$_{(cGAMP)}$ IC50/ THP1$_{(vir)}$ IC50 | hWB IC50 [nM] |
|---|---|---|---|---|---|---|
| 3.07 | 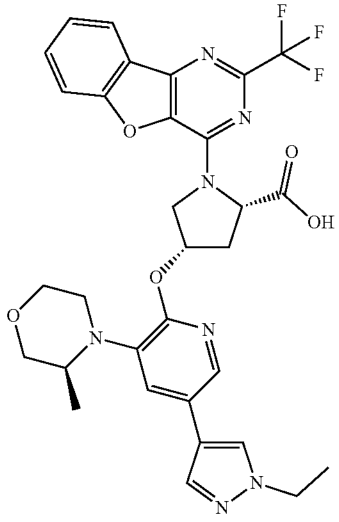 [SMILES: CCn1cc(-c2cnc(O[C@H]3C[C@@H](C(=O)O)N(c4nc(C(F)(F)F)nc5c4oc4ccccc45)C3)c(N3CCOC[C@@H]3C)c2)cn1] | 17 | 748 | 12339 | 16 | 1616 |
| 3.08 | 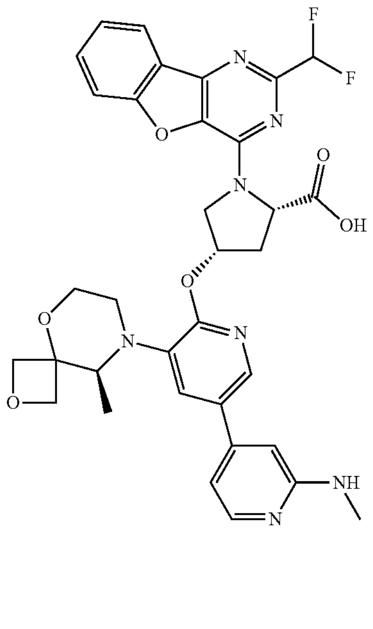 [SMILES: CNc1cc(-c2cnc(O[C@H]3C[C@@H](C(=O)O)N(c4nc(C(F)F)nc5c4oc4ccccc45)C3)c(N3CCOC4(COC4)[C@@H]3C)c2)ccn1] | 5 | 4 | 4789 | 1179 | 3 |

TABLE 1-continued
Pharmacological properties of the Example compounds of the invention
| Exam. No. | Structure | hcGAS IC50 [nM] | THP1$_{(vir)}$ IC50 [nM] | THP1$_{(cGAMP)}$ IC50 [nM] | Ratio THP1$_{(cGAMP)}$ IC50/ THP1$_{(vir)}$ IC50 | hWB IC50 [nM] |
|---|---|---|---|---|---|---|
| 3.09 | 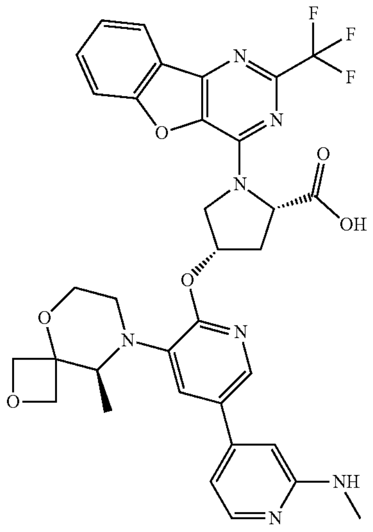 [SMILES: CNc1cc(-c2cnc(O[C@H]3C[C@@H](C(=O)O)N(c4nc(C(F)(F)F)nc5c4oc4ccccc45)C3)c(N3CCOC4(COC4)[C@@H]3C)c2)ccn1] | 9 | 8 | 4816 | 585 | 8 |
| 3.10 | 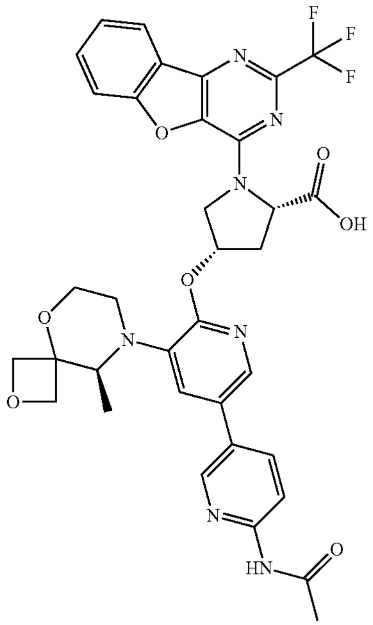 [SMILES: CC(=O)Nc1ccc(-c2cnc(O[C@H]3C[C@@H](C(=O)O)N(c4nc(C(F)(F)F)nc5c4oc4ccccc45)C3)c(N3CCOC4(COC4)[C@@H]3C)c2)cn1] | 8 | 5 | 7909 | 1713 | 10 |

TABLE 1-continued
| Pharmacological properties of the Example compounds of the invention | | | | | | |
|---|---|---|---|---|---|---|
| Exam. No. | Structure | hcGAS IC50 [nM] | $THP1_{(vir)}$ IC50 [nM] | $THP1_{(cGAMP)}$ IC50 [nM] | Ratio $THP1_{(cGAMP)}$ IC50/ $THP1_{(vir)}$ IC50 | hWB IC50 [nM] |
| 3.11 | 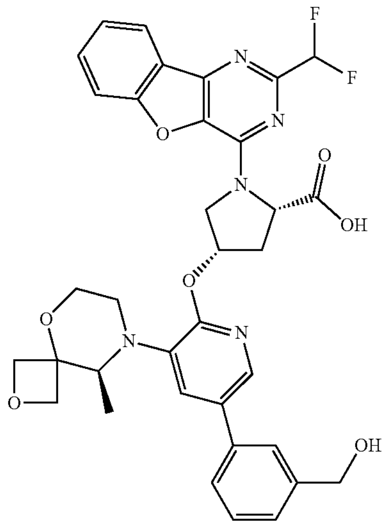 [SMILES: C[C@@H]1N(c2cc(-c3cccc(CO)c3)cnc2O[C@H]2C[C@@H](C(=O)O)N(c3nc(C(F)F)nc4c3oc3ccccc34)C2)CCOC12COC2] | 4 | 5 | 5289 | 1149 | 11 |
| 3.12 | 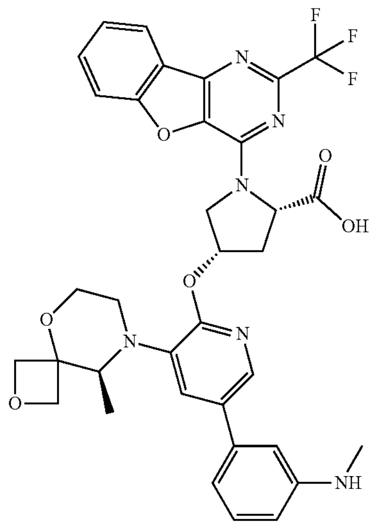 [SMILES: CNc1cccc(-c2cnc(O[C@H]3C[C@@H](C(=O)O)N(c4nc(C(F)(F)F)nc5c4oc4ccccc45)C3)c(N3CCOC4(COC4)[C@@H]3C)c2)c1] | 9 | 6 | 11138 | 1930 | 19 |

TABLE 1-continued
| Exam. No. | Structure | hcGAS IC50 [nM] | $THP1_{(vir)}$ IC50 [nM] | $THP1_{(cGAMP)}$ IC50 [nM] | Ratio $THP1_{(cGAMP)}$ IC50/ $THP1_{(vir)}$ IC50 | hWB IC50 [nM] |
|---|---|---|---|---|---|---|
| Pharmacological properties of the Example compounds of the invention | | | | | | |
| 3.13 | 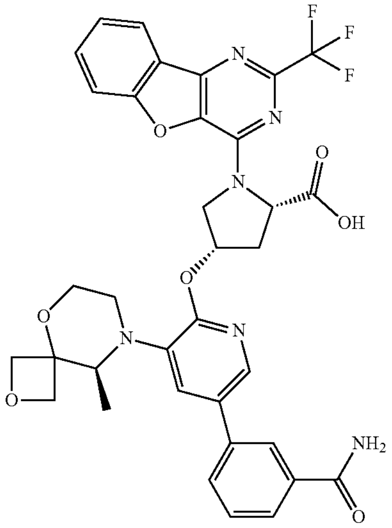 [SMILES: C[C@@H]1N(c2cc(-c3cccc(C(N)=O)c3)cnc2O[C@H]2C[C@@H](C(=O)O)N(c3nc(C(F)(F)F)nc4c3oc3ccccc34)C2)CCOC12COC2] | 9 | 25 | 8352 | 335 | 65 |
| 3.14 | 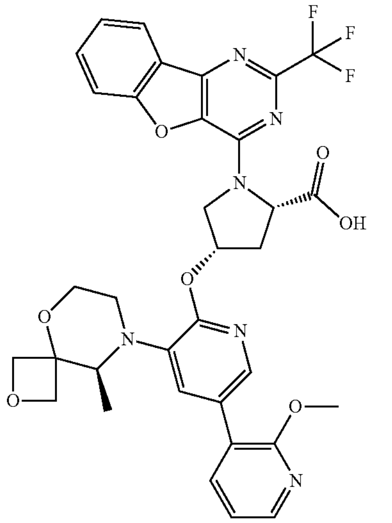 [SMILES: COc1ncccc1-c1cnc(O[C@H]2C[C@@H](C(=O)O)N(c3nc(C(F)(F)F)nc4c3oc3ccccc34)C2)c(N2CCOC3(COC3)[C@@H]2C)c1] | 11 | 10 | 7832 | 822 | 26 |

TABLE 1-continued
Pharmacological properties of the Example compounds of the invention
| Exam. No. | Structure | hcGAS IC50 [nM] | THP1$_{(vir)}$ IC50 [nM] | THP1$_{(cGAMP)}$ IC50 [nM] | Ratio THP1$_{(cGAMP)}$ IC50/ THP1$_{(vir)}$ IC50 | hWB IC50 [nM] |
|---|---|---|---|---|---|---|
| 3.15 | 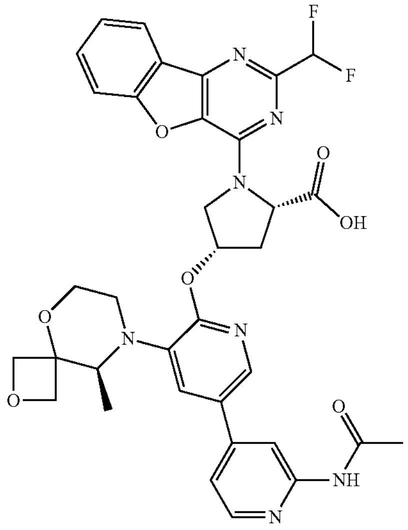 [SMILES: CC(=O)Nc1cc(-c2cnc(O[C@H]3C[C@@H](C(=O)O)N(c4nc(C(F)F)nc5c4oc4ccccc45)C3)c(N3CCOC4(COC4)[C@@H]3C)c2)ccn1] | 10 | 57 | 19921 | 348 | 22 |
| 3.16 | 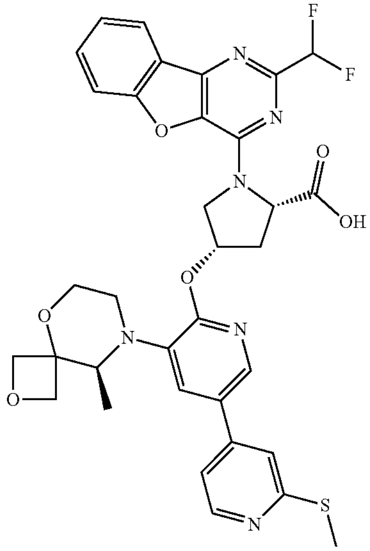 [SMILES: CSc1cc(-c2cnc(O[C@H]3C[C@@H](C(=O)O)N(c4nc(C(F)F)nc5c4oc4ccccc45)C3)c(N3CCOC4(COC4)[C@@H]3C)c2)ccn1] | 15 | 19 | 11849 | 629 | 38 |

TABLE 1-continued
Pharmacological properties of the Example compounds of the invention
| Exam. No. | Structure | hcGAS IC50 [nM] | THP1$_{(vir)}$ IC50 [nM] | THP1$_{(cGAMP)}$ IC50 [nM] | Ratio THP1$_{(cGAMP)}$ IC50/ THP1$_{(vir)}$ IC50 | hWB IC50 [nM] |
|---|---|---|---|---|---|---|
| 3.17 | 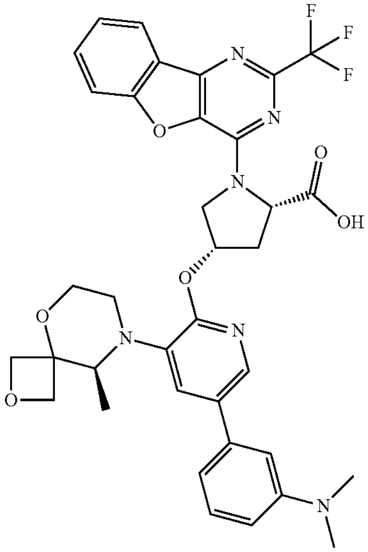 [SMILES: C[C@@H]1N(c2cc(-c3cccc(N(C)C)c3)cnc2O[C@H]2C[C@@H](C(=O)O)N(c3nc(C(F)(F)F)nc4c3oc3ccccc34)C2)CCOC12COC2] | 20 | 11 | 16809 | 1542 | 43 |
| 3.18 | 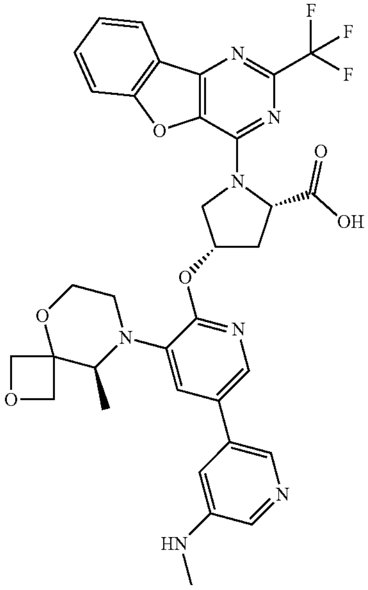 [SMILES: CNc1cncc(-c2cnc(O[C@H]3C[C@@H](C(=O)O)N(c4nc(C(F)(F)F)nc5c4oc4ccccc45)C3)c(N3CCOC4(COC4)[C@@H]3C)c2)c1] | 3 | 7 | 4758 | 645 | 44 |

TABLE 1-continued
Pharmacological properties of the Example compounds of the invention
| Exam. No. | Structure | hcGAS IC50 [nM] | $THP1_{(vir)}$ IC50 [nM] | $THP1_{(cGAMP)}$ IC50 [nM] | Ratio $THP1_{(cGAMP)}$ IC50/ $THP1_{(vir)}$ IC50 | hWB IC50 [nM] |
|---|---|---|---|---|---|---|
| 3.19 | 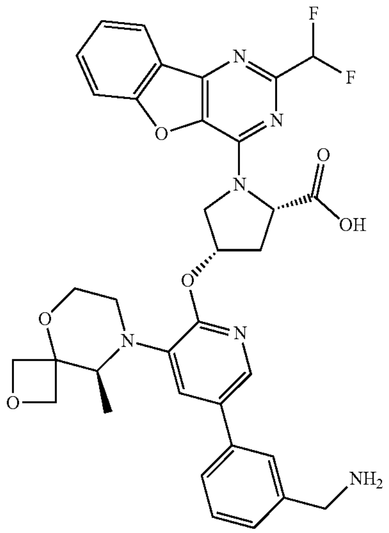 [SMILES: C[C@@H]1N(c2cc(-c3cccc(CN)c3)cnc2O[C@H]2C[C@@H](C(=O)O)N(c3nc(C(F)F)nc4c3oc3ccccc34)C2)CCOC12COC2] | 8 | 267 | >16593 | >62 | 47 |
| 3.20 | 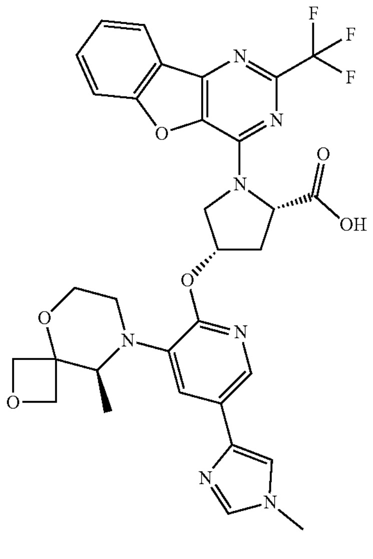 [SMILES: C[C@@H]1N(c2cc(-c3cn(C)cn3)cnc2O[C@H]2C[C@@H](C(=O)O)N(c3nc(C(F)(F)F)nc4c3oc3ccccc34)C2)CCOC12COC2] | 3 | 30 | 11521 | 383 | 50 |

TABLE 1-continued
Pharmacological properties of the Example compounds of the invention
| Exam. No. | Structure | hcGAS IC50 [nM] | $THP1_{(vir)}$ IC50 [nM] | $THP1_{(cGAMP)}$ IC50 [nM] | Ratio $THP1_{(cGAMP)}$ IC50/ $THP1_{(vir)}$ IC50 | hWB IC50 [nM] |
|---|---|---|---|---|---|---|
| 3.21 | 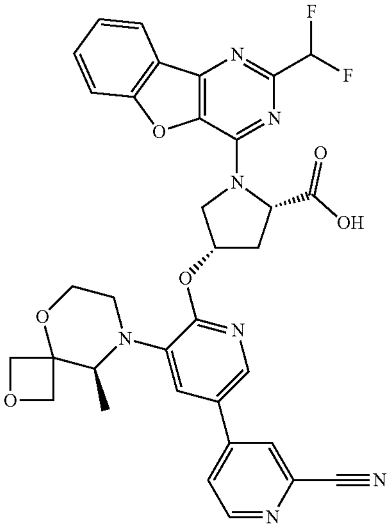 [SMILES: C[C@@H]1N(c2cc(-c3ccnc(C#N)c3)cnc2O[C@H]2C[C@@H](C(=O)O)N(c3nc(C(F)F)nc4c3oc3ccccc34)C2)CCOC12COC2] | 4 | 24 | 11689 | 483 | 55 |
| 3.22 | 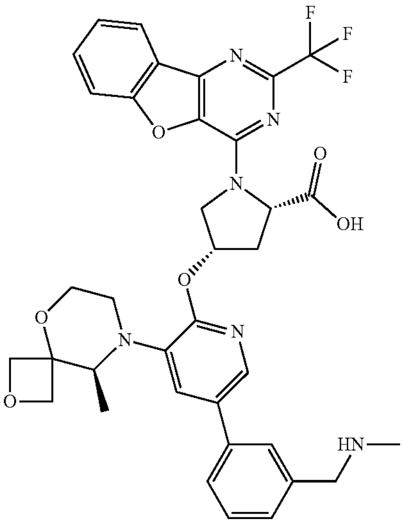 [SMILES: CNCc1cccc(-c2cnc(O[C@H]3C[C@@H](C(=O)O)N(c4nc(C(F)(F)F)nc5c4oc4ccccc45)C3)c(N3CCOC4(COC4)[C@@H]3C)c2)c1] | 16 | 177 | 8912 | 50 | 70 |

TABLE 1-continued
| Pharmacological properties of the Example compounds of the invention | | | | | | |
| --- | --- | --- | --- | --- | --- | --- |
| Exam. No. | Structure | hcGAS IC50 [nM] | $THP1_{(vir)}$ IC50 [nM] | $THP1_{(cGAMP)}$ IC50 [nM] | Ratio $THP1_{(cGAMP)}$ IC50/ $THP1_{(vir)}$ IC50 | hWB IC50 [nM] |
| 3.23 | 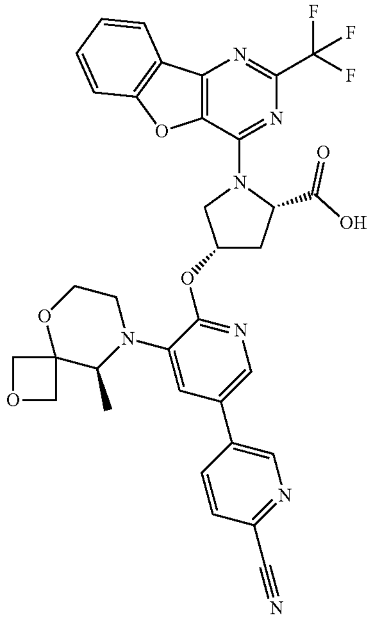 [SMILES: C[C@@H]1N(c2cc(-c3ccc(C#N)nc3)cnc2O[C@H]2C[C@@H](C(=O)O)N(c3nc(C(F)(F)F)nc4c3oc3ccccc34)C2)CCOC12COC2] | 8 | 10 | 10027 | 1029 | 70 |
| 3.24 | 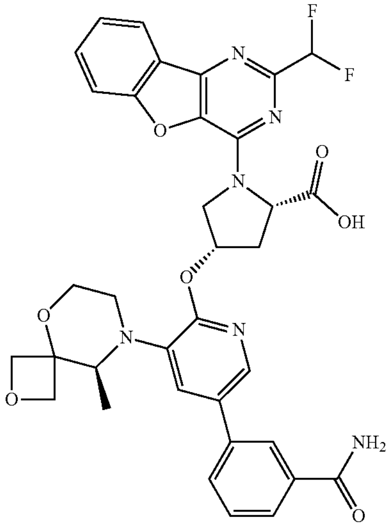 [SMILES: C[C@@H]1N(c2cc(-c3cccc(C(N)=O)c3)cnc2O[C@H]2C[C@@H](C(=O)O)N(c3nc(C(F)F)nc4c3oc3ccccc34)C2)CCOC12COC2] | 6 | 57 | 19222 | 336 | 322 |

TABLE 1-continued
| Exam. No. | Structure | hcGAS IC50 [nM] | $THP1_{(vir)}$ IC50 [nM] | $THP1_{(cGAMP)}$ IC50 [nM] | Ratio $THP1_{(cGAMP)}$ IC50/ $THP1_{(vir)}$ IC50 | hWB IC50 [nM] |
|---|---|---|---|---|---|---|
| Pharmacological properties of the Example compounds of the invention | | | | | | |
| 3.25 | 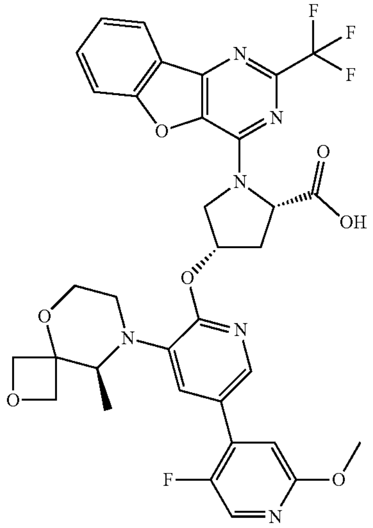 [SMILES: COc1cc(-c2cnc(O[C@H]3C[C@@H](C(=O)O)N(c4nc(C(F)(F)F)nc5c4oc4ccccc45)C3)c(N3CCOC4(COC4)[C@@H]3C)c2)c(F)cn1] | 9 | 19 | 9712 | 502 | 96 |
| 3.26 | 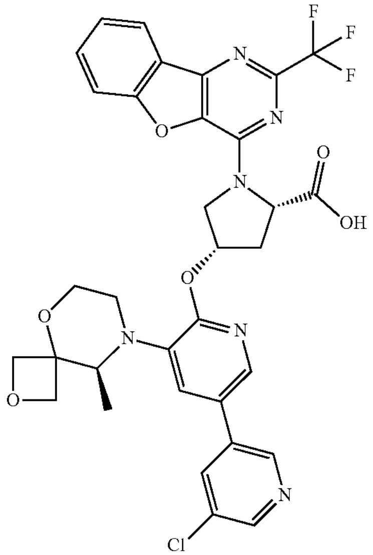 [SMILES: C[C@@H]1N(c2cc(-c3cncc(Cl)c3)cnc2O[C@H]2C[C@@H](C(=O)O)N(c3nc(C(F)(F)F)nc4c3oc3ccccc34)C2)CCOC12COC2] | 11 | 48 | 9238 | 193 | 1369 |

TABLE 1-continued
| Pharmacological properties of the Example compounds of the invention | | | | | | |
|---|---|---|---|---|---|---|
| Exam. No. | Structure | hcGAS IC50 [nM] | $THP1_{(vir)}$ IC50 [nM] | $THP1_{(cGAMP)}$ IC50 [nM] | Ratio $THP1_{(cGAMP)}$ IC50/ $THP1_{(vir)}$ IC50 | hWB IC50 [nM] |
| 3.27 | 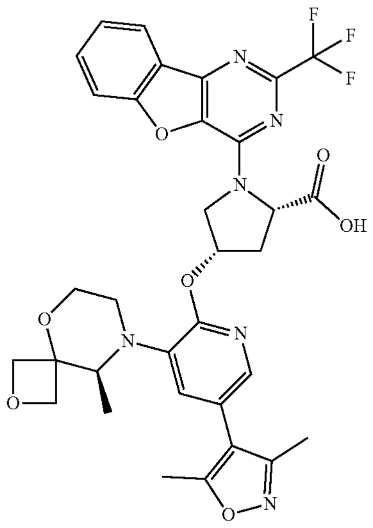 [SMILES: Cc1noc(C)c1-c1cnc(O[C@H]2C[C@@H](C(=O)O)N(c3nc(C(F)(F)F)nc4c3oc3ccccc34)C2)c(N2CCOC3(COC3)[C@@H]2C)c1] | 21 | 326 | 12478 | 38 | 1858 |
| 3.28 | 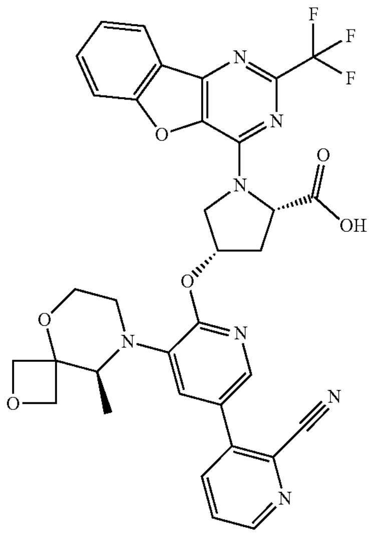 [SMILES: C[C@@H]1N(c2cc(-c3cccnc3C#N)cnc2O[C@H]2C[C@@H](C(=O)O)N(c3nc(C(F)(F)F)nc4c3oc3ccccc34)C2)CCOC12COC2] | 14 | 712 | 16375 | 23 | |

TABLE 1-continued
| Pharmacological properties of the Example compounds of the invention | | | | | | |
|---|---|---|---|---|---|---|
| Exam. No. | Structure | hcGAS IC50 [nM] | $THP1_{(vir)}$ IC50 [nM] | $THP1_{(cGAMP)}$ IC50 [nM] | Ratio $THP1_{(cGAMP)}$ IC50/ $THP1_{(vir)}$ IC50 | hWB IC50 [nM] |
| 3.29 | 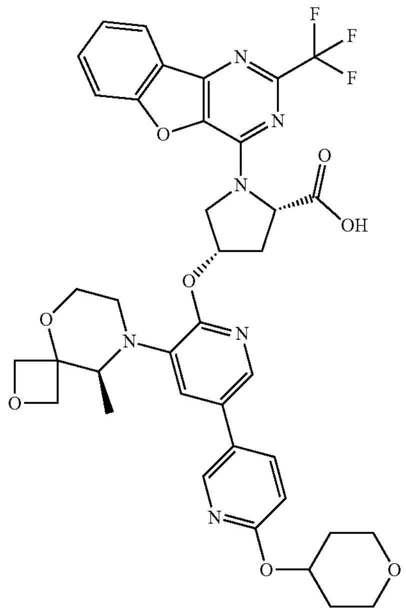 [SMILES: C[C@@H]1N(c2cc(-c3ccc(OC4CCOCC4)nc3)cnc2O[C@H]2C[C@@H](C(=O)O)N(c3nc(C(F)(F)F)nc4c3oc3ccccc34)C2)CCOC12COC2] | 66 | 591 | 6544 | 11 | 1574 |
| 3.30 | 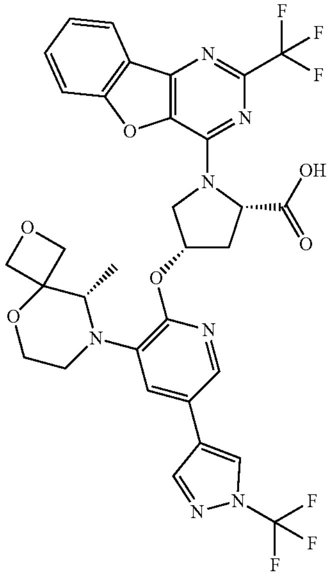 [SMILES: C[C@@H]1N(c2cc(-c3cnn(C(F)(F)F)c3)cnc2O[C@H]2C[C@@H](C(=O)O)N(c3nc(C(F)(F)F)nc4c3oc3ccccc34)C2)CCOC12COC2] | 26 | 15 | 12 626 | 829 | 84 |

TABLE 1-continued
Pharmacological properties of the Example compounds of the invention
| Exam. No. | Structure | hcGAS IC50 [nM] | $THP1_{(vir)}$ IC50 [nM] | $THP1_{(cGAMP)}$ IC50 [nM] | Ratio $THP1_{(cGAMP)}$ IC50/ $THP1_{(vir)}$ IC50 | hWB IC50 [nM] |
|---|---|---|---|---|---|---|
| 3.31 | 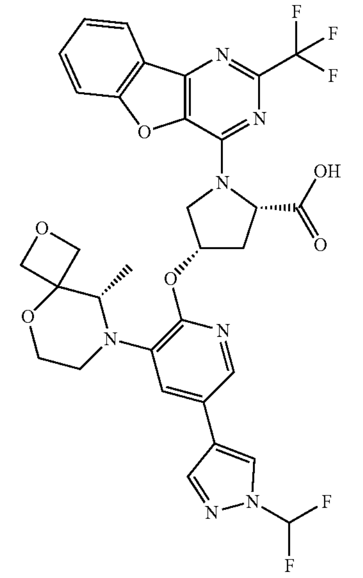 [SMILES: C[C@@H]1N(c2cc(-c3cnn(C(F)F)c3)cnc2O[C@H]2C[C@@H](C(=O)O)N(c3nc(C(F)(F)F)nc4c3oc3ccccc34)C2)CCOC12COC2] | 11 | 3 | 10 899 | 4120 | 28 |
| 3.32 | 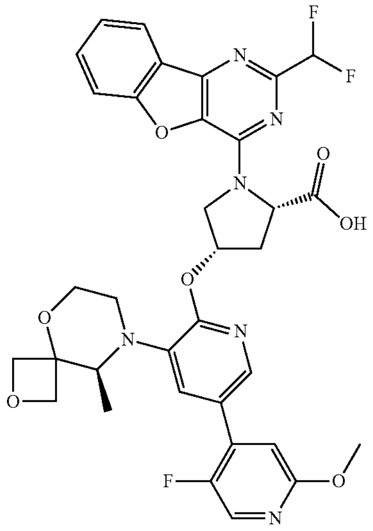 [SMILES: COc1cc(-c2cnc(O[C@H]3C[C@@H](C(=O)O)N(c4nc(C(F)F)nc5c4oc4ccccc45)C3)c(N3CCOC4(COC4)[C@@H]3C)c2)c(F)cn1] | 9 | 2 | 12885 | 5194 | 17 |

TABLE 1-continued
Pharmacological properties of the Example compounds of the invention
| Exam. No. | Structure | hcGAS IC50 [nM] | $THP1_{(vir)}$ IC50 [nM] | $THP1_{(cGAMP)}$ IC50 [nM] | Ratio $THP1_{(cGAMP)}$ IC50/ $THP1_{(vir)}$ IC50 | hWB IC50 [nM] |
|---|---|---|---|---|---|---|
| 4.01 | 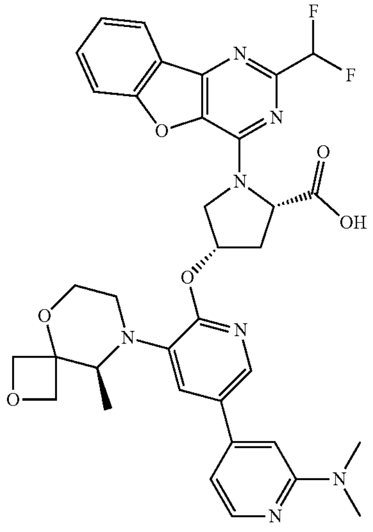 [SMILES: C[C@@H]1N(c2cc(-c3ccnc(N(C)C)c3)cnc2O[C@H]2C[C@@H](C(=O)O)N(c3nc(C(F)F)nc4c3oc3ccccc34)C2)CCOC12COC2] | 10 | <5 | 6676 | >1239 | 5 |
| 4.02 | 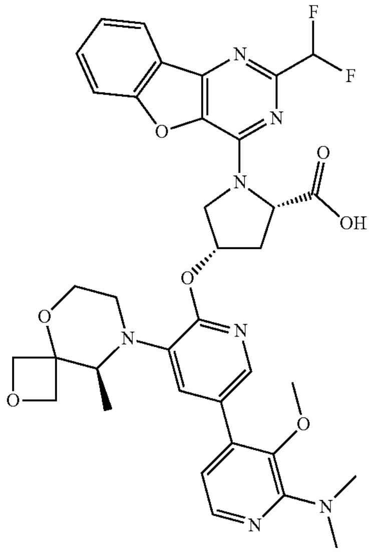 [SMILES: COc1c(-c2cnc(O[C@H]3C[C@@H](C(=O)O)N(c4nc(C(F)F)nc5c4oc4ccccc45)C3)c(N3CCOC4(COC4)[C@@H]3C)c2)ccnc1N(C)C] | 12 | 17 | 12562 | 735 | 42 |

TABLE 1-continued
Pharmacological properties of the Example compounds of the invention
| Exam. No. | Structure | hcGAS IC50 [nM] | $THP1_{(vir)}$ IC50 [nM] | $THP1_{(cGAMP)}$ IC50 [nM] | Ratio $THP1_{(cGAMP)}$ IC50/ $THP1_{(vir)}$ IC50 | hWB IC50 [nM] |
|---|---|---|---|---|---|---|
| 4.03 | 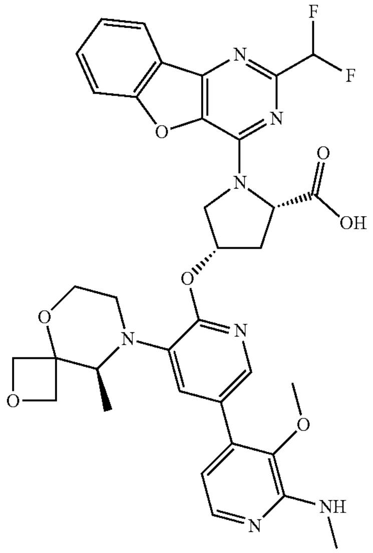 [SMILES: CNc1nccc(-c2cnc(O[C@H]3C[C@@H](C(=O)O)N(c4nc(C(F)F)nc5c4oc4ccccc45)C3)c(N3CCOC4(COC4)[C@@H]3C)c2)c1OC] | 8 | 199 | 7872 | 40 | 78 |
| 4.04 | 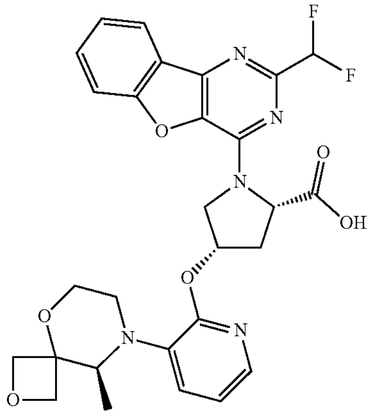 [SMILES: C[C@@H]1N(c2cccnc2O[C@H]2C[C@@H](C(=O)O)N(c3nc(C(F)F)nc4c3oc3ccccc34)C2)CCOC12COC2] | 2 | 386 | >16611 | >43 | 77 |
| 5.01 | 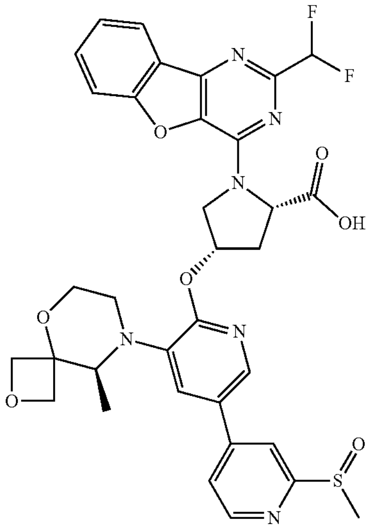 [SMILES: C[C@@H]1N(c2cc(-c3ccnc(S(C)=O)c3)cnc2O[C@H]2C[C@@H](C(=O)O)N(c3nc(C(F)F)nc4c3oc3ccccc34)C2)CCOC12COC2] | 5 | 579 | 22083 | 38 | 239 |

TABLE 1-continued
| Pharmacological properties of the Example compounds of the invention | | | | | | |
|---|---|---|---|---|---|---|
| Exam. No. | Structure | hcGAS IC50 [nM] | $THP1_{(vir)}$ IC50 [nM] | $THP1_{(cGAMP)}$ IC50 [nM] | Ratio $THP1_{(cGAMP)}$ IC50/ $THP1_{(vir)}$ IC50 | hWB IC50 [nM] |
| 6.01 | 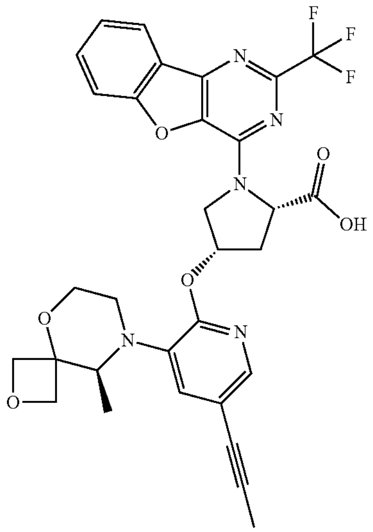 [SMILES: CC#Cc1cnc(O[C@H]2C[C@@H](C(=O)O)N(c3nc(C(F)(F)F)nc4c3oc3ccccc34)C2)c(N2CCOC3(COC3)[C@@H]2C)c1] | 10 | <5 | 20480 | 3801 | 25 |
| 6.02 | 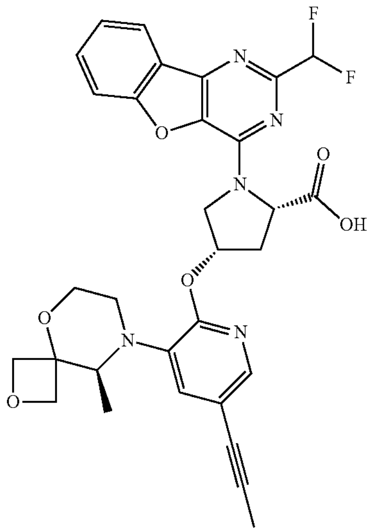 [SMILES: CC#Cc1cnc(O[C@H]2C[C@@H](C(=O)O)N(c3nc(C(F)F)nc4c3oc3ccccc34)C2)c(N2CCOC3(COC3)[C@@H]2C)c1] | 6 | <5 | >16 000 | >3000 | 8 |

TABLE 1-continued
Pharmacological properties of the Example compounds of the invention
| Exam. No. | Structure | hcGAS IC50 [nM] | $THP1_{(vir)}$ IC50 [nM] | $THP1_{(cGAMP)}$ IC50 [nM] | Ratio $THP1_{(cGAMP)}$ IC50/ $THP1_{(vir)}$ IC50 | hWB IC50 [nM] |
|---|---|---|---|---|---|---|
| 6.03 | 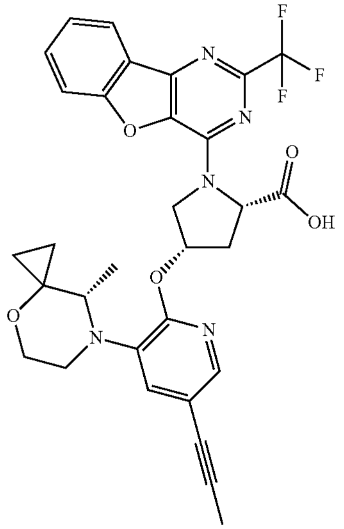 [SMILES: CC#Cc1cnc(O[C@H]2C[C@@H](C(=O)O)N(c3nc(C(F)(F)F)nc4c3oc3ccccc34)C2)c(N2CCOC3(CC3)[C@@H]2C)c1] | 7 | 5 | 10947 | 2273 | 95 |
| 7.01 | 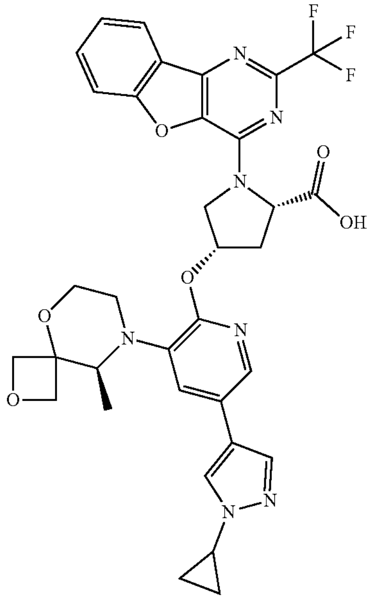 [SMILES: C[C@@H]1N(c2cc(-c3cnn(C4CC4)c3)cnc2O[C@H]2C[C@@H](C(=O)O)N(c3nc(C(F)(F)F)nc4c3oc3ccccc34)C2)CCOC12COC2] | 14 | 5 | 9257 | 1700 | 50 |

TABLE 1-continued
Pharmacological properties of the Example compounds of the invention
| Exam. No. | Structure | hcGAS IC50 [nM] | $THP1_{(vir)}$ IC50 [nM] | $THP1_{(cGAMP)}$ IC50 [nM] | Ratio $THP1_{(cGAMP)}$ IC50/ $THP1_{(vir)}$ IC50 | hWB IC50 [nM] |
|---|---|---|---|---|---|---|
| 7.02 | 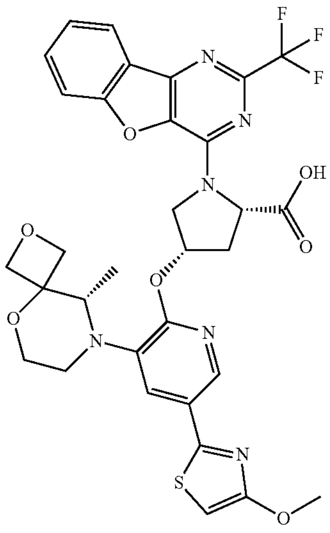 [SMILES: COc1csc(-c2cnc(O[C@H]3C[C@@H](C(=O)O)N(c4nc(C(F)(F)F)nc5c4oc4ccccc45)C3)c(N3CCOC4(COC4)[C@@H]3C)c2)n1] | 14 | 1 | 8320 | 7533 | 13 |
| 7.03 | 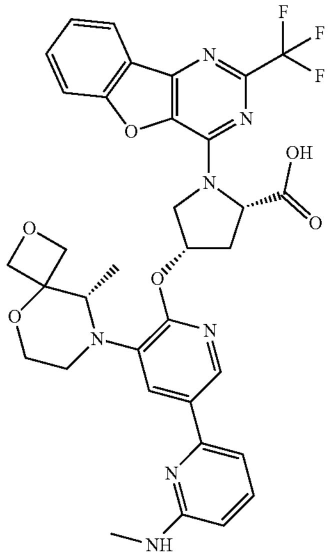 [SMILES: CNc1cccc(-c2cnc(O[C@H]3C[C@@H](C(=O)O)N(c4nc(C(F)(F)F)nc5c4oc4ccccc45)C3)c(N3CCOC4(COC4)[C@@H]3C)c2)n1] | 21 | 2 | >10009 | 4151 | 27 |

TABLE 1-continued
Pharmacological properties of the Example compounds of the invention
| Exam. No. | Structure | hcGAS IC50 [nM] | THP1$_{(vir)}$ IC50 [nM] | THP1$_{(cGAMP)}$ IC50 [nM] | Ratio THP1$_{(cGAMP)}$ IC50/ THP1$_{(vir)}$ IC50 | hWB IC50 [nM] |
|---|---|---|---|---|---|---|
| 7.04 | 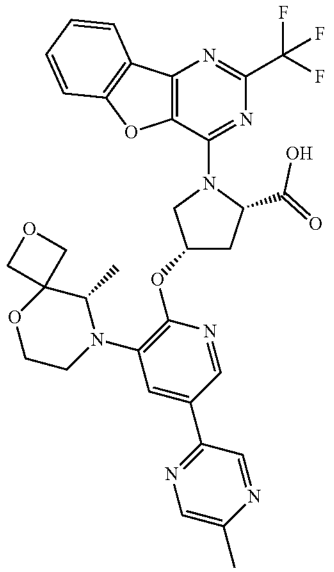 [SMILES: Cc1cnc(-c2cnc(O[C@H]3C[C@@H](C(=O)O)N(c4nc(C(F)(F)F)nc5c4oc4ccccc45)C3)c(N3CCOC4(COC4)[C@@H]3C)c2)cn1] | 12 | 2 | >10011 | 4084 | 22 |
| 7.05 | 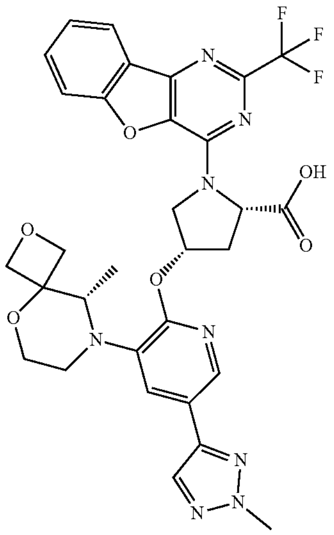 [SMILES: C[C@@H]1N(c2cc(-c3cnn(C)n3)cnc2O[C@H]2C[C@@H](C(=O)O)N(c3nc(C(F)(F)F)nc4c3oc3ccccc34)C2)CCOC12COC2] | 9 | 10 | 13172 | 1292 | 35 |

TABLE 1-continued
Pharmacological properties of the Example compounds of the invention
| Exam. No. | Structure | hcGAS IC50 [nM] | $THP1_{(vir)}$ IC50 [nM] | $THP1_{(cGAMP)}$ IC50 [nM] | Ratio $THP1_{(cGAMP)}$ IC50/ $THP1_{(vir)}$ IC50 | hWB IC50 [nM] |
|---|---|---|---|---|---|---|
| 8.01 | 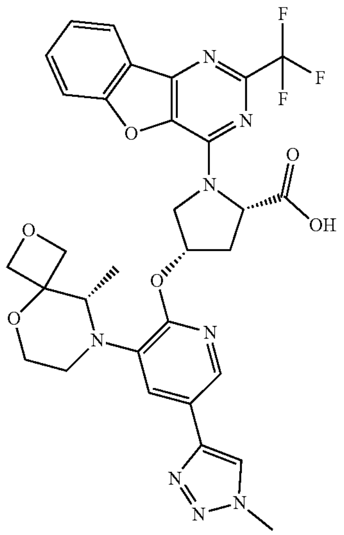 [SMILES: C[C@@H]1N(c2cc(-c3cn(C)nn3)cnc2O[C@H]2C[C@@H](C(=O)O)N(c3nc(C(F)(F)F)nc4c3oc3ccccc34)C2)CCOC12COC2] | 5 | 11 | 14921 | 1366 | 21 |
| 9.01 | 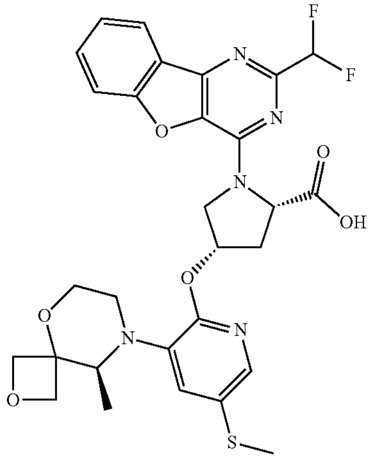 [SMILES: CSc1cnc(O[C@H]2C[C@@H](C(=O)O)N(c3nc(C(F)F)nc4c3oc3ccccc34)C2)c(N2CCOC3(COC3)[C@@H]2C)c1] | 6 | 16 | 19805 | 1254 | 38 |
| 10.01 | 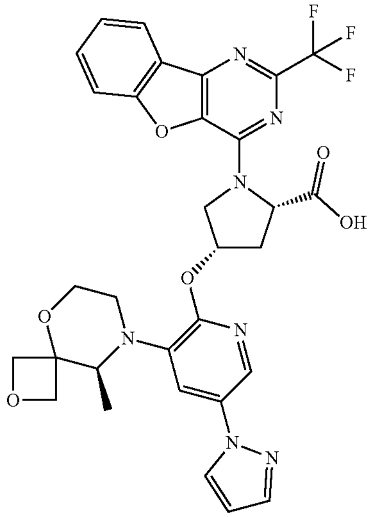 [SMILES: C[C@@H]1N(c2cc(-n3cccn3)cnc2O[C@H]2C[C@@H](C(=O)O)N(c3nc(C(F)(F)F)nc4c3oc3ccccc34)C2)CCOC12COC2] | 5 | 10 | >10000 | >1000 | 47 |

5.2 Comparison of the Example Compounds with Prior Art Compounds 5.2.1 Compounds of WO 2020/142729

In WO 2020/142729 cGAS-inhibitors with partially similar structures have been disclosed. On page 44 and 45 of WO 2020/142729 the "biochemical (in vitro) IC50-values" with regard to cGAS-inhibition (corresponding to "hcGAS IC50") have been disclosed. Hereby compounds with a "biochemical (in vitro) IC50-value" of less than 100 nM had been designated into "group A", compounds with a "biochemical (in vitro) IC50-value" of greater than 100 nM and less than 500 nM had been designated into "group B", compounds with a "biochemical (in vitro) IC50-value" of greater than 500 nM and less than 1 μM had been designated into "group C", compounds with a "biochemical (in vitro) IC50-value" of greater than 1 μM and less than 10 μM had been designated into "group D" and compounds with a "biochemical (in vitro) IC50-value" of greater than 10 μM had been designated into "group E" (see page 44 of WO 2020/142729).

On page 45 of WO 2020/142729 it is disclosed that only compound No. 25 could be designated to "group A" having a "biochemical (in vitro) IC50-value" of less than 100 nM. All other example compounds of WO 2020/142729 show "biochemical (in vitro) IC50-values" of greater than 100 nM.

5.2.2 Comparison Between the Examples of the Invention and the Examples of WO 2020/142729

Selected prior art compounds of WO 2020/142729 have been synthesized and then have been tested with respect to their pharmacological properties regarding their potency to inhibit the cGAS/STING pathway. In particular the "biochemical (in vitro) IC50-values" with regard to cGAS-inhibition (hcGAS IC50), the "cellular IC50-values with regard to inhibition of IFN induction in virus-stimulated THP1 cells" ($THP1_{(vir)}$ IC50), the "cellular IC50-value with regard to inhibition of IFN induction in cGAMP-stimulated THP1 cells" ($THP1_{(CGAMP)}$ IC50) and the "IC50-value with regard to inhibition of IFN induction in human whole blood" (hWB) have been experimentally determined for the structurally closest examples of WO 2020/142729 according to the assay methods as described in section 6 below (see Table 2).

TABLE 2

Pharmacological properties of a selection of Example compounds from WO 2020/142729

| Example No. (as disclosed in WO 2020/142729) | Structure | hcGAS IC50 [nM] | $THP1_{(vir)}$ IC50 [nM] | $THP1_{(cGAMP)}$ IC50 [nM] | hWB IC50 [nM] |
|---|---|---|---|---|---|
| 15 | 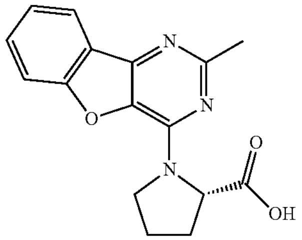 [SMILES: Cc1nc(N2CCC[C@H]2C(=O)O)c2oc3ccccc3c2n1] | 2700 | >17000 | >17000 | — |
| 25 | 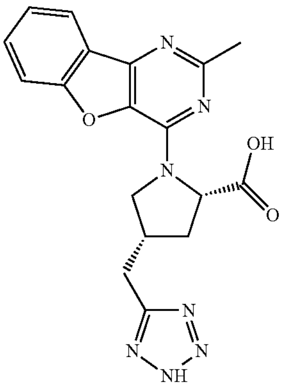 [SMILES: Cc1nc(N2C[C@@H](Cc3nn[nH]n3)C[C@H]2C(=O)O)c2oc3ccccc3c2n1] | 55 | >17000 | >17000 | >9992 |

TABLE 2-continued

| Pharmacological properties of a selection of Example compounds from WO 2020/142729 | | | | | |
|---|---|---|---|---|---|
| Example No. (as disclosed in WO 2020/142729) | Structure | hcGAS IC50 [nM] | $THP1_{(vir)}$ IC50 [nM] | $THP1_{(cGAMP)}$ IC50 [nM] | hWB IC50 [nM] |
| 28 | 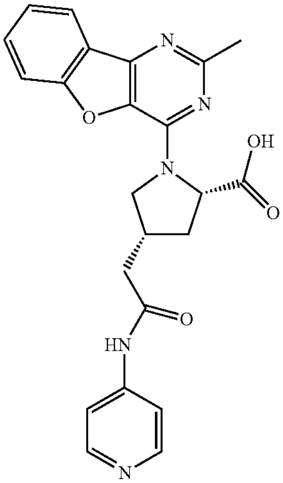 [SMILES: Cc1nc(N2C[C@@H](CC(=O)Nc3ccncc3)C[C@H]2C(=O)O)c2oc3ccccc3c2n1] | 630 | >32000 | >17000 | >9990 |
| 38 | 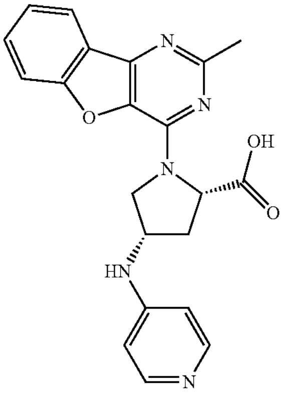 [SMILES: Cc1nc(N2C[C@@H](Nc3ccncc3)C[C@H]2C(=O)O)c2oc3ccccc3c2n1] | 3000 | >17000 | >17000 | >9990 |
| 58 | 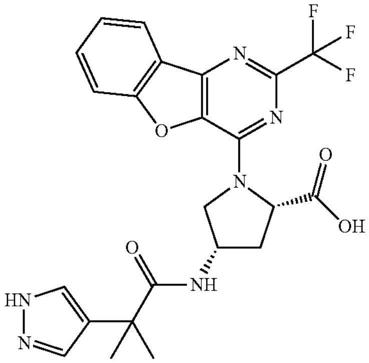 [SMILES: CC(C)(C(=O)N[C@H]1C[C@@H](C(=O)O)N(c2nc(C(F)(F)F)nc3c2oc2ccccc23)C1)c1cn[nH]c1] | 320 | 21000 | 23000 | >9982 |

The pharmacological properties for the Example compounds of the invention as summarized in Table 1 and the respective pharmacological properties for the compounds of WO 2020/142729 can be compared to each other, since they were experimentally determined according to the identical assay procedures as described in section 6 below.

From data as shown in Table 2 it is clear that all example compounds of WO 2020/142729 show "biochemical (in vitro) IC50-values" (=hcGAS IC50) that are significantly larger than 100 nM—with the only exception of Example No. 25 of WO 2020/142729 (in WO 2020/142729 designated in "Group A" having a "biochemical (in vitro) IC50-value" (=hcGAS IC50) of less than 100 nM). In contrast to that the Example compounds of the invention all have "biochemical (in vitro) IC50-values" (hcGAS IC50) of less than 100 nM. However, Example No. 25 of WO 2020/142729 which has a "biochemical (in vitro) IC50-value" (hcGAS IC50) of 55 nM, does not at all comply with the selection criterium of a "satisfying cellular inhibitory potency" shown by a $THP1_{(vir)}$ IC50 of lower than 1 μM, because $THP1_{(vir)}$ IC50 for Example No. 25 of WO 2020/142729 is 17 μM.

5.3 Prodrugs

It is known that esters of active agents with a carboxylic acid group may represent viable prodrugs which may i.e. show an improved oral absorption/bioavailability compared to the respective active agent. Frequently used prodrugs of active agents with a carboxylic acid group are for example methyl esters, ethyl esters, iso-propyl esters etc. (see Beaumont et al., Current Drug Metabolism, 2003, Vol. 4, Issue 6, 461-485).

Further, Nakamura et al., Bioorganic & Medicinal Chem., Vol. 15, Issue 24, p. 7720-7725 (2007), describes that also N-acylsulfonamide derivatives and N-acylsulfonylurea derivatives of a specific active agent with a free carboxylic acid group have the potential of being a viable prodrug.

Additionally, experimental hints have been found that also the methyl esters of the example compounds of formula (I) or of formula (I') represent viable prodrugs of the cGAS inhibitors of formula (I) or of formula (I').

Compounds P01, P02, P03 and P04 are methyl esters of the Example compounds 4.04, 1.10, 1.12 and 3.14, respectively and therefore may represent viable prodrugs of the respective Example compounds.

P01, P02, P03 and P04 have been synthesized and tested for their pharmacological properties with respect to their potency to inhibit the cGAS/STING pathway. Subsequently, the experimentally determined pharmacological properties of prodrugs P01, P02, P03 and P04 have been compared to the corresponding pharmacological properties of the respective Example compounds 4.04, 1.10, 1.12 and 3.14 as summarized in Table 3.

This comparison between the Example compound and its corresponding prodrug shows that the hcGAS IC50-values for the Example compounds are always around or even smaller than 10 nM, whereas the hcGAS IC50-values for the corresponding prodrugs are always extremely large, that means generally larger than 9000 nM. That large difference between Example compound on the one hand and its corresponding prodrug on the other hand is never observed for the respective $THP1_{(vir)}$ IC50-values which always stay in the same range between example compound and its corresponding prodrug (see Table 3 for Example No. 4.04 and its respective prodrug P01).

One possible explanation for that observation is that the example compounds (which represent the "drugs") all have a free carboxyl group which seems to be crucial for inhibition of cGAS activity, whereas in all "prodrugs" the carboxyl group is masked by a carboxy-methyl ester group. Consequently, the prodrugs lose their inhibitory potency in the "in vitro human cGAS enzyme assay" (see section 6.1 below), because in this assay intracellular enzymes that cleave the carboxy-methyl ester group are absent. Therefore the prodrugs show extremely large "biochemical (in vitro) IC50-values" (=hcGAS IC50) in this "in vitro human cGAS enzyme assay", whereas the corresponding Example compounds (which represent the drugs or active agents) show small "biochemical (in vitro) IC50-values" (=hcGAS IC50).

In the "human cGAS cell and the counter cell assay" (see section 6.2 below) endogenous cellular enzymes that cleave the carboxy-methyl ester group are present. Consequently not only the Example compounds themselves (that means the drugs or active agents themselves) show small $THP1_{(vir)}$ IC50-values, but also the corresponding prodrugs show relatively small "$THP1_{(vir)}$ IC50-values", because in this "human cGAS cell assay" the methyl ester of the prodrugs can be cleaved by endogenous intracellular enzymes into the corresponding drug/active agent that shows inhibitory potency again.

This explanation together with the measurements as shown in Table 3 imply that methyl ester derivatives of the compounds of formula (I) or of formula (I') really seem to represent viable prodrugs of the compounds of formula (I) or of formula (I') which themselves have no inhibitory potency regarding the in vitro human biochemical cGAS inhibition. However, upon cleavage of the methyl ester by endogenous intracellular enzymes the compounds of formula (I) or of formula (I') (the active agents) are formed, that exhibit again an inhibitory potency regarding the cGAS/STING pathway.

TABLE 3

Comparison between selected Example compound of the invention (= active agents) and their respective methyl ester prodrugs:

| Example No./ Prodrug No. | Structure | hcGAS IC50 [nM] | $THP1_{(vir)}$ IC50 [nM] | $THP1_{(cGAMP)}$ IC50 [nM] | hWB IC50 [nM] |
|---|---|---|---|---|---|
| P01 (Prodrug of Ex. 4.04) | 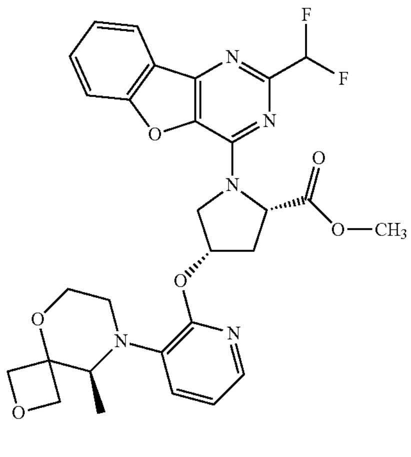 [SMILES: COC(=O)[C@@H]1C[C@H](Oc2ncccc2N2CCOC3(COC3)[C@@H]2C)CN1c1nc(C(F)F)nc2c1oc1ccccc12] | >9956 | 358 | 26058 | 1313 |

TABLE 3-continued
Comparison between selected Example compound of the invention (= active agents) and their respective methyl ester prodrugs:
| Example No./ Prodrug No. | Structure | hcGAS IC50 [nM] | $THP1_{(vir)}$ IC50 [nM] | $THP1_{(cGAMP)}$ IC50 [nM] | hWB IC50 [nM] |
|---|---|---|---|---|---|
| Ex. 4.04 | 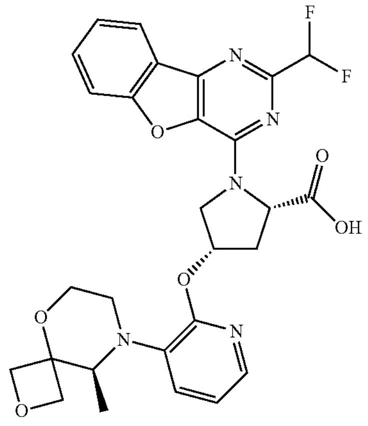 [SMILES: C[C@@H]1N(c2cccnc2O[C@H]2C[C@@H](C(=O)O)N(c3nc(C(F)F)nc4c3oc3ccccc34)C2)CCOC12COC2] | 2 | 386 | >16611 | 77 |
| P02 (Prodrug of Ex. 1.10) | 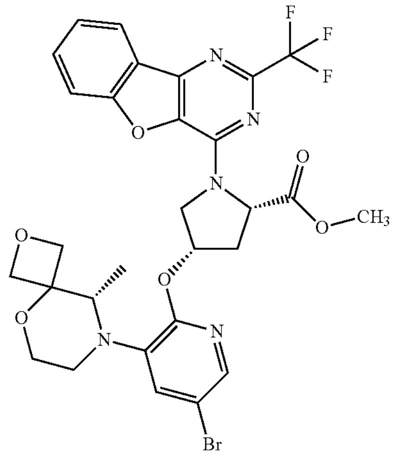 [SMILES: COC(=O)[C@@H]1C[C@H](Oc2ncc(Br)cc2N2CCOC3(COC3)[C@@H]2C)CN1c1nc(C(F)(F)F)nc2c1oc1ccccc12] | >9952 | 444 | 17109 | 5327 |
| Ex. 1.10 | 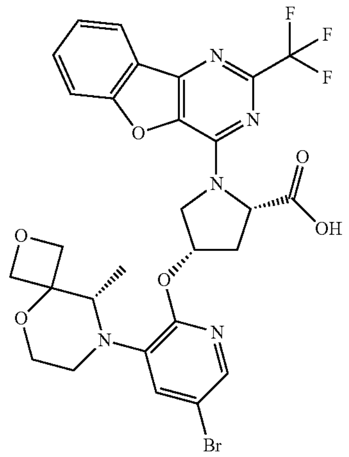 [SMILES: C[C@@H]1N(c2cc(Br)cnc2O[C@H]2C[C@@H](C(=O)O)N(c3nc(C(F)(F)F)nc4c3oc3ccccc34)C2)CCOC12COC2] | 5 | 91 | 16130 | 33 |

TABLE 3-continued
Comparison between selected Example compound of the invention (= active agents) and their respective methyl ester prodrugs:
| Example No./ Prodrug No. | Structure | hcGAS IC50 [nM] | $THP1_{(vir)}$ IC50 [nM] | $THP1_{(cGAMP)}$ IC50 [nM] | hWB IC50 [nM] |
|---|---|---|---|---|---|
| P03 (Prodrug of Ex. 1.12) | 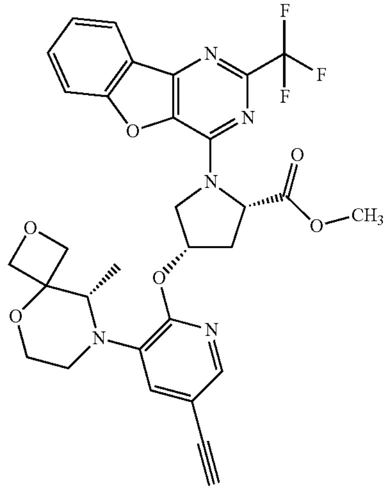 [SMILES: C#Cc1cnc(O[C@H]2C[C@@H](C(=O)OC)N(c3nc(C(F)(F)F)nc4c3oc3ccccc34)C2)c(N2CCOC3(COC3)[C@@H]2C)c1] | 9617 | 188 | 22845 | 1088 |
| Ex. 1.12 | 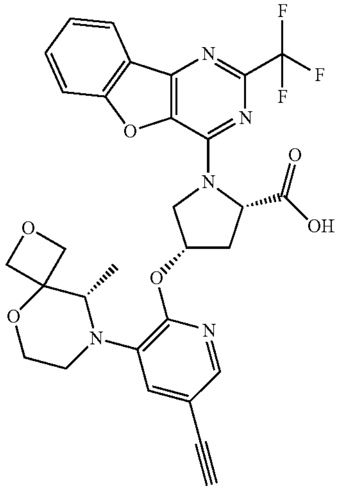 [SMILES: C#Cc1cnc(O[C@H]2C[C@@H](C(=O)O)N(c3nc(C(F)(F)F)nc4c3oc3ccccc34)C2)c(N2CCOC3(COC3)[C@@H]2C)c1] | 3 | 7 | 11892 | 15 |
| P04 (Prodrug of Ex. 3.14) | 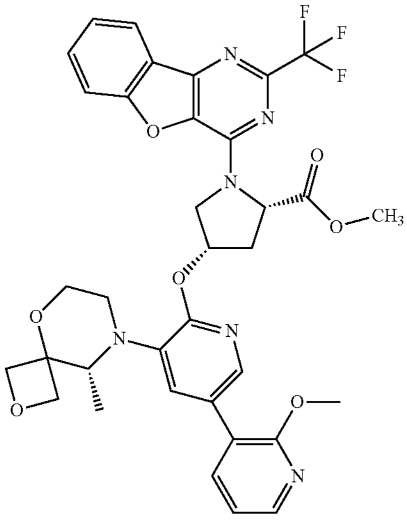 [SMILES: COC(=O)[C@@H]1C[C@H](Oc2ncc(-c3cccnc3OC)cc2N2CCOC3(COC3)[C@H]2C)CN1c1nc(C(F)(F)F)nc2c1oc1ccccc12] | >9954 | 67 | >16621 | 2747 |

TABLE 3-continued

Comparison between selected Example compound of the invention (= active agents) and their respective methyl ester prodrugs:

| Example No./ Prodrug No. | Structure | hcGAS IC50 [nM] | $THP1_{(vir)}$ IC50 [nM] | $THP1_{(cGAMP)}$ IC50 [nM] | hWB IC50 [nM] |
|---|---|---|---|---|---|
| Ex. 3.14 | 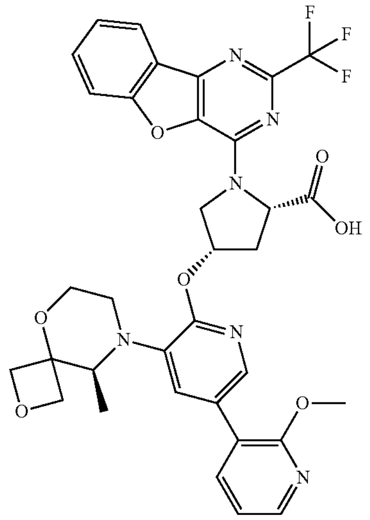 [SMILES: COc1ncccc1-c1cnc(O[C@H]2C[C@@H](C(=O)O)N(c3nc(C(F)(F)F)nc4c3oc3ccccc34)C2)c(N2CCOC3(COC3)[C@@H]2C)c1] | 11 | 10 | 7832 | 26 |

6 Biological Experiments

The activity of the compounds of the invention may be demonstrated using the following in vitro cGAS enzyme and cell assays:

6.1 Method: Human cGAS Enzyme Assay (hcGAS IC50 (In Vitro))

Human cGAS enzyme was incubated in the presence of a 45 base pair double stranded DNA to activate the enzyme and GTP and ATP as substrates. Compound activity was determined by measuring the effect of compounds on the formation of the product of the enzyme reaction, cGAMP, which is measured by a mass spectrometry method.

Enzyme preparation:

Human cGAS (amino acid 1-522) with an N-terminal 6x-His-tag and SUMO-tag was expressed in *E. coli* BL21 (DE3) pLysS (Novagen) cells for 16 h at 18° C. Cells were lysed in buffer containing 25 mM Tris (pH 8), 300 mM NaCl, 10 mM imidazole, 10% glycerol, protease inhibitor cocktail (Complete™, EDTA-free, Roche) and DNase (5 µg/mL). The cGAS protein was isolated by affinity chromatography on Ni-NTA agarose resin and further purified by size exclusion chromatography using a Superdex 200 column (GE Healthcare) equilibrated in 20 mM Tris (pH 7.5), 500 mM KCl, and 1 mM TCEP. Purified protein was concentrated to 1.7 mg/mL and stored at −80° C.

Assay Method

Compounds were delivered in 10 mM DMSO solution, serially diluted and transferred to the 384 well assay plate (Greiner #781201) using an Echo acoustic dispenser. Typically, 8 concentrations were used with the highest concentration at 10 µM in the final assay volume followed by ~1:5 dilution steps. DMSO concentration was set to 1% in the final assay volume. The 384 well assay plate contained 22 test compounds (column 1-22), and DMSO in column 23 and 24.

After the compound transfer, 15 µL of the enzyme-DNA-working solution (12 nM cGAS, 0.32 µM 45base pair DNA in assay buffer, 10 mM Tris pH 7.5/10 mM KCl/5 mM MgCl2/1 mM DTT) were added to each well from column 1-23 via a MultiDrop Combi dispenser. In column 24, 15 µl of assay buffer without enzyme/DNA were added as a low control.

The plates were then pre-incubated for 60 min at room temperature.

Following that, 10 µL of GTP (ThermoFisher #R0461)-ATP (Promega #V915B) mix in assay buffer were added to the assay plate (columns 1-24, 30 µM final concentration each) using a Multidrop Combi.

The plates were incubated again for 90 min at room temperature.

Following the incubation, the reaction was stopped by 80 µL of 0.1% formic acid in assay buffer containing 5 nM cyclic-di-GMP (Sigma #SML1228) used as internal standard for the mass spectrometry. The total volume/well was 105 µL.

Rapidfire MS Detection

The plates were centrifuged at 4000 rpm, 4° C., for 5 min.

The RapidFire autosampler was coupled to a binary pump (Agilent 1290) and a Triple Quad 6500 (ABSciex, Toronto, Canada). This system was equipped with a 10 µL loop, C18 [12 µL bed volume] cartridge (Agilent, Part No. G9210A) containing 10 mM NH4Ac (aq) water (pH7.4) as eluent A (pump 1 at 1.5 mL/min, pump 2 at 1.25 mL/min) and 10 mM NH4Ac in v/v/v 47.5/47.5/5 ACN/MeOH/H2O (pH7.4) as eluent B (pump 3 at 1.25 mL/min). Aspiration time: 250 ms; Load time: 3000 ms; Elute time: 3000 ms; Wash volume: 500 µL.

The MS was operated in positive ion mode with HESI ion source, with a source temperature of 550° C., curtain gas=35, gas 1=65, and gas 2=80. Unit mass resolution in SRM mode. The following transitions and MS parameters (DP: declustering potential and CE: collision energy) for cGAMP and DicGMP were determined:

Analyte: cGAMP at 675.1/524, DP=130, CE=30 and

Internal standard: cyclic-di-GMP at 690.1/540, DP=130, CE=30.

The formation of cGAMP was monitored and evaluated as ratio to cyclic-di-GMP.

Data Evaluation and Calculation:

For data evaluation and calculation, the measurement of the low control was set as 0% control and the measurement of the high control was set as 100% control. The IC50 values were calculated using the standard 4 parameter logistic regression formula. Calculation: [y=(a−d)/(1+(x/c)^b)+d], a=low value, d=high value; x=conc M; c=IC50 M; b=slope

6.2 Method: Human cGAS Cell Assay and cGAMP Stimulated Counter Cell Assay ($THP1_{(vir)}$ IC50 and $Thp1_{(cGAMP)}$ Ic50)

THP1-Dual™ cells (InvivoGen #thpd-nfis) expressing IRF dependent Lucia luciferase reporter were used as basis for both assays. For the detection of cellular cGAS activity cells were stimulated by a baculovirus (pFastbac-1, Invitrogen, no coding insert) infection that delivers the cGAS enzyme stimulating double-stranded DNA (measurement of $THP1_{(vir)}$ IC50).

For the counter assay, cells were stimulated by cGAMP (SigmaAldrich #SML1232) to activate the identical pathway independent and directly downstream of cGAS (measurement of $THP1_{(cGAMP)}$ IC50). Pathway activity was monitored by measuring the Lucia luciferase activity induced by either DNA stimulated cGAS enzyme activity (measurement of $THP1_{(vir)}$ IC50) or by cGAMP directly (measurement of $THP1_{(CGAMP)}$ IC50, counter assay).

Assay Method

Compounds were delivered in 10 mM DMSO solution, serially diluted and transferred to the 384 well assay plate (Greiner #781201) using an Echo acoustic dispenser. Typically, 8 concentrations were used with the highest concentration at 10 µM in the final assay volume followed by ~1:5 dilution steps. DMSO concentration was set to 1% in the final assay volume. The 384 well assay plate contained 21 test compounds (column 1-22), and DMSO in column 23 and 24.

Cells, cultivated according to manufacturer conditions, were harvested by centrifugation at 300 g/10 min and were then resuspended and diluted to 1.66E5 cells/ml in fresh cell culture medium (RPMI 1640 (Gibco #A10491-01), 10% FCS (Gibco #10500), 1× GlutaMax (Gibco #35050-061),1× Pen/Strep solution (Gibco #15140-122), 100 µg/ml Normocin (InvivoGen #ant-nr), 100 µg/ml Zeocin (InvivoGen #ant-zn), 10 µg/ml Blasticidin S (Life Technologies #A11139-03)). The baculovirus solution was then added 1:200 (have varied according to virus batch) to the cells (measurement of $THP1_{(vir)}$ IC50). Alternatively, for the counter assay cGAMP was added to the cells at a final concentration of 10 µM (measurement of $THP1_{(cGAMP)}$ IC50). 30 µL of the cell/virus-mix were added to each well of the compound plate from column 1-23 via MultiDrop Combi dispenser (5000 cells/well). In column 24, 30 µl/5000 cells/well without virus were added as a low control.

The plates were then incubated for 18 h at 37° C. in a humidified incubator.

Following that, 15 µL of QuantiLuc detection reagent (InvivoGen #rep-qlcg5) were added to each well using a MultiDrop Combi. Measurement was done immediately after the addition using an EnVision reader (US-luminescence read-mode).

Data Evaluation and Calculation:

For data evaluation and calculation, the measurement of the low control was set as 0% control and the measurement of the high control was set as 100% control. The IC50 values were calculated using the standard 4 parameter logistic regression formula. Calculation: [y=(a−d)/(1+(x/c)^b)+d], a=low value, d=high value; x=conc M; c=1C50 M; b=slope

6.3 Method: Human Whole Blood Assay (Human WB IC50)

For the detection of cellular cGAS activity human whole blood was stimulated by transfection with double stranded DNA. Pathway activity was monitored by measuring the IFNα2α production.

Assay Method

Compounds were delivered as 10 mM DMSO solution and serially diluted and transferred to the 96-well cell culture plate (Corning #3595), prefilled with 20 µl OptiMEM (Gibco, #11058-021) in each well, using an Echo acoustic dispenser. Typically, 8 concentrations were used with the highest concentration at 10 µM in the final assay volume followed by ~1:5 dilution steps. DMSO concentration was set to 0.1% in the final assay volume. The 96-well assay plate contained 10 test compounds, and DMSO in control wells.

Collection of human whole blood from 3 or more healthy donors (male or female, no medication for 7 days except contraceptive and thyroxine) as Na-Citrate blood (e.g. 3.8% in Monovettes from Sarstedt) was conducted in parallel. Whole blood was kept at room temperature for a maximum of 3 hours after collection until use in the assay.

160 µl of the whole blood samples was transferred to each well of the 96-well assay plates filled with compound/OptiMEM. All assay plates were prepared as duplicates with blood from different donors. Blood plates were kept at room temperature for 60 minutes and continuous shaking with 450 rpm, covered with the lid, but not sealed.

DNA-Fugene mix (Herring DNA, Sigma Aldrich #D6898-1G, Fugene (5×1 mL), Promega #E2312) was prepared in OptiMEM and incubated for 10 min at RT (125 ng DNA/20 µl and Fugene ratio 9.6:1). 20 µl of the DNA Fugene mix was added to each well, resulting in 125 ng DNA/well/200 µl, and Fugene Ratio 9.6:1. 20 µl OptiMEM and 9.6:1 Fugene was added to all low control wells.

After covering assay plates with area seals and the lid, blood plates were kept at room temperature for 30 minutes and continuous shaking with 450 rpm, followed by an overnight incubation of 22 h at 37° C. in the incubator, without shaking.

For the detection of IFNα-2α in human plasma, the biotinylated capture antibody (Antibody set IFNA2, Meso Scale Diagnostics #B21VH-3, including coating and capture antibody) was diluted 1:17.5 in Diluent 100 (Meso Scale Diagnostics #R50AA-4), according to the manufacturer's directions. U-Plex MSD GOLD 96-well Small Spot Strepavidin SECTOR Plates (Meso Scale Diagnostics #L45SA-5) were coated with 25 µl diluted capture antibody. Coated plates were incubated for 60 min at room temperature under continuous shaking at 700 rpm. MSD IFNα-2a plates were washed three times with 150 µl wash buffer (1× HBSS, 0.05% Tween).

After blocking the plates with 100 μl block solution/well (1× HBSS with 0.2% Tween, 2% BSA) for 60 min at room temperature and continuous shaking at 700 rpm, plates were emptied as dry as possible by dumping just before continuing with the human plasma.

Whole Blood assay plates were centrifuged at 1600 rpm for 10 minutes. 25 μl of supernatant was transferred with a pipetting robot from each whole blood plate to the corresponding IFNα-2α plate. Plates were sealed with microplate seals and kept at room temperature again under continuous shaking at 700 rpm for two hours.

Next MSD IFNα-2α plates were washed three times with 150 μl wash buffer (1× HBSS, 0.05% Tween), before adding 25 μl MSD SULFO-TAG IFNα-2α Antibody solution (1:100 diluted in Diluent 3 (Meso Scale Diagnostics #R50AP-2) to each well of the plates.

Afterwards plates were sealed with microplate seals and kept at room temperature again under continuous shaking at 700 rpm for two hours. Finally, MSD IFNα-2α plates were washed three times with 150 μl wash buffer (1× HBSS, 0.05% Tween). 150 μl 2× Read buffer was added to each well and plates were immediately measured with the MSD Sector S600 Reader using the vendor barcode.

Data Evaluation and Calculation:

For data evaluation and calculation, % control calculation of each well was based on the mean of high (DNA stimulated control) and mean of low (unstimulated control) controls by using the following formula:

$$[\text{counts(sample)}-\text{counts(low)})/(\text{counts(high)}-\text{counts(low)})]*100$$

The IC50 values were calculated using the standard 4 parameter logistic regression formula. Calculation: [y=(a−d)/(1+(x/c)^b)+d], a=low value, d=high value; x=conc M; c=IC50 M; b=slope 7 Indications As has been found, the compounds of formula (I) or of formula (I') are characterized by their range of applications in the therapeutic field. Particular mention should be made of those applications for which the compounds of formula (I) or of formula (I') according to the invention are preferably used on the basis of their pharmaceutical activity as cGAS inhibitors. While the cGAS pathway is important for host defense against invading pathogens, such as viral infection and invasion by some intracellular bacteria, cellular stress and genetic factors may also cause production of aberrant cellular dsDNA, e.g. by nuclear or mitochondrial leakage, and thereby trigger autoinflammatory responses. Consequently, cGAS inhibitors have a strong therapeutic potential to be used in the treatment of diverse autoinflammatory and autoimmune diseases.

An et al., Arthritis Rheumatol. 2017 April; 69(4):800-807, disclosed that cGAS expression in peripheral blood mononuclear cells (PBMCs) was significantly higher in patients with the autoimmune disease systemic lupus erythematosus (SLE) than in normal controls. Targeted measurement of cGAMP by tandem mass spectrometry detected cGAMP in 15% of the tested SLE patients, but none of the normal or rheumatoid arthritis controls. Disease activity was higher in SLE patients with cGAMP versus those without cGAMP. Whereas higher cGAS expression may be a consequence of exposure to type I interferon (IFN), detection of cGAMP in SLE patients with increased disease activity indicates potential involvement of the cGAS pathway in disease expression.

Park et al., Ann Rheum Dis. 2018 October; 77(10):1507-1515, also discloses the involvement of the cGAS pathway in the development of SLE.

Thim-Uam et al., iScience 2020 Sep. 4; 23(9), 101530 (doi: 10.1016/j.isci.2020.101530), discloses that the STING pathway mediates lupus via the activation of conventional dendritic cell maturation and plasmacytoid dendritic cell differentiation.

Gao et al., Proc. Natl. Acad. Sci. USA. 2015 Oct 20; 112(42):E5699-705, describes that the activation of cGAS by self-DNA leads to certain autoimmune diseases such as interferonopathies.

Tonduti et al., Expert Rev. Clin. Immunol. 2020 February; 16(2):189-198 discloses that cGAS inhibitors have particular therapeutic potential in Aicardi-Goutières syndrome which is a lupus-like severe autoinflammatory immune-mediated disorder.

In Yu et al., Cell 2020 Oct. 29; 183(3):636-649, the link between TDP-43 triggered mitochondrial DNA and the activation of the cGAS/STING pathway in amyotrophic lateral sclerosis (ALS) is described.

Ryu et al., Arthritis Rheumatol. 2020 November; 72(11): 1905-1915, also shows that bioactive plasma mitochondrial DNA is associated with disease progression in specific fibrosing diseases such as systemic sclerosis (SSc) or interstitial lung deseases (ILDs), progressive fibrosing interstitial lung diseases (PF-ILDs), and idiopathic pulmonary fibrosis (IPF).

In Schuliga et al., Clin. Sci. (Lond). 2020 Apr. 17; 134(7):889-905, it is described that self-DNA perpetuates IPF lung fibroblast senescence in a cGAS-dependent manner.

Additional scientific hints linking the cause for other fibrosing diseases such as non-alcoholic steatotic hepatitis (NASH) with the cGAS/STING pathway have been described in Yu et al., J. Clin. Invest. 2019 Feb. 1; 129(2): 546-555, and in Cho et al., Hepatology. 2018 October; 68(4): 1331-1346.

Nascimento et al., Sci. Rep. 2019 Oct. 16; 9(1):14848, discloses that self-DNA release and STING-dependent sensing drives inflammation due to cigarette smoke in mice hinting at a link between the cGAS-STING pathway and chronic obstructive pulmonary disease (COPD).

Ma et al., Sci. Adv. 2020 May 20; 6(21):eaaz6717, discloses that ulcerative colitis and inflammatory bowel disease (IBD) may be restrained by controlling cGAS-mediated inflammation.

Gratia et al., J. Exp. Med. 2019 May 6; 216(5):1199-1213, shows that Bloom syndrome protein restrains innate immune sensing of micronuclei by cGAS. Consequently cGAS-inhibitors have a therapeutic potential in treating Bloom's syndrome.

Kerur et al., Nat. Med. 2018 January; 24(1):50-61, describes that cGAS plays a significant role in noncanonical-inflammasome activation in age-related macular degeneration (AMD).

Further, the cGAS inhibitors of formula (I) or of formula (I') also have a therapeutic potential in the treatment of cancer (see Hoong et al., Oncotarget. 2020 Jul. 28; 11(30): 2930-2955, and Chen et al., Sci. Adv. 2020 Oct. 14; 6(42): eabb8941).

Additionally, the cGAS inhibitors of formula (I) or of formula (I') have also a therapeutic potential in the treatment of heart failure (Hu et al., Am. J. Physiol. Heart Circ. Physiol. 2020 Jun. 1; 318(6):H1525-H1537).

Further scientific hints at a correlation between Parkinsons disease and the cGAS/STING pathway (Sliter et al., Nature. 2018 September; 561(7722):258-262) and between Sjogren's syndrome and the cGAS/STING pathway (Papinska et al., J. Dent. Res. 2018 July; 97(8):893-900) exist.

Furthermore, cGAS inhibitors of formula (I) or of formula (I') have also a therapeutic potential in the treatment of COVID-19/SARS-CoV-2 infections as shown in Di Domizio et al., Nature. 2022 Jan. 19. doi: 10.1038/s41586-022-04421-w: "The cGAS-STING pathway drives type I IFN immunopathology in COVID-19", and in Neufeldt et al., Commun Biol. 2022 Jan. 12; 5(1):45. doi: 10.1038/s42003-021-02983-5: "SARS-CoV-2 infection induces a pro-inflammatory cytokine response through cGAS-STING and NF-kappaB".

Additionally, cGAS inhibitors of formula (I) or of formula (I') have a therapeutic potential in the treatment of renal inflammation and renal fibrosis as shown in Chung et al., Cell Metab. 2019 30:784-799: "Mitochondrial Damage and Activation of the STING Pathway Lead to Renal Inflammation and Fibrosis", and in Maekawa et al., Cell Rep. 2019 29:1261-1273: "Mitochondrial Damage Causes Inflammation via cGAS-STING Signaling in Acute Kidney Injury".

Furthermore, cGAS inhibitors of formula (I) or of formula (I') have a therapeutic potential in the treatment of cancer as shown in Bakhoum et el., Nature. 2018 Jan. 25; 553(7689): 467-472: "Chromosomal instability drives metastasis through a cytosolic DNA response", and in Liu et al., Nature. 2018 November; 563(7729):131-136: "Nuclear cGAS suppresses DNA repair and promotes tumorigenesis".

Additionally, cGAS inhibitors of formula (I) or of formula (I') have a therapeutic potential in the treatment of dysmetabolism, because $STING^{gt}$ animals show reduced macrophage infiltration in adipose tissue upon subchronic high caloric intake (HFD) and $STING^{gt}$ and IRF3-deficiency leads to a decrease in blood glucose and insulin and reduced body weight (Mao et al, Arterioscler Thromb Vasc Biol, 2017; 37 (5): 920-929).

Furthermore, cGAS inhibitors of formula (I) or of formula (I') have a therapeutic potential in the treatment of vascular diseases and leads to vascular repair/regeneration, because the release of mitochondrial DNA into the cytosol of endothelial cells results in cGAS/STING pathway activation and suppression of endothelial proliferation. Futher, knockout of the cGAS gene restores endothelial repair/regeneration in a mouse model of inflammatory lung injury (Huang et al, Immunity, 2020, March 2017; 52 (3): 475-486.e5. doi: 10.1016/j.immuni.2020,02.002).

Additionally, cGAS inhibitors of formula (I) or of formula (I') have a therapeutic potential in the treatment of age-related and obesity-related cardiovascular diseases (Hamann et al, Immun Ageing, 2020, Mar. 14; 17: 7; doi: 10.1186/s12979-020-00176-y.eCollection 2020).

Consequently the compounds of formula (I) or of formula (I') as cGAS inhibitors can be used in the therapy of autoinflammatory and autoimmune diseases such as systemic lupus erythematosus (SLE), interferonopathies, Aicardi-Goutieres syndrome, age-related macular degeneration (AMD), amyotrophic lateral sclerosis (ALS), inflammatory bowel disease (IBD), chronic obstructive pulmonary disease (COPD), Bloom's syndrome, Sjogren's syndrome and Parkinson disease.

Additionally the compounds of formula (I) or of formula (I') as cGAS inhibitors can be used in the therapy of fibrosing disease such as systemic sclerosis (SSc), interferonopathies, non-alcoholic steatotic hepatitis (NASH), interstitial lung disease (ILD), preferably progressive fibrosing interstitial lung disease (PF-ILD), in particular idiopathic pulmonary fibrosis (IPF).

Further, the compounds of formula (I) or of formula (I') as cGAS inhibitors can be used in the therapy of age-related macular degeneration (AMD), heart failure, COVID-19/SARS-CoV-2 infection, renal inflammation, renal fibrosis, dysmetabolism, vascular diseases, cardiovascular diseases and cancer.

8 Combinations

The compounds of formula (I) or of formula (I') may be administered to the patient alone or in combination with one or more other pharmacologically active agents.

In a preferred embodiment of the invention the compounds of formula (I) or of formula (I') may be combined with one or more pharmacologically active agents selected from the group of anti-inflammatory agents, anti-fibrotic agents, anti-allergic agents/anti-histamines, bronchodilators, beta 2 agonists/betamimetics, adrenergic agonists, anticholinergic agents, methotrexate, mycophenolate mofetil, leukotriene modulators, JAK inhibitiors, anti-interleukin antibodies, non-specific immunotherapeutics such as interferones or other cytokines/chemokines, cytokine/chemokine receptor modulators (i.e. cytokine receptor agonists or antagonists), Toll-like receptor agonists (=TLR agonists), immune checkpoint regulators, anti-TNF antibodies (Humira™), and anti-BAFF agents (Belimumab and Etanercept).

Anti-fibrotic agents are preferably selected from Pirfenidone and tyrosine kinase inhibitors such as Nintedanib, wherein Nintedanib is preferred in particular.

Preferred examples of anti-inflammatory agents are NSAIDs and corticosteroids.

NSAIDs are preferably selected from ibuprofen, naproxen, diclofenac, meloxicam, celecoxib, acetylsalicylic acid (Aspirin™), indomethacin, mefenamic acid and etoricoxib.

Corticosteroids are preferably selected from Flunisolide, Beclomethasone, Triamcinolone, Budesonide, Fluticasone, Mometasone, Ciclesonide, Rofleponide and Dexametasone.

Antiallergic agents/anti-histamines are preferably selected from Epinastine, Cetirizine, Azelastine, Fexofenadine, Levocabastine, Loratadine, Ebastine, Desloratidine and Mizolastine.

Beta 2 agonists/betamimetics may be either long acting beta 2 Agonists (LABAs) or short acting beta agonists (SABAs). Particularly preferred beta 2 agonists/betamimetics are selected from Bambuterol, Bitolterol, Carbuterol, Clenbuterol, Fenoterol, Formoterol, Hexoprenalin, Ibuterol, Pirbuterol, Procaterol, Reproterol, Salmeterol, Sulfonterol, Terbutalin, Tolubuterol, Olodaterol, and Salbutamol, in particular Olodaterol.

Anticholinergic agents are preferably selected from ipratropium salts, tiotropium salts, glycopyrronium salts, and theophylline, wherein tiotropium bromide is preferred in particular.

Leukotriene modulators are preferably selected from Montelukast, Pranlukast, Zafirlukast, Ibudilast and Zileuton.

JAK inhibitors are preferably selected from Baricitinib, Cerdulatinib, Fedratinib, Filgotinib, Gandotinib, Lestaurtinib, Momelotinib, Pacritinib, Peficitinib, Ruxolitinib, Tofacitinib, and Upadacitinib.

Anti-interleukin antibodies are preferably selected from anti-IL23 antibodies such as Risankizumab, anti-IL17 antibodies, anti-IL1 antibodies, anti-IL4 antibodies, anti-IL13 antibodies, anti-IL-5 antibodies, anti-IL-6 antibodies such as Actemra™, anti-IL-12 antibodies, anti-IL-15 antibodies.

9 Formulations

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, intrasternal, and subcutaneous injection or infusion. Inhalation refers to administration into the patient's lungs whether inhaled through the mouth or through the nasal passages. Topical administration includes application to the skin. The compounds of the invention may be administered via eye drops to treat Sjogren's syndrome.

Suitable forms for administration are for example tablets, capsules, solutions, syrups, emulsions or inhalable powders or aerosols. The content of the pharmaceutically effective compound(s) in each case should be in the range from 0.1 to 90 wt. %, preferably 0.5 to 50 wt. % of the total composition, i.e. in amounts which are sufficient to achieve the dosage range specified hereinafter.

The preparations may be administered orally in the form of a tablet, as a powder, as a powder in a capsule (e.g. a hard gelatin capsule), as a solution or suspension. When administered by inhalation the active substance combination may be given as a powder, as an aqueous or aqueous-ethanolic solution or using a propellant gas formulation.

Preferably, therefore, pharmaceutical formulations are characterized by the content of one or more compounds of formula (I) or of formula (I') according to the preferred embodiments above.

It is particularly preferable if the compounds of formula (I) or of formula (I') are administered orally, and it is also particularly preferable if they are administered once or twice a day. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example kollidone or shellac, gum arabic, talc, titanium dioxide or sugar. To achieve delayed release or prevent incompatibilities the core may also consist of a number of layers. Similarly, the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavor enhancer, e.g. a flavoring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Capsules containing one or more active substances or combinations of active substances may for example be prepared by mixing the active substances with inert carriers such as lactose or sorbitol and packing them into gelatin capsules. Suitable suppositories may be made for example by mixing with carriers provided for this purpose, such as neutral fats or polyethylene glycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral administration the tablets may, of course, contain, apart from the abovementioned carriers, additives such as sodium citrate, calcium carbonate and dicalcium phosphate together with various additives such as starch, preferably potato starch, gelatin and the like. Moreover, lubricants such as magnesium stearate, sodium lauryl sulphate and talc may be used at the same time for the tableting process. In the case of aqueous suspensions, the active substances may be combined with various flavor enhancers or colorings in addition to the excipients mentioned above.

The invention claimed is:

1. A compound of formula (I), (I)

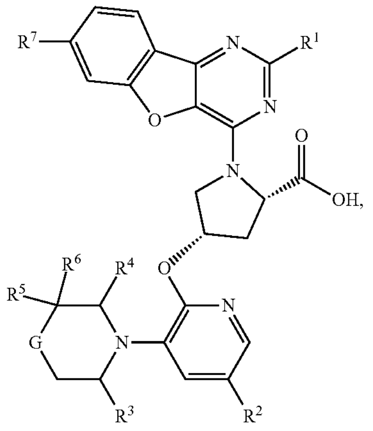

wherein $R^1$ is selected from methyl, ethyl, halomethyl, haloethyl and halogen, wherein G is selected from O, $NR^8$, $CH_2$, and $CR^8R^9$, wherein $R^2$ is selected from H, halogen, cyclopropyl, $C_{1-3}$-alkyl, —$C_{2-5}$-alkynyl, —S-methyl and CN, wherein $R^3$ is H or methyl, $R^4$ is H or methyl, $R^5$ is selected from H, methyl, —CN, -methylene-OH and —$CF_3$, or $R^5$ may be absent, $R^6$ is selected from H, methyl, —CN, -methylene-OH and —$CF_3$, or $R^5$ and $R^6$ together with the C-atoms in between form a ring selected from oxetane, tetrahydrofurane and cyclopropane, $R^7$ is selected from H, halogen, $(C_{1-3})$-alkyl and halo-$(C_{1-3})$-alkyl, $R^8$ is selected from CN, H and methyl, $R^9$ is selected from H, methyl and halogen or $R^9$ may be absent, or G is $CR^8R^9$, $R^5$ and $R^9$ are absent, and $R^8$ and $R^6$ and the two C-atoms in between $R^8$ and $R^6$ form an annulated five-membered aromatic or non-aromatic heterocycle comprising one, two or three heteroatoms each independently selected from N, S and O, or G is $CR^8R^9$ and $R^8$ and $R^9$ form together with the C-atom in between $R^8$ and $R^9$ a diazirine ring;

or a pharmaceutically acceptable salt thereof.

2. The compound according to claim 1 of formula (I'), (I')

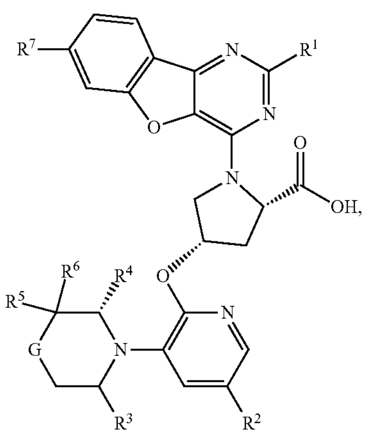

wherein $R^1$, $R^2$, $R^3$, $R^4$, $R^5$, $R^6$, $R^7$, $R^8$, $R^9$ and G are defined as in claim 1;

or a pharmaceutically acceptable salt thereof.

3. The compound of formula (I) according to claim 1, wherein $R^7$ is selected from H, F, Cl, methyl, ethyl, halomethyl and haloethyl;

or a pharmaceutically acceptable salt thereof.

4. The compound of formula (I) according to claim 1, wherein $R^1$ is selected from halomethyl, haloethyl and methyl;

or a pharmaceutically acceptable salt thereof.

5. The compound according to claim 3, wherein $R^1$ is a fluoromethyl selected from the group consisting of $-CF_3$, $-CHF_2$ and $-CH_2F$;

or a pharmaceutically acceptable salt thereof.

6. The compound of formula (I) according to claim 1, wherein at least one of $R^3$ and $R^4$ is methyl;

or a pharmaceutically acceptable salt thereof.

7. The compound of formula (I) according to claim 1, wherein one of $R^3$ and $R^4$ is methyl and the other one is H;

or a pharmaceutically acceptable salt thereof.

8. The compound of formula (I) according to claim 1, wherein G is O;

or a pharmaceutically acceptable salt thereof.

9. The compound of formula (I) according to claim 1, wherein G is O, and wherein one of $R^3$ or $R^4$ is methyl and the other one is H;

or a pharmaceutically acceptable salt thereof.

10. The compound according to claim 8, wherein $R^4$ is methyl and $R^3$ is H, wherein $R^5$ and $R^6$ together with the C-atoms in between form an oxetane ring;

or a pharmaceutically acceptable salt thereof.

11. The compound of formula (I) according to claim 1, wherein $R^2$ is selected from the group consisting of H, ethynyl, 1-propynyl, —S-methyl, halogen;

or a pharmaceutically acceptable salt thereof.

12. The compound of formula (I) according to claim 1, wherein $R^2$ is ethynyl;

or a pharmaceutically acceptable salt thereof.

13. The compound of formula (I) according to claim 1, wherein $R^4$ is methyl and $R^3$ is H, wherein G is O, wherein $R^5$ and $R^6$ together form an oxetane ring wherein $R^2$ is selected from the group consisting of H, ethynyl, 1-propynyl, —S-methyl, halogen;

or a pharmaceutically acceptable salt thereof.

14. The compound of formula (I) according to claim 1, wherein

G is $CR^8R^9$, and wherein $R^8$ and $R^6$ and the two C-atoms in between $R^8$ and $R^6$ form an annulated five-membered aromatic heterocycle comprising one or two heteroatoms each independently selected from N and O which is selected from an annulated isoxazolyl ring, an annulated pyrazolyl ring, an annulated pyrrolyl ring and an annulated furanyl ring, and wherein $R^9$ and $R^5$ are absent;

or a pharmaceutically acceptable salt thereof.

15. The compound of formula (I) according to claim 1, which is selected from the group consisting of

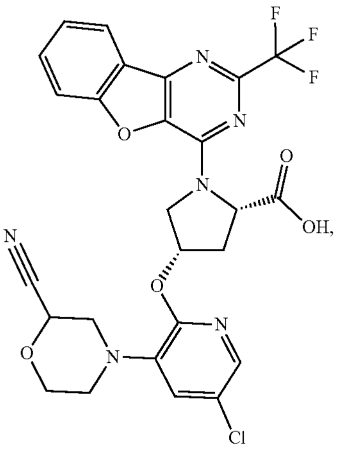

-continued
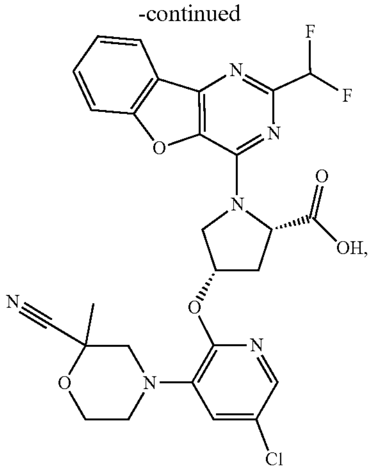
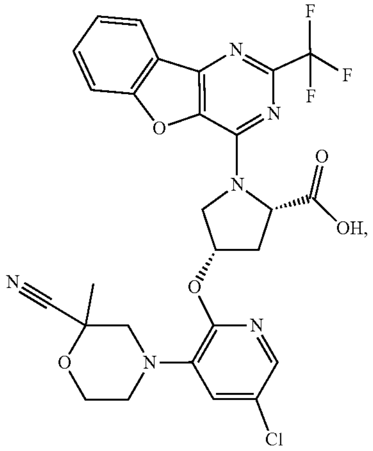
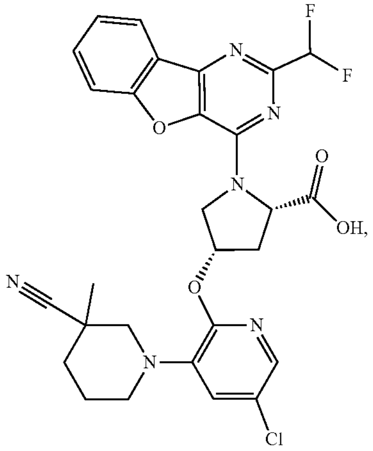
-continued
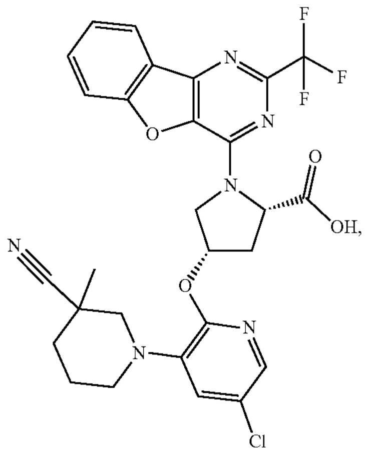
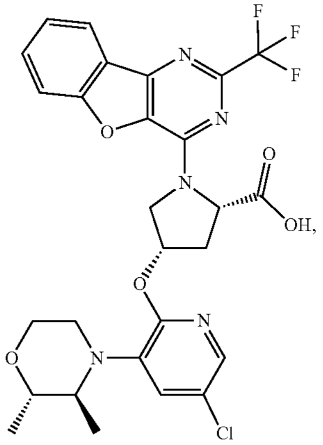
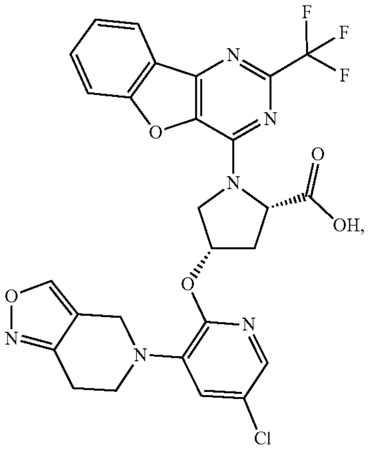

-continued
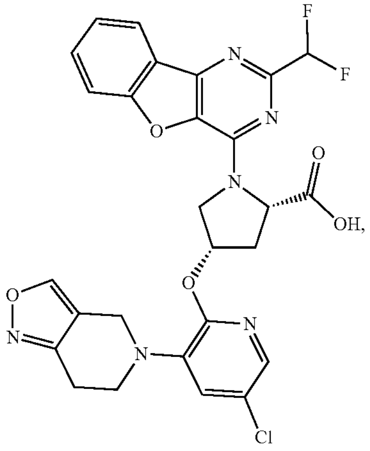
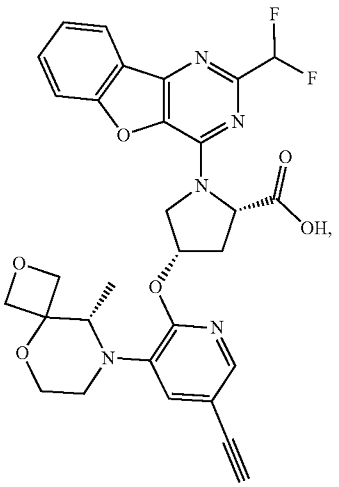
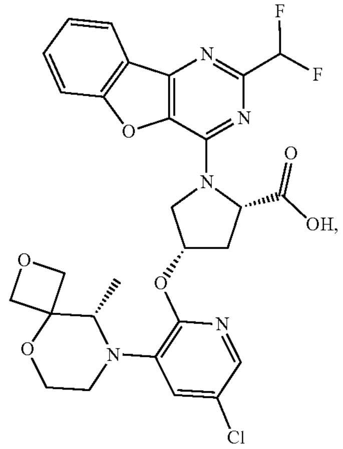
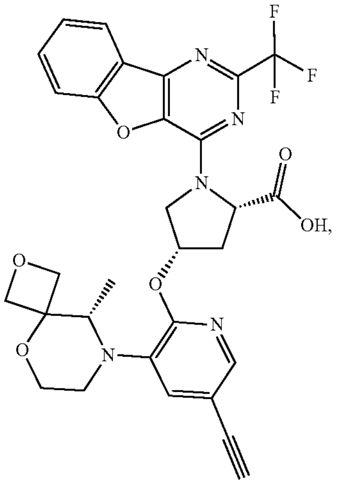
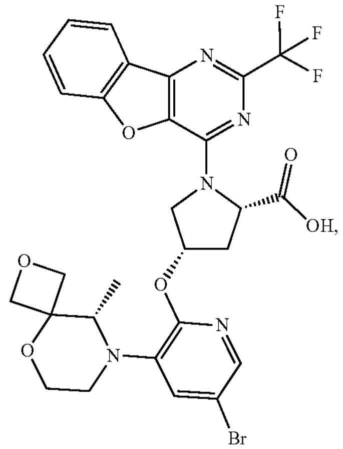
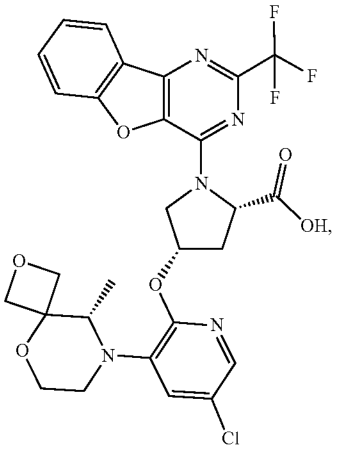
-continued -continued
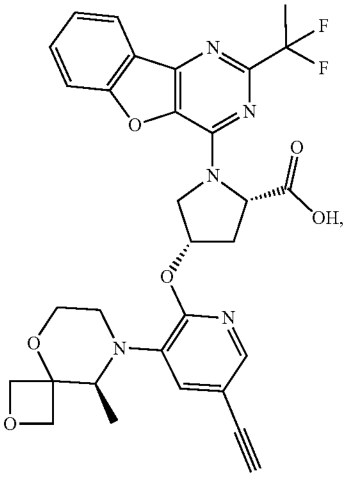
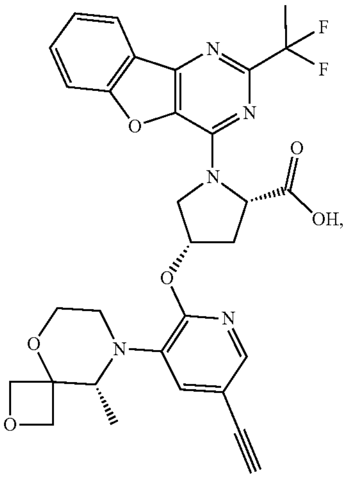
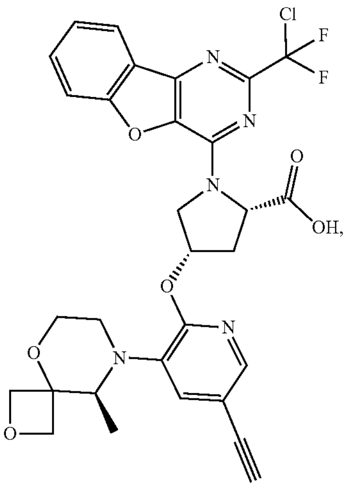
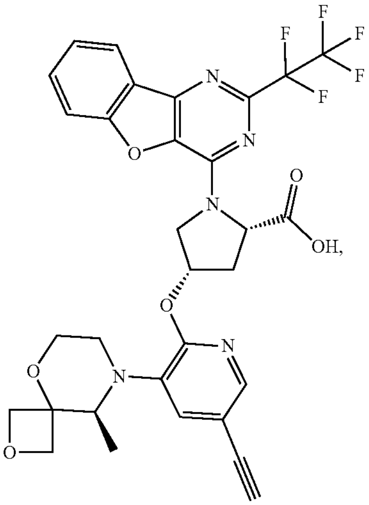
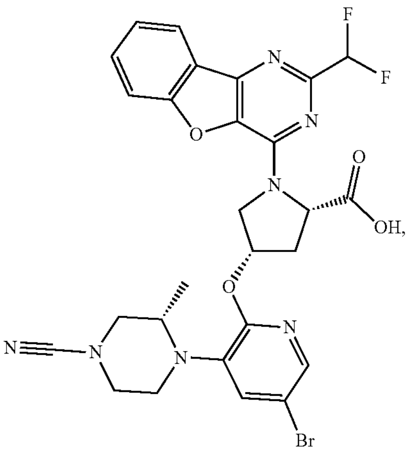
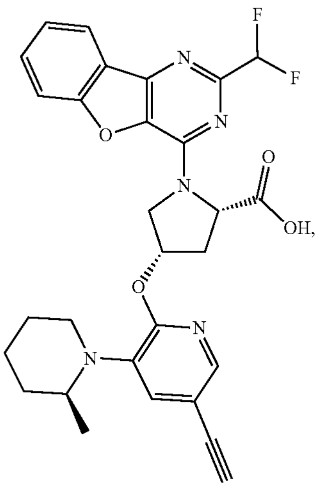
-continued -continued
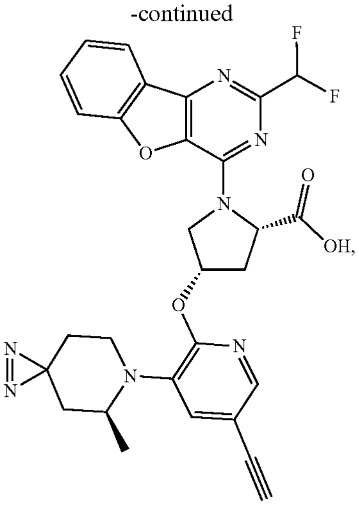
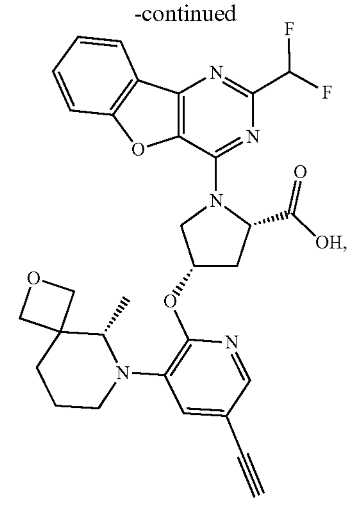
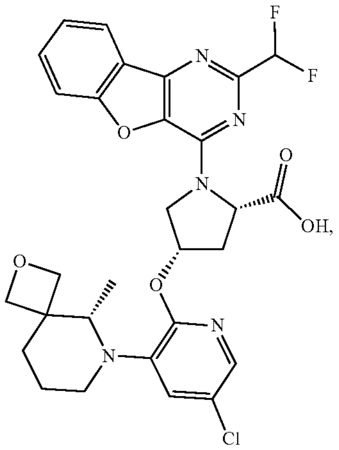
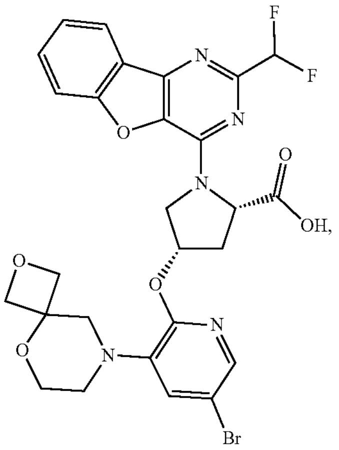
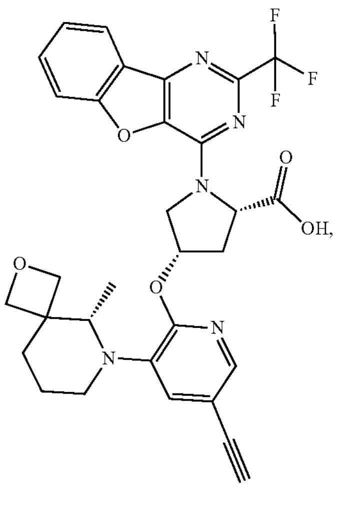
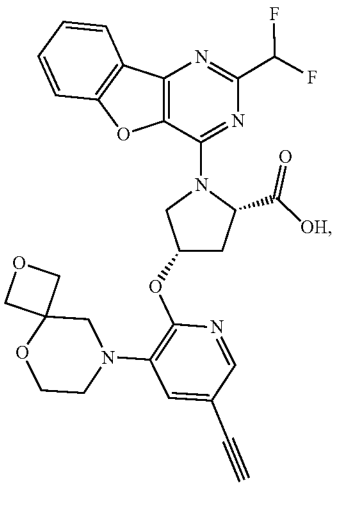

-continued
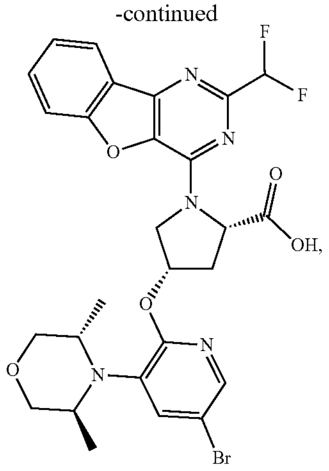
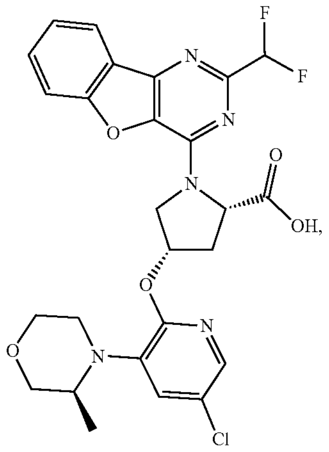
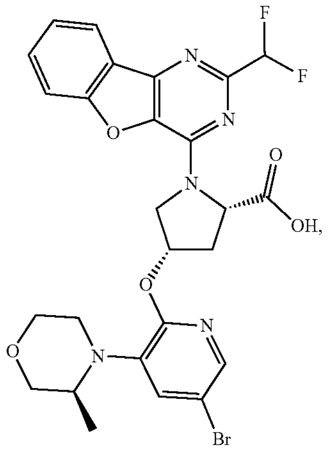
-continued
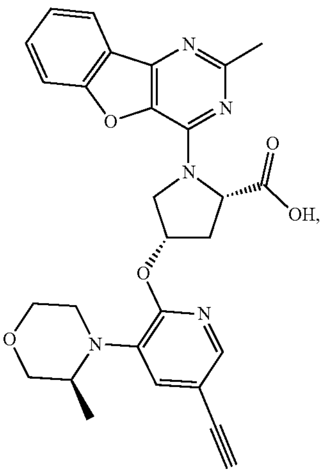
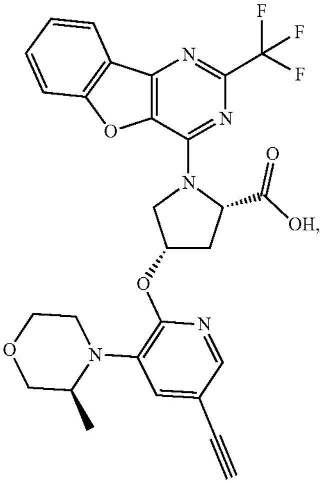
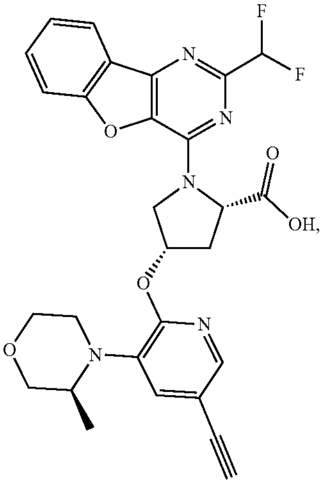

-continued
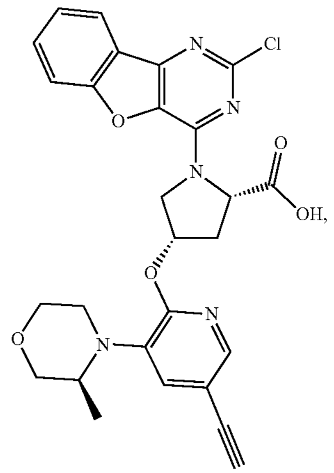
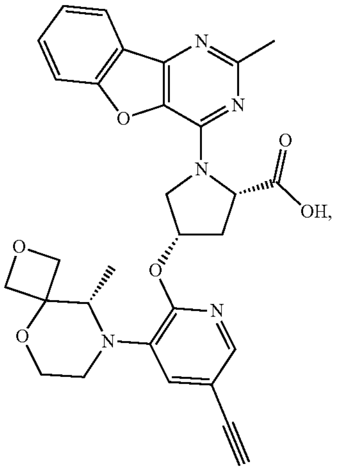
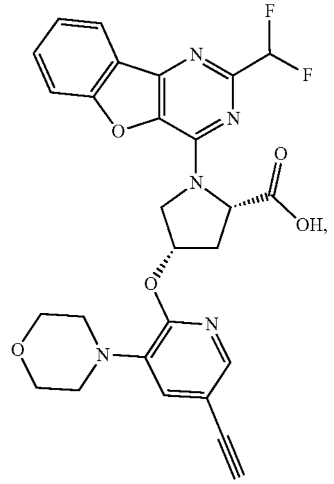
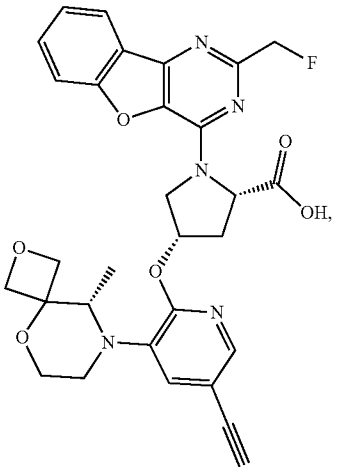
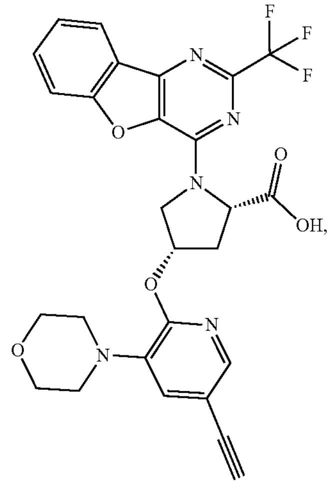
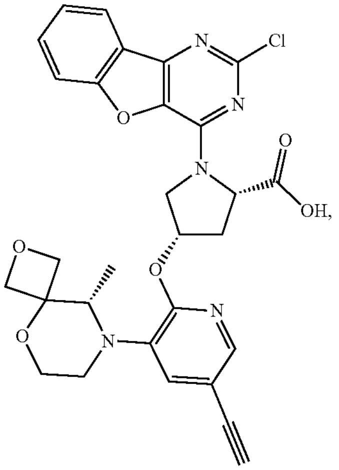

-continued
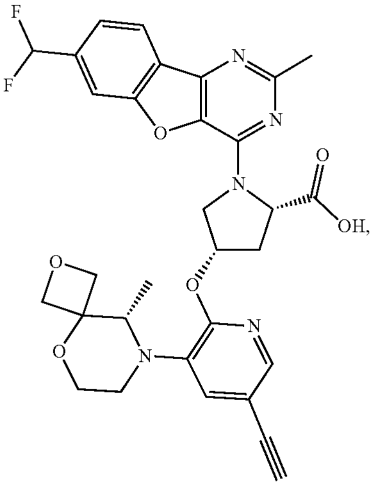
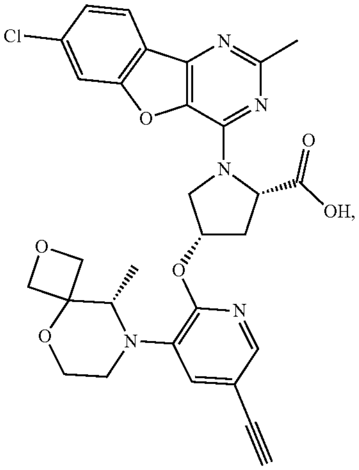
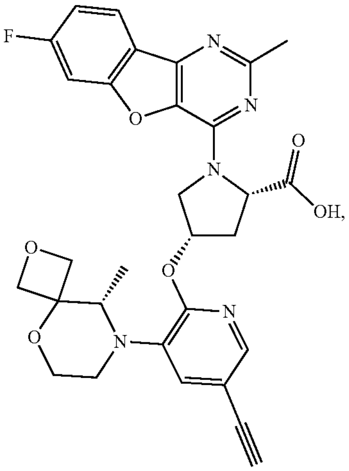
-continued
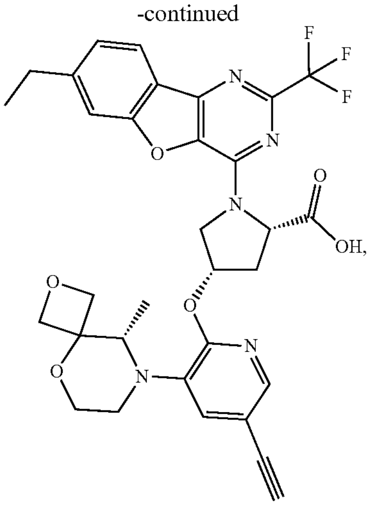
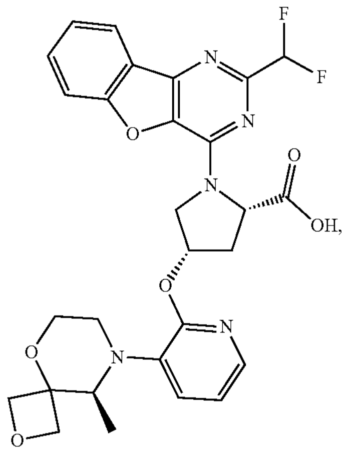
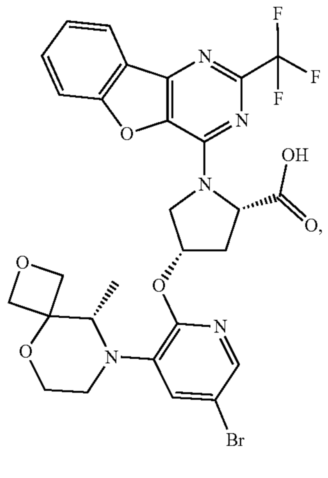

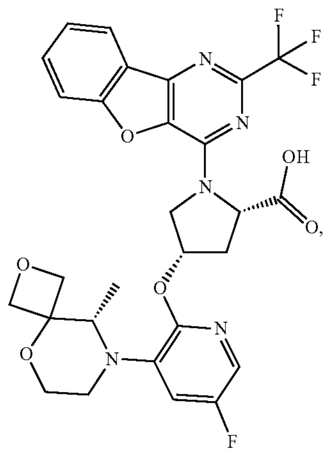
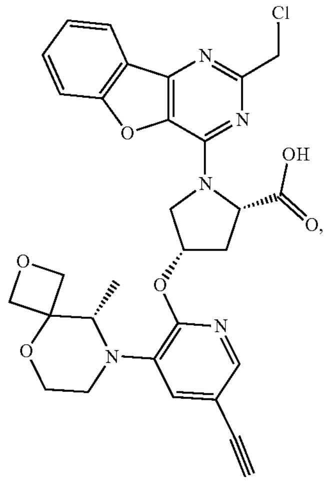
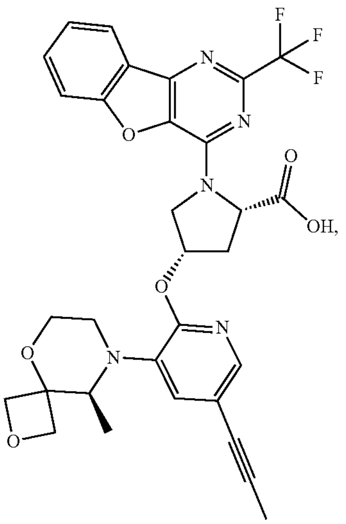
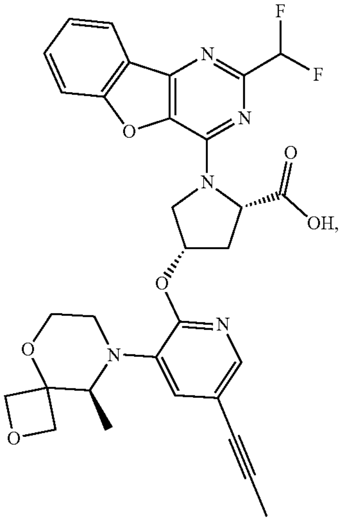
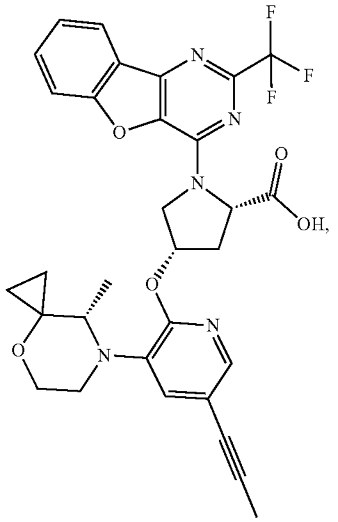
and
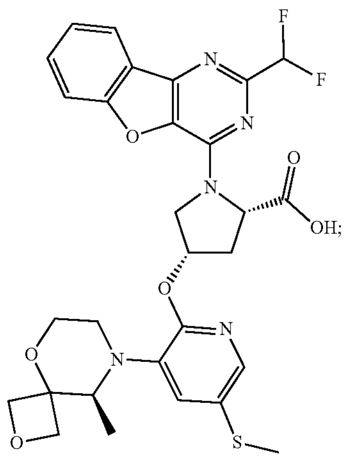
or a pharmaceutically acceptable salt thereof.

16. A compound of formula (A)

(A)

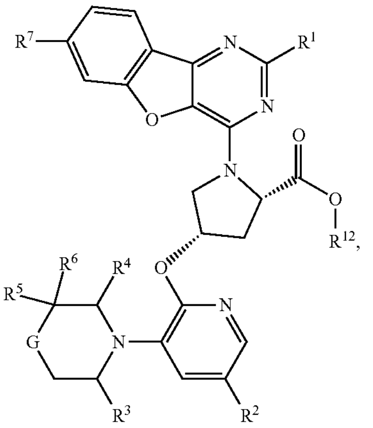

or of formula (A')

(A')

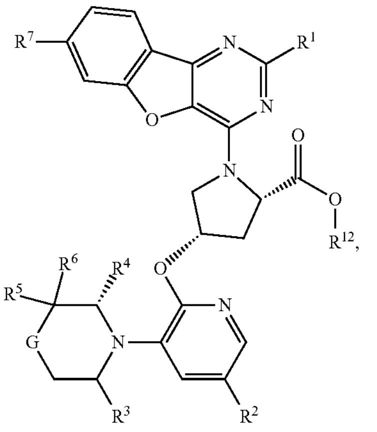

wherein $R^1$ is selected from methyl, ethyl, halomethyl, haloethyl and halogen, wherein G is selected from O, $NR^8$, $CH_2$, and $CR^8R^9$, wherein $R^2$ is selected from H, halogen, cyclopropyl, $C_{1-3}$-alkyl,-$C_{2-5}$-alkynyl,-S-methyl and CN, wherein $R^3$ is H or methyl, $R^4$ is H or methyl, $R^5$ is selected from H, methyl,-CN,-methylene-OH and-$CF_3$, or $R^5$ may be absent, $R^6$ is selected from H, methyl,-CN,-methylene-OH and-$CF_3$, or $R^5$ and R6 together with the C-atoms in between form a ring selected from oxetane, tetrahydrofurane and cyclopropane, $R^7$ is selected from H, halogen, $(C_{1-3})$-alkyl and halo-$(C_{1-3})$-alkyl, $R^8$ is selected from CN, H and methyl, $R^9$ is selected from H, methyl and halogen or $R^9$ may be absent, or G is $CR^8R^9$, $R^5$ and $R^9$ are absent, and $R^8$ and $R^6$ and the two C-atoms in between $R^8$ and R6 form an annulated five-membered aromatic or non-aromatic heterocycle comprising one, two or three heteroatoms each independently selected from N, S and O, or G is $CR^8R^9$ and $R^8$ and $R^9$ form together with the C-atom in between $R^8$ and $R^9$ a diazirine ring, and wherein $R^{12}$ is $C_{1-4}$-alkyl, aryl,-$CH_2$-aryl, or NH-$SO_2$-$C_{1-3}$-alkyl.

17. The compound of formula (A) or of formula (A') according to claim 16, wherein $R^{12}$ is methyl.

18. The compound of formula (I) according to claim 1, which is

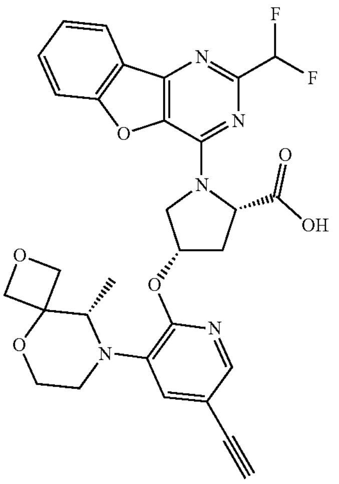 [SMILES: C#Cc1cnc(O[C@H]2C[C@@H](C(=O)O)N(c3nc(C(F)F)nc4c3oc3ccccc34)C2)c(N2CCOC3(COC3)[C@@H]2C)c1]

or a pharmaceutically acceptable salt thereof.

19. The compound of formula (I) according to claim 1, which is

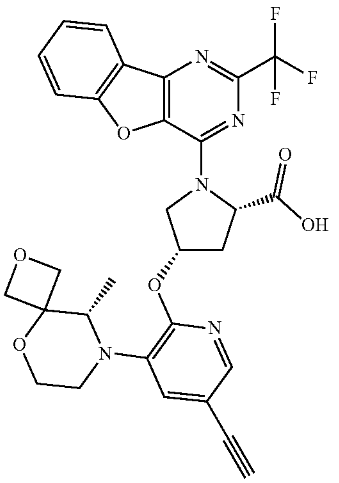 [SMILES: C#Cc1cnc(O[C@H]2C[C@@H](C(=O)O)N(c3nc(C(F)(F)F)nc4c3oc3ccccc34)C2)c(N2CCOC3(COC3)[C@@H]2C)c1]

or a pharmaceutically acceptable salt thereof.

20. The compound of formula (I) according to claim 1, which is

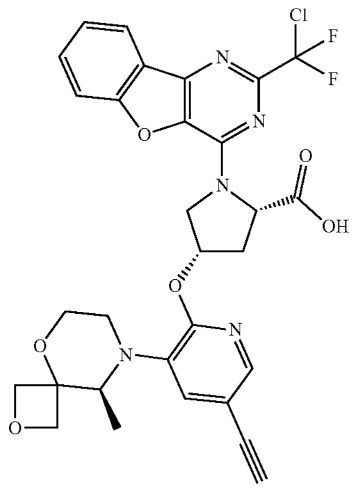 [SMILES: C#Cc1cnc(O[C@H]2C[C@@H](C(=O)O)N(c3nc(C(F)(F)Cl)nc4c3oc3ccccc34)C2)c(N2CCOC3(COC3)[C@@H]2C)c1]

or a pharmaceutically acceptable salt thereof.

21. The compound of formula (I) according to claim 1, which is

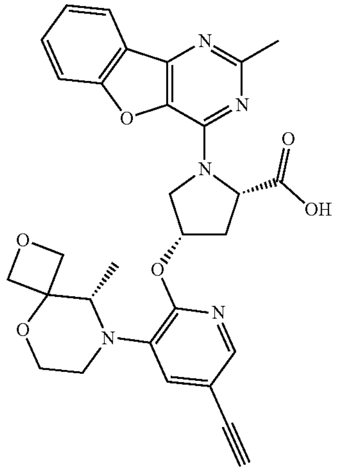 [SMILES: C#Cc1cnc(O[C@H]2C[C@@H](C(=O)O)N(c3nc(C)nc4c3oc3ccccc34)C2)c(N2CCOC3(COC3)[C@@H]2C)c1]

or a pharmaceutically acceptable salt thereof.

22. The compound of formula (I) according to claim 1, which is

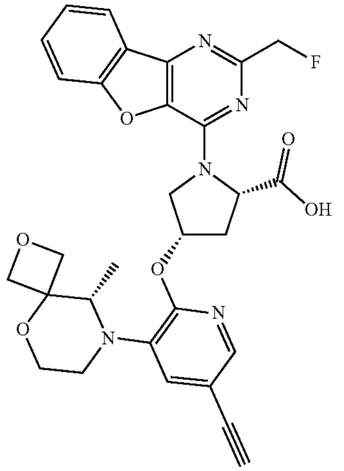 [SMILES: C#Cc1cnc(O[C@H]2C[C@@H](C(=O)O)N(c3nc(CF)nc4c3oc3ccccc34)C2)c(N2CCOC3(COC3)[C@@H]2C)c1]

or a pharmaceutically acceptable salt thereof.

23. The compound of formula (I) according to claim 1, which is

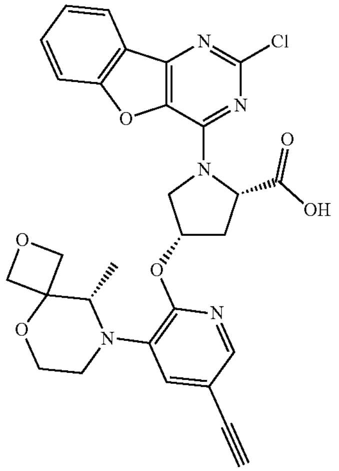 [SMILES: C#Cc1cnc(O[C@H]2C[C@@H](C(=O)O)N(c3nc(Cl)nc4c3oc3ccccc34)C2)c(N2CCOC3(COC3)[C@@H]2C)c1]

or a pharmaceutically acceptable salt thereof.

24. The compound of formula (I) according to claim 1, which is

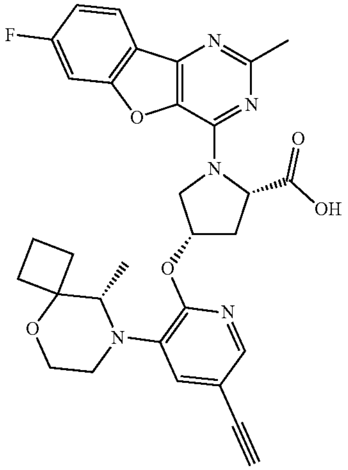 [SMILES: C#Cc1cnc(O[C@H]2C[C@@H](C(=O)O)N(c3nc(C)nc4c3oc3cc(F)ccc34)C2)c(N2CCOC3(CCC3)[C@@H]2C)c1]

or a pharmaceutically acceptable salt thereof.

25. The compound of formula (I) according to claim 1, which is

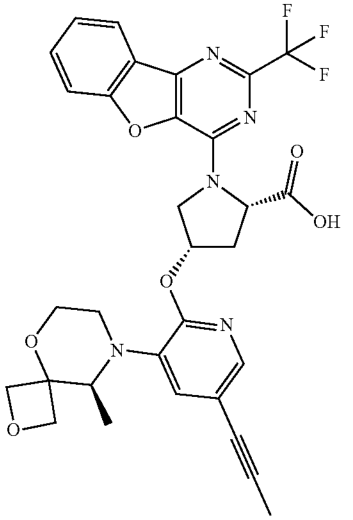 [SMILES: CC#Cc1cnc(O[C@H]2C[C@@H](C(=O)O)N(c3nc(C(F)(F)F)nc4c3oc3ccccc34)C2)c(N2CCOC3(COC3)[C@@H]2C)c1]

or a pharmaceutically acceptable salt thereof.

26. The compound of formula (I) according to claim 1, which is
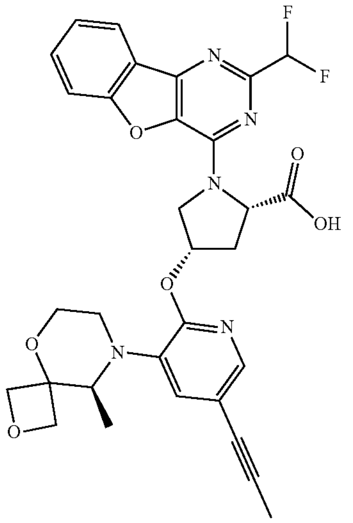 [SMILES: CC#Cc1cnc(O[C@H]2C[C@@H](C(=O)O)N(c3nc(C(F)F)nc4c3oc3ccccc34)C2)c(N2CCOC3(COC3)[C@@H]2C)c1]
or a pharmaceutically acceptable salt thereof.
27. A compound of formula:
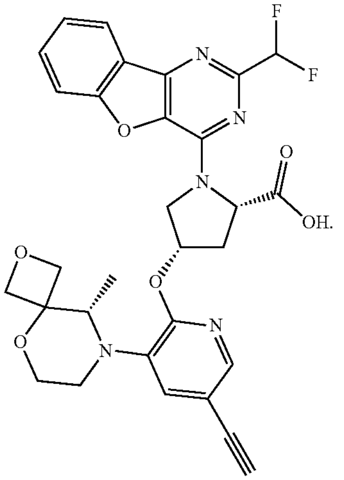 [SMILES: C#Cc1cnc(O[C@H]2C[C@@H](C(=O)O)N(c3nc(C(F)F)nc4c3oc3ccccc34)C2)c(N2CCOC3(COC3)[C@@H]2C)c1]
28. A compound of formula:
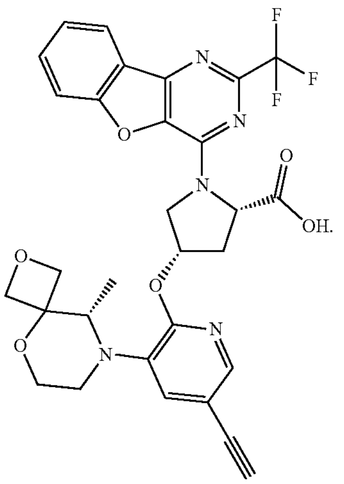 [SMILES: C#Cc1cnc(O[C@H]2C[C@@H](C(=O)O)N(c3nc(C(F)(F)F)nc4c3oc3ccccc34)C2)c(N2CCOC3(COC3)[C@@H]2C)c1]
29. A compound of formula:
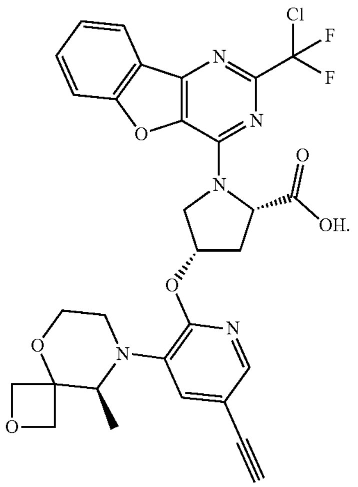 [SMILES: C#Cc1cnc(O[C@H]2C[C@@H](C(=O)O)N(c3nc(C(F)(F)Cl)nc4c3oc3ccccc34)C2)c(N2CCOC3(COC3)[C@@H]2C)c1]
30. A compound of formula:
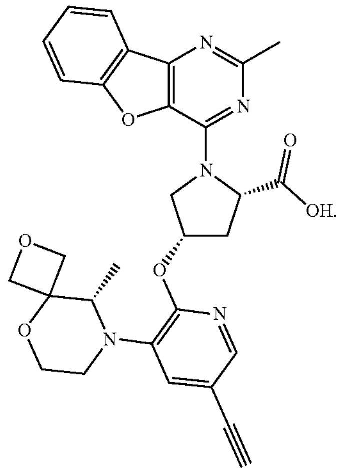 [SMILES: C#Cc1cnc(O[C@H]2C[C@@H](C(=O)O)N(c3nc(C)nc4c3oc3ccccc34)C2)c(N2CCOC3(COC3)[C@@H]2C)c1]
31. A compound of formula:
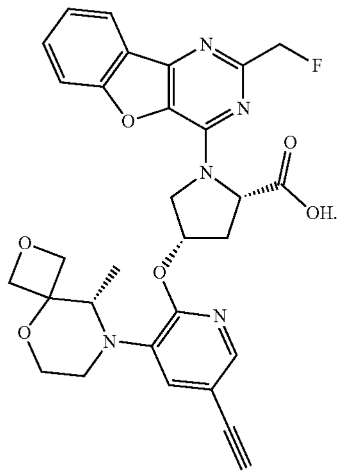 [SMILES: C#Cc1cnc(O[C@H]2C[C@@H](C(=O)O)N(c3nc(CF)nc4c3oc3ccccc34)C2)c(N2CCOC3(COC3)[C@@H]2C)c1]

32. A compound of formula:

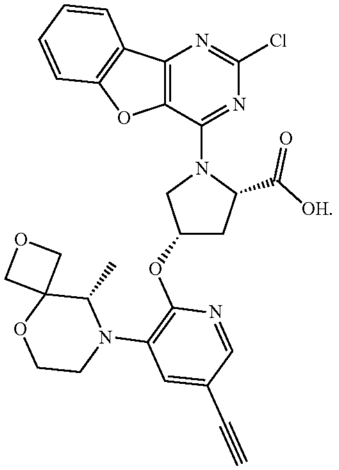 [SMILES: C#Cc1cnc(O[C@H]2C[C@@H](C(=O)O)N(c3nc(Cl)nc4c3oc3ccccc34)C2)c(N2CCOC3(COC3)[C@@H]2C)c1]

33. A compound of formula:

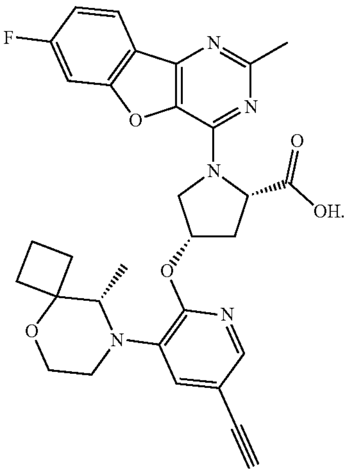 [SMILES: C#Cc1cnc(O[C@H]2C[C@@H](C(=O)O)N(c3nc(C)nc4c3oc3cc(F)ccc34)C2)c(N2CCOC3(CCC3)[C@@H]2C)c1]

34. A compound of formula:

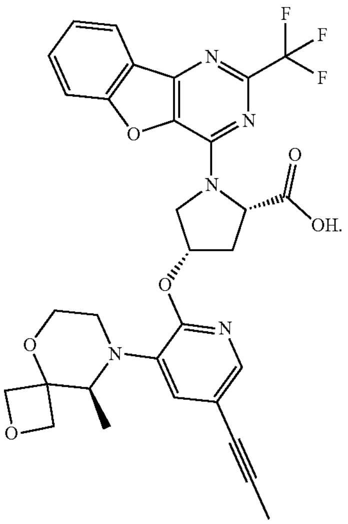 [SMILES: CC#Cc1cnc(O[C@H]2C[C@@H](C(=O)O)N(c3nc(C(F)(F)F)nc4c3oc3ccccc34)C2)c(N2CCOC3(COC3)[C@@H]2C)c1]

35. A compound of formula:

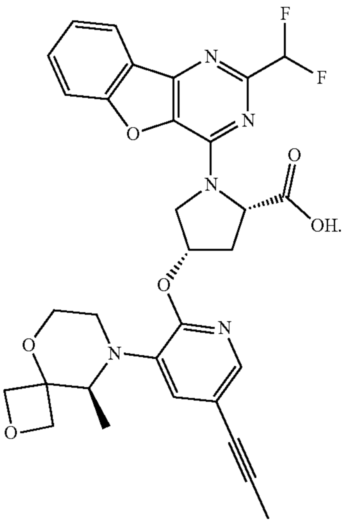 [SMILES: CC#Cc1cnc(O[C@H]2C[C@@H](C(=O)O)N(c3nc(C(F)F)nc4c3oc3ccccc34)C2)c(N2CCOC3(COC3)[C@@H]2C)c1]

36. A pharmaceutical composition comprising a compound of formula (I) according to claim 1 and optionally one or more pharmaceutically acceptable carriers and/or excipients.

37. A pharmaceutical composition comprising a compound of formula (I) according to claim 1 in combination with one or more active agents selected from the group consisting of anti-inflammatory agents, anti-fibrotic agents, anti-allergic agents/anti-histamines, bronchodilators, beta 2 agonists/betamimetics, adrenergic agonists, anticholinergic agents, methotrexate, mycophenolate mofetil, leukotriene modulators, JAK inhibitors, anti-interleukin antibodies, non-specific immunotherapeutics, interferons or other cytokines/chemokines, cytokine/chemokine receptor modulators, toll-like receptor agonists, immune checkpoint regulators, an anti-TNF antibody, and an anti-BAFF antibody.

38. The pharmaceutical composition according to claim 37, wherein the compound of formula (I) is combined with one or more anti-fibrotic agents selected from the group consisting of Pirfenidon and Nintedanib.

39. The pharmaceutical composition according to claim 37, wherein the compound of formula (I) is combined with one or more anti-inflammatory agents selected from the group consisting of NSAIDs and corticosteroids.

40. The pharmaceutical composition according to claim 37, wherein the compound of formula (I) is combined with one or more active agents selected from the group of bronchodilators, beta 2 agonists/betamimetics, adrenergic agonists and anticholinergic agents.

41. The pharmaceutical composition according to claim 37, wherein the compound of formula (I) is combined with one or more anti-interleukin antibodies selected from the group consisting of anti-IL-23 antibodies, anti-IL-17 antibodies, anti-IL-1 antibodies, anti-IL-4 antibodies, anti-IL-13 antibodies, anti-1L-5 antibodies, anti-IL-6 antibodies, anti-IL-12 antibodies and anti-IL-15 antibodies.

42. A method of treating in a subject a disease that can be treated by the inhibition of cGAS, said method comprising administering to the subject a compound of formula (I) according to claim 1.

43. A method of treating in a subject a disease selected from the group consisting of systemic lupus erythematosus (SLE), interferonopathies, Aicardi-Goutières syndrome, age-related macular degeneration (AMD), amyotrophic lateral sclerosis (ALS), inflammatory bowel disease (IBD), chronic obstructive pulmonary disease (COPD), Bloom's syndrome, Sjogren's syndrome, Parkinsons disease, heart failure and cancer, systemic sclerosis (SSc), non-alcoholic steatotic hepatitis (NASH), interstitial lung disease (ILD), progressive fibrosing interstitial lung disease (PF-ILD), and idiopathic pulmonary fibrosis (IPF), said method comprising administering to the subject a compound of formula (I) according to claim 1.

44. A method of treating in a subject a disease selected from the group consisting of systemic lupus erythematosus (SLE), interferonopathies, Aicardi-Goutières syndrome, age-related macular degeneration (AMD), amyotrophic lateral sclerosis (ALS), inflammatory bowel disease (IBD), chronic obstructive pulmonary disease (COPD), Bloom's syndrome, Sjogren's syndrome and Parkinsons disease, said method comprising administering to the subject a compound of formula (I) according to claim 1.

45. A method of treating in a subject a fibrosing disease selected from the group consisting of systemic sclerosis (SSc), non-alcoholic steatotic hepatitis (NASH), interferonopathies, Aicardi-Goutières syndrome, interstitial lung disease (ILD), progressive fibrosing interstitial lung disease (PF-ILD), and idiopathic pulmonary fibrosis (IPF), said method comprising administering to the subject a compound of formula (I) according to claim 1.

46. A method of treating in a subject a disease selected from the group consisting of age-related macular degeneration (AMD), heart failure, COVID-19/SARS-COV-2 infection, renal inflammation, renal fibrosis, dysmetabolism, vascular diseases, cardiovascular diseases and cancer, said method comprising administering to the subject a compound of formula (I) according to claim 1.

47. A method of treating in a subject a disease selected from the group consisting of interferonopathies, systemic sclerosis (SSc), and non-alcoholic steatotic hepatitis (NASH), said method comprising administering to the subject a compound selected from the group consisting of:

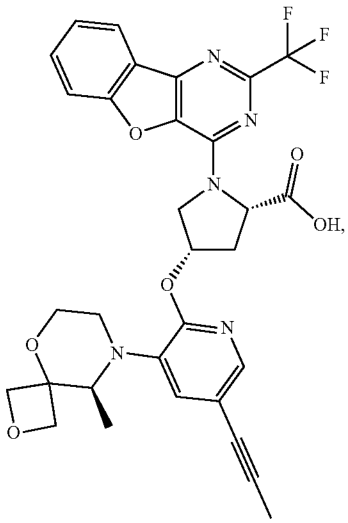

and

-continued

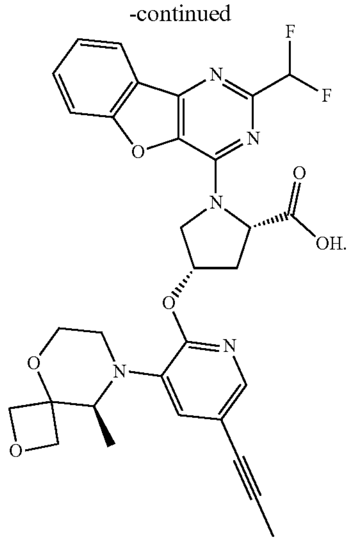

48. The pharmaceutical composition of claim 36, wherein the compound of formula (I) is the following compound:

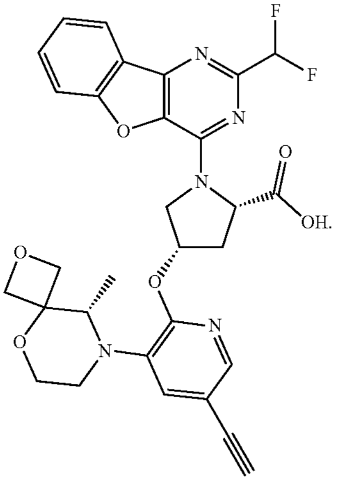 [SMILES: C#Cc1cnc(O[C@H]2C[C@@H](C(=O)O)N(c3nc(C(F)F)nc4c3oc3ccccc34)C2)c(N2CCOC3(COC3)[C@@H]2C)c1]

49. The pharmaceutical composition of claim 36, wherein the compound of formula (I) is the following compound:

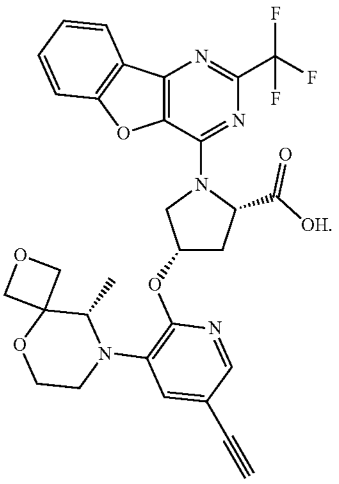 [SMILES: C#Cc1cnc(O[C@H]2C[C@@H](C(=O)O)N(c3nc(C(F)(F)F)nc4c3oc3ccccc34)C2)c(N2CCOC3(COC3)[C@@H]2C)c1]

50. The pharmaceutical composition of claim 36, wherein the compound of formula (I) is the following compound:

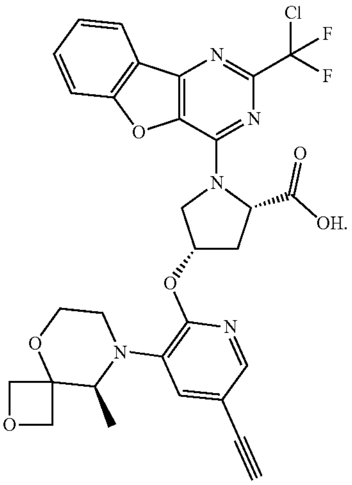 [SMILES: C#Cc1cnc(O[C@H]2C[C@@H](C(=O)O)N(c3nc(C(F)(F)Cl)nc4c3oc3ccccc34)C2)c(N2CCOC3(COC3)[C@@H]2C)c1]

51. The pharmaceutical composition of claim 36, wherein the compound of formula (I) is the following compound:

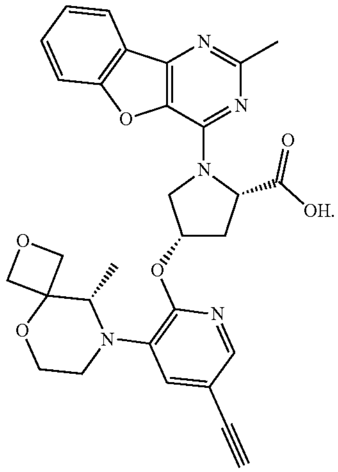 [SMILES: C#Cc1cnc(O[C@H]2C[C@@H](C(=O)O)N(c3nc(C)nc4c3oc3ccccc34)C2)c(N2CCOC3(COC3)[C@@H]2C)c1]

52. The pharmaceutical composition of claim 36, wherein the compound of formula (I) is the following compound:

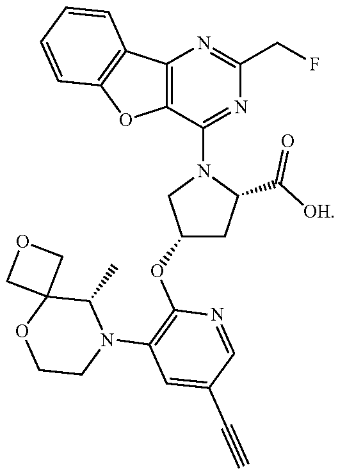 [SMILES: C#Cc1cnc(O[C@H]2C[C@@H](C(=O)O)N(c3nc(CF)nc4c3oc3ccccc34)C2)c(N2CCOC3(COC3)[C@@H]2C)c1]

53. The pharmaceutical composition of claim 36, wherein the compound of formula (I) is the following compound:

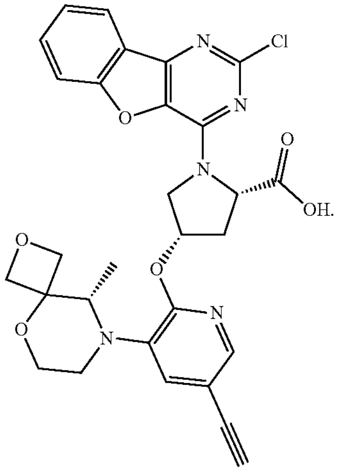 [SMILES: C#Cc1cnc(O[C@H]2C[C@@H](C(=O)O)N(c3nc(Cl)nc4c3oc3ccccc34)C2)c(N2CCOC3(COC3)[C@@H]2C)c1]

54. The pharmaceutical composition of claim 36, wherein the compound of formula (I) is the following compound:

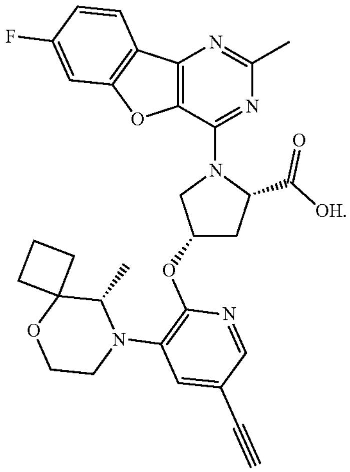 [SMILES: C#Cc1cnc(O[C@H]2C[C@@H](C(=O)O)N(c3nc(C)nc4c3oc3cc(F)ccc34)C2)c(N2CCOC3(CCC3)[C@@H]2C)c1]

55. The pharmaceutical composition of claim 36, wherein the compound of formula (I) is the following compound:

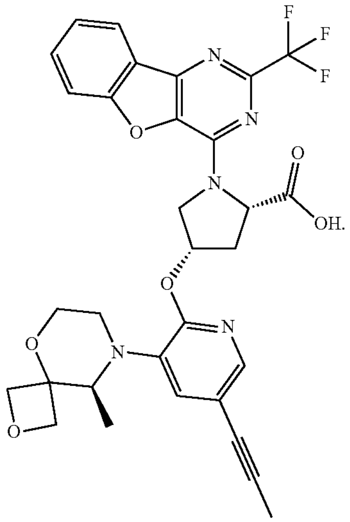 [SMILES: CC#Cc1cnc(O[C@H]2C[C@@H](C(=O)O)N(c3nc(C(F)(F)F)nc4c3oc3ccccc34)C2)c(N2CCOC3(COC3)[C@@H]2C)c1]

56. The pharmaceutical composition of claim 36, wherein the compound of formula (I) is the following compound:

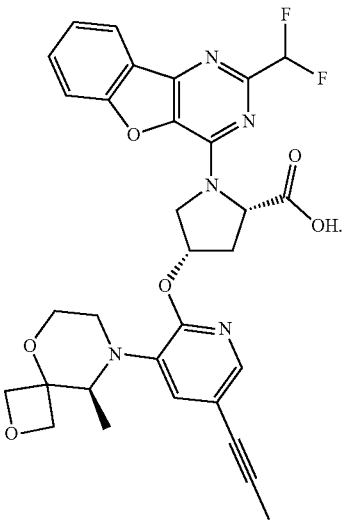 [SMILES: CC#Cc1cnc(O[C@H]2C[C@@H](C(=O)O)N(c3nc(C(F)F)nc4c3oc3ccccc34)C2)c(N2CCOC3(COC3)[C@@H]2C)c1]

57. A method of treating in a subject a disease selected from the group consisting of systemic lupus erythematosus (SLE), interferonopathies, systemic sclerosis (SSc), and non-alcoholic steatotic hepatitis (NASH), said method comprising administering to the subject the following compound:

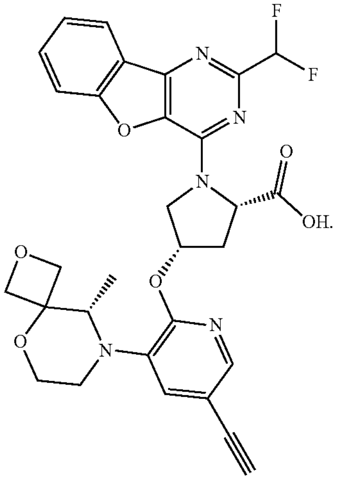 [SMILES: C#Cc1cnc(O[C@H]2C[C@@H](C(=O)O)N(c3nc(C(F)F)nc4c3oc3ccccc34)C2)c(N2CCOC3(COC3)[C@@H]2C)c1]

58. A method of treating in a subject a disease selected from the group consisting of systemic lupus erythematosus (SLE), interferonopathies, systemic sclerosis (SSc), and non-alcoholic steatotic hepatitis (NASH), said method comprising administering to the subject the following compound:

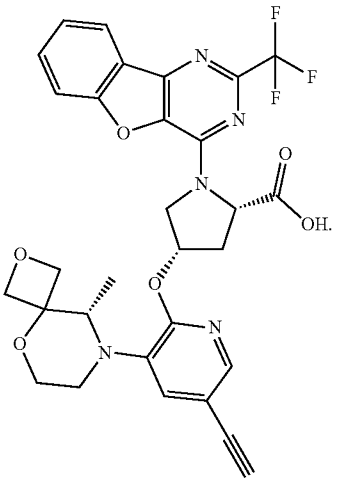 [SMILES: C#Cc1cnc(O[C@H]2C[C@@H](C(=O)O)N(c3nc(C(F)(F)F)nc4c3oc3ccccc34)C2)c(N2CCOC3(COC3)[C@@H]2C)c1]

59. A method of treating in a subject a disease selected from the group consisting of systemic lupus erythematosus (SLE), interferonopathies, systemic sclerosis (SSc), and non-alcoholic steatotic hepatitis (NASH), said method comprising administering to the subject the following compound:

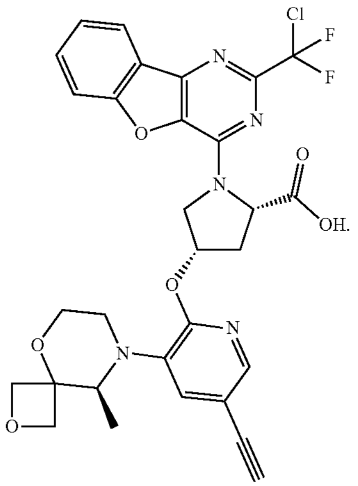 [SMILES: C#Cc1cnc(O[C@H]2C[C@@H](C(=O)O)N(c3nc(C(F)(F)Cl)nc4c3oc3ccccc34)C2)c(N2CCOC3(COC3)[C@@H]2C)c1]

60. A method of treating in a subject a disease selected from the group consisting of systemic lupus erythematosus (SLE), interferonopathies, systemic sclerosis (SSc), and non-alcoholic steatotic hepatitis (NASH), said method comprising administering to the subject the following compound:

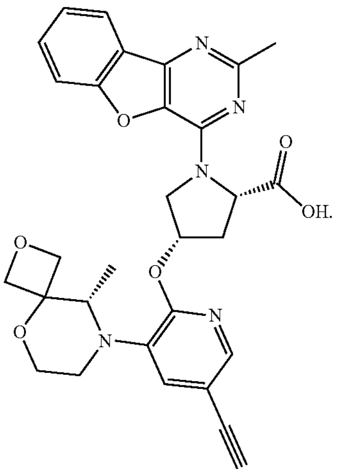 [SMILES: C#Cc1cnc(O[C@H]2C[C@@H](C(=O)O)N(c3nc(C)nc4c3oc3ccccc34)C2)c(N2CCOC3(COC3)[C@@H]2C)c1]

61. A method of treating in a subject a disease selected from the group consisting of systemic lupus erythematosus (SLE), interferonopathies, systemic sclerosis (SSc), and non-alcoholic steatotic hepatitis (NASH), said method comprising administering to the subject the following compound:

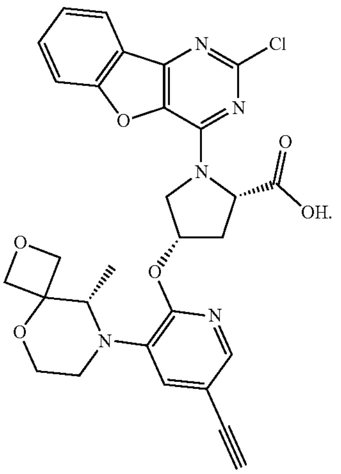

62. A method of treating in a subject a disease selected from the group consisting of systemic lupus erythematosus (SLE), interferonopathies, systemic sclerosis (SSc), and non-alcoholic steatotic hepatitis (NASH), said method comprising administering to the subject the following compound:

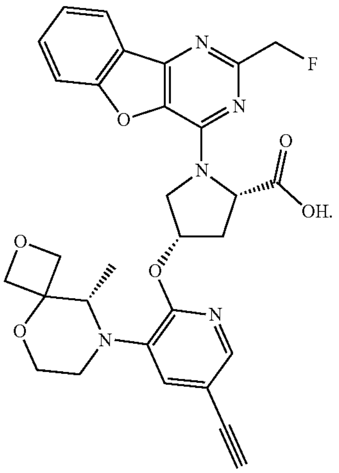 [SMILES: C#Cc1cnc(O[C@H]2C[C@@H](C(=O)O)N(c3nc(CF)nc4c3oc3ccccc34)C2)c(N2CCOC3(COC3)[C@@H]2C)c1]

63. A method of treating in a subject a disease selected from the group consisting of systemic lupus erythematosus (SLE), interferonopathies, systemic sclerosis (SSc), and non-alcoholic steatotic hepatitis (NASH), said method comprising administering to the subject the following compound:

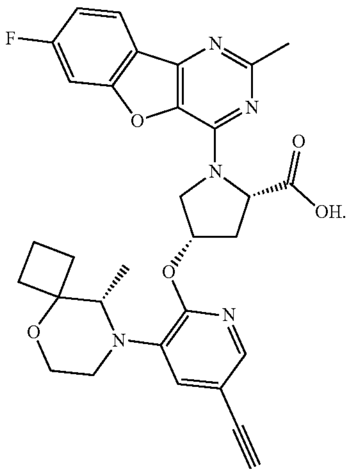 [SMILES: C#Cc1cnc(O[C@H]2C[C@@H](C(=O)O)N(c3nc(C)nc4c3oc3cc(F)ccc34)C2)c(N2CCOC3(CCC3)[C@@H]2C)c1]

64. A method of treating in a subject a disease selected from the group consisting of systemic lupus erythematosus (SLE), interferonopathies, systemic sclerosis (SSc), and non-alcoholic steatotic hepatitis (NASH), said method comprising administering to the subject the following compound:

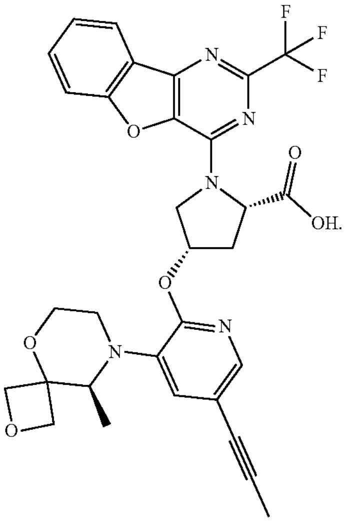 [SMILES: CC#Cc1cnc(O[C@H]2C[C@@H](C(=O)O)N(c3nc(C(F)(F)F)nc4c3oc3ccccc34)C2)c(N2CCOC3(COC3)[C@@H]2C)c1]
65. A method of treating in a subject a disease selected from the group consisting of systemic lupus erythematosus (SLE), interferonopathies, systemic sclerosis (SSc), and non-alcoholic steatotic hepatitis (NASH), said method comprising administering to the subject the following compound:
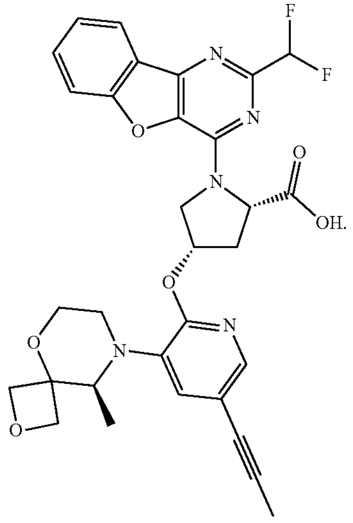 [SMILES: CC#Cc1cnc(O[C@H]2C[C@@H](C(=O)O)N(c3nc(C(F)F)nc4c3oc3ccccc34)C2)c(N2CCOC3(COC3)[C@@H]2C)c1]
* * * * *